United States Patent
Phalipon et al.

(10) Patent No.: US 9,446,109 B2
(45) Date of Patent: Sep. 20, 2016

(54) GLYCOCONJUGATES AND THEIR USE AS POTENTIAL VACCINES AGAINST INFECTION BY SHIGELLA FLEXNERI

(75) Inventors: Armelle Phalipon, Paris (FR); Farida Nato, Antony (FR); Laurence Mulard, Le Kremlin Bicetre (FR); Philippe Sansonetti, Paris (FR); Françoise Baleux, Paris (FR); Frédéric Belot, Grenoble (FR); Cyrille Grandjean, Covëron (FR)

(73) Assignee: INSERM (Institut National De La Sante Et De La Recherche Medicale), Paris (FR)

( * ) Notice: Subject to any disclaimer, the term of this patent is extended or adjusted under 35 U.S.C. 154(b) by 1223 days.

(21) Appl. No.: 13/325,511

(22) Filed: Dec. 14, 2011

(65) Prior Publication Data
US 2013/0243751 A1 Sep. 19, 2013
US 2014/0161793 A2 Jun. 12, 2014

Related U.S. Application Data

(62) Division of application No. 10/563,221, filed as application No. PCT/IB2004/002657 on Jul. 2, 2004.

(51) Int. Cl.
| | |
|---|---|
| C12P 19/00 | (2006.01) |
| C12P 19/12 | (2006.01) |
| C07K 1/00 | (2006.01) |
| A61K 39/112 | (2006.01) |
| A61K 47/48 | (2006.01) |
| C07K 16/12 | (2006.01) |
| G01N 33/563 | (2006.01) |
| G01N 33/569 | (2006.01) |
| C07H 3/06 | (2006.01) |
| C08B 37/00 | (2006.01) |
| A61K 39/00 | (2006.01) |

(52) U.S. Cl.
CPC ....... *A61K 39/0283* (2013.01); *A61K 47/4823* (2013.01); *A61K 47/4833* (2013.01); *A61K 47/48146* (2013.01); *A61K 47/48261* (2013.01); *C07H 3/06* (2013.01); *C07K 16/1228* (2013.01); *C08B 37/006* (2013.01); *G01N 33/563* (2013.01); *G01N 33/56916* (2013.01); *A61K 2039/6031* (2013.01); *A61K 2039/6037* (2013.01); *A61K 2039/625* (2013.01); *C07K 2317/565* (2013.01)

(58) Field of Classification Search
CPC ................................................. A61K 39/0283
See application file for complete search history.

(56) References Cited

U.S. PATENT DOCUMENTS

2003/0235818 A1* 12/2003 Katritch et al. .................. 435/5

FOREIGN PATENT DOCUMENTS

| WO | WO 99/03871 | 1/1999 |
|---|---|---|
| WO | WO 99/32645 | 7/1999 |
| WO | WO 99/58679 | 11/1999 |
| WO | WO 02/080964 A1 | 10/2002 |
| WO | WO 03/100033 A2 | 12/2003 |
| WO | WO 2004/063335 A2 | 7/2004 |

OTHER PUBLICATIONS

Polotsky, V. Y. et al., "Comparison of Conjugates Composed of Lipopolysaccharide from *Shigella flexnari* Type 2a Detoxified by Two Methods and Bound to Tetanus Toxoid," Infection and Immunity, vol. 62, No. 1, pp. 210-214, (Jan. 1994).
Passwell, J. H. et al., "Safety and Immunogenicity of Improved *Shigella* O-Specific Polysaccharide-Protein Conjugate Vaccine in Adults in Israel," Infection and Immunity, vol. 69, No. 3, pp. 1351-1357, (Mar. 2001).
Pavliakova, D. et al., "Treatment with Succinic Anhydride Improves the Immunogenicity of *Shigella flexneri* Type 2a O-Specific Polysaccharide-Protein Conjugates in Mice," Infection and Immunity, vol. 67, No. 10, pp. 5526-5529, (Oct. 1999).
Taylor, D. N. et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (*Plesiomonas shigelloides*) Bound to Bacterial Toxoids," Infection and Immunity, vol. 61, No. 9, pp. 3678-3687, (Sep. 1993).
Carlin, N. I. A. et al., "Monoclonal Antibodies Specific for O-Antigenic Polysaccharides of *Shigella flexneri*: Clones Binding to II, II:3,4 and 7,8 Epitopes," Journal of Clinical Microbiology, vol. 18, No. 5, pp. 1183-1189, (Nov. 1983).
Yun, M., "Analysis of Biological Characteristics of Monoclonal Antibodies to *Shigella flexneri* 2a O-Side Chain of LPS," Chinese Journal of Microbiology and Immunology, Beijing, vol. 12, No. 5, pp. 322-324, (1992).
Pozsgay, V. et al., "Protein Conjugates of Synthetic Saccharides Elicit Higher Levels of Serum IgG Lipopolysaccharide Antibodies in Mice Than Do Those of the O-Specific Polysaccharide from *Shigella dysenteriae* Type 1," Proc. Natl. Acad. Sci. USA, vol. 96, pp. 5194-5197, (Apr. 1999).
Pozsgay, V., "Synthesis of Glycoconjugate Vaccines Against *Shigella dysenteriae* Type 1," J. Org. Chem., vol. 63, pp. 5983-5999, (1998).
Chu, C. et al., "Preparation, Characterization, and Immunogenicity of Conjugates Composed of the O-Specific Polysacharide of *Shigella dysenteriae* Type 1 (Shiga's Bacillus) Bound to Tetanus Toxoid," Infection and Immunity, vol. 59, No. 12, pp. 4450-4458, (Dec. 1991).
Mulard, L. A. et al., "Synthesis of the Methyl Glycosides of A Di-and Two Trisaccharide Fragments Specific for the *Shigella flexneri* Serotype 2a O-Antigen¹", J. Carbohydrate Chemistry, vol. 19, No. 7, pp. 849-877, (2000).
Costachel, C. et al., "Linear Synthesis of The Methyl Glycosides of Tetra- and Pentasaccharide Fragments Specific for the *Shigella flexneri* Serotype 2a o-Anigen¹", J. Carbohydrate Chemisty, vol. 19, No. 9, pp. 1131-1150, (2000).

(Continued)

*Primary Examiner* — Albert Navarro
(74) *Attorney, Agent, or Firm* — Finnegan, Henderson, Farabow, Garrett & Dunner, L.L.P.

(57) ABSTRACT

A conjugate molecule comprising an oligo- or polysaccharide covalently bound to a carrier and its use as potential vaccine against infection by *S. Flexneri*.

19 Claims, 35 Drawing Sheets

(56) References Cited

OTHER PUBLICATIONS

Segat-Dioury, F. et al., "Convergent Synthesis of the Methyl Glycosides of A Tetra- and a Pentasaccharide Fragment of the *Shigella flexneri* Serotype 2a *O*-Specific Polysaccharide," Tetrahedron: *Asymmetry*, vol. 13, pp. 2211-2222, (2002).

Bélot, F. et al., "Synthesis of the Methyl Glycoside of a Branched Octasaccharide Fragment Specific for the *Shigella flexneri* Serotype 2a *O*-Antigen," Tetrahedron Letters, vol. 43, pp. 8215-8218, (2002).

Phalipon, A. et al., "Shigellosis: Innate Mechanisms of Inflammatory Destruction of the Intestinal Epithelium, Adaptive Immune Response, and Vaccine Development," Critical Review in Immunology, vol. 23, No. 5 & 6, pp. 371-401, (2003).

Clément, M. J. et al., "Conformational Studies of the O-Specific Polysaccharide of *Shigella flexneri* 5a and of Four Related Synthetic Pentasaccharide Fragments Using NMR and Molecular Modeling," The Journal of Biology Chemistry, vol. 278, No. 48, Issue of Nov. 28, pp. 47928-47936, (2003).

Bélot, F. et al., "Blockwise Approach to Fragments of the O-Specific Polysaccharide of *Shigella flexneri* Serotype 2a: Convergent Synthesis of a Decasaccharide Representative of a Dimer of the Branched Repeating Unit[1]," J. Org. Chem., vol. 69, pp. 1060-1074, (2004).

Wright, K. et al., "Preparation of Synthetic Glycoconjugates as Potential Vaccines Against *Shigella flexneri* Serotype 2a Disease," Org. Biomol. Chem., vol. 2, pp. 1518-1527, (2004).

Islam, M. S. et al., "Production and Characterization of Monoclonal Antibodies with Diagnostic Potential Against *Shigella flexneri*," J. Clin. Lab. Immunol., vol. 29, pp. 199-206, (1989).

Hartman, A. B. et al., "Specificity of Monoclonal Antibodies Elicited by Mucosal Infection of BALB/c Mice with Virulent *Shigella flexneri* 2a," Clinical and Diagnostic Laboratory Immunology, vol. 3, No. 5, pp. 584-589, (Sep. 1996).

Kipriyanov, S. M. et al., "Generation and Production of Engineered Antibodies," Molecular Biotechnology, vol. 26, pp. 39-60, (2004).

\* cited by examiner a. TMSOTf, Et₂O, −35°C → rt; b. MeONa, MeOH-CH₂Cl₂, rt; c. Sn(OTf)₂, CH₃CN, rt; d. i. H₂NCH₂CH₂NH₂, EtOH, 60°C, ii. Ac₂O, EtOH; iii. MeONa, MeOH-CH₂Cl₂, rt; e. Me₂C(OMe)₂, PTSA, acetone, rt; f. see ref (L. A. Mulard, C. Costachel, P. J. Sansonetti, *J. Carbohydr. Chem.* 2000, *19*, 849-877); g. 4Å-MS, TfOH, CH₂Cl₂, −15°C → rt; h. 90% aq TFA, 0°C; i. MeONa, MeOH-CH₂Cl₂, rt ; j. H₂, 10% Pd/C, EtOH-AcOH, rt.

a. see ref. (F. Segat, L. A. Mulard, *Tetrahedron: Asymmetry* 2002, *13*, 2211-2222); *b.* (ClAc)$_2$O, Pyridine-CH$_2$Cl$_2$, 0°C; *c. i.* (COD)Ir$^+$(P(MePh$_2$)$_2$)PF$_6^-$, THF, *ii.* I$_2$, THF, rt; *d.* CCl$_3$CN, DBU, CH$_2$Cl$_2$, 0°C; *e.* 4Å-MS, TMSOTf, CH$_2$Cl$_2$, −60°C → rt; *f.* thiourea, MeOH-pyridine, 65°C.

a. i. (COD)Ir⁺(P(MePh₂)₂)PF₆⁻, THF, ii. I₂, THF, rt; b. CCl₃CN, K₂CO₃, CH₂Cl₂, 0°C; c. TMSOTf, Et₂O, −60°C → 0°C; d. thiourea, MeOH-pyridine, 65°C; e. guanidine, EtOH-CH₂Cl₂, rt; f. 4Å-MS, TMSOTf, Et₂O, −60°C → rt; g. 50% aq TFA, CH₂Cl₂, 0°C; h. 0.5M MeONa, MeOH, 55°C; i. 10% Pd/C, EtOH-EtOAc, 1M aq HCl, rt.

a. 50% aq TFA, CH$_2$Cl$_2$, 0°C; b. MeONa, MeOH, 55°C; c. 10% Pd/C, EtOH-EtOAc, 1M aq HCl, rt.

(a) cat. TMSOTf, anhydrous DCM, 0.5 h, 0°C, 97% (308), 99% (317); (b) i. cat. [Ir(COD){PCH$_3$(C$_6$H$_5$)$_2$}$_2$]$^+$PF$_6^-$, THF, rt, 20 h, ii. HgO, HgCl$_2$, acetone/water, rt, 2 h, 81% (318), 69% (320); (c) CCl$_3$CN, DBU, DCM, 0°C, 1 h, 78% (306), 86% (7); (d) i. NH$_3$, MeOH, 20h, 0°C, ii. Ac$_2$O, MeOH, iii. Ac$_2$O, Py, 90%; (e) cat. TMSOTf, CH$_3$CN, 0°C, 41% (2); (f) cat. TfOH, NIS, Et$_2$O, DCE, 0°C, 10% (304).

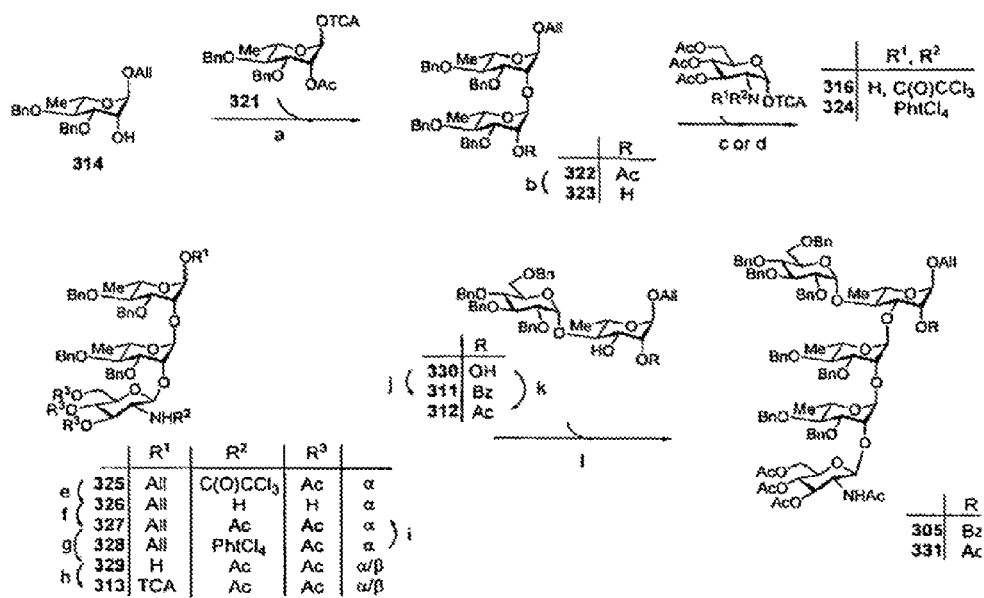

(a) cat. TMSOTf, anhydrous Et$_2$O, 3 h, −55 → −20°C, 92%; (b) MeONa, MeOH, 3 h, rt, 93%; (c) cat. TMSOTf, 4Å molecular sieves, DCE, 3 h, −20 → 0°C, 96%; (d) cat. TMSOTf, anhydrous Et$_2$O, 4 h, 0°C → rt, 65%; (e) i. MeONa, MeOH, Et$_3$N, rt, 18 h, rt, ii. Ac$_2$O, 0.5 h, 0°C → rt, 45%; (f) Py, Ac$_2$O, 18 h, 0°C → rt, 94%; (g) i. cat. [Ir(COD){PCH$_3$(C$_6$H$_5$)$_2$}$_2$]$^+$PF$_6^-$, THF, rt, 20 h, ii. HgO, HgCl$_2$, acetone/water, rt, 2 h, 83%; (h) CCl$_3$CN, DBU, DCM, 0°C, 40 min, 94%; (i) i. ethylenediamine, THF, EtOH, 55°C, 4 h, ii. Ac$_2$O, rt, 1.5 h, iii. Py, Ac$_2$O, 0°C, overnight, 68%; (j) i. PhC(OMe)$_3$, CSA, DCM, ii. 50% aq. TFA, DCM, 87%; (k) i. MeC(OMe)$_3$, CSA, DCM, ii. 50% aq. TFA, DCM, 90%; (l) BF$_3$.Et$_2$O, anhydrous Et$_2$O, 4Å molecular sieves, 0°C → rt, 18 h, 44%.

FIGURE 13

(a) ClAc₂O, Py, 0°C → rt, overnight, 57%; (b) pMeOBnCl, NaH, DMF, rt, overnight, 97%; (c) i. cat. [Ir(COD){PCH₃(C₆H₅)₂}₂]⁺PF₆⁻, THF, rt, 20 h, ii. HgO, HgCl₂, acetone/water, rt, 2 h, 84% (333), 73% (336); (d) CCl₃CN, DBU, DCM, 0°C, 1 h, 83% (334), 82% (337); (e) cat. TMSOTf, anhydrous Et₂O, −60°C → rt, overnight, 22% (338), 44% (339).

(a) cat. TMSOTf, anhydrous Et₂O, −50°C → rt, overnight, 84% (342), 90% (344); (b) HBF₄/Et₂O, MeOH, rt, 4 days, 84% (310), 84% (340); (c) Guanidine, DCM, rt; (d) cat. TMSOTf, anhydrous DCM, 4Å molecular sieves, 0°C → rt, 3 h, 98%; (e) i. cat. [Ir(COD){PCH₃(C₆H₅)₂}₂]⁺PF₆⁻, THF, rt, 20 h, ii. HgO, HgCl₂, acetone/water, rt, 2 h; (f) CCl₃CN, DBU, DCM, 0°C, 1 h, 66% (2 steps).

(a) MeONa, MeOH, rt, 0.5 h; (b) 2-methoxypropene, CSA, DMF, 72% (2 steps); (c) cat. TfOH, anhydrous DCE, 4Å molecular sieves, $-35°C \rightarrow -10°C$, 2.5 h; (d) TFA, water/DCM, 0°C, 3 h, 72% (2 steps); (e) MeONa, MeOH, DCM, 55°C; (f) i. $H_2$, Pd/C, EtOH, EtOAc, 1M HCl, rt, 72 h, ii. $H_2$, Pd/C, MeOH, $Et_3N$, rt, 24 h. (g) MeONa, MeOH, DCM, 55°C, overnight, 37% (3 steps).

2)-αLRhap-(1,2)-αLRhap-(1,3)-[αDGlcp-(1,4)]-αLRhap-(1,3)-βDGlcNAcp-(1
　　A　　　　　B　　　　　　E　　　　　C　　　　　　D

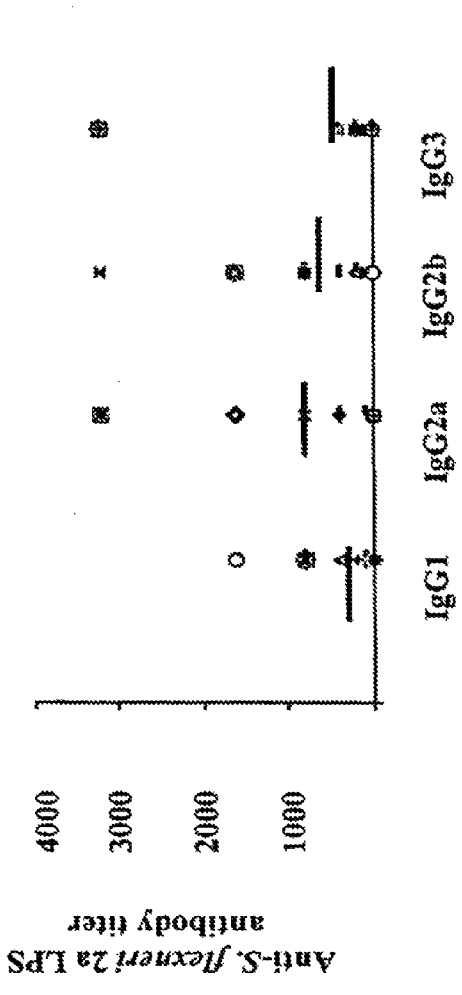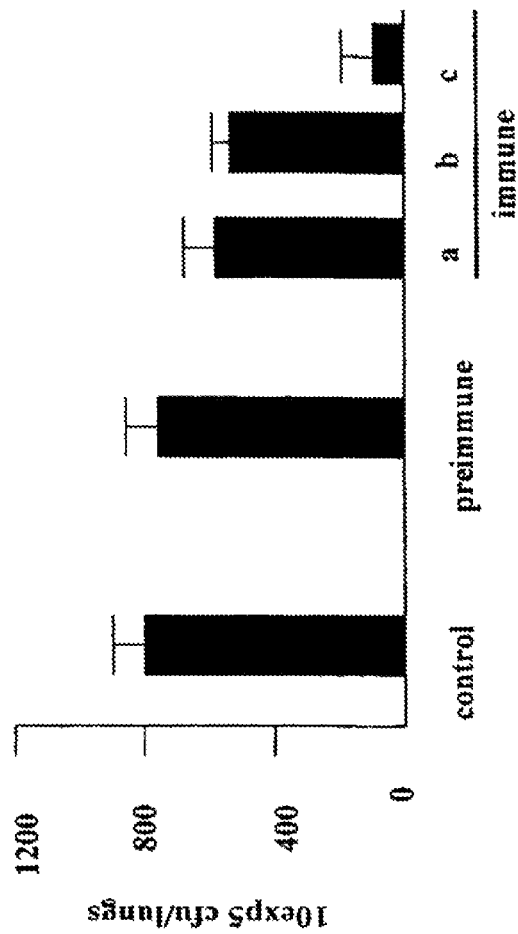
FIGURE 30A
FIGURE 30B

SEQUENCE LISTING

<160> NUMBER OF SEQ ID NOS: 41

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcaaggctta ctagttgaag atttgggctc aactttcttg tcgac         45

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttctgacta gtgggcactc tgggctc         27

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggggtacta gtcttgggta ttctaggctc         30

<210> SEQ ID NO 4
<211> LENGTH: 26
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 4
gaggtgcagc tcgaggagtc aggacc                                              26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaggtccagc tcgagcagtc tggacc                                              26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggtccaac tcgagcagcc tggggc                                              26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaggttcagc tcgagcagtc tggggc                                              26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggtgaagc tcgaggaatc tggagg                                              26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaggtaaagc tcgaggagtc tggagg                                              26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
```

```
            primer

<400> SEQUENCE: 10
gaagtgcagc tcgaggagtc tggggg                                          26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaggttcagc tcgagcagtc tggagc                                          26

<210> SEQ ID NO 12
<211> LENGTH: 5
<212> TYPE: PRT
<213> ORGANISM: Mus musculus

<400> SEQUENCE: 12

Asn Tyr Trp Met Ser
 1               5

<210> SEQ ID NO 13
<211> LENGTH: 5
<212> TYPE: PRT
<213> ORGANISM: Mus musculus

<400> SEQUENCE: 13

Tyr Ser Ser Ile His
 1               5

<210> SEQ ID NO 14
<211> LENGTH: 5
<212> TYPE: PRT
<213> ORGANISM: Mus musculus

<400> SEQUENCE: 14

Asp Tyr Ser Leu His
 1               5

<210> SEQ ID NO 15
<211> LENGTH: 5
<212> TYPE: PRT
<213> ORGANISM: Mus musculus

<400> SEQUENCE: 15

Asp Tyr Ser Met His
 1               5

<210> SEQ ID NO 16
<211> LENGTH: 19
<212> TYPE: PRT
<213> ORGANISM: Mus musculus

<400> SEQUENCE: 16

Glu Ile Arg Leu Lys Ser Asp Asn Tyr Ala Thr Tyr Tyr Ala Glu Ser
 1               5                  10                  15

Val Lys Gly

<210> SEQ ID NO 17
<211> LENGTH: 17
```

-continued

```
<212> TYPE: PRT
<213> ORGANISM: Mus musculus

<400> SEQUENCE: 17

Trp Ile Asn Thr Ala Thr Gly Glu Pro Thr Tyr Pro Asp Asp Phe Lys
 1               5                  10                  15
Gly

<210> SEQ ID NO 18
<211> LENGTH: 17
<212> TYPE: PRT
<213> ORGANISM: Mus musculus

<400> SEQUENCE: 18

Trp Ile Asn Thr Glu Thr Gly Glu Pro Ala Tyr Ala Asp Asp Phe Lys
 1               5                  10                  15
Gly

<210> SEQ ID NO 19
<211> LENGTH: 17
<212> TYPE: PRT
<213> ORGANISM: Mus musculus

<400> SEQUENCE: 19

Trp Val Asn Thr Gln Thr Gly Glu Pro Ser Tyr Ala Asp Asp Phe Lys
 1               5                  10                  15
Gly

<210> SEQ ID NO 20
<211> LENGTH: 4
<212> TYPE: PRT
<213> ORGANISM: Mus musculus

<400> SEQUENCE: 20

Pro Met Asp Tyr
 1

<210> SEQ ID NO 21
<211> LENGTH: 8
<212> TYPE: PRT
<213> ORGANISM: Mus musculus

<400> SEQUENCE: 21

Tyr Asp Tyr Ala Gly Phe Tyr Trp
 1               5

<210> SEQ ID NO 22
<211> LENGTH: 7
<212> TYPE: PRT
<213> ORGANISM: Mus musculus

<400> SEQUENCE: 22

Tyr Arg Tyr Asp Gly Ala Tyr
 1               5

<210> SEQ ID NO 23
<211> LENGTH: 7
<212> TYPE: PRT
<213> ORGANISM: Mus musculus

<400> SEQUENCE: 23

Tyr Arg Tyr Asp Gly Ala His
 1               5
```

```
<210> SEQ ID NO 24
<211> LENGTH: 16
<212> TYPE: PRT
<213> ORGANISM: Mus musculus

<400> SEQUENCE: 24

Arg Ser Ser Lys Ser Leu Leu His Ser Asp Gly Ile Thr Tyr Leu Tyr
1               5                   10                  15

<210> SEQ ID NO 25
<211> LENGTH: 10
<212> TYPE: PRT
<213> ORGANISM: Mus musculus

<400> SEQUENCE: 25

Ser Ala Ser Ser Ser Val Gly Tyr Ile His
1               5                   10

<210> SEQ ID NO 26
<211> LENGTH: 10
<212> TYPE: PRT
<213> ORGANISM: Mus musculus

<400> SEQUENCE: 26

Arg Ala Thr Ser Ser Val Gly Tyr Ile Asn
1               5                   10

<210> SEQ ID NO 27
<211> LENGTH: 9
<212> TYPE: PRT
<213> ORGANISM: Mus musculus

<400> SEQUENCE: 27

Arg Ala Arg Ser Ser Val Gly Tyr Met
1               5

<210> SEQ ID NO 28
<211> LENGTH: 7
<212> TYPE: PRT
<213> ORGANISM: Mus musculus

<400> SEQUENCE: 28

His Leu Ser Asn Leu Ala Ser
1               5

<210> SEQ ID NO 29
<211> LENGTH: 7
<212> TYPE: PRT
<213> ORGANISM: Mus musculus

<400> SEQUENCE: 29

Asp Thr Ser Lys Leu Ala Ser
1               5

<210> SEQ ID NO 30
<211> LENGTH: 7
<212> TYPE: PRT
<213> ORGANISM: Mus musculus

<400> SEQUENCE: 30

Ala Thr Ser Asn Leu Ala Ala
1               5
```

```
<210> SEQ ID NO 31
<211> LENGTH: 7
<212> TYPE: PRT
<213> ORGANISM: Mus musculus

<400> SEQUENCE: 31

Ala Thr Ser Asn Gln Ala Ser
 1               5

<210> SEQ ID NO 32
<211> LENGTH: 9
<212> TYPE: PRT
<213> ORGANISM: Mus musculus

<400> SEQUENCE: 32

Ala His Asn Val Glu Leu Pro Arg Thr
 1               5

<210> SEQ ID NO 33
<211> LENGTH: 9
<212> TYPE: PRT
<213> ORGANISM: Mus musculus

<400> SEQUENCE: 33

Gln Gln Trp Ser Arg Asn Pro Leu Thr
 1               5

<210> SEQ ID NO 34
<211> LENGTH: 9
<212> TYPE: PRT
<213> ORGANISM: Mus musculus

<400> SEQUENCE: 34

Gln Gln Trp Ser Ser Asp Pro Phe Thr
 1               5

<210> SEQ ID NO 35
<211> LENGTH: 19
<212> TYPE: PRT
<213> ORGANISM: Mus musculus

<400> SEQUENCE: 35

Glu Ile Arg Leu Lys Ser Asn Asn Tyr Ala Thr His Tyr Ala Glu Ser
 1               5                  10                  15

Val Lys Gly

<210> SEQ ID NO 36
<211> LENGTH: 9
<212> TYPE: PRT
<213> ORGANISM: Mus musculus

<400> SEQUENCE: 36

Gly Gly Ala Val Gly Ala Met Asp Tyr
 1               5

<210> SEQ ID NO 37
<211> LENGTH: 16
<212> TYPE: PRT
<213> ORGANISM: Mus musculus

<400> SEQUENCE: 37

Arg Ser Ser Gln Ser Leu Leu His Ser Asp Gly Asn Thr Tyr Leu His
 1               5                  10                  15
```

```
<210> SEQ ID NO 38
<211> LENGTH: 7
<212> TYPE: PRT
<213> ORGANISM: Mus musculus

<400> SEQUENCE: 38

Lys Val Ser Asn Arg Phe Ser
 1               5

<210> SEQ ID NO 39
<211> LENGTH: 8
<212> TYPE: PRT
<213> ORGANISM: Mus musculus

<400> SEQUENCE: 39

Ser Gln Thr Thr His Val Pro Thr
 1               5

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Cyclohexyl-Ala
<220> FEATURE:
<221> NAME/KEY: MOD_RES
<222> LOCATION: (14)
<223> OTHER INFORMATION: Aminocaproic acid

<400> SEQUENCE: 40

Ala Lys Xaa Val Ala Ala Trp Thr Leu Lys Ala Ala Ala Xaa
 1               5                  10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Cyclohexyl-Ala

<400> SEQUENCE: 41

Lys Xaa Val Ala Ala Trp Thr Leu Lys Ala Ala
 1               5                  10
```

GLYCOCONJUGATES AND THEIR USE AS POTENTIAL VACCINES AGAINST INFECTION BY *SHIGELLA FLEXNERI*

CROSS-REFERENCE TO RELATED APPLICATIONS

This is a division of application Ser. No. 10/563,221, filed Jul. 14, 2008, now issued U.S. Pat. No. 8,124,380, which is a U.S. National Stage entry of PCT/IB2004/02657, which is incorporated herein by reference, and which claims priority to Canadian Application Nos. 2,434,685, filed Jul. 4, 2003, and 2,434,668, filed Jul. 7, 2003.

FIELD OF THE INVENTION

This invention relates to compositions and methods for eliciting an immunogenic response in mammals, including responses that provide protection against, or reduce the severity of bacterial infections. More particularly it relates to the use of oligo- or polysaccharides obtained from natural sources and/or through synthesis or recombinant technology, and conjugates thereof to induce serum antibodies having protective activity against *Shigella flexneri,* in particular *S. flexneri* serotype 2a. These saccharides and/or conjugates thereof are useful as vaccines to induce serum antibodies which have protective activity against *S. flexneri,* in particular *S. flexneri* type 2a, and are useful to prevent and/or treat shigellosis caused by *S. flexneri.*

The present invention also relates to diagnostic tests for shigellosis using one or more of the oligo- or polysaccharides, conjugates or antibodies described above.

BACKGROUND OF THE INVENTION

Since the discovery of *Shigella dysenteriae* type 1 (Shiga's *bacillus*) more than a century ago (R. Shields and W. Burnett, *Zentl. Bakterio.,* 1898, 24, 817-828), shigellosis or bacillary dysentery has been known as a serious infectious disease, occurring in humans only (T. G. Keusch and M. L. Bennish, Shigellosis, Plenum Medical Book Company, New York, 1991, p. 593-620). In a recent survey of the literature published between 1966 and 1997 (K. L. Kotloff, J. P. Winickoff, B. Ivanoff, J. D. Clemens, D. L. Swerdlow, P. J. Sansonetti, G. K. Adak and M. M. Levine, *Bull. WHO,* 1999, 77, 651-666), the number of episodes of shigellosis occurring annually throughout the world was estimated to be 164.7 million, of which 163.2 million were in developing countries. Up to 1.1 million annual deaths were associated with shigellosis during the same period. Occurrence of the disease is seen as a correlate of sanitary conditions, and those are not likely to improve rapidly in areas at risk.

The financial status of the populations in which shigellosis exists in its endemic forms, as well as the emerging resistance to antimicrobial drugs (M. U. Khan, *Int. J. Epidemiol.,* 1985, 14, 607-613; B. A. Iwalokun, G. O. Gbenle, S. I. Smith, A. Ogunledun, K. A. Akinsinde and E. A. Omonigbehin, *J. Health Popul. Nutr.,* 2001, 19, 183-190), limit the impact of the latter. Of the four species of *Shigellae, S. flexneri* is the major responsible for the endemic form of the disease, with serotype 2a being the most prevalent. The critical importance of the development of a vaccine against *Shigellae* infections was first outlined in 1987 (World Health and Organization, *Bull. W.H.O.,* 1987, 65, 17-25). Due to increasing resistance of all groups of *Shigellae* to antibiotics (S. Ashkenazi, M. May-Zahav, J. Sulkes and Z. Sanwa, *Antimicrob. Agents Chernother.,* 1995, 39, 819-823) vaccination remained a high priority as stated by the World Health Organization ten years later (WHO, *Weekly Epidemiol. Rec.,* 1997, 72, 73-79). In the meantime, several experimental vaccines have gone through field evaluation (T. S. Coster, C. W. Hoge, L. L. van der Verg, A. B. Hartman, E. V. Oaks, M. M. Venkatesan, D. Cohen, G. Robin, A. Fontaine-Thompson, P. J. Sansonetti and T. L. Hale, *Infect. Immun.,* 1999, 67, 3437-3443; J. H. Passwell, E. Harlev, S. Ashkenazi, C. Chu, D. Miron, R. Ramon, N. Farzan, J. Shiloach, D. A. Bryla, F. Majadly, R. Roberson, J. B. Robbins and R. Schneerson, *Infect. Immun.,* 2001, 69, 1351-1357) but there are as yet no licensed vaccines for shigellosis.

*Shigella*'s lipopolysaccharide (LPS) is a major surface antigen of the bacterium. The corresponding O—SP domain (O—SP) is both an essential virulence factor and the target of the infected host's protective immune response (D. Cohen, M. S. Green, C. Block, T. Rouach and I. Ofek, *J. Infect. Dis.,* 1988, 157, 1068-1071; D. Cohen, M. S. Green, C. Block, R. Slepon and I. Ofek, *J. Clin. Microbiol.,* 1991, 29, 386-389). Indeed, using the pulmonary murine model for shigellosis, it was demonstrated that the presence locally, preliminary to infection, of a secretory antibody of isotype A specific for an epitope located on the O—SP moiety of the LPS of *S. flexneri* 5a, prevented any host homologous infection (A. Phalipon, M. Kauffmann, P. Michetti, J.-M. Cavaillon, M. Huerre, P. Sansonetti and J.-P. Krahenbuhl, *J. Exp. Med.,* 1995, 182, 769-778). Based on the former hypothesis that serum IgG anti-LPS antibodies may confer specific protection against shigellosis (J. B. Robbins, C. Chu and R. Schneerson, *Clin. Infect. Dis.,* 1992, 15, 346-361), several polysaccharide-protein conjugates, targeting either *Shigella sonnei, S. dysenteriae* 1 or *S. flexneri* serotype 2a, were evaluated in humans (J. H. Passwelle, E. Harlev, S. Ashkenazi, C. Chu, D. Miron, R. Ramon, N. Farzan, J. Shiloach, D. A. Bryla, F. Majadly, R. Roberson, J. B. Robbins and R. Schneerson, *Infect. Immun.,* 2001, 69, 1351-1357; D. N. Taylor, A. C. Trofa, J. Sadoff, C. Chu, D. Bryla, J. Shiloach, D. Cohen, S. Ashkenazi, Y. Lerman, W. Egan, R. Schneerson and J. B. Robbins, *Infect. Immun.,* 1993, 61, 3678-3687). In the case of *S. sonnei,* recent field trials allowed Robbins and co-workers to demonstrate the efficacy of a vaccine made of the corresponding detoxified LPS covalently linked to recombinant exoprotein A (D. Cohen, S, Ashkenazi, M. S. Green, M. Gdalevich, G. Robin, R. Slepon, M. Yavzori, N. Orr, C. Block, I. Ashkenazi, J. Sherner, D. N. Taylor, T. L. Hale, J. C. Sadoff, D. Pavliovka, R. Schneerson and J. B. Robbins, *The Lancet,* 1997, 349, 155-159). Conversion of polysaccharide T-independent antigens to T-dependent ones through their covalent attachment to a carrier protein has had a tremendous impact in the field of bacterial vaccines. Several such neoglycoconjugate vaccines are currently in use against *Haemophilus influenzae* b (R. W. Ellis and D. M. Granoff, *Development and clinical use of Haemophilus b conjugate vaccines*, Dekker, New York, 1994), *Neisseria meningitidis* (P. Richmond, R. Borrow, E. Miller, S. Clark, F. Sadler, A. Fox, N. Begg, R. Morris and K. Cartwright, *J. Infect. Dir.,* 1999, 179, 1569-1572) and *Streptococcus pneumoniae* (M. B. Renels, K. M. Edwards, H. L. Keyserling, K. S. Reisinger, D. A. Hogerman, D. V. Madore, I. Chang, P. R. Paradiso, F. J. Malinoski and A. Kimura, *Pediatrics,* 1998, 101, 604-611). These polysaccharide-protein conjugate vaccines are highly complex structures, whose immunogenicity depends on several parameters amongst which are the length and nature of the saccharide component as well as its loading on the protein. It is reasonably admitted that control of these parameters is somewhat difficult when dealing with polysaccharides purified from bacterial cell cultures. As recent progress in carbohydrate synthesis allows access to complex saccharides, it has been suggested that the use of well-defined synthetic oligosaccharides may allow a better control, and consequently the optimisation, of these parameters. Indeed, available data on *S. dysenteriae* type 1 indicate that neoglycoconjugates incorporating di-, tri- or tetramers of the O—SP repeating unit were more immunogenic than a detoxified LPS-human serum albumin conjugate of reference (V. Pozsgay, C. Chu, L. Panell, J. Wolfe, J. B. Robbins and R. Schneerson, *Proc. Natl. Acad. Sci.* USA, 1999, 96, 5164-5197).

Besides, recent reports demonstrate that short oligosaccharides comprising one repeating unit may be immunogenic in animal models (B. Benaissa-Trouw, D. J. Lefeber, J. P. Kamerling, J. F. G. Vliegenthart, K. Kraaijeveld and H. Snippe, *Infect. Immun.*, 2001, 69, 4698-4701; F. Mawas, J. Niggemann, C. Jones, M. J. Corbet, J. P. Kamerling and J. F. G. Vliegenthart, *Infect. Immun.*, 2002, 70, 5107-5114). Another critical parameter in the design of neoglycoconjugate vaccines is the carrier protein. As potential applications for these vaccines are expanding, the need for new carrier proteins licensed for human use is growing (J. B. Robbins, R. Schneerson, S. C. Szu and V. Pozsgay in *Polysaccharide-protein conjugate vaccines*, vol. (S. Plotkin and B. Fantini Eds), Elsevier, Paris, 1996, pp. 135-143). That synthetic peptides representing immunodominant T-cell epitopes could act as carriers in polysaccharide and oligosaccharide conjugates has been suggested (G. J. P. H. Boons, P. Hoogerhout, J. T. Poolman, G. A. van der. Marel and J. H. van Boom, *Bioorg. Med. Chem.*, 1991, 1, 303-308) and later on demonstrated (E. Lett, S. Gangloff, M. Zimmermann, D. Wachsmann and J.-P. Klein, *Infect. Immun.*, 1994, 62, 785-792; A. Kandil, N. Chan, M. Klein and P. Chong, *Glycoconjugate J.*, 1997, 14, 13-17). Besides, the use of T-cell epitopes offers several advantages, including potential access to well-defined conjugates with no risk of epitopic suppression, as this latter phenomenon appeared to be a major drawback of protein carriers (T. Barington, M. Skettrup, L. Juul and C. Heilmann, *Infect. Immunol.*, 1993, 61, 432-438; M.-P. Schutze, C. Leclerc, M. Jolivet, F. Audibert and L. Chedid, *J. Immunol.*, 1985, 135, 2319-2322). Polypeptides containing multiple T-cell epitopes have been generated in order to address the extensive polymorphism of HLA molecules (P. R. Paradiso, K. Dermody and S. Pillai, *Vaccine Res.*, 1993, 2, 239-248). In other strategies, universal T-helper epitopes compatible with human use have been characterized, for example from tetanus toxoid (D. Valmori, A. Pessi, E. Bianchi and G. P. Corradin, *J. Immunol.*, 1992, 149, 717-721), or engineered such as the pan HLA DR-binding epitope (PADRE) (J. Alexander, J. Sidney, S. Southwood, J. Ruppert, C. Oseroff, A. Maewal, K. Snoke, H. M. Serra, R. T. Kubo, A. Sette and H. M. Grey, *Immunity*, 1994, 1, 751-761). Recently, covalent attachment of the human milk oligosaccharide, lacto-N-fucopentose II, to PADRE resulted in a linear glycopeptide of comparable immunogenicity to that of a glycoconjugate employing human serum albumine (HAS) as the carrier (J. Alexander, A.-F. d. Guercio, A. Maewal, L. Qiao, J. Fikes, R. W. Chesnut, J. Paulson, D. R. Bundle, S. DeFrees and A. Sette, *J. Immunol.*, 2000, 164, 1625-1633).

Based on these converging data, the inventors have focused on the development of well-defined neoglycoconjugate as an alternative to polysaccharide protein conjugate vaccines targeting infections caused by *S. flexneri* serotype 2a. The target neoglycoconjugates were constructed by covalently linking an immunocarrier, serving as T-helper epitope(s), to appropriate carbohydrate (oligo- or polysaccharide) haptens, serving as B epitopes mimicking the *S. flexneri* 2a O—Ag. To this end, a rationale approach involving a preliminary study of the interaction between the bacterial O—SP and homologous protective monoclonal antibodies, was employed to define the carbohydrate haptens.

SUMMARY OF THE INVENTION

Abbreviation: LPS: lipopolysaccharide; O—SP: O-specific polysaccharide; TT: tetanus toxoid; DCC: dicyclohexyl carbodiimide; Rhap: rhamnopyranosyl; Glcp: glucopyranosyl; GlcNAcp: 2-acetamido-2-deoxy-glucopyranosyl.

In the instant invention, the list of polysaccharides designated L1 consists of:
 $(X)_x$—{B(E)C}—$(Y)_y$
 $(X)_x$—{(E)CD}—$(Y)_y$
 $(X)_x$—{AB(E)C}—$(Y)_y$
 $(X)_x$—{B(E)CD}—$(Y)_y$
 $(X)_x$—{(E)CDA}—$(Y)_y$
 $(X)_x$—{DAB(E)C}n—$(Y)_y$
 $(X)_x$—{B(E)CDA}n—$(Y)_y$
 $(X)_x$—{(E)CDAB}n—$(Y)_y$
 $(X)_x$—{AB(E)CD}n—$(Y)_y$
 $(X)_x$—{DAB(E)CD}—$(Y)_y$
 $(X)_x$—{B(E)CDAB(E)C}—$(Y)_y$
wherein:
A is an alphaLRhap-(1,2) residue
B is an alphaLRhap-(1,3) residue
C is an alphaLRhap-(1,3) residue
E is an alphaDGlcp-(1,4) residue
D is a betaDGlcNAcp-(1,2) residue
x and y are independently selected among 0 and 1
X and Y are independently selected among A, B, C, D, E, AB, B(E), (E)C, CD, DA, AB(E), B(E)C, (E)CD, CDA, AB(E)C, B(E)CD, (E)CDA, CDAB, DAB(E) and wherein n is an integer comprised between 1 and 10 covalently bound to a carrier.
Saccharides selected from the group consisting of:
{B(E)CD}
{(E)CDAB}n
{AB(E)CD}n
wherein A, B, C, D, E and n have the same meaning as above are new and are another object of the invention.

It is an object of the present invention to produce an antigen based on natural, modified-natural, synthetic, semi-synthetic or recombinant oligo- or polysaccharides which have subunits, selected from the list L1. Preferably, these oligo- or polysaccharides of the invention are antigenically similar to an antigenic determinant of the O—SP of *S. flexneri* type 2a which contains [AB(E)CD] subunits. It is also an object of the invention to provide molecules, for example oligo- or polysaccharides, which are structurally related and/or antigenically similar to those oligo- and polysaccharides from the list L1. The oligo- or polysaccharides may be conjugated to an immunocarrier to form conjugates. These conjugates thereof are immunogenic and elicit serum antibodies that are protective against *S. flexneri*, in particular *S. flexneri* type 2a and which are useful in the prevention and treatment of shigellosis caused by *S. flexneri*. These oligo- or polysaccharides and conjugates thereof, and the antibodies which they elicit, are also useful for studying *S. flexneri*, in particular *S. flexneri* type 2a, in vitro or its products in patients. The oligo- or polysaccharides may also be conjugated to other carriers which are suitable for labelling or immobilizing said oligo- or polysaccharides on a solid phase.

It is yet another object of the present invention to provide an immunogen that elicits antibodies which are protective against S. flexneri, in particular S. flexneri type 2a and which react with, or bind to the O—SP of S. flexneri type 2a, wherein the immunogen is based on a natural, modified natural, synthetic, semi-synthetic or recombinant oligo- or polysaccharide containing one or more subunits selected from the list L1 or a structurally related, immunologically similar, oligo- or polysaccharide, and/or conjugate thereof.

It is yet another object of the present invention to provide antibodies which have protective activity against S. flexneri, in particular S. flexneri type 2a, and which react with, or bind to the O—SP of S. flexneri type 2a, wherein the antibodies may be elicited by immunization with a natural, modified natural, or synthetic oligo- or polysaccharide containing subunits from the list L1 or a structurally related, immunologically similar, oligo- or polysaccharide, and/or conjugate thereof.

It is yet another object of the present invention to provide oligo- or polysaccharides or conjugates thereof with a carrier which are useful as vaccines to prevent and/or treat shigellosis.

It is yet another object of the present invention to prepare antibodies for the treatment of established shigellosis. Antibodies elicited by the molecules of the invention are able to provide passive protection to an individual exposed to S. flexneri, in particular S. flexneri type 2a, to prevent, treat, or ameliorate infection and disease caused by the microorganism.

It is yet another object of the present invention to provide diagnostic tests and/or kits for shigellosis caused by S. flexneri, in particular S. flexneri type 2a, using one or more of the oligo- or polysaccharides, conjugates, or antibodies of the present invention.

It is yet another object of the present invention to provide an improved method for synthesizing an oligo- or polysaccharide containing one ore more subunits of the list L1.

According to the present invention, methods are provided to isolate, substantially purify and/or synthesize natural, modified-natural, synthetic, semi-synthetic or recombinant oligo- or polysaccharides containing subunits of the L1 list or structurally related, immunologically similar, oligo- or polysaccharides. Preferably, these oligo- and polysaccharides are structurally related and/or immunologically similar to an antigenic determinant of the O—SP of S. flexneri type 2a.

Methods are also provided to conjugate the natural, modified-natural, synthetic, semi-synthetic or recombinant oligo- or polysaccharide of the invention with a carrier.

DETAILED DESCRIPTION OF THE INVENTION

Oligo- and Polysaccharides:

This invention provides a synthetic, semi-synthetic, natural, modified-natural or recombinant oligo- or polysaccharide containing subunits from the list L1.

Methods for synthesizing S. flexneri 2a di- tri-, tetra, penta and octasaccharides are know from the prior art (F. Segat Dioury et al., *Tetrahedron, Asymmetry*, 13, 2002, 2211-2222; C. Costachel et al., *J. Carbohydrate Chemistry*, 19(9), 2000, 1131-1150; L. Mulard et al., *J. Carbohydrate Chemistry*, 19(7), 2000, 849-877; F. Belot et al., *Tetrahedron Letters*, 43, 2002, 8215-8218; L. Mulard et al., *Tetrahedron*, 58, 2002, 2593-2604; L. Mulard et al., *J. Carbohydrate Chemistry*, 19(2), 2000, 193-200).

An improved method to synthesize oligo- or polysaccharides is set forth in the examples below. Notably the synthesis of a decasaccharide was performed by condensation of two pentasaccharide intermediates.

Definitions:

"oligosaccharide" as defined herein, is a carbohydrate containing from two to twenty monosaccharide units linked together, "oligosaccharide" is used herein in a liberal manner to denote the saccharides described herein; this usage differs from the standard definition that oligosaccharides may contain up to and including ten monosaccharide units (Joint Commission on Biological Nomenclature, Eur. J. Biochem. 1982, 126, 433-437).

"polysaccharide" as defined herein, is a carbohydrate containing more than twenty monosaccharide subunits linked together.

"structurally-related" oligo- or polysaccharide as defined herein, is a modified oligo- or polysaccharide from the list characterized by its ability to immunologically mimic the antigenic determinant of the O—SP of S. flexneri, in particular S. flexneri type 2a. Such modified oligo- or polysaccharide can be obtained by structure alterations that render the modified polysaccharide antigenically similar to the antigenic determinant of the O—SP of S. flexneri 2a . Such a modified oligo- or polysaccharide can be obtained, for example, by means of a specific spacer constraining said oligosaccharide into the conformation it bears in the native O—SP.

"immunoreact" means specific binding between an antigenic determinant-containing molecule and a molecule containing an antibody combining site such as a whole antibody molecule or a portion thereof.

"antibody" refers to immunoglobulin molecules and immunologically active or functional fragments of immunoglobulin molecules comprising an antigen recognition and binding site. Exemplary antibody molecules are intact immunoglobulins molecules, substantially intact immunoglobulin molecules and active fragments of an immunoglobulin molecule, including those portions known in the art as Fab, Fab', F(ab')$_2$ and scFv, as well as chimeric antibody molecules.

"immunologically similar to" or "immunologically mimic" refers to the ability of an oligo- or polysaccharide of the invention to immunoreact with, or bind to, an antibody of the present invention that recognizes and binds to a native antigenic determinant on the O—SP of S. flexneri type 2a.

functional group refers to groups of atoms characterized by their specific elemental composition and connectivity. Said functional groups confer reactivity upon the molecule that contains them. Common functional groups include: Primary amines: R—NH$_2$; Primary Imines: —C(=NH)—R'; Azo: [Azo, —N=N—R'; Nitrile, —C≡N; Carboxylic acid, Carboxyl: —C(=O)OH), carboxylic acid and derivatives thereof like ester: —C(=O)O—R' or activated ester; Carbonyl: [Aldehyde: —C(=O)H; Ketone, —C(=O)—R'], or derivatives thereof as masked carbonyl such as acetal or thioacetal; Alkenes: —CH=CH—R'; Alkynes: —C≡C—R'; Isocyanates: —N=C=O; Isothiocyanate: —N=C=S; Thioacyl —SCO—R', Thiol —SH, dithiol: —S—S—R'; Azide —N$_3$; Hydrazide: —CONHNH$_2$, Hydrazine, Maleimide, O-alkyl hydroxylamine, halogen, "carrier" refers to any molecule which can be covalently bound to an oligo- or polysaccharide of the invention to form the glycoconjugate of the invention. It includes immunocarriers for use as vaccine and other carriers for preparing diagnostic reagents.

"immunocarrier" refers to an immunogenic molecule or a fragment of a molecule which is recognized by T cells and is able to induce an antibody response.

"other carriers for preparing diagnostic reagents" refers to agents commonly used to immobilize molecules onto a solid phase or to label molecules.

"a label" refers to any substance which can produce a signal which can be detected by any appropriate mean.

"glyconjugate" refers to an oligo- or polysaccharide from the list L1 covalently bound to a carrier.

"prevention and treatment" refers to the prevention of infection or reinfection, reduction or elimination of the symptoms, and reduction or complete elimination of the pathogen. Treatment may be effected prophylactically (prior to infection) or therapeutically (following infection).

Oligo- and Polysaccharide Conjugates (Glycoconjugate)

The oligo- or polysaccharides of the invention can be bound covalently to a protein or peptide carrier. This covalent bond can be a direct bond between the oligo- or polysaccharide and the peptide or protein.

According to another variant, the oligo- or polysaccharide of the L1 list can be linked to the protein or peptide via a spacer molecule. The oligo or polysaccharide can be functionalized by an —O—R—Z group, wherein R is an alkyl group comprising 1 to 12 carbon atoms, preferably 1 to 6 carbon atoms, preferably an ethyl group, and Z is a functional group which reacts with a functional group of the protein or peptide carrier. Preferably Z is —NH$_2$.

The oligo and polysaccharide of the list L1 bearing an —O-alkyl-Z and preferably those bearing an —O-alkyl-NH$_2$ spacer molecule are another object of the instant invention.

Notably molecules :
{B(E)C}—O—R—NH$_2$
{(E)CD}—O—R—NH$_2$
{AB(E)C}—O—R—NH$_2$
{B(E)CD}—O—R—NH$_2$
{(E)CDA}—O—R—NH$_2$
{DAB(E)C}n—O—R—NH$_2$
{B(E)CDA}n—O—R—NH$_2$
{(E)CDAB}n—O—R—NH$_2$
{AB(E)CD}n—O—R—NH$_2$
{DAB(E)CD}—O—R—NH$_2$
{B(E)CDAB(E)C}—O—R—NH$_2$
wherein A, B, C, D, E and n have the same meaning as above are of special interest.

The oligo- or polysaccharide functionalized by an —O-alkyl-NH$_2$ group, is then transformed in manner known to the man skilled in the art in an —O-alkyl-NH—CO—CH$_2$—R', wherein —R' is selected among a S-acetyl group, a linear haloalkyl group having from 1 to 7, and preferably 1 to 3 atoms of carbone, and preferably wherein the halogen is Br, and linear carboxylic acid group having preferably 2 to 3 atoms of carbon, For example, the functionalized oligo- or polysaccharides with a S-acetyl group can be deprotected resulting in the free thiol to be reacted with a carrier which is functionalized by a haloacetyl or a maleimide group. Another strategy consists in establishing a bond between the oligo- or polysaccharide and the protein or peptide via a spacer bearing a β-alanine.

According to another variant of the invention, oligo- and polysaccharides of the L1 list are terminated by an —OQ group, wherein Q is selected among alkyl and alkenyl groups comprising 1 to 12 carbon atoms. Preferably Q is selected among methyl and allyl. Particularly, a saccharide derivative selected from the group consisting of:
{B(E)CD}—OQ
{(E)CDAB}n—OQ
{AB(E)CD}n—OQ
{DAB(E)C}m—OQ
{B(E)CDA}m—OQ
{DAB(E)CD}—OQ
wherein A, B, C, D, E and n have the same meaning as above and m is comprised from 2 and 10.

Methods for binding oligo- and/or polysaccharides to a non-toxic non-host protein are well known in the art. For example, in U.S. Pat. No. 5,204,098 and U.S. Pat. No. 5,738,855 it is taught that an oligo- or polysaccharide containing at least one carboxyl group, through carbodiimide condensation, may be thiolated with cystamine, or aminated with adipic dihydrazide, diaminoesters, ethylenediamine and the like. Groups which could be introduced by the method, or by other methods known in the art, include thiols, hydrazides, amines and carboxylic acids. Both the thiolated and the aminated intermediates are stable, may be freeze dried, and stored in cold. The thiolated intermediate may be reduced and covalently linked to a polymeric carrier containing a disulfide group, such as a 2-pyridyldithio group. The aminated intermediate may be covalently linked to a polymeric carrier containing a carboxyl group through carbodiimide condensation.

The oligo- or polysaccharide can be covalently bound to a carrier with or without a linking molecule. To conjugate without a linker, for example, a carboxyl-group-containing oligo- or polysaccharide and an amino-group-containing carrier are mixed in the presence of a carboxyl activating agent, such as a carbodiimide, in a choice of solvent appropriate for both the oligo- or polysaccharide and the carrier, as is known in the art (Szu, S. C., A. L. Stone, J. D. Robbins, R. Schneerson, and J. B. Robbins, 1987, Vi capsular polysaccharide-protein conjugates for prevention of typhoid fever. *J. Exp. Med.*, 166:1510-1524). The oligo- or polysaccharide is preferably conjugated to a carrier using a linking molecule. A linker or crosslinking agent, as used in the present invention, is preferably a small linear molecule having a molecular weight of approximately <500 daltons and is non-pyrogenic and non-toxic in the final product form.

To conjugate with a linker or crosslinking agent, either or both of the oligo- or polysaccharide and the carrier may be covalently bound to a linker first. The linkers or crosslinking agents are homobifunctional or heterobifunctional molecules, (see references provided in Bioconjugate Techniques, G. T. Hermanson, Ed, Academic Press, San Diego, 1995). e.g., adipic dihydrazide, ethylenediamine, cystamine, N-succinimidyl 3-(2-pyridyldithio)propionate (SPDP), N-succinimidyl-[N-(2-iodoacetyl)-β-alanyl]propionate-propionate (SIAP), succinimidyl 4-(N-maleimido-methyl)cyclohexane-1-carboxylate (SMCC), 3,3'-dithiodipropionic acid, and the like. Among the class of heterobifunctional linkers are omega-hydroxy alkanoic acids.

According to the type of bonding between the oligo- or polysaccharide and the carrier, there is the possibility of preparing a conjugate molecule wherein the ratio of the oligo- or polysaccharide versus the carrier can vary between 1:1 and 30:1. Preferably, this ratio is comprised between 5:1 and 20:1.

A carrier can be a natural, modified-natural, synthetic, semi-synthetic or recombinant material containing one or more functional groups, for example primary and/or secondary amino groups, azido groups, or carboxyl group. The carrier can be water soluble or insoluble. Carriers that fulfil these criteria are well-known to those of ordinary skill in the art.

Immunocarriers are chosen to increase the immunogenicity of the oligo- or polysaccharide and/or to raise antibodies against the carrier which are medically beneficial.

Suitable immunocarriers according to the present invention include proteins, peptides, polysaccharides, polylactic acids, polyglycolic acids, lipid aggregates (such as oil droplets or liposomes), and inactivated virus particles.

According to an advantageous embodiment of the glycoconjugate molecule of the invention, it is covalently bound to a protein or a peptide comprising at least one T-helper cell epitope, for use as a vaccine against *S. flexneri* infection.

Protein carriers known to have potent T-cell epitopes, include but are not limited to bacterial toxoids such as tetanus, diphtheria and cholera toxoids, *Staphylococcus* exotoxin or toxoid, *Pseudomonos aeruginosa* Exotoxin A and recombinantly produced, genetically detoxified variants thereof, outer membrane proteins (OMPs) of *Neisseria meningitidis* and *Shigella flexneri* proteins. The recombinantly-produced, non-toxic mutant strains of *Pseudomonos aeruginosa* Exotoxin A (rEPA) are described in Fattom et al., Inf. Immun., 1993, 61, 1023-1032. The CMR 197 carrier is a well characterized non-toxic diphtheria toxin mutant that is useful in glycoconjugate vaccine preparations intended for human use (Bixler et al., Adv. Exp. Med. Biol., 1989, 251, 175-; Constantino et al., Vaccine, 1992). Other exemplary protein carriers include the Fragment C of tetanus toxin, and the Class 1 or Class 2/3 OMPs. Also CRM 9 carrier has been disclosed for human immunisation. (Passwell J H et al. Pediatr Infect Dis J. (2003) 22, 701-6).

Synthetic peptides representing immunodominant T-cell epitopes can also act as carriers in polysaccharide and oligosaccharide conjugates. The peptide carriers include polypeptides containing multiple T-cell epitopes addressing the extensive polymorphism of HLA molecules (Paradiso et al., Vaccine Res., 1993, 2, 239-248), and universal T-helper epitopes compatible with human use. Exemplary T-helper epitopes, include but are not limited to natural epitopes characterized from tetanus toxoid (Valmori et al., J. Immunol., 1992, 149, 717-721) and non-natural epitopes or engineered epitopes such as the pan HLA DR-binding epitope PADRE (KXVAAWTLKAA; Immunity, 1994, 1, 751-761).

Other types of carrier include but are not limited to biotin. The oligo- or polysaccharides conjugated to biotin or to a label are especially designed for diagnosing *S. flexneri* infections.

Vaccine

The invention provides an immunogenic composition comprising a glycoconjugate as defined above, in a physiologically acceptable vehicle.

The vaccine composition includes one or more pharmaceutically acceptable excipients or vehicles such as water, saline, glycerol, ethanol. Additionally, auxiliary substances, such as wetting or emulsifying agents, pH buffering substances, and the like, may be present in such vehicles.

The glycoconjugate of the present invention which induces protective antibodies against *S. flexneri* infection, in particular *S. flexneri* type 2a are administered to a mammal subject, preferably a human, in an amount sufficient to prevent or attenuate the severity, extent of duration of the infection by *S. flexneri*, in particular *S. flexneri* type 2a.

Each vaccine dose comprises a therapeutically effective amount of oligo- or polysaccharide conjugate. Such amount will vary depending on the subject being treated, the age and general condition of the subject being treated, the capacity of the subject's immune response to synthesize antibodies, the degree of protection desired, the severity of the condition to be treated, the particular oligo- or polysaccharide conjugate selected ant its mode of administration, among other factors. An appropriate effective amount can be readily determined by one of skill in the art. A therapeutically effective amount will fall in a relatively broad range that can be determined through routine trials.

More particularly the oligo- or polysaccharide conjugate of the invention will be administered in a therapeutically effective amount that comprises from 1 to 1000 µg of oligo- or polysaccharide, preferably 1 to 50 µg.

An optimal amount for a particular vaccine can be ascertained by standard studies involving measuring the anti-LPS 2a antibody titers in subjects.

Following an initial vaccination, subjects may receive one or two booster injections at about four week intervals.

According to a preferred embodiment of said immunogenic composition, said glycoconjugates comprises a pentasaccharide or a multimer thereof such as a decasaccharide or a pentadecasaccharide The immunogenic composition of the invention may be administered with or without adjuvant. Adjuvants can be added directly to the vaccine compositions or can be administered separately, either concurrently with or shortly after, administration of the vaccine. Such adjuvants include but are not limited to aluminium salts (aluminium hydroxide), oil-in-water emulsion formulations with or without specific stimulating agents such as muramyl peptides, saponin adjuvants, cytokines, detoxified mutants of bacterial toxins such as the cholera toxin, the pertussis toxin, or the *E. coli* heatlabile toxin.

The immunogenic composition of the invention may be administered with other immunogens or immunoregulatory agents, for example, immunoglobulins, cytokines, lymphokines and chemokines.

According to another preferred embodiment of said immunogenic composition, it comprises at least an immunogen which afford protection against another pathogen, such as for example, *S. flexneri* serotype 1b, 3a and 6, *S.* species such as *S. dysenteriae* 1 and *S. sonnei* or pathogens responsible for diarrhoeal disease in humans [*Vibrio cholerae* (cholera), *Salmonella typhimurium* (typhoid), rotavirus, Enterotoxic strains of *E. Coli* (ETEC)].

Typically, the vaccine compositions are prepared as injectables either as liquid solutions or suspensions; or as solid forms suitable for solution or suspension in liquid vehicle prior to injection. The preparation may be emulsified or encapsulated in liposomes for enhanced adjuvant effect.

Once formulated, the vaccine compositions may be administered parenterally, by injection, either subcutaneous, intramuscular or intradermal.

Alternative formulations suitable for other mode of administration include oral and intranasal formulations.

Antibodies

The invention provides monoclonal IgG antibodies immunoreactive with a serotype 2a-specific antigenic determinant of the O—SP of *S. flexneri* type 2a (O—SP or O—Ag) which are produced by an hybridoma cell line deposited under the accession number I-3147, I-3198, I-3199, I-3200 and I-3201, on Apr. 20, 2004, at the Collection Nationale de Cultures de Microorganismes, INSTITUT PASTEUR, 25 rue du Docteur Roux, 75724 PARIS CEDEX 15, FRANCE.

The invention encompasses also the hybridoma cell line producing the here above defined monoclonal IgG antibodies.

The monoclonal IgG antibodies according to the invention are representative of the different IgG subclasses;
the hybridoma cell line I-3197 produces an IgG2a antibody denominated hereafter A2-1,
the hybridoma cell line I-3198 produces an IgG3 antibody denominated hereafter C1-7,
the hybridoma cell line I-3199 produces an IgG1 antibody denominated hereafter D15-7,
the hybridoma cell line I-3200 produces an IgG2b antibody denominated hereafter E4-1,
the hybridoma cell-line I-3201 produces an IgG1 antibody denominated hereafter F22-4.

The invention provides also chimeric antibodies comprising (i) a fragment of the heavy and/or light chain(s) which is identical with or homologous to the sequences of one of the here above defined mouse monoclonal IgG antibody, and (ii) the remainder of the heavy and or light chain(s) which is identical with or homologous to the sequences of an antibody from another species or belonging to another antibody class or subclass.

Accordingly, an advantageous embodiment of said chimeric antibody, is a humanized antibody which contains minimal sequences from mouse origin. For the most part humanized antibodies are human immunoglobulins in which the residues from one or more CDR(s) are replaced by residues from one or more CDR(s) of one of the here above defined mouse monoclonal IgG antibodies. Furthermore, humanized antibody may comprise residues which are found neither in the human antibody, nor in the imported CDR(s) or framework (FR) sequences. These modifications are made to further refine and optimize antibody performance. In general, the humanized antibody will comprise substantially all of at least one, and typically two, variable domains in which all or substantially all of the CDR regions correspond to those of the mouse monoclonal IgG antibody as here above defined, and all or substantially all of the FR regions are those of a human immunoglobulin consensus sequence. The humanized antibody optimally also will comprise at least a domain of an immunoglobulin constant region (Fc), typically that of a human immunoglobulin.

Preferably, said humanized antibody comprises the constant region from an IgG or an IgA, or at least the CH3 domains thereof.

More preferably, when said constant region is from an IgA, said humanized antibody comprises also a J chain so as to form dimeric IgA and/or a secretory component, so as to form secretory IgA.

According to another advantageous embodiment of said chimeric antibody it comprises a Fab fragment from said mouse monoclonal IgG antibody and a constant region from a human IgA, or at least the CH3 domains thereof.

The invention provides also fragments from the here above defined monoclonal IgG antibodies and deriving chimeric antibodies. Preferred fragments are functional fragments comprising the antigen recognition and binding site such as: Fv or half of the Fv comprising only three Complementarity-Determining-Regions (CDRs), Fab and Fab'$_2$.

Accordingly, an advantageous embodiment of said fragments is the CDR defined by the sequences SEQ ID NO: 12 to 34.

The invention provides also the polynucleotides (DNA or RNA) encoding the heavy and/or light chain from the here above defined antibodies, or a fragment thereof such as: a variable region (VL, VH) or a portion thereof such as a framework and/or CDR, and a constant region or a portion thereof such as a constant domain (CL, CH1, CH2, CH3).

The invention provides also the vectors comprising said polynucleotides.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors A vector according to the present invention comprises, but is not limited to, a YAC (yeast artificial chromosome), a BAC (bacterial artificial), a baculovirus vector, a phage, phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art.

Preferably said vectors are expression vectors, wherein a sequence encoding an antibody of the invention is placed under control of appropriate transcriptional and translational control elements to permit production or synthesis of said protein. Therefore, said polynucleotide is comprised in an expression cassette. More particularly, the vector comprises a replication origin, a promoter operatively linked to said encoding polynucleotide, a ribosome site, an RNA-splicing site (when genomic DNA is used), a polyadenylation site and a transcription termination site. It also can comprise an enhancer. Selection of the promoter will depend upon the cell in which the polypeptide is expressed.

The invention also concerns a prokaryotic or eukaryotic host cell that is modified by a polynucleotide or a vector as defined above, preferably an expression vector.

As used herein, a cell refers to a prokaryotic cell, such as a bacterial cell, or eukaryotic cell, such as an animal, plant or yeast cell.

The invention also concerns a non-human transgenic animal or a transgenic plant, wherein all or part of the cells are modified by a polynucleotide or a vector as defined above.

The polynucleotide sequence encoding the polypeptide of the invention may be prepared by any method known by the man skilled in the art. For example, it is amplified from a cDNA template, by polymerase chain reaction with specific primers. Preferably the codons of said cDNA are chosen to favour the expression of said protein in the desired expression system.

The recombinant vectors comprising said polynucleotide may be obtained and introduced in a host cell by the well-known recombinant DNA and genetic engineering techniques.

The antibody of the invention may be obtained by culturing the host cell containing an expression vector comprising a polynucleotide sequence encoding said polypeptide, under conditions suitable for the expression of the polypeptide, and recovering the polypeptide from the host cell culture.

Passive Protection

The invention provides a pharmaceutical composition comprising an antibody, as defined above or a functional fragment thereof, and a physiologically acceptable vehicle.

The antibodies of the present invention which have a protective effect against *S. flexneri* infection, in particular *S.* flexneri type 2a are administered to a mammal subject, preferably a human, in an amount sufficient to prevent or attenuate the severity, extent of duration of the infection by S. flexneri, in particular S. flexneri type 2a.

The administration of the antibody may be either prophylactic (prior to the anticipated exposure to S. flexneri) or therapeutical (after the initiation of the infection, at or shortly after the onset of the symptoms).

The dosage of the antibodies will vary depending upon factors as the subject's age, weight and species. In general, the dosage of the antibody is in the range of from about 1 mg/kg to 10 mg/kg body weight.

Preferably, said antibody is a humanized antibody of the IgG or the IgA class.

The route of administration of the antibody may be oral or systemic, for example, subcutaneous, intramuscular or intravenous.

Diagnosis

The antibodies and the oligo- or polysaccharides according to the present invention are used, in vitro, as S. flexneri type 2a specific diagnostic reagents in standard immunoassays.

The antibodies according to the present invention are used to test for the presence of S. flexneri type 2a in biological samples, for establishing the diagnosis of shigellosis in an individual presenting a diarrhoeal disease.

Alternatively, the oligo- or polysaccharides according to the present invention are used to test the presence of S. flexneri type 2a-specific antibodies. Oligo- or polysaccharides may be used for epidemiological studies, for example for determining the geographic distribution and/or the evolution of S. flexneri type 2a infection worldwide, as well as for evaluating the S. flexneri type 2a-specific antibody response induced by an immunogen.

The antibodies and the oligo or polysaccharides according to the present invention may be advantageously labelled and/or immobilized onto a solid phase, according to standard protocols known to the man skilled in the art. Such labels include, but are not limited to, enzymes (alkaline phosphatase, peroxydase), luminescent or fluorescent molecules. For example an oligo- or polysaccharide conjugated to biotine, according to the present invention may be immobilized onto a solid phase, to detect the presence of S. flexneri type 2a-specific antibodies in biological samples.

Such immunoassays include, but are not limited to, agglutination assays, radioimmunoassay, enzyme-linked immunosorbent assays, fluorescence assays, western-blots and the like.

Such assays may be for example, of direct format (where the labelled antibody/oligo- or polysaccharide is reactive with the antigen/antibody to be detected), an indirect format (where a labelled secondary antibody is reactive with said antibody/oligo- or polysaccharide), a competitive format (addition of a labelled antibody/oligo- or polysaccharide), or a sandwich format (where both labelled and unlabelled antibodies are used).

For all therapeutic, prophylactic and diagnostic uses, the oligo- or polysaccharides of the invention, alone or linked to a carrier, as well as antibodies and other necessary reagents and appropriate devices and accessories may be provided in kit form so as to be readily available and easily used.

Detailed Description of the Preparation of the Molecules

The instant invention is based on the characterization of the antigenic determinants of S. flexneri 2a O—SP recognized by serotype-specific protective monoclonal antibodies. The synthesis, as their methyl glycosides, of a panel of oligosaccharides representative of fragments of S. flexneri 2a O—SP was thus undertaken to be used as probes in the study of antibody recognition.

$$\text{A} \quad\quad \text{B} \quad\quad \text{E} \quad\quad \text{C} \quad\quad \text{D}$$
$$\text{2)-}\alpha\text{-L-Rhap-(1}\rightarrow\text{2)-}\alpha\text{-L-Rhap-(1}\rightarrow\text{3)-[}\alpha\text{-D-Glcp-(1}\rightarrow\text{4)]-}\alpha\text{-L-Rhap-(1}\rightarrow\text{3)-}\beta\text{-D-GlcNAcp(1}\rightarrow$$

The O—SP of S. flexneri 2a is a heteropolysaccharide defined by the pentasaccharide repeating unit I. {(D. A. R. Simmons, Bacteriol. Reviews 1971, 35, 117-148; A. A. Lindberg, A. Karnell, A. Weintraub, Rev. Infect. Dis. 1991, 13, S279-S284) It features a linear tetrasaccharide backbone, which is common to all S. flexneri O-antigens, except serotype 6, and comprises a N--acetyl glucosamine and three rhamnose residues, together with an α-D-glucopyranose residue branched at position 4 of rhamnose C. We have already reported on the synthesis of the methyl glycosides of various fragments of the O—SP, including the known EC disaccharide, (J. M. Berry, G. G. S. Dutton, Can. J. Chem. 1974, 54, 681-683; G. M. Lipkind, A. S. Shashkov, A. V. Nikolaev, S. S. Mamyan, N. K. Kochetkov, Bioorg. Khim. 1987, 13, 1081-1092; L. A. Mulard, C. Costachel, P. J. Sansonetti, J. Carbohydr. Chem. 2000, 19, 849-877) the ECD (L. A. Mulard, C. Costachel, P. J. Sansonetti, J. Carbohydr. Chem. 2000, 19, 849-877) and B(E)C (L. A. Mulard, C. Costachel, P. J. Sansonetti, J. Carbohydr. Chem. 2000, 19, 849-877) trisaccharides, the ECDA (F. Segat, L. A. Mulard, Tetrahedron: Asymmetry 2002, 13, 2211-2222) and AB(E)C (C. Costachel, P. J. Sansonetti, L. A. Mulard, J. Carbohydr. Chem. 2000, 19, 1131-1150) tetrasaccharides, the B(E)CDA (F. Segat, L. A. Mulard, Tetrahedron: Asymmetry 2002, 13, 2211-2222) and DAB(E)C (C. Costachel, P. J. Sansonetti, L. A. Mulard, J. Carbohydr. Chem. 2000, 19, 1131-1150) pentasaccharides and more recently the B(E)CDAB(E)C octasaccharide (F. Bélot, C. Costachel, K. Wright, A. Phalipon, L. A. Mulard, Tetrahedron. Lett. 2002, 43, 8215-8218).

In the following, we report on the synthesis of the ECDAB, AB(E)CD pentasaccharides as well on that of the B(E)CD tetrasaccharide as their methyl glycosides, 1, 2 and 3, respectively. We also report on the synthesis of a pentasaccharide DAB(E)C building block (201) and that of the corresponding trichloroacetimidate donor 203. The decasaccharide D'A'B'(E')C'DAB(E)C fragment, was prepared as its methyl glycoside (301).

1—Synthesis of Oligo- and Polysaccharides According to the Invention

A—Synthesis of a Tetra- and Two Pentasaccharide Fragments of the O-specific Polysaccharide of Shigella flexneria Serotype 2a:

The synthesis of the methyl glycosides of the ECDAB, AB(E)CD pentasaccharides and that of the B(E)CD tetrasaccharide, 101, 102 and 103, respectively, is reported in the following.

Analysis of the targets shows that all the glycosylation reactions to set up involve 1,2-trans glycosidic linkages except for that at the E-C junction which is 1,2-cis. Consequently, the syntheses described herein rely on key EC disaccharide building blocks as well as on appropriate A, B and D monosaccharide synthons.

Synthesis of the linear ECDAB-OMe pentasaccharide (101): Based on earlier findings in the series which have demonstrated that the C-D linkage was an appropriate disconnection site. (F. Segat, L. A. Mulard, *Tetrahedron: Asymmetry* 2002, 13, 2211-2222; F. Bélot, C. Costachel, K. Wright, A. Phalipon, L. A. Mulard, *Tetrahedron. Lett.* 2002, 43, 8215-8218; F. Bélot, K. Wright, C. Costachel, A. Phalipon, L. A. Mulard, *J. Org. Chem.* 2004, 69, 1060-1074) Consequently, the synthesis of 101 was designed (FIG. 1) based on the glycosylation of the known EC trichloroacetimidate donor 114, (L. A. Mulard, C. Costachel, P. J. Sansonetti, *J. Carbohydr. Chem.* 2000, 19, 849-877) obtained in three steps (69%) from the key diol 113, (F. Segat, L. A. Mulard, *Tetrahedron: Asymmetry* 2002, 13, 2211-2222) and the DAB trisaccharide acceptor 112. The latter was obtained by the stepwise condensation of known monosaccharide precursors, readily available by selective protection, deprotection and activation sequences. Thus, TMSOTf-catalysed condensation of the rhamnopyranoside acceptor 104 (V. Pozsgay, J.-R. Brisson, H. J. Jennings, *Can. J. Chem.* 1987, 65, 2764-2769) with the trichloroacetimidate donor 5 (J. C. Castro-Palomino, M. H. Rensoli, V. V. Bencomo, *J. Carbohydr. Chem.* 1996, 15, 137-146) in diethyl ether to give the fully protected rhamnobioside 106, and subsequent de-O-acetylation gave the AB disaccharide acceptor 107 in 91% overall yield, which compares favourably with the previously described preparation using the corresponding 1-O-acetyl donor. (V. Pozsgay, J.-R. Brisson, H. J. Jennings, *Can. J. Chem.* 1987, 65, 2764-2769) Analogously to previous work in a related series, (F. Bélot, K. Wright, C. Costachel, A. Phalipon, L. A. Mulard, *J. Org. Chem.* 2004, 69, 1060-1074) the known glucosaminyl trichloroacetimidate donor 109, (J. C. Castro-Palomino, R. R. Schmidt, *Tetrahedron Lett.* 1995, 36, 5343-5346) was chosen as the precursor to residue D. Conventional glycosylation of 107 with 109 was best performed in acetonitrile using tin trifluoromethanesulfonate ($Sn(OTf)_2$) as the catalyst (A. Lubineau, A. Malleron, *Tetrahadron Lett.* 1985, 26, 1713-1716) to give the fully protected trisaccharide 110 in 72% yield (extracted from the $^1$H NMR spectrum). When TMSOTf was used instead of $Sn(OTf)_2$, 110 was formed in lower yield (52%) outlining the sensitivity of the tetrachlorophtaloyl group to these stronger conditions, as previously noted. (L. Lay, L. Manzoni, R. R. Schmidt, *Carbohydr. Res.* 1998, 310, 157-171) A three step process including heating 110 with ethylenediamine in dry ethanol,(J. S. Debenham, R. Madsen, C. Roberts, B. Fraser-Reid, *J. Am. Chem. Soc.* 1995, 117, 3302-3303) ensuing N-acetylation with acetic anhydride, and de-O-acetylation under Zemplén conditions, furnished the triol 111 (51% from 107). It was next protected at positions $4_D$ and $6_D$ by regioselective introduction of an isopropylidene acetal upon reaction with 2,2-dimethoxypropane under acid-catalysis to give 112 (96%). The latter acetal-protecting group was selected based on data previously obtained when synthesizing shorter fragments in the series which had outlined the interest of using 4,6-O-isopropylidene-glucosaminyl intermediates instead of the more common benzylidene analogues. (L, A. Mulard, C. Costachel, P. J. Sansonetti, *J. Carbohydr. Chem.* 2000, 19, 849-877) Once the two key building blocks were made available, their condensation was performed in dichloromethane in the presence of a catalytic amount of TMSOTf to give the fully protected pentasaccharide 115 (84%). Conventional stepwise deprotection involving (i) acidic hydrolysis of the isopropylidene acetal using 90% aq TFA to give diol 116 (95%), (ii) conversion of the latter into the corresponding tetraol 117 under Zemplén conditions (86%), and (iii) final hydrogenolysis of the benzyl protecting groups, gave the linear pentasaccharide target 101 in 81% yield.

Synthesis of the AB(E)CD pentasaccharide 102 and of the B(E)CD tetrasaccharide 103. For reasons mentioned above, the glucosaminyl acceptor 118, (L. A. Mulard, C. Costachel, P. J. Sansonetti, *J. Carbohydr. Chem.* 2000, 19, 849-877) protected at its 4 and 6 hydroxyl groups by an isopropylidene acetal was the precursor of choice for residue D (FIG. 2). In the past, introduction of residue B at position $3_C$ was performed on a $2_C$-O-benzolyated EC acceptor resulting from the regioselective acidic hydrolysis of the corresponding 2,3-orthoester intermediate. (F. Segat, L. A. Mulard, *Tetrahedron: Asymmetry* 2002, 13, 2211-2222; C. Costachel, P. J. Sansonetti, L. A. Mulard, *J. Carbohydr. Chem.* 2000, 19, 1131-1150) It rapidly occurred to us that opening of the intermediate phenyl orthoester was not compatible with the presence of $4_D,6_D$-O-isopropylidene acetal. For that reason, the trichloroacetimidate donor 119, suitably benzoylated at position $2_C$ and orthogonally protected by a chloroacetyl group at position $3_C$ was used as the EC building block instead of the previously used 114. Protection at the 2-OH of the rhamnosyl precursor to residue B was also crucial in the synthesis of 102. Indeed, most of our previous work in the series relied on the use of the known 2-O-acetyl rhamnopyranosyl donor 105, In the reported syntheses, (C. Costachel, P. J. Sansonetti, L. A. Mulard, *J. Carbohydr. Chem.* 2000, 19, 1131-1150) selective de-O-acetylation at position $2_B$ in the presence of a $2_C$-O-benzoate was best performed by treatment with methanolic $HBF_4.OEt_2$ for five days. Clearly, such de-O-acetylation conditions are not compatible with the presence of an isopropylidene acetal on the molecule. To overcome this limitation, the corresponding 2-O-chloroacetyl rhamnopyranosyl trichloroacetimidate 120 was selected as an alternate donor. In theory, the latter could also serve as an appropriate precursor to residue A.

Regioselective conversion of diol 113 into its 2-O-benzoylated counterpart 121 was performed as described (FIG. 3). (F. Segat, L. A. Mulard, *Tetrahedron: Asymmetry* 2002, 13, 2211-2222) Treatment of the latter with chloroacetic anhydride and pyridine gave the orthogonally protected 122 (95%), which was smoothly de-O-allylated to yield the corresponding hemiacetal 123 (91%) by a two-step process, involving (i) iridium (I)-promoted isomerisation (J. J. Oltvoort, C. A. A. van Boeckel, J. H. der Koring, J. van Boom, *Synthesis* 1981 305-308) of the allyl glycoside and (ii) subsequent hydrolysis in the presence of iodine. (M. A. Nashed, L. Anderson, *J. Chem. Soc. Chem. Commun.* 1982 1274-1282) The selected trichloroacetimidate leaving group was successfully introduced by treatment of 123 with trichloroacetonitrile in the presence of DBU, which resulted in the formation of 119 (84%) together with the recovery of some starting hemiacetal (14%) since partial hydrolysis during column chromatography could not be avoided. TMSOTf-mediated glycosylation of donor 119 and acceptor 118 furnished the fully protected ECD trisaccharide (124, 80%), which was readily converted to the required acceptor 125 upon selective deblocking of the chloroacetyl protecting group with thiourea (97%). Following the two-step protocol described above for the preparation of 119, the known allyl rhamnopyranoside 127, (P. Westerduin, P. E. der Haan, M. J. Dees, J. H. van Boom, *Carbohydr. Res.* 1988, 180, 195-205) bearing a 2-O-chloroacetyl protecting group, was converted to the hemiacetal 128 (85%) (FIG. 4). Next, treatment of the latter with trichloroacetonitrile and a slight amount of DBU gave at best donor 120 in a yield of 73%. Although the isolated yield of 120 was not better (72%), running the activation step in the presence of $K_2CO_3$ instead of DBU resulted in a more reproducible isolated yield of the activated donor. Glycosylation of the ECD acceptor 125 and the B donor 120 was attempted under various conditions of solvent and catalyst. Whatever the conditions, hardly separable mixtures of compounds were obtained, among which the yield of the target tetrasaccharide reached 45-50%. Running the condensation in $Et_2O$ in the presence of TMSOTf as the promoter were the best conditions tested, although the expected tetrasaccharide 129 was often slightly contaminated with glycosylation intermediates such as the silylated 126 or the orthoester 135 (FIG. 5), as suggested from mass spectroscopy analysis and NMR data. In fact, the nature of the latter was fully ascertained at the next step in the synthesis. Indeed, full recovery of the starting material was observed upon treatment of 135 with thiourea. On the contrary, treatment of a mixture of the condensation products 129 and supposedly 126 under the same conditions led to the expected tetrasaccharide acceptor 131 and the trisaccharide acceptor 125 (not described). The βB-tetrasaccharide isomer could not be detected at this stage, indicating that the corresponding chloroacetylated βB-anomer was probably not part of the initial mixture. Formation of the starting 125 during the dechloroacetylation step was not unexpected, since loss of a trimethylsilyl group under similar treatment was observed for a model compound (not described). Although the fluoride analog corresponding to donor 120 has been used successfully in a prior report, (P. Westerduin, P. E. der Haan, M. J. Dees, J. H. van Boom, *Carbohydr. Res*, 1988, 180, 195-205) the poor yield of 129 may be, in part, associated to the sensitivity of the chloroacetyl group to the glycosylation conditions. Thus, in order to investigate the poor outcome of the condensation reaction, the donor properties of the chloroacetylated 120 were compared to that of the more common acetylated 105. When methyl rhamnopyranoside 104 was condensed with 120 as described for the preparation of 106, the rhamnobioside 108 was isolated in 67% yield. This result tends to suggest that indeed the acetylated 5 is a more powerful donor than 120.

Starting from 120 and 125, the isolated yield of the tetrasaccharide acceptor 131 was 34%, which encouraged us to reconsider the use of 105 as a precursor to residues B and A in the synthesis of 102. Condensation of 105 and 125 in $CH_2Cl_2$ using TMSOTf as the promoter furnished the corresponding tetrasaccharide 130 (72%). However, even though the yield of 131 was better than that of 129, slight contamination by the silylated side-product 126 was again apparent, outlining the somewhat poor reactivity of the ECO acceptor. Subsequent treatment of 130 with a 0.4 M ethanolic solution of guanidine (N. Kunesh, C. Miet, J. Poisson, *Tetrahadron Lett*. 1987, 28, 3569-3572) resulted in selective $2_B$-O-deacetylation to give 131 in a satisfactory 83% yield, which outlined the interest of the method. However, previous experience in other closely related series has shown that the selectivity of the method was highly dependent on the nature of the substrate. Clearly, the 2-O-acetylated donor 105 was preferred to the chloroacetate analogue 120. Condensation of the tetrasaccharide acceptor 131 and donor 105 in the presence of TMSOTf gave the fully protected pentasaccharide 132 in a yield of 52%. TFA-mediated hydrolysis of the isopropylidene acetal followed by transesterification of the ester groups and subsequent conventional hydrogenolysis of the benzyl ethers finally gave the target pentasaccharide 2 (88%).

Alternatively, the fully protected tetrasaccharide 130 was converted to the diol 136 by acidic removal of the isopropylidene acetal (85%), and subsequently to the corresponding tetrol 137 upon transesterification (83%). Final hydrogenolysis of the benzyl groups furnished the target tetrasaccharide 103 (71%) (FIG. 6).

Noteworthy, in the case of intermediates 133 and 136, removal of the esters required heating of the reaction mixtures, whereas de-O-acylation of 117 proceeded smoothly at rt. Occurring most probably as a consequence to the branched nature of compounds 133 and 136, steric hindrance and isolation of the acyl groups (Z. Szurmai, A. Liptak, G. Snatzke, *Carbohydr. Res*. 1990, 200, 201-208) may best explain the phenomenon. Steric hindrance may also account for the poor outcome of the condensation of the ECD acceptor 125 with the B donors 120 and 105. Interestingly, $^{13}C$ NMR data support this hypothesis. Although no altered signals could be seen in the $^{13}C$ NMR spectrum of the ECD acceptor 125 or in the $^{13}C$ NMR spectra of the fully protected precursor 124, significant disturbance of several signals in the $^{13}C$ NMR spectra of the tetra- and pentasaccharides were seen repeatedly. At the protected and partially protected stage, major altered signals are those tentatively assigned to $C-3_C$ and $C-4_C$. Besides, signals assigned to $C-2_D$, $C-3_D$ as well as to $C-1_B$ are significantly broader than expected. Loss of conformational flexibility at the C ring is not totally unexpected especially since the carbons involved are those corresponding to the branching points. Of particular interest however, was the observation that residue D, the N-acetyl-glucosaminyl residue, was also partially constrained. Full conformational freedom of residue D is recovered when the B(E)CD and AB(E)CD oligosaccharides are in their free form. However, this observation does not stand true for residue C since characteristic broad signals for $C-3_C$ and $C-4_C$ as well for $C-1_B$ and $C-1_E$ are still present in the $^{13}C$ NMR spectra of compounds 102 and 103, respectively. Overall, these observations suggest a somewhat compact organisation at the branching point of the B(E)CD structure. It is worth mentioning that none of these disturbed signals are seen in the $^{13}C$ NMR spectra of the oligosaccharides corresponding to the linear ECDAB fragment.

The synthesis of the methyl glycoside (102) of the repeating unit I of the *S. flexneri* 2a O—SP, together with that of the corresponding frame-shifted pentasaccharide 101 and tetrasaccharide 103 were described. All the methyl glycosides of the di- to pentasaccharides obtained by circular permutation of the monosaccharide residues partaking in the linear backbone of 1, and comprising the EC portion, are now available in the laboratory. Their binding to a set of protective monoclonal IgG antibodies will be reported elsewhere.

B—Synthesis of a Pentasaccharide Building Block of the O-specific Polysaccharide of *Shigella flexneri* Serotype 2a: DAB(E)C In the following, a synthesis of the DAB(E)C pentasaccharide 201, which is protected in an orthogonal fashion at position $O-3_D$ with an acetyl group and at the reducing end by an allyl group. At this stage, the acetamido function is already present at position $2_D$. Compound 201 may be converted to the corresponding alcohol 202, which acts as an donor and a masked donor, or to the trichloroacetimidate 203 which acts as an acceptor allowing subsequent chain elongation at the non-reducing end (FIG. 7). Previous work in the laboratory has shown that in order to construct the DAB(E)C sequence, the linear approach involving stepwise elongation at the non-reducing end, was more suitable than the blockwise one.

D-glucosamine unit (D). In order to limit the number of steps at the pentasaccharide level, we reasoned that an appropriate precursor to residue D should have (i) permanent protecting groups at positions 4 and 6, (ii) a participating group at position 2 and (iii) an orthogonal protecting group at position 3, allowing easy cleavage. As they allow a wide range of protecting group manipulations previously to ultimate activation, thioglycosides are highly convenient masked donors. Recently, two sets of non-malodorous thioglycosyl donors have been proposed (H. Dohi, Y. Nishida, T. Takeda, K. Kobayashi, Carbohydr. Res. 2002, 337, 983-989; H. Matsui, J.-I. Furukawa, T. Awano, N. Nishi, N. Sakairi, Chem. Lett. 2000, 29, 326-327), among which the thiododecanyl moiety was selected (FIG. 8). Thus, the known peracetylated trichloroacetamide 204 (G. Blatter, J.-M. Beau, J.-C. Jacquinet, Carbohyd. Res. 1994, 260, 189-202) was reacted with dodecanthiol in the presence of $BF_3.OEt_2$ to give thioglycoside 205 in high yield (97%). Zemplén deacetylation cleanly afforded the corresponding triol 206, which was selectively protected at position 4 and 6 upon reaction with 2,2-dimethoxypropane to give 207 (80% from 204). Indeed, previous observations in the series have demonstrated that 4,6-O-isopropylidene-D-glucosaminyl derivatives were highly suitable precursors to residue D. (L. A. Mulard, C. Costachel, P. J. Sansonetti, Carbohydr. Chem. 2000, 19, 849-877; F. Bélot, C. Costachel, K. Wright, A. Phalipon, L. A. Mulard, Tetrahedron. Lett. 2002, 43, 8215-8218) Next, conventional acetylation of 207 gave the required thioglycoside donor 208.

L-Rhamnose units (A, B): Previous work in the series was mostly based on the use of the 2-O-acetyl trichloroacetimidate rhamnopyranosyl donor 213. (C. Costachel, P. J. Sansonetti, L. A. Mulard, J. Carbohydr. Chem. 2000, 19, 1131-1150; F. Bélot, K. Wright, C. Costachel, A. Phalipon, L. A. Millard, J. Org. Chem, 2004, 69, 1060-1074) Condensation yields were excellent. However, the acetyl protecting group is not fully orthogonal to the benzoyl one, which is a weak point in the strategy since selective de-O-acetylation is required twice. The levulinate on the contrary is fully orthogonal to either benzyl or allyl ethers, and to benzoates. The 2-O-levulinoyl trichloroacetimidate donor 212 was thus evaluated as an alternative to 213. It was prepared from the known allyl rhamnopyranoside 209 (P. Westerduin, P. E. der Haan, M. J. Dees, J. H. van Boom, Carbohydr. Res. 1988, 180, 195-205) in three steps (FIG. 9). Indeed, treatment of 209 with levulinic acid gave the fully protected 210 (95%), deallylation of which proceeded in two steps based on (i) isomerisation of the allyl group into the prop-1-enyl ether using an iridium complex, (J. J. Oltvoort, C. A. A. van Boeckel, J. H. der Koning, J. van Boom, Synthesis 1981 305-308) and (ii) subsequent oxidative cleavage of the latter to give the hemiacetal 211 (85-95%). (M. A. Nashed, L. Anderson, J. Chem. Soc. Chem. Commun. 1982 1274-1282) Reaction of the latter with trichloroacetonitrile in the presence of 1,8-diazabicyclo[5.4.0]undec-7-ene (DBU) resulted in the required donor 212 (95%).

Synthesis of the pentasaccharide 201 (FIG. 10): The known allyl glycoside 214, acting as an EC acceptor, temporarily protected at the anomeric position and having a participating group at position $2_C$, was prepared as described in 63% yield from allyl 2,3-O-isopropylidene-α-L-rhamnopyranoside. (F. Segat, L. A. Mulard, Tetrahedron: Asymmetry 2002, 13, 2211-2222) Its condensation with the trichloroacetimidate donor 212, performed in the presence of a catalytic amount of TMSOTf, afforded the fully protected trisaccharide 215 (80-95%), and subsequently the known B(E)C acceptor 216 (F. Bélot, K. Wright, C. Costachel, A. Phalipon, L. A. Mulard, J. Org. Chem. 2004, 69, 1060-1074) upon selective removal of the O-levulinoyl group with hydrazine hydrate (80-94%). Starting from 216, this two-step process was repeated to give first the fully protected 217 (54-90%), then the known AB(E)C acceptor 218 (F. Bélot, K. Wright, C. Costachel, A. Phalipon, L. A. Mulard, J. Org. Chem. 2004, 69, 1060-1074) in 80-94% yield. Considering that selective deblocking at positions $2_B$ and $2_A$ was completed in overnight runs instead of the 5 days required for each corresponding chemoselective O-deacetylation steps, the use of the 2-O-levulinoyl donor 212 appeared as a suitable alternative to that of 213. Using a mixture of NIS and triflic acid as the promoter, condensation of the tetrasaccharide acceptor 218 with the thioglycoside donor 208 gave the key intermediate 219 in 58% yield. Although alternative conditions in terms of promoters and solvents (not described) were tested, this rather low yield could not be improved. $Bu_3SnH$ mediated radical dechlorination of 219 in the presence of a catalytic amount of AIBN readily afforded the corresponding acetamido key intermediate 201 (74%). On one hand, compound 201 may be efficiently converted to the acceptor building block 202 under Zemplén conditions. On the other hand, it was smoothly deallylated into the hemiacetal 220, following a two-step process as described above. Next, treatment of 220 with trichloroacetonitrile and DBU allowed its conversion to the building block 3 (82% from 201).

C—Convergent Synthesis of the Decasaccharide D'A'B'(E')C'DAB(E)C

Considering its dimeric nature, a convergent synthetic strategy to the target methyl glycoside of the decasaccharide D'A'B'(E')C'DAB(E)C (301) was considered. Indeed, retrosynthetic analysis, supported by previous work in the field, (Bélot, F.; Costachel, C.; Wright, K.; Phalipon, A.; Mulard, L. A. Tetrahedron. Lett, 2002, 43, 8215-8218; Kochetkov, N. K.; Byramova, N. E.; Tsvetkov, Y. E; Backinovsky, L. V. Tetrahedron 1985, 41, 3363-3375 ; Pinto, B. M.; Reimer, K. B.; Morissette, D. G.; Bundle, D. R. J. Org. Chem. 1989, 54, 2650-2656 ; Pinto, B. M.; Reimer, K. B.; Morissette, D. G.; Bundle, D. R. J. Chem. Soc. Perkin Trans. 1 1990, 293-299) indicated that disconnections at the C-D linkage, thus based on two DAB(E)C branched pentasaccharides corresponding to a frame-shifted repeating unit I, would be the most advantageous (FIG. 11). Such a strategy would involve a pentasaccharide acceptor easily derived from the known methyl glycoside 302 (Costachel, C.; Sansonetti, P. J.; Mulard, L. A. J. Carbohydr. Chem, 2000, 19, 1131-1150) or from the corresponding N-acetylated analogue 303 and a pentasaccharide donor bearing a 2-O-acyl protecting group at the reducing residue (C) in order to direct glycosylation towards the desired stereochemistry. Depending on the nature of the 2-N-acyl group in residue D, the latter could derive from the allyl glycosides 304 or 305. Besides, bearing in mind that the major drawbacks of the linear synthesis of pentasaccharide 302 reported so far (Costachel, C.; Sansonetti, P. J.; Mulard, L. A. J. Carbohydr. Chem. 2000, 19, 1131-1150) dealt with the selective deblocking of key hydroxyl groups to allow further chain elongation, we describe herein various attempts at a convergent synthesis of the fully protected DAB(E)C pentasaccharide as its methyl (302, 303) or allyl (304, 305) glycosides. Precedents concerning a related serotype of S. flexneri have indicated that disconnection at the D-A linkage should be avoided (Pinto, B. M.; Reimer, K. B.; Morissette, D. G.; Bundle, D. R. J.

*Org. Chem.* 1989, 54, 2650-2656 ; Pinto, B. M.; Reimer, K. B.; Morissette, D. G.; Bundle, D. R. *J. Chem. Soc. Perkin Trans.* 1 1990, 293-299). To our knowledge, disconnection at the B-C linkage was never attempted in the series. However, disconnection at the A-B linkage, based on the use of a combination of a bromide disaccharide donor and $Hg(CN)_2/HgBr_2$ as the promoter, was reported once. (N. K. Kochetkov, N. E. Byramova, Y. E. Tsvetkov, L. V. Backinovsky, *Tetrahedron* 1985, 41, 3363-3375) In the latter case concerning the synthesis of the linear DABC tetrasaccharide, the condensation of two disaccharide building blocks was found more effective than the stepwise strategy. Both routes were considered in the following study. The nature of the repeating unit I indicated that any blockwise synthesis involving such linkages would rely on donors lacking any participating group at position 2 of the reducing residue, thus the relevance of this strategy may be questioned. Nevertheless, although β-glycoside formation was observed occasionally, (Srivastava, O. P.; Hindsgaul, O. *Can. J. Chem.* 1986, 64, 2324-2330) the good α-stereoselectivity reported on several occasions in the literature for glycosylation reactions based on mannobiosyl donors (Ogawa, T.; Kitajma, T.; Nukada, T. *Carbohydr. Res.* 1983, 123, c5-c7 ;Ogawa, T.; Sugimoto, M.; Kitajma, T.; Sadozai, K. K.; Nukuda, T. *Tetrahadron Lett.* 1986, 27, 5639-5742) and derivatives such as perosaminyl analogues (Lei P. S; Ogawa, Y; Kovac, P. Carbohydr. Res. 1996, 281, 47-60; Kihlberg, J.; Eichler, E.; Bundle, D. R. *Carbohydr. Res.* 1991, 211, 59-75; Peters, T.; Bundle, D. R. *Can. J. Chem,* 1989, 67, 491-496) or rhamnopyranosyl donors that were either glycosylated at C-2 (Reimer, K. B.; Harris, S. L.; Varma, V.; Pinto, B. M. *Carbohydr. Res.* 1992, 228, 399-414), or blocked at this position with a non participating group (Varga, Z.; Bajza, I.; Batta, G.; Liptak, A. *Tetrahedron Lett.* 2001, 42, 5283-5286), encouraged the evaluation of the above mentioned block strategies. To follow up the work developed thus far in the *S. flexneri* 2a series, emphasis was placed on the use of the use of trichloroacetimidate (TCA) chemistry (Schmidt, R. R.; Kinzy, W. *Adv. Carbohydr. Chem. Biochem.* 1994, 50, 21-123).

Strategy based on the disconnection at the A-B linkage (FIG. 11, route a): Such a strategy involves the coupling of suitable DA donors to an appropriate B(E)C acceptor. Taking into account the glycosylation chemistry, two sets of disaccharide building blocks (306, 307, 308), easily obtained from known monosaccharide precursors which were readily available by standard protecting group/activation strategies, were selected (FIG. 11). Thus, condensation of the allyl rhamnopyranoside 314, (Westerduin, P.; der Haan, P. E.; Des, M. J.; van Boom, J. H. *Carbohydr. Res.* 1988, 180, 195-205) as precursor to residue A, with the glucosaminyl trichloroacetimidate 316, (Blatter, G.; Beau, J.-M.; Jacquinet, J.-C. *Carbohydr. Res.* 1994, 260, 189-202) as precursor to residue D, was performed in the presence of a catalytic amount of TMSOTf to give the fully protected disaccharide 317 (99%). Selective deallylation of 317 proceeded in two steps involving (i) iridium(I)-catalysed isomerisation of the allyl glycoside into the corresponding 1-O-propenyl glycoside (Oltvoort, J. J.; van Boeckel, C. A. A.; der Koning, J. H.; van Boom, *J. Synthesis* 1981, 305-308) and (ii) hydrolysis of the latter (Gigg, R.; Warren, C. D. *J. Chem. Soc. C* 1968, 1903-1911 ; Gigg, R.; Payne, S.; Conant, R. *J. Carbohydr. Chem.* 1983, 2, 207-223). The resulting hemiacetal 318 (81%) was converted into the trichloroacetimidate 306 (78%) by treatment with trichloro-acetonitrile in the presence of a catalytic amount of DBU (FIG. 12). Knowing from previous experience that conversion of the trichloroacetamide moiety at position 2 of residue D ($2_D$-N-trichloroacetyl) into the required $2_D$-N-acetyl group could be somewhat low-yielding, we took advantage of the blockwise approach to perform the above-mentioned transformation at an early stage in the synthesis. Thus, the disaccharide intermediate 317 was converted to the corresponding 319 (90%) upon overnight treatment with a saturated ammonia methanolic solution and subsequent per-acetylation. Conversion of 319 into the hemiacetal 320 (69%), and next into the required trichloroacetimidate donor 307 (86%), followed the procedure described above for the preparation of 306 from 317. Where glycosylation is concerned, the bifunctional role of thioglycosides as protected acceptors and masked donors is highly appreciated. (S. Oscarson, *Carbohydrates in chemistry and biology. Part* 1: *Chemistry of saccharides* 2000, 2, 93) Thus, the thiophenyl disaccharide 308 was considered as a possible alternative to the use of the more reactive trichloroacetimidates 306 and 307. It was synthesized in 97% yield by condensing the known thiophenyl rhamnopyranoside 315 (Lau, R.; Schucle, G.; Schwaneberg, U.; Ziegler, T. *Liebigs Ann. Org. Bioorg. Chem.* 1995, 10, 1745-1754) and 316 in the presence of a catalytic amount of TMSOTf (FIG. 12). To fulfil the requirements of the synthesis of 301, two different trisaccharide building blocks were used, namely either the known methyl glycoside 309 (Costachel, C.; Sansonetti, P. J.; Mulard, L. A. *J. Carbohydr. Chem.* 2000, 19, 1131-1150) or the corresponding allyl glycoside 310, obtained from the known $2_B$-O-acetylated trisaccharide 342 (see below and FIG. 15) (Segat, F.; Mulard, L. A. *Tetrahedron: Asymmetry* 2002, 13, 2211-2222). Condensation of the trisaccharide acceptor 309 and the trichloroacetimidate donor 306 was attempted under various conditions of solvent, temperature and promoter. The α-linked condensation product, i.e. the known pentasaccharide 302, (Costachel, C.; Sansonetti, P. J.; Mulard, L. A. *J. Carbohydr. Chem.* 2000, 19, 1131-1150) was at best isolated in 41% yield providing that the glycosylation reaction was run in acetonitrile in the presence of a catalytic amount of TMSOTf, following the inverted procedure protocol (Schmidt, R. R.; Toepfer, A. *Tetrahedron Lett.* 1991, 32, 3353-3356; Bommer, R.; Kinzy, W.; Schmidt, R. R. *Liebigs Ann. Chem.* 1991, 425-433) to minimize degradation of the donor. Although the α-selectivity of the glycosylation reaction was good, yields of pentasaccharide remained low, and as anticipated, use of the alternate trichloroacetimidate donor 307 to give 303 did not result in any improvement (not described). Rearrangement of the activated donor into the corresponding inert trichloroacetamide was observed previously in glycosylation reactions based on trichloroacetimidate donors lacking a participating group at position 2 of the reducing residue. (K. H. Sadozai, T. Nukada, Y. Ito, Y. Nakahara, T. Ogawa, *Carbohydr. Res.* 1986, 157, 101-123) Although the expected side-product was not isolated in any of the attempted glycosylation with 306 or 307, it was anticipated that the use of an alternate glycosylation chemistry would prevent such side-reaction, and possibly favour the condensation. However, reaction of thiophenyl donor 308 and acceptor 310 in the presence of N-iodosuccinimide and catalytic triflic acid did not prove any better as it resulted in mixtures of products from which the target 304 was isolated in very low yield, 10% at best. This strategy was thus not considered any further.

Strategy based on the disconnection at the B-C linkage (FIG. 11, route b). It was hypothesized that the good α-selectivity, but poor yields, of the condensation of the various DA donors with the B(E)C acceptors 309 and 310 might result from the poor nucleophilicity of the axial hydroxyl at position $2_B$. Thus, we next turned to the $3_C$-OH as a possible elongation site in the design of a block synthesis of pentasaccharide 305. Considering such a disconnection approach suggests the use of a DAB trisaccharide donor for coupling to an EC disaccharide acceptor. As the target pentasaccharide should serve as an appropriate donor in the construction of 301, we reasoned that an acyl participating group had to be present at its position $2_C$. Thus, two $2_C$-O-acylated EC building blocks, 311 or 312, were considered. In order to avoid any unnecessary deprotection step at the pentasaccharide level, the trisaccharide 313, bearing an acetamido functionality at position $2_D$, was selected as the donor. Indeed, as it involves the less readily available EC structure in fewer synthetic steps and does not rely on selective deprotection at the $2_A$ position, this path was found particularly attractive. Again, it relies on the use of appropriately functionalized known monosaccharide intermediates (FIG. 13).

The known key di-rhamnoside core structure 322 (Zhang, J.; Mao, J. M.; Chen, H. M.; Cai, M. S. *Tetrahedron: Asymmetry* 1994, 5, 2283-2290) was formed by glycosylation of the allyl rhamnoside 314 with the trichloroacetimidate donor 321 (Castro-Palomino, J. C.; Rensoli, M. H.; Bencomo, V. V. *J. Carbohydr. Chem.* 1996, 15, 137-146) in the presence of a catalytic amount of TMSOTf. It should be pointed out that using diethyl ether as the solvent, the isolated yield of 322 was 92%, which compares favourably with those obtained previously, 60% and 76.2% (Zhang, J.; Mao, J. M.; Chen, H. M.; Cai, M. S. *Tetrahedron: Asymmetry* 1994, 5, 2283-2290), when running the reaction in dichloromethane under promotion by TMSOTf BF$_3$.OEt$_2$, respectively. De-O-acetylation under Zemplén conditions afforded the $2_A$-O-unprotected acceptor 323 (Pinto, B. M.; Reimer, K. B.; Morissette, D. G.; Bundle, D. R. *J. Org. Chem.* 1989, 54, 2650-2656) in 93% yield.

As shown previously in the construction of the DA intermediate 317, the N-trichloroacetyl trichloroacetimidate 316 appears to be a highly suitable precursor to residue D when involved in the formation of the β-GlcNAc linkage at the poorly reactive $2_A$ position. Indeed, reaction of 316 with the acceptor 323 in 1,2-dichloroethane in the presence of TMSOTf went smoothly and gave the trisaccharide 325 in 96% yield. However, conversion of the N-trichloroacetyl group to the N-acetyl derivative 327 was rather less successful as the desired trisaccharide was obtained in only 42% yield when treated under conditions that had previously been used in the case of a related oligosaccharide (sodium methoxide, Et$_3$N, followed by re-N,O-acetylation). (Costachel, C.; Sansonetti, P. S.; Mulard, L. A. *J. Carbohydr. Chem.* 2000, 19, 1131-1150). This result led us to reconsider the protection pattern of the glucosamine donor. The N-tetrachlorophthalimide group has been proposed as an alternative to overcome problems associated with the widely spread phthalimido procedure when introducing a 2-acetamido-2-deoxy-β-D-glucopyranosidic linkage (Debenham, J. S.; Madsen, R.; Roberts, C,; Fraser-Reid, B. *J. Am. Chem. Soc.* 1995, 117, 3302-3303). Thus, the N-tetrachlorophthalimide trichloroacetimidate donor 324 was selected as an alternative. It was prepared as described from commercially available D-glucosamine (Castro-Palomino, J. C.; Schmidt, R. R. *Tetrahedron Lett.* 1995, 36, 5343-5346), apart from in the final imidate formation step, where we found the use of potassium carbonate as base to be more satisfactory than DBU. Glycosylation of 323 with 324 in the presence of TMSOTf resulted in the trisaccharide 328 in 65% yield. The tetrachlorophthaloyl group was then removed by the action of ethylenediamine, and subsequent re-N,O-acetylation gave the trisaccharide 327 in 65% yield. The latter was next converted into the donor 313 in two steps, analogous to those described for the preparation of 306 from 317. Indeed, de-O-allylation of 327 cleanly gave the hemiacetal 329 (83%), which was then activated into the required trichloroacetimidate (94%). It is worth mentioning that although they involve a different D precursor, both strategies give access to the intermediate 327 in closely related yields, 40 and 42%, respectively.

Initial attempts to form the pentasaccharide 305 from 313 and the previously described acceptor 311 (Segat, F.; Mulard, L. A. *Tetrahedron: Asymmetry* 2002, 13, 2211-2222) in the presence of TMSOTf as promoter were rather unsuccessful, resulting in at best 17% of the desired product, accompanied by decomposition of the donor into the hemiacetal 329 (75%). By using BF$_3$.OEt$_2$ as the promoter in place of TMSOTf, reaction of 311 with 313 at room temperature provided 305 in 44% yield, with the acceptor 311 and hemiacetal 329 also recovered in 54% and 29% yield, respectively. We considered that the poor reactivity of the acceptor was responsible for these results, since the $^{13}$C NMR of 305, showing several distorted signals (notably C-$1_B$, as well as most certainly C-$3_C$ and C-$4_C$), suggests restricted conformational flexibility around the position $3_C$. For that matter, the $2_C$-O-acetylated disaccharide 312 was considered as an alternate acceptor. Analogously to the preparation of 311, it was obtained from the known diol 330 through regioselective opening of the intermediate orthoester. However, coupling of the potentially less hindered acceptor 312 and the trisaccharide donor 313 resulted, at best, in the isolation of the condensation product 331 in 42% yield (not described), The modest yield of 305 and 331 obtained by this route made the alternative reaction path (FIG. 14) worth investigating, despite the more numerous synthetic steps required. Indeed, it was found rather appealing when evaluated independently in a closely related series (unpublished results). By this route, a tetrasaccharide acceptor can be formed from two disaccharide building blocks (EC and AB), and coupled with an appropriate monosaccharide donor as precursor to D.

Considering that selective deprotection of the $2_A$ hydroxyl group would occur in the course of the synthesis, glycosylation attempts were limited to the 2-O-benzoylated acceptor 311. The disaccharide donor necessary for this path could be derived from the building block 323, already in hand. The choice of temporary protecting group at position $2_A$ was determined by our experience of the stepwise synthesis of the corresponding methyl pentasaccharide, (Costachel, C.; Sansonetti, P. J.; Mulard, L. A. *J. Carbohydr. Chem.* 2000, 19, 1131-1150) where we noted that an acetate group at this position may not be fully orthogonal to the benzoate located at position $2_C$. The chosen group had also to support removal of the anomeric allyl group and the subsequent conversion to the trichloroacetimidate. At first, a chloroacetate group was anticipated to fulfil these requirements. Thus, the disaccharide 323 was treated with chloroacetic anhydride and pyridine to give the derivative 332 (57%). Anomeric deprotection to give the hemiacetal 333 (84%) and subsequent trichloroacetimidate activation of the latter into the donor 334 (83%) were performed in the same way as before. Coupling of 311 with 334, carried out in the presence of TMSOTf at –40° C., yielded a complex mixture of products. When the temperature was lowered to –60° C., the condensation product 338 could be isolated in 22% yield. Alternative donor protection was attempted. Treatment of 323 with p-methoxybenzyl chloride and sodium hydride gave the fully protected derivative 335 (97%), which was cleanly converted into the trichloroacetimidate donor 337 (82%) in two steps involving the hemiacetal intermediate 336 (73%). Glycosylation of 311 with 337 in the presence of TMSOTf at −40° C. gave the desired tetrasaccharide 339 in 44% yield. When the temperature was lowered to −60° C., the yield of 339 fell to 34% and a second major product 340 (21%) was observed in the mixture. Indeed, examination of the NMR spectra of this product revealed that the pMeOBn group had been lost. That 340 was the acceptor required for the next step brought the estimated yield of condensation to 55%. Nevertheless, the overall outcome of this blockwise strategy did not match our expectations, and this route was abandoned.

Linear strategy to the fully protected pentasaccharide 304 (FIG. 15): As preliminary studies have demonstrated, rapid access to suitable building blocks allowing the synthesis of higher-order oligosaccharides representative of fragments of the O—SP of *S. flexneri* 2a remains a challenge. Major conclusions drawn from our studies favour the design of a linear synthesis of the target 304. Indeed, when put together with our previous work, such as the synthesis of tetrasaccharide 341 (95%) (Costachel, C.; Sansonetti, P. J.; Mulard, L. A. *J. Carbohydr. Chem.* 2000, 19, 1131-1150) or that of trisaccharide 342 (97%) (Segat, F.; Mulard, L. A. *Tetrahedron: Asymmetry* 2002, 13, 2211-2222), all the above-described attempted couplings outlined the loss of efficiency of glycosylation reactions involving rhamnopyranosyl donors glycosylated at position 2 in comparison to those involving the corresponding acetylated donor. Thus, matching the linear strategy of the methyl pentasaccharide 2 described previously, (Costachel, C.; Sansonetti, P. J.; Mulard, L. A, *J. Carbohydr. Chem.* 2000, 19, 1131-1150) a synthesis of 304, based on donors bearing a participating group at O-2, was designed. Three key building blocks were selected. These were the readily accessible EC disaccharide acceptor 311 benzoylated at C-2 as required for the final condensation step leading to the fully protected decasaccharide intermediate; the rhamnopyranosyl trichloroacetimidate 321, which serves as a precursor to residues A and B, and bears a both temporary and participating group at position 2; and the trichloroacetamide glucosaminyl donor 316 as a precursor to residue D. As stated above, coupling of 311 and 321 gave 342 in high yield. As observed in the methyl glycoside series, (Costachel, C.; Sansonetti, P. J.; Mulard, L. A. *J. Carbohydr. Chem.* 2000, 19, 1131-1150) de-O-acetylation using MeONa or methanolic HCl was poorly selective. Although, guanidine/guanidinium nitrate was proposed as a mild and selective O-deacetylation reagent compatible with the presence of benzoyl protecting groups, (Ellervik, U.; Magnusson, G. *Tetrahedron Lett.* 1997, 38, 1627-1628) none of the conditions tested prevented partial debenzoylation leading to diol 343, as easily confirmed from NMR analysis (not described). The required alcohol 310 was readily obtained in an acceptable yield of 84% yield by a five-day acid catalysed methanolysis, using $HBF_4$ in diethyl ether/methanol, (Costachel, C.; Sansonetti, P. J.; Mulard, L. A. *J. Carbohydr. Chem.* 2000, 19, 1131-1150 ; Pozsgay, V.; Coxon, B. *Carbohydr. Res.* 1994, 257, 189-215) of the fully protected intermediate 342. Repeating this two-step process using 310 as the acceptor and 321 as the donor resulted first in the intermediate 344 (90%), and next in the tetrasaccharide acceptor 340 (84%). Glycosylation of the latter with 316 gave the fully protected pentasaccharide 304 in high yield (98%), thus confirming that the combination of the trichloroacetamide participating group and the trichloroacetirnidate activation mode in 316 results in a potent donor to be used as a precursor to residue D in the *S. flexneri* series, where low-reactive glycosyl acceptors are concerned. Following the above described procedure, selective anomeric deprotection of 304 furnished the hemiacetal 345 which was smoothly converted to the trichloroacetimidate donor 346 (66% from 304). From these data, the linear synthesis of 34, truly benefiting from the use of 321 as a common precursor to residue A and B, appears as a reasonable alternative to the block syntheses which were evaluated in parallel.

Synthesis of the target decasaccharide 301: Having a pentasaccharide donor in hand, focus was next placed on the synthesis of an appropriate pentasaccharide acceptor. In our recent description of the convergent synthesis of the B'(E') C'DAB(E)C octasaccharide, (F. Bélot, C. Costachel, K. Wright, A. Phalipon, L. A. Mulard, *Tetrahedron. Lett.* 2002, 43, 8215-8218) the pentasaccharide 348, bearing a $4_D,6_D$-O-isopropylidene protecting group, was found a most convenient acceptor which encouraged its selection in the present work. Briefly, 348 was prepared in two steps from the known 302. Thus, mild transesterification of 302 under Zemplén conditions allowed the selective removal of the acetyl groups to give triol 347, which was converted to the required acceptor 348 (72% from 302) upon subsequent treatment with 2-methoxypropene. Relying on previous optimisation of the glycoxylation step (Bélot, F.; Costachel, C.; Wright, K.; Phalipon, A.; Mulard, L. A. *Tetrahedron. Lett.* 2002, 43, 8215-8218), the condensation of 348 and 346 was performed in the presence of a catalytic amount of trifle acid. However, probably due to the closely related nature of the donor and acceptor, the reaction resulted in an inseparable mixture of the fully protected 349 and the hemiacetal 345 resulting from partial hydrolysis of the donor. Most conveniently, acidic hydrolysis of the mixture, allowing the selective removal of the isopropylidene group in 349, gave the intermediate diol 350 in a satisfactory yield of 72% for the two steps. According to the deprotection strategy used for the preparation of the closely related octasaccharide (Bélot, F.; Costachel, C.; Wright, K.; Phalipon, A.; Mulard, L. A. *Tetrahedron. Lett.* 2002, 43, 8215-8218), diol 350 was engaged in a controlled de-O-acylation process upon treatment with hot methanolic sodium methoxide. However, partial cleavage of the trichloroacetyl moiety, leading to an inseparable mixture, was observed which prevented further use of this strategy. Indeed, it was assumed that besides being isolated and therefore resistant to Zemplén transacetylation conditions (Liptak, A.; Szurmai, Z.; Nanasi, P.; Neszmelyi, A. *Carbohydr. Res.* 1982, 99 ; Szurmai, Z.; Liptak, A.; Snatzke, G. *Carbohydr. Res.* 1990, 200, 201-208 ; Szurmai, Z.; Kerékgyarto, J.; Harangi, J.; Liptak, A. *Carbohydr. Res.* 1987, 174, 313-325), the $2_C$-O-benzoyl groups were most probably highly hindered which contributed to their slow deprotection. Alternatively, 350 was submitted to an efficient two-step in-house process involving first, hydrogenolysis under acidic conditions which allowed the removal of the benzyl groups and second, basic hydrochlorination which resulted in the conversion of the N-trichloroacetyl groups into the required N-acetyl ones, thus affording 352. Subsequent transesterification gave the final target 301 in 37% yield from 350 (FIG. 16).

D—Synthesis of the 2-aminoethyl Glycoside of a Hapten Representative of the O-specific Polysaccharide of *Shigella flexneri* Serotype 2a and of a Corresponding PADRE-conjugate Studies on the recognition of synthetic fragments of the O—SP by protective homologous monoclonal antibodies suggested that sequences larger than one repeating unit were more antigenic, thus probably better mimicking the natural polysaccharide than shorter ones. Indeed, it is anticipated that better mimics of the O—SP, in terms of both antigenicity and conformation, would lead to conjugates of higher immunogenicity. For that reason, the preparation of conjugates comprising oligosaccharides larger than one repeating unit was undertaken.

We report herein on the synthesis of the 2-aminoethyl glycosides of a hexasaccharide (402) and on that of the corresponding fully synthetic conjugate (401) using the PADRE as a universal T-helper peptide (see section E for the background). We have demonstrated that disconnection at the C-D linkage was appropriate for the construction of large fragments of the *S. flexneri* 2a O—SP (F. Bélot, K. Wright, C. Costachel, A. Phalipon, L. A. Mulard, *J. Org. Chem.* 2004, 69, 1060-1074). Based on our experience in the field, a strategy to target 401, implicating the DAB(E)C building block bearing the required acetamido function at position $2_D$ (406) as donor and the recently disclosed acceptor 405 (K. Wright, C. Guerreiro, I. Laurent, F. Baleux, L. A. Mulard, *Org. Biomol. Chem.* 2004, 2, 1518-1527) as a precursor to the spacer-armed D residue (FIG. 17). Although permanent blocking of OH-$4_D$ and OH-$6_D$ with an isopropylidene acetal may appear somewhat unusual, this choice was a key feature of the strategy. It was based on former observations in the methyl glycoside series, demonstrating that its use could overcome some of the known drawbacks of the corresponding benzylidene acetal, (Bundle, D. R.; Josephson, S. *Can. J. Chem.* 1979, 57, 662-668 ; Mulard, L. A.; Costachel, C.; Sansonetti, P. J. *J. Carbohydr. Chem.* 2000, 19, 849-877) including its poor solubility.

Synthesis of the hexasaccharide 402 (FIG. 18): The key pentasaccharide donor 406 was obtained from the recently disclosed precursor 407 (see section F, compound 611). The latter was converted to the hemiacetal 408 following a two-step process including iridium complex promoted isomerisation of the allyl moiety into the proper-1-yl, (Oltvoort, J. J.; van Boeckel, C. A. A.; der Koning, J. H.; van Boom, J. *Synthesis* 1981, 305-308) and hydrolysis of the latter upon treatment with aqueous iodine (Nashed, M. A.; Anderson, L. *J. Chem. Soc. Chem. Commun.* 1982, 1274-1282). Subsequent reaction of 408 with trichloroacetonitrile in the presence of catalytic 1,8-diazabicyclo[5.4.0]undec-7-ene (DBU) cleanly gave the trichloroacetimidate donor 406 (85% from 407). Previous glycosidation attempts in the series indicated that when run at low temperature or room temperature, reactions using the D acceptor 405 occasionally resulted in a rather poor yield of the condensation product. This was tentatively explained by the still rather poor solubility of 405. When using 1,2-dichloroethane (1,2-DCE) as the solvent, the condensation could be performed at higher temperature, which proved rewarding. Indeed, optimized coupling conditions relied on the concomitant use of a catalytic amount of triflic acid in the presence of 4 Å molecular sieves as the promoter and 1,2-DCE as the solvent, while the condensation was performed at 80° C. The fully protected hexasaccharide 409 was isolated in a satisfactory 78% yield. That the hemiacetal 408, resulting from the hydrolysis of the excess donor could be recovered was of great advantage is one considers scaling up the process (not described). Acidic hydrolysis of the isopropylidene acetal smoothly converted 409 into the corresponding diol 410 (94%). Resistance of isolated benzoyl groups to Zemplén transesterification has been reported (Lipták, A.; Szurmai, Z.; Nanasi, P.; Neszmelyi, A. *Carbohydr. Res.* 1982, 99, 13-21; Szurmai, Z.; Kerékgyarto, J.; Harangi, J.; Lipták, A. *Carbohydr. Res.* 1987, 174, 313-325 ; Szurmai, Z.; Lipták, A.; Snatzke, G. *Carbohydr. Res.* 1990, 200, 201-208). It was also observed previously in the series, upon attempted removal of a benzoyl group located at position $2_C$ (F. Bélot, K. Wright, C. Costachel, A. Phalipon, L. A. Mulard, *J. Org. Chem.* 2004, 69, 1060-1074). Again, the $2_C$-O-benzoyl group in 410 was particularly resistant to Zemplén de-O-acylation, and successful transesterification required a week. In that case, heating was avoided in order to prevent any potential migration of the acyl group which would lead to the N-deacylated product. Conversion of the hexaol 411 into the target 402 (77%) was successfully accomplished upon concomitant hydrogenolysis of the remaining benzyl protecting group and reduction of the azido moiety into the corresponding amine. As observed earlier, the latter was best performed under acidic conditions.

Synthesis of the fully synthetic glycoconjugate 401 (FIG. 17): 4-(N-maleimido)-n-butanoyl was selected as the linker, and incorporated using commercially available 404 by covalent linkage to the side chain amino group of a Lysine residue added at the C-terminus of the PADRE sequence (PADRE-Lys). The latter was assembled using standard Fmoc chemistry for solid-phase peptide synthesis (Chan, W. C.; White, P. D. *Fmoc solid phase peptide synthesis;* Oxford University Press: New York, 2000). Standard side chain protecting groups were used, except for that of the C-terminal Lysine side chain which was protected by the 1-(4,4dimethyl-2,6-dioxocyclohex-1-ylidene)-3-methylbutyl (ivDde) group (Chhabra, S. R.; Hothi, B.; Evans, D. J.; White, P. D.; Bycroft, B. W.; Chan, W. C. *Tetrahedron Lett.* 1998, 39, 1603-1606) to allow specific introduction of the maleimide group. The thiol functionality was introduced onto the carbohydrate haptens as a masked thiol function (acetylthioester), which is easily generated in situ during the conjugation process Thus, reaction of 402 with S-acetylthioglycolic acid pentafluorophenyl ester (SAMA-oPfp) resulted in the site-selective elongation of the aminoethyl spacer via a thioacetyl acetamido linker. Derivatization could be monitored by RP-HPLC with detection at 215 nm. Under these conditions, the required thioacetyl-armed intermediate, 412 was isolated in 53% yield. Its structure was confirmed based on MS and NMR analysis. Conjugation of the carbohydrate haptens to the maleimido activated PADRE-Lys (403) was run in phosphate buffer at pH 6.0 in presence of hydroxylamine (H. F. Brugghe, H. A. M. Timmermans, L. M. A. van Unen, G. J. T. Hove, G. W. der Werken, J. T. Poolman, P. Hoogerhout, *Int. J. Peptide Protein Res.* 1994, 43, 166) and monitored by RP-HPLC. Lastly, RP-HPLC purification gave the target neoglycopeptide 401 as a single product, whose identity was assessed based on MS analysis, in yields of 58%.

E—Preparation of Chemically Defined Glycopeptides as Potential Synthetic Conjugate Vaccines Against *Shigella flexneri* Serotype 2a Disease The target neoglycopeptides were constructed by covalently linking a short peptide, serving as a T-helper epitope, to appropriate carbohydrate haptens, serving as B epitopes mimicking the *S. flexneri* 2a O—Ag. Our approach is based on rational bases involving a preliminary study of the interaction between the bacterial O—SP and homologous protective monoclonal antibodies, which helped to define the carbohydrate haptens.

Fragments ECD, B(E)CD and AB(E)CD were selected as haptens that will act as B-epitopes in the conjugates. Three fully synthetic linear neoglycopeptides 501, 502 and 503, corresponding to haptens ECD, B(E)CD, and AB(E)CD, respectively, were synthesized according to a strategy built up on the concept of chemoselective ligation which allows the selective one-point attachment of the free B and T epitopes in aqueous media. All conjugates involve the peptide PADRE (J. Alexander, J. Sidney, S. Southwood, J. Ruppert, C. Oseroff, A. Maewal, K. Snoke, H. M. Serra, R. T. Kubo, A. Sette, H. M. Grey, *Immunity* 1994, 1, 751-761; J. Alexander, A.-F. d. Guercio, A. Maewal, L. Qiao, J. Fikes, R. W. Chesnut, J. Paulson, D. R. Bundle, S. DeFrees, A. Sette, *J. Immunol.* 2000, 164, 1625-1633) as the universal T-cell epitope.

Retrosynthetic analysis of the saccharidic haptens (FIG. 19): Analysis of *S. flexneri* 2a O—SP suggests that, due to the 1,2-cis glycosidic linkage involved, construction of the EC disaccharide is probably the most demanding. Besides, prior work in this laboratory has shown that the C-D glycosidic linkage was an appropriate disconnection site when dealing with the blockwise synthesis of oligosaccharide fragments of *S. flexneri* O-2a SP. (F. Segat, L. A. Mulard, *Tetrahedron: Asymmetry* 2002, 13, 2211-2222) These observations supported the design of a synthetic strategy common to all three targets. Basically, it relies on (i) the condensation of an EC (504), (C. Costachel, P. J. Sansonetti, L. A. Mulard, *J. Carbohydr. Chem.* 2000, 19, 1131-1150) B(E)C (505) (F. Bélot, C. Costachel, K. Wright, A. Phalipon, L. A. Mulard, *Tetrahedron. Lett.* 2002, 43, 8215-8218) or AB(E)C (506) donor to a D acceptor (507), functionalized at the anomeric position with an azidoethyl spacer; (ii) elongation of the spacer with introduction of a masked thiol group to allow its coupling onto a PADRE peptide derivatized by a maleimido group on a C-terminal Lysine (508). The carbohydrate synthesis relies on the trichloroacetimidate methodology and the use of known building blocks whenever possible.

Synthesis of the aminoethyl ECD building block 518 (FIG. 20): The now easily accessible disaccharide donor 504, with a benzoyl participating group at position $2_C$, was used as the precursor to the EC moiety in the construction of 501. It was prepared, as described, (Costachel, C.; Sansonetti, P. J.; Mulard, L. A. *J. Carbohydr. Chem.* 2000, 19, 1131-1150) in 5 steps and 45% overall yield from 2,3,4,6-tetra-O-benzyl-β-D-glucopyranosyl trichloroacetimidate (509) (R. R. Schmidt, J. Michel, M. Roos, *Liebigs Ann. Chem.* 1984 1343-1357; R. R. Schmidt, J. Michel, *Tetrahedron Lett.* 1984, 25, 821-824) and allyl 2,3-O-isopropylidene-α-L-rhamnopyranoside (510) (R. Gigg, S. Payne, R. Conant, *J. Carbohydr. Chem.* 1983, 2, 207-223) through the key intermediate diol 511 (69% from 510). Introduction of the azidoethyl spacer on a glucosaminyl intermediate was performed according to a known procedure (Eklind, T.; Gustafsson, R.; Tidén, A.-K.; Norberg, T.; Åberg, P.-M. *J. Carbohydr. Chem.* 1996, 15, 1161-1174) by coupling of azidoethanol onto the oxazoline 512 to give the triacetate 513. (T. Eklind, R. Gustafsson, A.-K. Tidén, T. Norberg, P.-M. Åberg, *J. Carbohydr. Chem.* 1996, 15, 1161-1174) We have shown on several occasions in the *S. flexneri* series, that regioselective protection of the 4- and 6-OH groups of precursors to residue D with an isopropylidene acetal was appropriate, especially when such precursors are involved in a blockwise synthesis based on the disconnection at the C-D linkage. Thus, Zemplén deacetylation of 513 gave the triol 514 which was converted to the key acceptor 507 (81% from 513) upon reaction with 2,2-dimethoxypropane under acid catalysis. When the latter was glycosylated with the donor 504 in the presence of $BF_3.OEt_2$ in $CH_2Cl_2$, the fully protected trisaccharide 515 was isolated in 58% yield together with the diol 516 (30%), resulting from partial loss of the isopropylidene acetal. When 504 and 507 were glycosylated in the presence of a catalytic amount of TMSOTf, no side-reaction was observed, and the condensation product 515 was obtained in 86% yield. Quantitative conversion of 515 into 516 was more conveniently achieved by acidic hydrolysis of the former with 95% aq TFA. Debenzoylation of 516 gave the tetraol 517 (94%) which was subsequently transformed into the aminoethyl-trisaccharide 518 (69%) by hydrogenation in the presence of palladium-on-charcoal (Pd/C) and 1M aq HCl to convert the formed amine to its hydrochloride salt. Indeed, others have pointed out that hydrogenolysis using Pd/C in the presence of a free amine was sluggish and low-yielding (Stahl, W.; Sprengard, U.; Kretschmar, G.; Kunz, H. *Angew. Chem. Int. Ed.* 1994, 33, 2096-2098 ; Spikjer, N. M.; Keuning, C. A.; Hooglugt, M. *Tetrahedron* 1996, 52, 5945-5960 ; Li, Q.; Li, H.; Lou, Q.-H.; Su, B.; Cai, M.-S.; Li, Z.-J. *Carbohydr. Res.* 2002, 337, 1929-1934). In order to prevent any side-reaction at a latter stage of the synthesis, isolation of pure 518 was subsequently submitted to reversed-phase HPLC (RP-HPLC).

Synthesis of the aminoethyl B(E)CD building block 525 (FIG. 21): The known rhamnopyranosyl tricholoracetimidate 520, acetylated at its 2-, 3-, and 4-OH groups thus acting as a chain terminator, was chosen as the precursor to residue B. Benzoylation of diol 511 to give 519 was performed by regioselective opening of the cyclic orthoester intermediate as described (Segat, F.; Mulard, L. A. *Tetrahedron: Asymmetry* 2002, 13, 2211-2222), Glycosylation of the latter by donor 520, with activation by a catalytic amount of TMSOTf proceeded smoothly in $Et_2O$ to yield the fully protected trisaccharide 521 (89%), which was de-O-allylated into the hemiacetal 522 (80%) following a two step process involving (i) iridium(I)-catalysed isomerisation of the allyl glycoside to the prop-1-enyl glycoside (Oltvoort, J. J.; van Boeckel, C. A. A.; der Koning, J. H.; van Boom, J. Synthesis 1981, 305-308) and (ii) subsequent hydrolysis (Gigg, R.; Payne, S.; Conant, R. *J. Carbohydr. Chem.* 1983, 2, 207-223 ; Gigg, R,; Warren, C. D. *J. Chem. Soc. C* 1968, 1903-1911). The selected trichloroacetimidate leaving group was introduced by treatment of 522 with trichloroacetonitrile in the presence of a catalytic amount of DBU, which resulted in the formation of 505 (99%). Condensation of the latter with acceptor 507 was performed in $CH_2Cl_2$ in the presence of a catalytic amount of trifluoromethanesulfonic acid (TfOH) to give the required tetrasaccharide 523 (76%). Acidic hydrolysis of the latter using 95% aq TFA gave the intermediate diol 524 in 95% yield. Deacylation of the resulting diol under Zemplén conditions followed by debenzylation and concomitant conversion of the azide into the corresponding amine to give the key aminoethyl-armed tetrasaccharide 525 (77%) was performed by treatment of 524 with hydrogen in the presence of Pd/C under acidic conditions. Again, compound 525 was purified by RP-HLPC before elongation of the spacer or conjugation.

Synthesis of the aminoethyl AB(E)CD building block 537 (FIG. 22): The synthesis of 537 is based on the condensation of acceptor 507 and donor 506, which resulted from the selective deallylation and anomeric activation of the key intermediate tetrasaccharide 533. The latter was obtained according to two routes following either a block strategy (route 1) based on the condensation of an AB disaccharide donor (530) and the EC disaccharide acceptor 519, or a linear strategy (route 2) involving the stepwise elongation of 519. The construction of the donor 530 was based on the use of the known allyl rhamnopyranoside 526 (Westerduin, P.; der Haan, P. E.; Dees, M. J.; van Boom, J. H. *Carbohydr. Res.* 1988, 180, 195-205), having permanent protecting groups at position 3 and 4, as the precursor to residue B, and the trichloroacetimidate chain terminator 527 (Ziegler, T.;

Bien, F.; Jurish, C. *Tetrahedron: Asymmetry* 1998, 9, 765-780), acting as a precursor to residue A. Condensation of the two entities in the presence of a catalytic amount of TMSOTf resulted in the fully protected 528 (96%), which was selectively de-O-allylated into 529 (84%) according to the protocol described above for the preparation of 522. Subsequent treatment of 529 with trichloroacetonitrile and a catalytic amount of DBU gave the required 530 (96%). Glycosylation of 519 with the latter under TMSOTf promotion afforded the fully protected tetrasaccharide 533 in 55% yield. No β-anomer was detected. Route 1 was considered initially in order to prevent extensive consumption of the EC disaccharide 511. Given the relatively low yield of coupling of 519 and 530, route 2 was considered as well. Of all precursors to 534, only that to residue B, namely the donor and potential acceptor 531, differed from those used in route 1. Conventional glycosylation of disaccharide 519 and 531 and subsequent selective deacetylation using methanolic HBF$_4$, gave the acceptor 532 in 70% yield from 519. The trisaccharide 532 was glycosylated with trichloroacetimidate 527 in an analogous fashion to glycosylation of 519 with 530, yielding 533 (92%). Anomeric de-O-allylation of this key intermediate, as described above for the preparation of 522, gave the corresponding hemiacetal 534 (90%) which was converted into the required trichloroacetimidate 506 (88%) upon treatment with trichloroacetonitrile and DBU. Condensation of donor 506 with the glucosaminyl acceptor 507 was performed under promotion by TfOH or TMSOTf, which resulted in the fully protected pentasaccharide 535 in 62% and 80% yield, respectively. Following the process described for the preparation of 525, compound 535 was submitted to acetolysis (97%) and subsequent Zemplén deacylation to give the partially deblocked 536 (87%), which was next converted to the aminoethyl-spacer pentasaccharide 537 upon treatment with hydrogen in the presence of Pd/C. Final RP-HPLC purification resulted in the isolation of 537 in 53% yield.

Synthesis of the target neoglycopeptides 501-503 (FIG. 23): In all cases, chemoselective ligation of the B and T epitopes was achieved through coupling of the carbohydrate haptens pre-functionalized with a thiol function and a maleimido group properly introduced at the C terminus of the T helper peptide. Such a strategy was chosen in order to exploit the high reactivity and specificity of thiol groups towards the maleimide functionality (Martian, D. H. *J. Chem. Soc. C* 1949, 1515), which allows specific and high-yielding modification of the former in the presence of other nucleophiles (Hermanson, G. T. *Bioconjugate techniques*; Academic Press: New York, 1996). It was used previously under various forms in the coupling of carbohydrate haptens to either proteins (Ragupathi, G.; Koganty, R. R.; Qiu, D.; Llyod, K. O.; Livingston, P. O. *Glycoconjugate J.* 1998, 15, 217-221 ; Shin, I.; Jung, H.; Lee, M. *Tetrahedron Lett.* 2001, 42, 1325-1328) or peptides (Kandil, A.; Chan, N.; Klein, M.; Chong, P. *Glycoconjugate* 1997, 14, 13-17). To our knowledge, in all the reported cases the rnaleimide functionality was introduced onto the carbohydrate hapten. On the contrary, our strategy relies on the introduction of this activating group on the T helper peptide. The immunogenicity of various maleimide-derived coupling reagents was evaluated in a model system. Based on the reported data, (Peeters, J. M.; Hazendonk, T. C.; Beuvery, E. C.; Tesser, G. I. *J. Immunol. Methods* 1989, 120, 133-143) 4-(N-maleimido)-n-butanoyl was selected as the linker, and incorporated by covalent linkage to the side chain amino group of a Lysine residue added at the C-terminus of the PADRE sequence (PADRE-Lys). It is worth mentioning that the strategy described herein somewhat differs from that described by others when demonstrating the usefulness of PADRE in the construction of immunogenic neoglycopeptides (Alexander, J.; Guercio, A.-F. d.; Maewal, A.; Qiao, L.; Fikes, J.; Chesnut, R. W.; Paulson, J.; Bundle, D. R.; DeFrees, S.; Sette, A. *J Immunol.* 2000, 164, 1625-1633).

The Lysine-modified PADRE was assembled using standard Fmoc chemistry for solid-phase peptide synthesis (Chan, W. C.; White, P. D. *Fmoc solid phase peptide synthesis*; Oxford University Press: New York, 2000). Standard side chain protecting groups were used, except for that of the C-terminal Lysine side chain which was protected by the 1-(4,4-dimethyl-2,6-dioxocyclohex-1-ylidene)-3-methylbutyl (ivDde) group (Chhabra, S. R.; Hothi, B.; Evans, D. J.; White, P. D.; Bycroft, B. W.; Chan, W. C. *Tetrahedron Lett.* 1998, 39, 1603-1606). Indeed, this orthogonal protecting group strategy allows specific introduction of the malelmide group on the C-terminal Lysine, upon selective cleavage of the ivDde by hydrazine. The thiol functionality was introduced onto the carbohydrate haptens as a masked thiol function (acetylthioester), which is easily generated in situ during the conjugation process. Thus, reaction of 518, 525, and 537 with S-acetylthioglycolic acid pentafluorophenyl ester (SAMA-θPfp) resulted in the site-selective elongation of their aminoethyl spacer via a thioacetyl acetamido linker. Derivatization could be monitored by RP-HPLC with detection at 215 nm. Under these conditions, the required thioacetyl-armed intermediates, 538, 539 and 540 were isolated in 53%, 74%, and 75% yield, respectively. Their structure was confirmed based on MS and NMR analysis. Conjugation of the carbohydrate haptens to the maleimido activated PADRE-Lys (508) was run in phosphate buffer at pH 6.0 in presence of hydroxylamine H. F. Brugghé, H. A. M. Timmermans, L. M. A. van Unen, G. J. T. Hove, G. W. der Werken, J. T. Poolman, P. Hoogerhout, *Int. J. Peptide Protein Res.* 1994, 43, 166-172) and monitored by RP-HPLC. Lastly, RP-HPLC purification gave the target neoglycopeptides 501, 502, and 503 as single products, which identity was assessed based on MS analysis, in yields of 58%, 48% and 46%, respectively.

F—Synthesis of Two Linear PADRE-conjugates Bearing a Deca- or a Pentadecasaccharide B Epitope as Potential Synthetic Vaccine Against *Shigella flexneri* Serotype 2a Infection We report herein on the synthesis of the PADRE conjugates of a deca- (601) and a pentadecasaccharide (602), corresponding to a dimer [AB(E)CD]$_2$ and a trimer [AB(E)CD]$_3$ of the branched pentasaccharide 1, respectively (FIG. 24). The synthesis is based on a modular approach involving three partners. Basically, it relies on (i) the use of appropriate haptens functionalized at the anomeric position with an arninoethyl spacer, 603 and 604, respectively; (ii) the incorporation of a thioacetyl acetamido linker as a masked thiol functionality, and (iii) the use of a PADRE peptide derivatized by a maleimido group on a C-terminal lysine (605).

Considering the targets 603 and 604, a disconnection at the D-A linkage would appear most appropriate. However, others have shown that such a disconnection strategy was not suitable even when involving di- or trisaccharide building blocks (B. M. Pinto, K. B. Reimer, D. G. Morissette, D. R. Bundle, *J. Org. Chem.* 1989, 54, 2650 ; B. M. Pinto, K. B. Reimer, D. G. Morissette, D. R. Bundle, *Carbohydr. Res.* 1990, 196, 156), thus this route was avoided. More recently, disconnections at the A-B, B-C and C-D linkages were evaluated in this laboratory when synthesizing successfully the methyl glycoside of the frame-shifted decasaccharide D'A'B'(E')C'DAB(E)C (F. Bélot, K. Wright, C. Costachel, A.

Phalipon, L. A. Mulard, *J. Org. Chem.* 2004, 69, 1060-1074). It was demonstrated on that occasion that disconnection at the C-D linkage was indeed appropriate for the construction of large fragments of the *S. flexneri* 2a O—SP. Based on our experience in the field, we designed a blockwise strategy to targets 603 and 604, implicating an AB(E)C tetrasaccharide donor (606), a DAB(E)C potential acceptor acting as a donor (607), and the recently disclosed acceptor 608 (K. Wright, C. Guerreiro, I. Laurent, F. Baleux, L. A. Mulard, *Org. Biomol. Chem.* 2004, 2, 1518-1527), bearing a masked aminoethyl spacer, as a precursor to the reducing end D residue (FIG. 24). Although permanent blocking of OH-$4_D$ and OH-$6_D$ with an isopropylidene acetal may appear somewhat unusual, this choice was a key feature of the strategy. It was based on former observations in the methyl glycoside series, demonstrating that its use could overcome some of the known drawbacks of the corresponding benzylidene acetal (F. Segat, L. A. Mulard, *Tetrahedron: Asymmetry* 2002, 13, 2211-2222) J. Banoub, D. R. Bundle, *Can. J. Chem.* 1979, 57, 2091), including its poor solubility. In order to reduce the number of synthetic steps, it was found appropriate to access the AB(E)C donor and the DAB(E)C building block from a common key AB(E)C tetrasaccharide intermediate 609. Most of all, the design of the pentasaccharide building block 607 was a key element to success. Indeed, a leading concept of the overall strategy was to limit the number of transformations at later stages in the syntheses. Concerning the choice of 607, the reader's attention is thus drawn to (i) the permanent blocking of position $4_D$ and $6_D$ as an isopropylidene acetal, (ii) the introduction of a participating benzoyl group, resistant to Zemplén deacylation, at position $2_A$, (iii) the temporary protection of position $3_D$ as an orthogonal acetate, (iv) the early introduction of the required $2_D$ acetamido functionality, and (v) the activation of the anomeric position as a trichloroacetimidate. Indeed, it should be outlined that the syntheses disclosed herein are based on the use of the trichloroacetimidate (TCA) chemistry, (R. R. Schmidt, W. Kinzy, *Adv. Carbohydr. Chem. Biochem.* 1994, 50, 21-123) and that known building blocks were used whenever possible.

Synthesis of the tetrasaccharide building block 606 (FIG. 25): Preparation of 606 was conveniently achieved from the previously described tetrasaccharide 609, (F, Bélot, K. Wright, C. Costachel, A. Phalipon, L. A. Mulard, *J. Org. Chem.* 2004, 69, 1060-1074) in a non optimized yield of 56%, according to a conventional protocol, namely selective removal of the anomeric allyl group and subsequent activation upon reaction of the resulting hemiacetal with trichloroacetonitrile in the presence of catalytic 1,8-diazabicyclo [5.4.0]undec-7-ene (DBU).

Synthesis of the pentasaccharide building block 607 (FIG. 25): Starting from 609, we recently described the synthesis of the DAB(E)C building block 610 bearing a trichloroacetamide function at position $2_D$. This crucial intermediate could be obtained in high yield when running the condensation on a 5 g scale. It was used successfully as the donor in the synthesis of the D'A'B'(E')C'DAB(E)C decasaccharide, once converted to the corresponding trichloroacetimidate.(F. Bélot, K. Wright, C. Costachel, A. Phalipon, L. A. Mulard, *J. Org. Chem.* 2004, 69, 1060-1074) However, for the present purpose we reasoned that conversion of the trichloroacetamide moiety into the required acetamide at an early stage in the synthesis was preferable. Thus, reductive free-radical dechlorination of 610 using Bu$_3$SnH in the presence of catalytic AIBN allowed the conversion of the N-trichloroacetyl moiety into N-acetyl, to give the known 611 (68%), previously obtained according to an alternative and somewhat lower yielding strategy (F. Bélot, K. Wright, C. Costachel, A. Phalipon, L. A. Mulard, *J. Org. Chem,* 2004, 69, 1060-1074). Controlled de-O-acetylation of 611 under Zemplén conditions gave the triol 612, which was next converted to the corresponding alcohol 613 upon reaction with 2,2-dimethoxypropane (81% from 611). Conventional acetylation at position $3_D$ then gave the fully protected intermediate 614 (94%), the good overall yield of this three-step conversion (611→614, 76%) outlining its interest. The latter was transformed into the hemiacetal 615 (82%) following a two-step process including Iridium complex promoted isomerisation of the allyl moiety into the corresponding propen-1-yl (J. J. Oltvoort, C. A. A. van Boeckel, J. H. der Koning, J. van Boom, *Synthesis* 1981, 305), and hydrolysis of the latter upon treatment with mercuric chloride, since it was originally demonstrated that labile isopropylidene groups were stable to such neutral conditions (R. Gigg, C. D. Warren, *J. Chem. Soc. C* 1968, 1903). Subsequent reaction of 615 with trichloroacetonitrile in the presence of catalytic 1,8-diazabicyclo[5.4.0]undec-7-ene (DBU) cleanly gave the key building block 607 (85% from 614).

Synthesis of the aminoethyl decasaccharide 603 (FIG. 26); Previous glycosidation attempts in the series indicated that when run at low temperature or room temperature, reactions using the D acceptor 608 occasionally resulted in a somewhat poor yield of the condensation product. This was tentatively explained by the still rather low solubility of 608. When using 1,2-dichloroethane (1,2-DCE) as the solvent, the condensation could be performed at higher temperature, which proved rewarding. Indeed, optimized coupling conditions of 607 and 608, used in slight excess, relied on the concomitant use of a catalytic amount of triflic acid in the presence of 4 Å molecular sieves as the promoter and 1,2-DCE as the solvent, while the condensation was performed at 75° C., according to a known protocole (F. Bélot, D. Rabuka, M. Fukuda, O. Hindsgaul, *Tetrahadron Lett.* 2002, 43, 7743) which had recently been adapted to the use of acceptor 608 in the *S. flexneri* series. The fully protected hexasaccharide 616 was isolated in a satisfactory 76% yield. The resistance of the two isopropylidene acetals to the harsh acidic conditions of the glycosidation reaction is noteworthy. That the hemiacetal 615, resulting from the hydrolysis of the excess donor could be recovered was of great advantage if one considers scaling up the process (not described). Resistance of isolated benzoyl groups to Zemplén transesterification has been reported (A. Liptak, Z. Szurmai, P. Nanasi, A. Neszmelyi, *Carbohydr. Res.* 1982, 99 ; Z. Szurmai, Kerékgyarto, J. Harangi, A. Liptak, *Carbohydr. Res.* 1987, 174, 313; Z. Szurmai, A. Liptak, G. Snatzke, *Carbohydr. Res.* 1990, 200, 201). It was also observed previously in the series, upon attempted removal of a benzoyl group located at position $2_C$. Thus, as anticipated selective deacetylation at the 3-OH of the non reducing residue, gave the D'AB(E)CD acceptor 617 in a yield of 97%, which confirmed the orthogonality of the various protecting groups in use at this stage. Condensation of the latter and 606 was performed in 1,2-DCE using triflic acid as the promoter. One may note that although the condensation involves the construction of the C-D linkage, thus somewhat resembling the preparation of the hexasaccharide 616, heating was not required and the glycosylation went smoothly at 10° C. to give the fully protected decasaccharide 618 (82%). Acidic hydrolysis of the acetals gave the tetraol 619 (75%). Transesterification of the acyl groups was best performed by overnight heating of 619 in methanolic sodium methoxide. Final hydrogenolysis of the benzyl groups and concomitant conversion of the azido group into the corresponding amine gave the target 603 (71% from 619). As observed earlier, (Q, Li, H. Li, Q.-H. Lou, B. Su, M.-S. Cai, Li, *Carbohydr. Res.* 2002, 337, 1929) the latter transformation was best performed under acidic conditions.

Synthesis of the aminoethyl pentadecasaccharide 604 (FIG. 27): The rather convenient access to the building block 607 allowed the targeting of larger sequences. Thus, having the hexasaccharide acceptor 617 in hands, the two-step glycosylation/deacetylation process involving 607 was repeated, Analogously to the condensation step leading to the fully protected decasaccharide, condensation of 617 and the pentasaccharide donor 607 in the presence of triflic acid was run at a temperature below 5° C. Under such conditions, the fully protected undecasaccharide 621 was isolated in an excellent yield of 90%, outlining once more the compatibility of rather labile isopropylidene groups with the glycosylation conditions in use. Zemplén transesterification at the non reducing $3_D$-OH of the latter, resulting in the required acceptor 622 (91%), proved as efficient. Condensation of this key intermediate with the tetrasaccharide trichloroacetimidate donor 606 was performed according to the same protocols, using triflic acid as the promoter. The fully protected pentadecasaccharide 623 was isolated in a satisfactory yield of 82%. Conversion of 623 to the target 604 was performed by running the stepwise sequence described for the preparation of 603. Acidic hydrolysis of the isopropylidene groups afforded the hexaol 624 (83%). Again, running the transesterification step at high temperature allowed to overcome the resistance of the isolated 2-benzoyl groups to methanolic transesterification. Lastly, conventional hydrogenolysis of the benzyl groups and concomitant reduction of the azide moiety allowed the smooth conversion of de-O-acylated intermediate into the pentadecasaccharide hapten 604 (65% from 624). Interestingly, although the number of synthetic steps involved may be somewhat challenging, those are in average high yielding, making large amounts of 604 reachable.

Synthesis of the target conjugates 601 and 602 (FIG. 24): Chemoselective ligation of the carbohydrate B and peptide T epitopes was achieved through coupling of the carbohydrate haptens pre-functionalized with a thiol function and a maleimido group properly introduced at the C terminus of the T helper peptide, which allows specific and high-yielding modification of the former in the presence of other nucleophiles (G. T. Hermanson, *Bioconjugate techniques*, Academic Press, New York, 1996). Based on reported data on the immunogenicity of various maleimide-derived coupling agents (J. M. Peeters, T. G. Hazendonk, E. C. Beuvery, G. I. Tesser, *J. Immunol. Methods* 1989, 120, 133), 4-(N-maleimido)-n-butanoyl was selected as the linker. It was covalently linked to the side chain amino group of a lysine residue added to the C-terminus of the PADRE sequence (PADRE-Lys) according to an in-house process (K. Wright, C. Guerreiro, I. Laurent, F. Baleux, L. A. Mulard, *Org. Biomol. Chem.* 2004, 2, 1518), differing from that described previously by others (J. Alexander, A.-F. d. Guercio, A. Maewal, L. Qiao, J. Fikes, R. W. Chesnut, J. Paulson, D. R. Bundle, S. DeFrees, A. Sette, *J. Immunol.* 2000, 164, 1625). Reaction of 603 and 604 with S-acetylthioglycolic acid pentafluorophenyl ester (SAMA-Pfp) resulted in the site-selective elongation of their aminoethyl spacer with a thioacetamido linker, yielding 620 (FIGS. 26) and 625 (FIG. 27) in 61% and 63% yield, respectively. Derivatization could be monitored by RP-HPLC with detection at 215 nm and structure confirmation was based on MS and NMR analysis. Conjugation of the carbohydrate haptens to the maleimido activated PADRE-Lys (605) was run in phosphate buffer at pH 6.0 in the presence of hydroxylamine (H. F. Brugghe, H. A. M. Timmermans, L. M. A. van Unen, G. J. T. Hove, G. W. der Werken, J. T. Poolman, P. Hoogerhout, *Int. J. Peptide Protein Res.* 1994, 43, 166) and monitored by RP-HPLC. Lastly, RP-HPLC purification gave the target neoglycopeptides 601 and 602 as single products, whose identity was assessed by MS analysis, in yields of 44% and 67%, respectively.

G. Syntheis of Biotinylated Analogues of Oligosaccharides Representative of Fragments of the O—SP of *S. flexneri* 2a The tri- (ECD), tetra- (B(E)CD), penta- (AB(E)CD), hexa- (D'AB(E)CD), deca- ({AB(E)CD}$_2$) and pentadecasaccharide ({AB(E)CD}$_3$) were synthesized as their biotine conjugates 708-713, respectively (FIG. 28). Analogously to that used for the preparation of the corresponding glycopeptides, the synthetic strategy relied on a chemoselective ligation step between a commercially available maleimide-activated biotine derivative 707 and the saccharides functionalized as thiols. The known thioacetates 701-703, disclosed in our reports on the synthesis of the PADRE-conjugates (K. Wright, C. Guerreiro, I. Laurent, F. Baleux, L. A. Mulard, *Org. Biomol. Chem.* 2004, 2, 1518), 704 (see part D, compound 413), and 705-706 (see part F, compounds 620 and 625, respectively) were used as precursors to the required thiols. Accordingly, conjugation of the carbohydrate haptens to the maleimido activated biotine (707) was run in phosphate buffer at pH 6.0 in presence of hydroxylamine (H. F. Brugghe, H. A. M. Timmermans, L. M. A. van Unen, G. J. T. Hove, C. W. der Werken, J. T. Poolman, P. Hoogerhout, *Int. J. Peptide Protein Res.* 1994, 43, 166) and monitored by RP-HPLC. Lastly, RP-HPLC purification gave the target conjugates as single products, whose identity was assessed based on MS analysis.

H. Synthesis of a *Shigella flexneri* 2a Pentasaccharide-PADRE Conjugate Using an Alternate Conjugation Chemistry We report herein on the synthesis of the (2-bromoethyl) carbonylaminoethyl glycoside of the pentasaccharide AB(E) CD (802) and on that of the corresponding fully synthetic conjugate (801) using the PADRE as a universal T-helper peptide (see section E for the background). The target 801 was obtained by chemoselective ligation of 802 to the side chain thiol group of a cysteine residue added at the C-terminus of the PADRE sequence (PADRE-Cys, 803).

(3-Bromopropionyl) was selected as the linker, and incorporated using the succinimidyl intermediate 804, itself prepared in one step from commercially available 3-bromopropionic acid (86%). Thus, reaction of 805 with 804 resulted in the site-selective elongation of the aminoethyl spacer via a 3-bromopropionyl linker. Derivatization could be monitored by RP-HPLC with detection at 215 nm. Under these conditions, the intermediate 802 was isolated in 69% yield. Its structure was confirmed based on MS and NMR analysis (not described). The PADRE-Cys sequence was assembled using standard Fmoc chemistry for solid-phase peptide synthesis (Chan, W. C.; White, P. D. *Fmoc solid phase peptide synthesis*; Oxford University Press: New York, 2000). Standard side chain protecting groups were used. Conjugation of the carbohydrate hapten 802 to the PADRE-Cys (803) was run in anhydrous DMF and monitored by RP-HPLC. Lastly, preparative RP-HPLC purification gave the target neoglycopeptide 801 (57%) as a single product, whose identity was assessed based on MS analysis.

EXPERIMENTAL

Legend of Figures:

FIG. 1: Synthesis of the linear ECDAB-OMe pentasaccharide 101

FIG. 2: Retrosynthetic analysis of pentasaccharide 102

FIG. 3: Synthesis of the trisaccharide 125 (intermediate for the synthesis of the pentasaccharide 102

FIG. 4: Synthesis of the AB(E)CD pentasaccharide 102

FIG. 5: Representation of the orthoester 135

FIG. 6: Synthesis of the B(E)CD tetrasaccharide 103

FIG. 7: Pentasaccharides 201 (DAB(E)C), 202, 203

FIG. 8: Synthesis of compound 208

FIG. 9: Synthesis of compound 212

FIG. 10: Synthesis of the pentasaccharide 203

FIG. 11: Retrosynthetic analysis of the target decasaccharide D'A'B'(E')C'DAB(E)C 301

FIG. 12: Synthesis of the pentasaccharides 302, 303, 304

FIG. 13: Synthesis of the pentasaccharide 313

FIG. 14: Synthesis of the tetrasaccharides 338, 339, 340, 341

FIG. 15: Synthesis of the pentasaccharide 346

FIG. 16: Synthesis of the decasaccharide D'A'B'(E')C'D-AB(E)C 301

FIG. 17: Retrosynthetic analysis of the target conjugate 401

FIG. 18: Synthesis of the hexasaccharide 402

FIG. 19: Retrosynthetic analysis of the target conjugates 501, 502, 503

FIG. 20: Synthesis of the aminoethyl ECD building block 518

FIG. 21: Synthesis of the aminoethyl tetrasaccharide 525

FIG. 22: Synthesis of the aminoethyl pentasaccharide 537

FIG. 23: Synthesis of the conjugates 501, 502, 503

FIG. 24: Retrosynthetic analysis of the target conjugates 601, 602

FIG. 25: Synthesis of the pentasaccharides 606 and 607

FIG. 26: Synthesis of the decasaccharide 620

FIG. 27: Synthesis of the pentadecasaccharide 625

FIG. 28A: Synthesis of the conjugates 701 to 713

FIG. 28B: Synthesis of the conjugate 801.

FIG. 29 illustrates the structure of the repeating units of the O—SP of S. flexneri serotype 2a.

FIGS. 30A and 30B illustrate the protection conferred by immune serum specific for S. flexneri 2a LPS intranasally administered prior to i.n. challenge.

FIG. 30A. Serum IgG subclasses elicited in mice upon i.p. immunization with killed S. flexneri 2a bacteria. represents the mean value of the antibody titer (n=10 mice).

FIG. 30B. Protection assessed by reduction of lung-bacterial load in mice receiving anti-S. flexneri 2a LPS immune serum raised upon i.p. immunization, 1 h prior to i.n. challenge with a sublethal dose of S. flexneri 2a bacteria, a, b, c, correspond to immune sera exhibiting an anti-S. flexneri 2a LPS IgG antibody titer of $\frac{1}{4,000}$, $\frac{1}{16,000}$ and $\frac{1}{64,000}$, respectively. Standard deviation is indicated (n=10 mice per group).

Figure 31A:
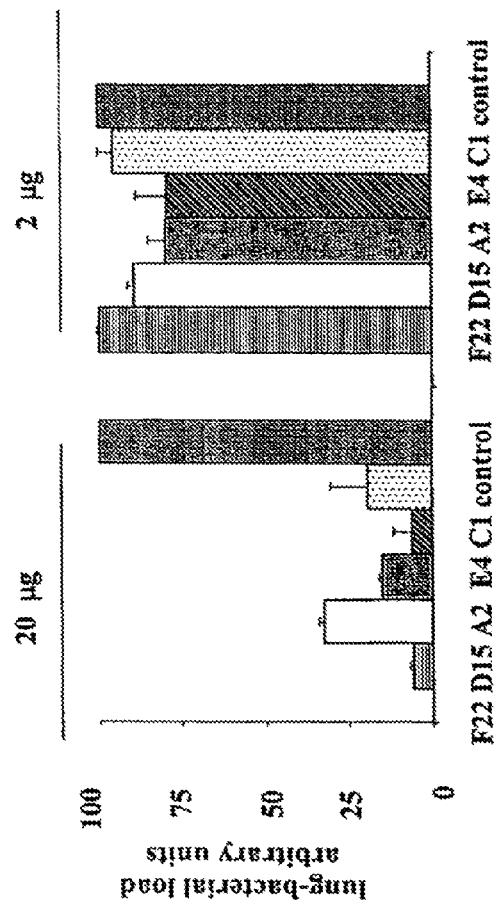
Figure 31B:
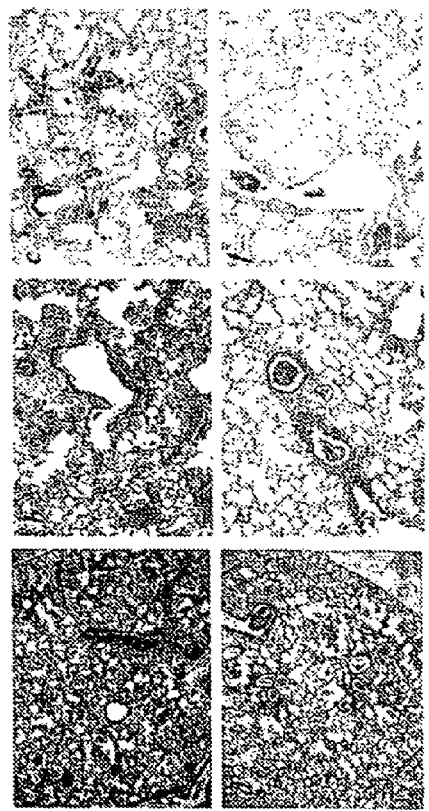

FIG. 31A and FIG. 31B illustrate the protection conferred by different subclasses of mIgG specific for S. flexneri 2a serotype determinants. FIG. 31A: mice receiving intranasally 20 μg and 2 μg of purified mIgG (F22, D15, A2, E4 or C1), respectively, 1 h prior to i.n. challenge with a sublethal dose of S. flexneri 2a bacteria. Lung-bacterial load was expressed using arbitrary units with 100 corresponding to the bacterial count in lungs of control mice. Standard deviations are represented (n=10 mice per group; 3 independent experiments). FIG. 31B: Histopathological study of mouse lungs. Upper row: control mice. Lower row: mice receiving mIgG. HE staining: a and d magnification×40; b and e magnification×100. Immunostaining using an anti-LPS antibody specific for S. flexneri serotype 2a: c and f magnification×100.

Figure 32A:
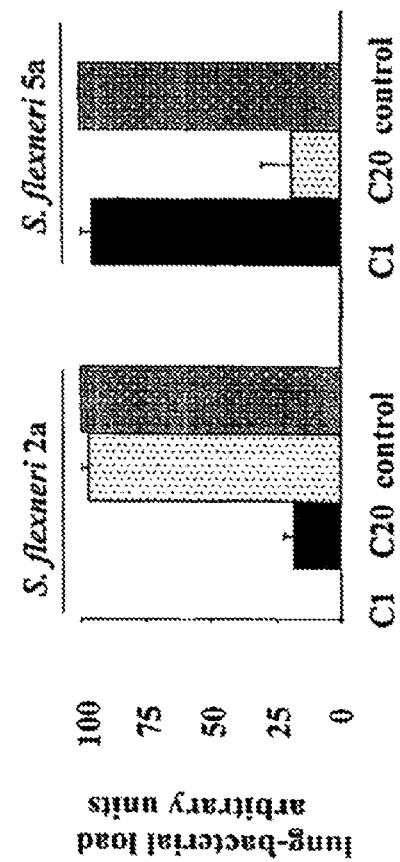
Figure 32B:
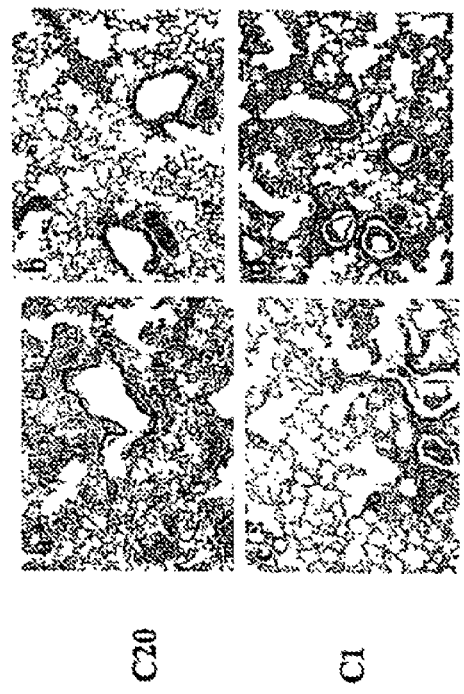

FIG. 32A and FIG. 32B illustrate the serotype-specific protection conferred by the anti-O—SP mIgGs. FIG. 32A: Mice were receiving i.n. 20 μg of each of the purified mIgG, C20 and C1-7, 1 h prior to i.n. challenge with a sublethal dose of S. flexneri serotype 2a (A) or serotype 5a (B) bacteria. Lung-bacterial load was expressed using arbitrary units with 100 corresponding to the bacterial count in lungs of control mice. Standard deviations are represented (n=10 mice per group; 3 independent experiments). FIG. 32B: Histopathological study of mouse lungs, a and b: mice receiving mIgGC20 specific for S. flexneri serotype 5a and challenged with S. flexneri serotype 2a and 5a, respectively, c and d: mice receiving mIgGC1-7 specific for S. flexneri 2a prior to challenge with S. flexneri serotype 2a and 5a, respectively. HE staining, magnification×100.

Figure 33:
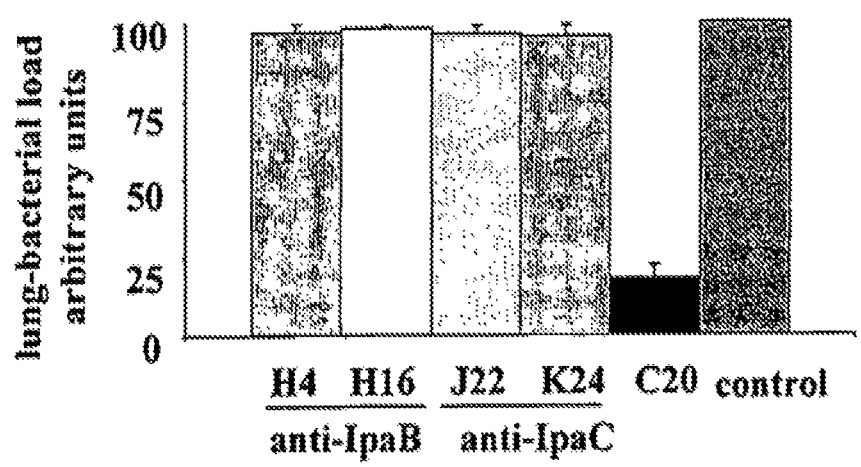

FIG. 33 illustrates the protection conferred by mIgG specific for S. flexneri IpaB or IpaC invasins. Mice were receiving i.n. 20 μg of each of the purified mIgG, H4, H16, J22, K24, and C20, 1 h prior to i.n. challenge with a sublethal dose of S. flexneri serotype 5a. Lung-bacterial load was expressed using arbitrary units with 100 corresponding to the bacterial count in lungs of control mice. Standard deviations are represented (n=10 mice per group).

Figure 34:
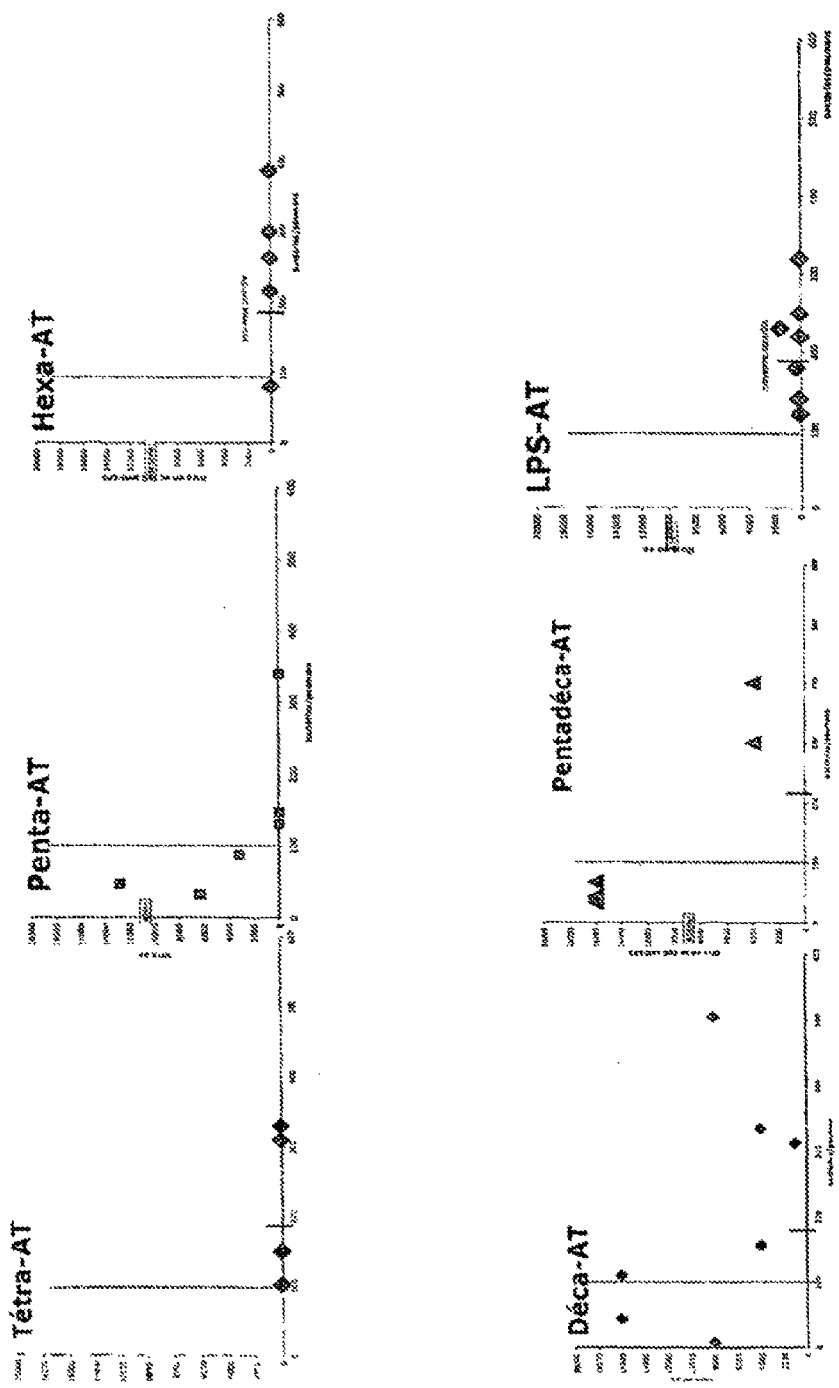

FIG. 34 illustrates the protection conferred by oligosaccharides-tetanus toxoid conjugates in the mouse model of pulmonary infection. For each mice tested, the bacteria load 24 hours after the challenge is indicated as a function of the anti-LPS 2a antibody titer before the challenge.

I—Synthesis of Oligosaccharides, Polysaccharides and Conjugates According to the Invention General Methods. Melting points were determined in capillary tubes with an electrothermal apparatus and are uncorrected. Optical rotations were measured for CHCl$_3$ solutions at 25° C., expect where indicated otherwise. TLC on precoated slides of Silica Gel 60 F$_{254}$ (Merck) was performed with solvent mixtures of appropriately adjusted polarity. Detection was effected when applicable, with UV light, and/or by charring with orcinol (35 mM) in 4N aq H$_2$SO$_4$. Preparative chromatography was performed by elution from columns of Silica Gel 60 (particle size 0.040-0.063 mm). RP-HPLC (215 nm or 230 nm) used a Kromasil 5 μm C18 100 Å 4.6×250 mm analytical column (1mL.min$^{-1}$). NMR spectra were recorded at 20° C. on a Brucker Avance 400 spectrometer (400 MHz for $^1$H, 100 MHz for $^{13}$C) at 20° C. Unless indicated otherwise, NMR spectra were run for solutions in CDCl$_3$ using TMS (0.00 ppm for both $^1$H and $^{13}$C) as an external reference. Dioxane (67.4 ppm for $^{13}$C) and trimethylsilyl-3-propionic acid sodium salt (0.00 ppm for $^1$H) were used as external references for solutions in D$_2$O. Proton-signal assignments were made by first-order analysis of the spectra, as well as analysis of 2D $^1$H-$^1$H correlation maps (COSY) and selective TOCSY experiments. In the NMR spectra, of the two magnetically non-equivalent geminal protons at C-6, the one resonating at lower field is denoted H-6a and the one at higher field is denoted H-6b. The $^{13}$C NMR assignments were supported by 2D $^{13}$C-$^1$H correlations maps (HETCOR). Interchangeable assignments in the $^{13}$C NMR spectra are marked with an asterisk in listing of signal assignments. Sugar residues in oligosaccharides are serially lettered according to the lettering of the repeating unit of the O—SP and identified by a subscript in listing of signal assignments. Low resolution mass spectra were obtained by either chemical ionisation (CI-MS) using $NH_3$ as the ionising gas, by electrospray mass spectrometry (ES-MS), by fast atom bombardment mass spectrometry (FAB-MS) recorded in the positive-ion mode using dithioerythridol/dithio-L-threitol (4:1, Magic Bullet) as the matrix in the presence of NaI, and Xenon as the gas. HRMS were obtained by Matrix Assisted Laser Desorption Ionisation (MALDI).

Abréviations
TCA: trichloroacetimidate
EtOAc: Ethyl acetate
1,2-DCE: 1,2-dichloroethane
DCM: Dichloromethane
THF: Tetrahydrofuran
DMF: N,N-dimethyl formamide
rt: room temperature A—Synthesis of the Methyl Glycosides of a Tetra- and Two Pentasaccharide Fragments of the O-specific Polysaccharide of *Shigella flexneri* Serotype 2a:

Appropriate solvents for chromatography consisted of A, dichloromethane-methanol; B, cyclohexane-ethyl acetate, C, cyclohexane-acetone, D, water-acetonitrile, E, iso-propanol-ammonia-water; F, 0.01 M aq TFA-acetonitrile.

Methyl (3,4-di-O-benzyl-2-O-chloroacetyl-α-L-rhamnopyranosyl)-(1→2)-3,4-di-O-benzyl-α-L-rhamnopyranoside (108). Activated powered 4 Å molecular sieves (200 mg) was added to a solution of alcohol (V. Pozsgay, J.-R. Brisson, H. J. Jennings, *Can. J. Chem.* 1987, 65, 2764-2769) 104 (60 mg, 167 μmol) and trichloroacetimidate donor 120 (113 mg, 0.2 mmol) in dry $Et_2O$ (2 mL) and the solution was stirred at rt for 30 min then cooled to −40° C. TMSOTf (9 μL, 50 μmol) was added and the mixture was stirred for 1 h at −30° C., then for 2 h while the bath temperature was coming back to rt. TLC (solvent B, 4:1) showed the presence of less polar product than 104. The mixture was neutralized by addition of $Et_3N$, and filtered on a pad of Celite. Concentration of the filtrate and column chromatography of the residue (solvent B, 4:1) gave 86 mg of 108 as a colourless oil (67%). $[\alpha]_D$−13.6 (c 1.0); $^1$H NMR δ 7.42-7.32 (m, 20H, Ph), 5.64 (dd, 1H, $J_{1,2}$=1.9, $J_{2,3}$=3.2 Hz, H-$2_A$), 5.07 (d, 1H, H-$1_A$), 4.98-4.93 (m, 2H, $OCH_2$), 4.83-4.61 (m, 6H, $OCH_2$), 4.64 (bs, 1H, H-$1_B$), 4.18 (d, 1H, J=15.2 Hz, $CH_2Cl$), 4.13 (d, 1H, $OCH_2Cl$), 3.90 (dd, 1H, $J_{3,4}$=9.3 Hz, H-$3_B$), 3.89 (m, 1H, partially overlapped, $J_{5,6}$=6.3 Hz, H-$5_A$), 3.73 (dq, 1H, $J_{4,5}$=9.5, $J_{5,6}$=6.2 Hz, H-$5_B$), 3.48 (pt, 1H, $J_{3,4}$=9.4 Hz, H-$4_B$), 3.45 (pt, 1H, $J_{3,4}$=$J_{4,5}$=9.4 Hz, H-$4_A$), 3.36 (s, 3H, $OCH_3$), 1.37 (d, 3H, H-$6_A$), 1.35 (d, 3H, H-$6_B$); $^{13}$C NMR δ 165.5 (CO), 137.4-126.4 (Ph), 100.2 (C-$1_A$), 99.2 (C-$1_B$), 80.4, 80.3, 80.2 (2C, C-$4_A$, $4_B$, $3_B$), 77.9 (C-$3_A$), 75.8, 75.7 (2C, $OCH_2$), 74.8 (C-$2_B$), 72.6, 72.5 (2C, $OCH_2$), 71.2 (C-$2_A$), 68.7 (C-$5_A$), 68.2 (C-$5_B$), 55.0 ($OCH_3$), 41.4 ($CH_2Cl$), 18.4 (2C, C-$6_A$, $6_B$). FABMS for $C_{43}H_{49}ClNO_{10}$ (M, 760.3) m/z 783.3 $[M+Na]^+$. Anal. Calcd for $C_{43}H_{49}ClNO_{10}$: C, 67.84; H, 6.49%. Found: C, 68.03; H, 7.02.

Methyl (3,4-di-O-benzyl-α-L-rhamnopyranosyl)-(1→2)-3,4-di-O-benzyl-α-L-rhamnopyranoside (107). Activated powered 4 Å molecular sieves was added to a solution of alcohol 104 (322 mg, 0.90 mmol) and trichloroacetimidate donor (J. C. Castro-Palomino, M. H. Rensoli, V. Verez Bencomo, *J. Carbohydr. Chem.* 1996, 15, 137-146) 105 (573 mg, 1.08 mmol) in dry $Et_2O$ (9 mL) and the solution was stirred at rt for 30 min then cooled to −35° C. TMSOTf (48 μL, 266 μmol) was added and the mixture was stirred for 4 h, while the bath temperature was coming back to rt. TLC (solvent B, 23:2) showed that only little starting material remained and the mixture was neutralized by addition of $Et_3N$, and filtered on a pad of Celite. Concentration of the filtrate and column chromatography of the residue (solvent B, 9:1) gave 647 mg of slightly contaminated 106. The later (626 mg) was dissolved in a mixture of $CH_2Cl_2$ (2 mL) and MeOH (5 mL) and 1M methanolic sodium methoxide (300 μL) was added. The mixture was stirred overnight, neutralized with Amberlite IR 120 ($H^+$), filtered and concentrated. Chromatography of the residue (solvent G, 89:11) gave syrupy 107 (554 mg, 91% from 104). Analytical data were as described. (V. Pozsgay, J.-R. Brisson, H. J. Jennings, *Can. J. Chem.* 1987, 65t 2764-2769)

Methyl (3,4.6-tri-O-acetyl-2-deoxy-2-tetrachlorophtalimido-β-D-glucopyranosyl)-(1→2)-(3,4-di-O-benzyl-α-L-rhamnopyranosyl)-(1→2)-3,4-di-O-benzyl-α-L-rhamnopyranoside (110). A solution of disaccharide 107 (179 mg, 0.26 mmol) and trichloroacetimidate donor (J. C. Castro-Palomino, R. R. Schmidt, *Tetrahedron Lett.* 1995, 36, 5343-5346) 109 (436 mg, 0.60 mmol) in dry $CH_3CN$ (9 mL) was stirred at rt for 30 min in the presence of activated 4 Å molecular sieves (1.2 g). Tin(II) trifluoromethanesulfonate $[Sn(OTf)_2]$ (75 mg, 180 μmol) was added and the mixture was stirred at rt for 4 h, then neutralized with $Et_3N$. Filtration on a pad of Celite, concentration of the filtrate and column chromatography of the residue (solvent B, 87:13) gave 110 (324 mg) as a slightly contaminated white foam (72% as estimated from the $^1$H NMR spectrum). An analytical sample had $[\alpha]_D$+23.3 (c 1.0); $^1$H NMR δ 7.43-7.17 (m, 20H, Ph), 5.92 (d, 1H, J=9.2, J=10.5 Hz, H-$3_D$), 5.24 (d, 1H, $J_{1,2}$=8.4 Hz, H-$1_D$), 5.14 (dd, 1H, J=9.7, J=9.4 Hz, H-$4_D$), 5.00 (bs, 1H, H-$1_A$), 4.79 (d, 1H, J=10.8 Hz, $OCH_2$), 4.65 (s, 2H, $OCH_2$), 4.55 (d, 1H, J=11.2 Hz, $OCH_2$), 4.53 (bs, 1H, H-$1_B$), 4.46-4.36 (m, 3H, H-$2_D$, $OCH_2$), 4.28 (d, 1H, J=12.4 Hz, $OCH_2$), 4.26 (d, 1H, J=10.6 Hz, $OCH_2$), 4.06 (dd, 1H, $J_{6a,6b}$=12.5, $J_{5,6a}$=6.8 Hz, H-$6a_D$), 3.91 (bs, 1H, H-$2_B$), 3.85-3.69 (m, 5H, H-$2_A$, $3_B$, $3_A$, $6b_D$, $5_A$*), 3.59 (dq, 1H, $J_{4,5}$=9.4, $J_{5,6}$=6.2 Hz, H-$5_B$*), 3.40 (m, 1H, H-$5_D$), 3.27 (s, 3H, $OCH_3$), 3.18 (m, 2H, H-$4_A$, $4_B$), 2.03, 2.01, 1.94 (3s, 9H, $C(O)CH_3$), 1.27, 1.25 (2d, 6H, H-$6_A$, $6_B$); $^{13}$C NMR δ 170.5, 170.4, 170.3, 163.8, 162.6 (5C, CO), 140.3-128.0 (Ph), 101.1 (C-$1_A$), 100.0 (C-$1_D$), 99.8 (C-$1_B$), 80.7 (2C, C-$4_A$, $4_B$), 79.7 (C-$2_A$), 78.9 (C-$3_B$), 78.1 (C-$3_A$), 76.2 (C-$2_B$), 75.3, 75.2, 72.7, 71.4 (4C, $OCH_2$), 71.3 (C-$5_D$), 70.1 (C-$3_D$), 68.5 (C-$5_A$*), 68.4 (C-$4_D$), 67.4 (C-$5_B$*), 61.3 (C-$6_D$), 55.4 (C-$2_D$), 54.6 ($OCH_3$), 20.7, 20.6 (3C, C(O)$CH_3$), 18.0, 17.7 (2C, C-$6_A$, $6_B$). FABMS for $C_{61}H_{63}Cl_4NO_{18}$ (M, 1237.3) m/z 1259.9 $[M+Na]^+$. Anal. Calcd for $C_{61}H_{63}Cl_4NO_{18} \cdot H_2O$: C, 58.24; H, 5.21; N, 1.11%. Found: C, 58.21; H, 4.91; N, 1.01%.

Methyl (2-acetamido-2-deoxy-β-D-glucopyranosyl)-(1→2)-(3,4-di-O-benzyl-α-L-rhamnopyranosyl)-(1→2)-3,4-di-O-benzyl-α-L-rhamnopyranoside (111). A solution of disaccharide 107 (179 mg, 0.26 mmol) and trichloroacetimidate donor 109 (436 mg, 0.60 mmol) in dry $CH_3CN$ (9 mL) was stirred at rt for 30 min in the presence of activated 4 Å molecular sieves (1.2 g). Tin(II) trifluoromethanesulfonate $[Sn(OTf)_2]$ (75 mg, 180 μmol) was added and the mixture was stirred at rt for 4 h, then neutralized with $Et_3N$. Filtration on a pad of Celite, concentration of the filtrate and column chromatography of the residue (solvent B, 87:13) gave 110 (324 mg) as a slightly contaminated product. The latter was solubilized in dry ethanol (13 mL) and diethylamide (200 μL, 3.0 mmol) was added and the mixture was stirred overnight at 60° C. The mixture was cooled to rt and acetic anhydride (1.0 mL, 10.6 mmol) was added and the mixture was stirred at this temperature for 2 h. The suspension was was filtered and volatiles were evaporated and coevaporated repeatedly with toluene and cyclohexane. The crude residue was taken up in a minimum of $CH_2Cl_2$ and MeOH (10 mL). 1N methanolic sodium methoxide was added until the pH was 10 and the solution was stirred overnight at rt, neutralized with IR 120 ($H^+$), filtered and concentrated. Chromatography of the residue (solvent A, 24:1) gave foamy 111 (135 mg, 51% from 107). $[\alpha]_D$ –15.0 (c 1.0); $^1$H NMR δ 7.44-7.28 (m, 20H, Ph), 8.88 (bs, 1H, $NH_D$), 5.28 (bs, 1H, H-$1_A$), 4.93-4.61 (m, 8H, $OCH_2$), 4.59 (s, 1H, $J_{1,2}$=1.3 Hz, H-$1_B$), 4.41 (d, 1H, $J_{1,2}$=8.3 Hz, H-$1_D$), 4.06 (m, 2H, H-$2_A$, $2_B$), 4.00 (dd, 1H, $J_{2,3}$=3.3, $J_{3,4}$=9.4 Hz, H-$3_A$), 3.86 (dd, 1H, $J_{2,3}$=2.9, $J_{3,4}$=9.4 Hz, H-$3_B$), 3.79 (dq, 1H, $J_{4,5}$=9.4, $J_{5,6}$=6.2 Hz, H-$5_A$*), 3.67 (m, 2H, H-$5_B$*, $6a_D$), 3.51 (m, 1H, H-$2_D$), 3.49-3.38 (m, 6H, H-$6b_D$, $4_D$, $3_D$, $4_B$, $4_A$), 3.31 (s, 3H, $OCH_3$), 3.29 (m, 1H, H-$5_D$), 1.55 (s, 3H, C(O)$CH_3$), 1.35 (d, 6H, H-$6_A$, $6_B$); $^{13}$C NMR δ 173.6 (CO), 138.5-127.6 (Ph), 103.2 (C-$1_D$), 100.2 (C-$1_A$), 99.9 (C-$1_B$), 81.3, 80.7 (2C, C-$4_A$, $4_B$), 79.9 (2C, C-$3_A$, $3_B$), 79.0 (C-$2_A$), 77.2 (C-$3_D$), 75.8 (C-$5_D$), 75.7, 75.2, 74.6 (3C, $OCH_2$), 73.4 (C-$2_B$), 72.3 ($OCH_2$), 71.8 (C-$4_D$), 68.2, 67.7 (C-$5_A$, $5_B$), 62.5 (C-$6_D$), 58.9 (C-$2_D$), 54.6 ($OCH_3$), 22.3 C(O)$CH_3$), 17.9, 17.7 (2C, C-$6_A$, $6_B$). FABMS for $C_{49}H_{61}NO_{14}$ (M, 887.44) m/z 910.1 $[M+Na]^+$. Anal. Calcd for $C_{49}H_{61}NO_{14}$.$H_2O$: C, 64.96; H, 7.01; N, 1.55%. Found: C, 65.19; H, 6.83; N, 1.51%.

Methyl (2-acetamido-2-deoxy-4,6-O-isopropylidene-β-D-glucopyranosyl)-(1→2)-(3,4-di-O-benzyl-α-L-rhamnopyranosyl)-(1→2)-3,4-di-O-benzyl-α-L-rhamnopyranoside (112). 2,2-dimethoxypropane (4.9 mL, 39.8 mmol) and para-toluenesulfonic acid (18 mg, 95 μmol) were added to a solution of the triol 111 (964 mg, 1.09 mmol) in acetone (3 mL) and the mixture was stirred at rt for 1 h. $Et_3N$ was added, and volatiles were evaporated. Column chromatography of the residue (solvent A, 99:1) gave the acceptor 112 as a white solid (969 mg, 96%) which could be crystallized from $AcOEt$:$iPr_2O$; mp 164-165° C. $[\alpha]_D$ –25.9 (c 1.0); $^1$H NMR δ 7.45-7.31 (m, 20H, Ph), 6.98 (d, 1H, $J_{NH,2}$=2.4 Hz, NH), 6.37 (bs, 1H, OH), 5.07 (d, 1H, $J_{1,2}$=1.9 Hz, H-$1_A$), 4.90 (d, 1H, J=10.8 Hz, $OCH_2$), 4.85 (d, 1H, J=10.1 Hz, $OCH_2$), 4.84 (d, 1H, J=10.8 Hz, $OCH_2$), 4.76 (d, 1H, $OCH_2$), 4.69 (d, 1H, $OCH_2$), 4.68 (s, 2H, $OCH_2$), 4.65 (d, 1H, $OCH_2$), 4.61 (d, 1H, $J_{1,2}$=1.6 Hz, H-$1_B$), 4.48 (d, 1H, $J_{1,2}$=8.3 Hz, H-$1_D$), 4.09 (dd, 1H, H-$2_A$), 4.01 (dd, 1H, $J_{2,3}$=3.2, $J_{3,4}$=9.4 Hz, H-$3_A$), 3.91 (dd, 1H, H-$2_B$), 3.89-3.84 (m, 2H, $J_{5,6}$=6.3, $J_{4,5}$=9.4, $J_{2',3'}$=3.3, $J_{3',4'}$=9.4 Hz, H-$5_A$, $3_B$), 3.68 (dq, partially overlapped, $J_{5,6}$=6.2, $J_{4,5}$=9.5 Hz, H-$5_B$), 3.66-3.58 (m, 5H, H-$6a_D$, $6b_D$, $2_D$, $3_D$, $4_D$), 3.44 (pt, 1H, H-$4_A$), 3.41 (pt, 1H, H-$4_B$), 3.32 (s, 3H, $OCH_3$), 3.16 (m, 1H, H-$5_D$), 1.60 (s, 3H, C(O)$CH_3$), 1.54, 1.48 (2s, 6H, C($CH_3$)$_2$), 1.35 (d, 6H, H-$6_A$, $6_B$); $^{13}$C NMR δ 173.9 (CO), 138.8-128.0 (Ph), 103.7 (C-$1_D$), 101.3 (C-$1_A$), 100.3 (C($CH_3$)$_2$), 100.2 (C-$1_B$), 81.9 (C-$4_A$), 80.8 (C-$4_B$), 80.5 (C-$3_A$), 79.7 (C-$3_B$), 79.4 (C-$2_A$), 76.2 ($OCH_2$), 76.0 (C-$2_B$), 75.6, 75.1 (2C, $OCH_2$), 74.7 (C-$4_D$), 74.4 (C-$3_D$), 72.6 ($OCH_2$), 68.6 (C-$5_A$), 68.0, 67.9 (2C, C-$5_B$, $5_D$), 62.2 (C-$6_D$), 60.6 (C-$2_D$), 55.1 ($OCH_3$), 29.5 (C($CH_3$)$_2$), 22.7 (C(O)$CH_3$), 19.4 (C($CH_3$)$_2$), 18.5, 18.2 (2C, C-$6_A$, $6_B$). FABMS for $C_{52}H_{65}NO_{14}$ (M, 927.44) m/z 950.1 $[M+Na]^+$. Anal. Calcd for $C_{52}H_{65}NO_{14}$: C, 67.30; H, 7.06; N, 1.51%. Found: C, 67.12; H, 6.98; N, 1.44%.

Methyl (2,3,4,6-tetra-O-benzyl-α-D-glucopyranosyl)-(1→4)-(2,3-di-O-benzoyl-α-L-rhamnopyranosyl)-(1→3)-2-acetamido-2-deoxy-4,6-O-isopropylidene-β-D-glucopyranosyl)-(1→2)-(3,4-di-O-benzyl-α-L-rhamnopyranosyl)-(1→2)-3,4-di-O-benzyl-α-L-rhamnopyranoside (115). Activated powdered 4 Å molecular sieves were added to a solution of the trisaccharide acceptor 112 (202 mg, 0.22 mmol) and the disaccharide donor 114 (263 mg, 0.25 mmol) in anhydrous $CH_2Cl_2$ (5 mL) and the suspension was stirred for 30 min at –15° C. TfOH (7 μL, 34 μmol) was added and the mixture was stirred for 2 h while the bath temperature was slowly coming back to 10° C. TLC (solvent D, 49:1) showed that no 112 remained. $Et_3N$ was added and after 30 min, the suspension was filtered through a pad of Celite. Concentration of the filtrate and chromatography of the residue (solvent B, 9:1→17:5) gave the fully protected pentasaccharide 115 (330 mg, 84%) as a white foam; $[\alpha]_D$+63.3 (c 1.0); $^1$H NMR δ 8.07-6.96 (m, 50H, Ph), 5.82 (d, 1H, $J_{NH,2}$=7.4 Hz, NH), 5.63 (dd, 1H, $J_{2,3}$=3.5, $J_{3,4}$=9.5 Hz, H-$3_C$), 5.43 (dd, 1H, $J_{1,2}$=1.6 Hz, H-$2_C$), 5.09 (bs, 1H, H-$1_A$), 5.02 (d, 1H, $J_{1,2}$=3.4 Hz, H-$1_E$), 4.99 (d, 1H, $J_{1,2}$=8.3 Hz, H-$1_D$), 4.95 (d, 1H, $J_{1,2}$=1.1 Hz, H-$1_C$), 4.94-4.63 (m, 13H, $OCH_2$), 4.63 (s, 1H, H-$1_B$), 4.37 (d, 1H, J=11.0 Hz, $OCH_2$), 4.29 (dq, 1H, $J_{4,5}$=9.5, $J_{5,6}$=6.2 Hz, H-$5_C$), 4.25 (d, 1H, J=9.5 Hz, $OCH_2$), 4.23 (pt, 1H, $J_{3,4}$=$J_{4,5}$=9.5 Hz, H-$3_D$), 4.01 (m, 1H, H-$2_A$), 3.97-3.86 (m, 5H, H-$3_A$, $2_B$, $3_E$, $4_C$, $OCH_2$), 3.82 (m, 1H, H-$3_B$, $5_A$), 3.71-3.57 (m, 7H, H-$5_D$, $4_E$, $5_B$, $4_D$, $6a_D$, $6b_D$), 3.54-3.41 (m, 3H, H-$2_E$, $4_A$, $2_D$) 3.38-3.31 (m, 2H, H-$4_B$, $6a_E$), 3.31 (s, 3H, $OCH_3$), 3.17 (m, 1H, H-$5_D$), 3.08 (d, 1H, $J_{6a,6b}$=10.1 Hz, H-$6b_E$), 1.84 (s, 3H, C(O)$CH_3$), 1.46 (s, 3H, C($CH_3$)$_2$), 1.45 (d, 3H, $J_{5,6}$=5.9 Hz, H-$6_C$), 1.35 (m, 6H, $J_{5,6}$=5.9 Hz, H-$6_A$, C($CH_3$)$_2$), 1.31 (d, 3H, $J_{5,6}$=6.2 Hz, H-$6_B$); $^{13}$C NMR δ 171.7, 165.9, 165.8 (3C, CO), 138.9-127.9 (Ph), 102.3 (C-$1_D$, J=167 Hz), 101.5 (C-$1_A$, J=170 Hz), 100.3 (C-$1_B$, J=170 Hz), 99.8 (C($CH_3$)$_2$), 99.6 (C-$1_E$, J=172 Hz), 98.2 (C-$1_C$, J=172 Hz), 82.0 (C-$3_E$), 81.2, 80.9, 80.7 (3C, C-$4_A$, $4_B$, $2_E$), 80.0, 79.7, 79.3 (3C, C-$3_B$, $3_A$, $4_C$), 78.1, 77.8, 77.4 (3C, C-$2_A$, $4_E$, $3_D$), 75.9, 75.8, 75.6 (3C, $OCH_2$), 75.5 (C-$2_B$), 75.0, 74.4, 73.7 (3C, $OCH_2$), 73.2 (2C, C-$4_D$, $OCH_2$), 72.2 ($OCH_2$), 71.7, 71.6 (3C, C-$2_C$, $3_C$, $5_E$), 68.8 (C-$5_B$), 68.0 (C-$6_E$), 68.0 (2C, C-$5_A$, $5_B$), 67.6 (C-$5_D$), 62.5 (C-$6_D$), 58.9 (C-$2_D$), 55.0 ($OCH_3$), 29.5 (C($CH_3$)$_2$), 23.8 (C(O)$CH_3$), 19.8 (C($CH_3$)$_2$), 18.6 (C-$6_C$), 18.5 (C-$6_A$), 18.3 (C-$6_B$). FAB-MS for $C_{106}H_{117}NO_{25}$ (M, 1803.79) m/z 1826.4 $[M+H]^+$. Anal. Calcd for $C_{106}H_{117}NO_{25}$.$H_2O$: C, 69.83; H, 6.58; N, 0.77%. Found: C, 69.86; H, 6.33; N, 0.71%.

Methyl (2,3,4,6-tetra-O-benzyl-α-D-glucopyranosyl)-(1→4)-(2,3-di-O-benzoyl-α-L-rhamnopyranosyl)-(1→3)-(2-acetamido-2-deoxy-β-D-glucopyranosyl)-(1→2)-(3,4-di-O-benzyl-α-L-rhamnopyranosyl)-(1→2)-3,4-di-O-benzyl-α-L-rhamnopyranoside (116). 90% aq TFA (750 μL) was added at 0° C. to a solution of the fully protected 115 (588 mg, 326 μmol) in $CH_2Cl_2$ (6.7 mL) and the mixture was stirred at this temperature for 1 h. TLC (solvent B, 1.5:1) showed that no 115 remained. Volatiles were evaporated by repeated addition of toluene. Chromatography of the residue (solvent B, 4:1→1:1) gave 116 (544 mg, 95%) as a white foam; $[\alpha]_D$+58.8 (c 1.0); $^1$H NMR δ 8.06-7.06 (m, 50H, Ph), 5.82 (d, 1H, $J_{NH,2}$=7.1 Hz, NH), 5.65 (dd, 1H, $J_{2,3}$=3.8, $J_{3,4}$=9.0 Hz, H-$3_C$), 5 53 (m, 1H, H-$2_C$), 5.34 (bs, 1H, H-$1_A$), 5.04 (d, 1H, $J_{1,2}$=8.3 Hz, H-$1_D$), 5.00 (m, 2H, H-$1_C$, $1_E$), 4.97-4.63 (m, 13H, $OCH_2$), 4.48 (bs, 1H, H-$1_B$), 4.40 (d, 1H, J=8.4 Hz, $OCH_2$), 4.29 (d, 1H, J=8.0 Hz, $OCH_2$), 4.28-4.21 (m, 2H, H-$3_D$, $5_C$), 4.10 (m, 1H, H-$2_B$), 4.04 (m, 1H, H-$2_A$), 3.99 (d, 1H, $OCH_2$), 3.95-3.89 (m, 3H, H-$3_A$, $3_E$, $4_C$), 3.87 (dd, 1H, $J_{2,3}$=2.7, $J_{3,4}$=9.7 Hz, H-$3_B$), 3.81-3.64 (m, 5H, H-$5_E$, $5_A$, $6a_D$, $4_E$, $5_B$), 3.54 (dd, 1H, $J_{1,2}$=3.2, $J_{2,3}$=9.7 Hz, H-$2_E$), 3.51 (pt, 1H, $J_{3,4}$=$J_{4,5}$=9.5 Hz, H-$4_A$), 3.45-3.37 (m, 4H, H-$4_B$, $4_D$, $6a_E$, $2_D$), 3.33 (m, 5H, H-$5_D$, $6b_D$, $OCH_3$), 3.12 (d, 1H, $J_{6a,6b}$=10.6 Hz, H-$6b_E$), 2.28 (bs, 1H, OH), 1.97 (bs, 1H, OH), 1.84 (s, 3H, C(O)$CH_3$), 1.54 (d, 3H, $J_{5,6}$=6.1 Hz, H-$6_C$), 1.37 (m, 6H, H-$6_B$, $6_A$); $^{13}$C NMR δ 171.5, 165.8, 165.6 (3C, CO), 138.8-127.9 (Ph), 101.6 (C-$1_D$), 100.8 (C-$1_A$), 100.5 (C-$1_B$), 100.1 (C-$1_E$*), 99.9 (C-$1_C$*), 84.9 (C-$3_D$), 82.1 (C-$3_E$), 80.9, 80.7, 80.6, 80.5 (4C, C-$4_B$, $3_B$, $4_A$, $2_E$), 79.7 (C-$4_C$), 79.3 (C-$3_A$), 77.8 (2C, C-$2_A$, $4_E$), 76.0, 75.9 (2C, OCH$_2$), 75.8 (C-$5_D$), 75.6, 75.1, 74.6, 73.7, 73.1 (5C, OCH$_2$), 72.8 (C-$2_B$), 72.6 (OCH$_2$), 71.8 (C-$5_E$), 71.6 (C-$4_D$), 71.3 (C-$3_C$), 71.1 (C-$2_C$), 69.4 (C-$5_C$), 68.8 (C-$5_A$), 68.3 (C-$5_B$), 68.1 (C-$6_E$), 63.0 (C-$6_D$), 57.6 (C-$2_D$), 55.0 (OCH$_3$), 23.8 (C(O)CH$_3$), 18.8 (C-$6_C$), 18.6, 18.5 (2C, C-$6_A$, $6_B$). FAB-MS for C$_{103}$H$_{113}$NO$_{25}$ (M, 1763.76) m/z 1786.2 [+H]$^+$. Anal. Calcd for C$_{103}$H$_{113}$NO$_{25}$.2 H$_2$O: C, 68.69; H, 6.55; N, 0.78%. Found: C, 68.74; H, 6.45; N, 0.65%.

Methyl (2,3,4,6-tetra-O-benzyl-α-D-glucopyranosyl)-(1→4)-α-L-rhamnopyranosyl-(1→3)-(2-acetamido-2-deoxy-β-D-glucopyranosyl)-(1→2)-(3,4-di-O-benzyl-α-L-rhamnopyranosyl)-(1→2)-3,4-di-O-benzyl-α-L-rhamnopyranoside (117). 1M Methanolic sodium methoxide was added to a solution of 116 (277 mg, 157 μmol) in a 1:1 mixture of CH$_2$Cl$_2$ and MeOH (6 mL) until the pH was 10. The mixture was stirred overnight at rt and neutralized with Amberlite IR-120 (H$^+$). The crude material was chromatographed (solvent A, 49:1) to give 117 (211 mg, 86%) as a white foam; [α]$_D$+23.8 (c 1.0); $^1$H NMR δ 7.33-7.16 (m, 40H, Ph), 5.34 (d, 1H, J$_{NH,2}$=7.6 Hz, NH), 5.18 (bs, 1H, H-$1_A$), 4.79 (d, partially overlapped, 1H, H-$1_E$), 4.67 (bs, 1H, H-$1_C$), 4.50 (d, partially overlapped, 1H, H-$1_D$), 4.49 (bs, 1H, H-$1_B$), 4.88-4.33 (m, 16H, OCH$_2$), 3.98-3.81 (m, 6H, H-$2_A$, $2_B$, $5_E$, $3_A$, $3_E$, $5_B$*), 3.77-3.70 (m, 3H, H-$3_B$, $2_C$, $5_C$*), 3.65 (dq, 1H, J$_{4,5}$=9.4, J$_{5,6}$=6.2 Hz, H-$5_A$*), 3.62-3.51 (m, 4H, H-$2_D$, 6a$_D$, 6a$_E$, 6b$_E$), 3.48-3.27 (m, 7H, H-$2_E$, $4_E$, $3_D$, $4_A$, $4_B$, $3_C$, $4_C$), 3.23-3.12 (m, 6H, H-$4_D$, 6b$_D$, $5_D$, OCH$_2$), 2.76 (bs, 1H, OH), 1.72 (bs, 3H, OH), 1.65 (s, 3H, NHAc), 1.32, 1.25 (2d, 9H, H-$6_C$, $6_B$, $6_A$); $^{13}$C NMR δ 170.6 (CO), 138.5-128.0 (Ph), 103.0 (C-$1_D$), 101.8 (C-$1_C$), 100.7 (C-$1_A$), 100.4 (C-$1_B$), 99.6 (C-$1_E$), 87.3 (C-$3_D$), 85. (C-$4_C$*), 82.0 (C-$3_E$), 81.2, 80.7, 80.5, 80.2, 797, 78.1, 77.9 (7C, C-$2_B$, $3_A$, $3_B$, $4_A$, $4_B$, $2_E$, $4_E$), 76.2 (C-$5_D$), 76.1, 75.9, 75.6, 75.4, 74.0, 73.9, 73.6 (7C, OCH$_2$), 73.0 (C-$2_A$), 72.8 (OCH$_2$), 71.7, 71.2, 71.1, 69.8 (4C, C-$4_D$, $5_E$, $2_C$, $3_C$), 68.8, 68.2 (3C, C-$5_A$, $5_B$, $5_C$), 63.1 (C-$6_D$), 55.6 (C-$2_D$), 55.0 (OCH$_2$), 23.7 (C(O)CH$_3$), 18.6, 18.3, 18.1 (3C, C-$6_A$, $6_B$, $6_C$). FAB-MS for C$_{89}$H$_{105}$NO$_{23}$ (M, 1555.71) m/z 1578.2 [M+H]$^+$. Anal. Calcd for C$_{89}$H$_{105}$NO$_{23}$: C, 68.66; H, 6.80; N, 0.90%. Found: C, 68.41; H, 6.78; N, 0.61%.

Methyl α-D-glucopyranosyl-(1→4)-α-L-rhamnopyranosyl-(1→3)-2-acetamido-2-deoxy-β-D-glucopyranosyl-(1→2)-α-L-rhamnopyranosyl-(1→2)-α-L-rhamnopyranoside (101). The benzylated tetrasaccharide 117 (352 mg, 226 μmol) was dissolved in a mixture of ethanol (14 mL) and AcOH (1 mL), treated with 10% Pd-C catalyst (200 mg), and the suspension was stirred for 5 days at rt. TLC (solvent A, 1:1) showed that the starting material had been transformed into a more polar product. The suspension was filtered on a pad of Celite. The filtrate was concentrated and coevaporated repeatedly with cyclohexane. Reverse phase chromatography of the residue (solvent D, 100:0→49:1), followed by freeze-drying, gave the target tetrasaccharide 101 as an amorphous powder (153 mg, 81%). RP-HPLC gave a single product eluting at Rt: 15.21 min (solvent F, 1:0→80:20 over 20 min); [α]$_D$−3.2 (c 1.0. methanol); $^1$H NMR (D$_2$O) δ 5.08 (d, 1H, J$_{1,2}$=1.2 Hz, H-$1_A$), 4.97 (d, 1H, J$_{1,2}$=3.9 Hz, H-$1_E$), 4.79 (d, 1H, J$_{1,2}$=1.3 Hz, H-$1_C$), 4.69 (m, 2H, H-$1_B$, $1_D$), 4.07 (dd, 1H, J$_{2,3}$=3.3 Hz, H-$2_A$), 4.02 (dq, 1H, J$_{4,5}$=9.3, J$_{5,6}$=6.2 Hz, H-$5_C$), 3.93 (m, 1H, H-$5_E$), 3.86 (m, 2H, H-$2_B$, $3_A$), 3.82-3.73 (m, 7H, H-$3_C$, $2_D$, 6a$_E$, 6b$_E$, $3_B$, $2_C$, 6a$_D$), 3.70-3.59 (m, 4H, H-$5_A$, $3_E$, 6b$_D$, $5_B$), 3.56 (pt, 1H, J$_{3,4}$=J$_{4,5}$=9.4 Hz, H-$3_D$), 3.49 (dd, 1H, J$_{2,3}$=9.6 Hz, H-$2_E$), 3.46-3.38 (m, 5H, H-$4_C$, $4_B$, $5_D$, $4_E$), 3.32 (s, 3H, OCH$_3$), 3.24 (pt, 1H, J$_{3,4}$=J$_{4,5}$=9.6 Hz, H-$4_A$), 2.00 (s, 3H, C(O)CH$_3$), 1.25 (d, 3H, partially overlapped, H-$6_C$), 1.23 (d, 3H, partially overlapped, H-$6_B$), 1.18 (d, 3H, J$_{5,6}$=6.2 Hz, H-$6_A$); $^{13}$C NMR (D$_2$O) δ 175.0 (CO), 102.3 (C-$1_D$, J=162 Hz), 101.5 (C-$1_C$, J=170 Hz), 101.3 (C-$1_A$, J=173 Hz), 100.0 (C-$1_E$, J=170 Hz), 99.9 (C-$1_B$, J=172 Hz), 81.9 (C-$3_D$), 81.4 (C-$4_C$), 79.2 (C-$2_A$), 79.0 (C-$2_B$), 76.2, 73.1, 72.2, 72.0, 71.4, 70.4, 70.0, 69.8, 69.7, 69.6, 69.3, 68.9, 68.7 (14C, $3_A$, $4_A$, $5_A$, $3_B$, $4_B$, $5_B$, $2_C$, $3_C$, $4_D$, $5_D$, $2_E$, $3_E$, $4_E$, $5_E$), 68.4 (C-$5_C$), 60.5 (2C, C-$6_D$, $6_E$), 56.0 (C-$2_D$), 55.3 (OCH$_3$), 22.6 (C(O)CH$_3$), 17.0 (3C, C-$6_A$, $6_B$, $6_C$). HRMS (MALDI) Calcd for C$_{27}$H$_{47}$NO$_{19}$+Na: 858.3214. Found: 858.3206.

3,4-Di-O-benzyl-2-O-chloroacetyl-α-L-rhamnopyranose (128). 1,5-Cyclooctadiene-bis(methyldiphenylphosphine) iridium hexafluorophosphate (IR(I), 25 mg) was dissolved in dry THF (5 mL) and the resulting red solution was degassed in an argon stream. Hydrogen was then bubbled through the solution, causing the colour to change to yellow. The solution was then degassed again in an argon stream. A solution of rhamnopyranoside (P. Westerduin, P. E. der Haan, M. J. Dees, J. H. van Boom, *Carbohydr. Res.* 1988, 180, 195-205) 127 (3.28 g, 7.12 mmol) in THF (30 mL) was degassed and added. The mixture was stirred overnight at rt, and a solution of iodine (3.6 g, 14.2 mmol) in a mixture of THF (70 mL) and water (20 mL) was added. The mixture was stirred at rt for 1 h, then concentrated. The residue was taken up in CH$_2$Cl$_2$ and washed twice with 5% aq NaHSO$_4$. The organic phase was dried and concentrated. The residue was purified by column chromatography (solvent B, 9:1) to give 128 (2.53 g, 85%). $^1$H NMR δ 7.40-7.28 (m, 10H, Ph), 5.57 (bd, 0.2H, H-2β), 5.45 (dd, 0.8H, J$_{1,2}$=2.0 Hz, H-2α), 5.13 (bd, 0.8H, H-1α), 4.92 (d, 1H, J=10.9 Hz, OCH$_2$α, OCH$_2$β), 4.79 (d, 0.2H, J=11.2 Hz, OCH$_2$β), 4.74 (d, 1H, J=11.2 Hz, OCH$_2$α, H-1β), 4.65 (d, 0.8H, OCH$_2$α), 4.64 (d, 0.2H, OCH$_2$β), 4.58 (d, 0.8H, OCH$_2$α), 4.54 (d, 0.2H, OCH$_2$β), 4.30 (d, 0.2H, J=15.1 Hz, CH$_2$Clβ), 4.26 (d, 0.2H, CH$_2$Clβ), 4.20 (s, 1.6H, CH$_2$Clα), 4.08 (dd, 0.8H, J$_{2,3}$=3.3, J$_{3,4}$=9.6 Hz, H-3α), 4.04 (dq, 0.8H, J$_{4,5}$=9.5 Hz, H-5α), 3.66 (dd, 0.2H, J$_{2,3}$=3.2, J$_{3,4}$=8.7 Hz, H-3β), 3.44 (pt, 2H, H-4α, 5β, OH-1α, 1β), 3.38 (pt, 0.2H, J$_{4,5}$=9.5 Hz, H-4β), 1.37 (d, 0.6H, J$_{5,6}$=5.7 Hz, H-6β), 1.34 (d, 2.4H, J$_{5,6}$=6.2 Hz, H-6α); $^{13}$C NMR δ 167.8 (COβ), 167.4 (COα), 138.6-128.2 (Ph), 93.0 (C-1β), 92.4 (C-1α), 80.3 (C-4α), 80.2 (C-3β), 79.6 (C-4β), 77.8 (C-3α), 75.9 (OCH$_2$β), 75.8 (OCH$_2$α), 72.5 (OCH$_2$α), 72.3 (0.4C, C-5β, OCH$_2$β), 71.9 (C-2-β), 71.7 (C-2α), 68.2 (C-5α), 41.3 (CH$_2$Clα, CH$_2$Clβ), 18.3 (C-6α, 6β); FAB-MS for C$_{22}$H$_{25}$ClO$_6$ (M, 420.5) m/z 443.1 [M+Na]$^+$. Anal. Calcd for C$_{22}$H$_{25}$ClO$_6$: C, 62.78; H, 5.94%. Found: C, 62.92; H, 6.11%.

3,4-Di-O-benzyl-2-O-chloroacetyl-α/β-L-rhamnopyranosyl trichloroacetimidate (120). (a) The hemiacetal 128 (700 mg, 1.66 mmol) was dissolved in CH$_2$Cl$_2$ (6 mL) and the solution was cooled to 0° C. Trichloroacetonitrile (1.7 mL) and DBU (26 μL) were added. The mixture was stirred at rt for 2 h. Toluene was added, and co-evaporated twice from the residue. The crude material was purified by flash chromatography (solvent B 4:1+0.1% Et$_3$N) to give 120 as a white foam (687 mg, 73%, α/β: 4/1).

(b) The hemiacetal 128 (858 mg, 2.04 mmol) was dissolved in CH$_2$Cl$_2$ (11 mL) and freshly activated K$_2$CO$_3$ (1.1 g, 8.0 mmol) was added. The suspension was cooled to 0° C., and trichloroacetonitrile (1.0 mL) was added. The mixture was stirred vigorously at rt for 5 h. The suspension was filtered on a pad of Celite, and concentrated. The crude material was purified by flash chromatography (solvent B, 9:1+0.1% Et$_3$N) to give 120 as a white foam (840 mg, 72%, α/β: 9/1 from the $^1$H NMR spectrum). $^1$H NMR (α-anomer) δ 8.71 (s, 1H, NH), 7.40-7.30 (m, 10H, Ph), 6.24 (d, 1H, J$_{1,2}$=1.8 Hz, H-1), 5.57 (dd, 1H, H-2), 4.94 (d, 1H, J=10.8

Hz, OCH$_2$), 4.76 (d, 1H, J=11.2 Hz, OCH$_2$), 4.67 (d, 1H, OCH$_2$), 4.62 (d, 1H, OCH$_2$), 4.22 (s, 2H, CH$_2$Cl), 4.04 (dd, 1H, J$_{2,3}$=3.2 Hz, H-3), 3.99 (dq, 1H, J$_{4,5}$=9.6 Hz, H-5), 3.53 (pt, H, H-4), 1.37 (d, 3H, J$_{4,5}$=6.2 Hz, H-6); $^{13}$C NMR (α-anomer) δ 166.9 (CO), 160.4 (C=NH), 138.4-128.3 (Ph), 95.2 (C-1), 91.1 (CCl$_3$), 79.5 (C-4), 77.6 (C-3), 76.1, 72.9 (2C, OCH$_2$), 71.2 (C-5), 69.8 (C-2), 41.1 (CH$_2$Cl), 18.3 (C-6).

Allyl (2,3,4,6-tetra-O-benzyl-α-D-glucopyranosyl)-(1→4)-2-O-benzoyl-3-O-chloroacetyl-α-L-rhamnopyranoside (122). To a solution of the known 121(F. Segat, L. A. Mulard, *Tetrahedron: Asymmetry* 2002, 13, 2211-2222) (7.10 g, 8.55 mmol) in a mixture of CH$_2$Cl$_2$ (40 mL) and pyridine (5 mL) at 0° C. was added chloroacetic anhydride (3.65 g, 21.3 mmol), and the mixture was stirred at this temperature for 2 h. TLC (solvent C, 9:1) showed the complete disappearance of the starting material. MeOH (10 ml) was added, and after 30 min, volatiles were evaporated. Column chromatography (solvent B, 1:0→4:1) of the crude yellow oil afforded 122 as a colourless foam (7.34 g, 95%). [α]$_D$+47.5 (c 1.0); $^1$H NMR δ 8.12-7.13 (m, 25H, Ph), 5.95 (m, 1H, CH=), 5.50-5.42 (m, 2H, J$_{2,3}$=3.6 Hz, H-2$_C$, 3$_C$), 5.37 (m, 1H, =CH$_2$), 5.28 (m, 1H, =CH$_2$), 4.96 (d, 1H, J=11.0 Hz, OCH$_2$), 4.93 (d, 1H, J$_{1,2}$=1.5 Hz, H-1$_C$), 4.90 (d, 1H, J$_{1,2}$=3.3 Hz, H-1$_E$), 4.87-4.81 (m, 3H, OCH$_2$), 4.67 (d, 1H, J=12.1 Hz, OCH$_2$), 4.64 (d, 1H, J=12.8 Hz, OCH$_2$), 4.47 (d, 1H, J=10.8 Hz, OCH$_2$), 4.43 (d, 1H, J=12.0 Hz, OCH$_2$), 4.25 (m, 2H, OCH$_2$), 4.09 (d, 1H, J=15.5 Hz, CH$_2$Cl), 3.99-3.93 (m, 3H, CH$_2$Cl, H-5$_C$, 3$_C$), 3.84 (m, 1H, H-5$_E$), 3.78-3.74 (m, 2H, H-6a$_E$, 4$_E$), 3.70 (pt, 1H, J$_{4,5}$=J$_{3,4}$=9.3 Hz, H-4$_C$), 3.58-3.54 (m, 2H, H-6$_E$, 2$_E$), 1.50 (d, 3H, J$_{5,6}$=6.2 Hz, H-6$_C$); $^{13}$C NMR δ 167.0, 166.0 (2C, CO), 139.1-128.0 (Ph, All), 118.5 (All), 99.5 (C-1$_E$), 96.8 (C-1$_C$), 81.9 (C-3$_E$), 81.0 (C-2$_E$), 79.7 (C-4$_C$), 77.7 (C-4$_E$), 76.0, 75.4, 74.1, 73.8 (4C, OCH$_2$), 73.5 (C-3$_C$), 71.8 (C-5$_E$), 70.9 (C-2$_C$), 68.8 (OCH$_2$), 68.1 (C-6$_E$), 67.7 (C-5$_C$), 41.5 (CH$_2$Cl), 18.6 (C-6$_C$); FAB-MS for C$_{52}$H$_{55}$O$_{12}$ (M, 906.5) m/z 929.3 [M+Na]$^+$. Anal. Calcd for C$_{52}$H$_{55}$ClO$_{12}$: C, 68.83; H, 6.11%. Found: C, 68.74; H, 6.19%.

(2,3,4,6-Tetra-O-benzyl-α-D-glucopyranosyl)-(1→4)-2-O-benzoyl-3-O-chloroacetyl-α/β-L-rhamnopyranose (123). A solution of 122 (7.21 g, 7.95 mmol) in THF (80 mL) containing activated iridium complex (60 mg) was treated as described for the preparation of 128. The mixture was stirred at rt for 3 h, at which point a solution of iodine (4.0 g, 15.7 mmol) in a mixture of THF (90 mL) and water (24 mL) was added. The mixture was stirred at rt for 30 min, then concentrated. The residue was taken up in CH$_2$Cl$_2$ and washed twice with 5% aq NaHSO$_4$, then with brine. The organic phase was dried and concentrated. The residue was purified by column chromatography (solvent B, 4:1) to give 123 (6.7 g, 97%) as a slightly yellow foam. $^1$H NMR δ 8.10-7.09 (m, 25H, Ph), 5.47 (dd, 1H, J$_{2,3}$=3.5, J$_{3,4}$=9.3 Hz, H-3$_C$), 5.41 (bs, 1H, H-2$_C$), 5.03 (bs, 1H, H-1$_C$), 4.94 (d, 1H, J=10.9 Hz, OCH$_2$), 4.87 (d, 1H, J$_{1,2}$=3.4 Hz, H-1$_E$), 4.85 (d, 1H, OCH$_2$), 4.80 (m, 2H, OCH$_2$), 4.64 (m, 2H, OCH$_2$), 4.45 (d, 1H, J=10.7 Hz, OCH$_2$), 4.41 (d, 1H, J=12.1 Hz, OCH$_2$), 4.16 (dq, 1H, J$_{4,5}$=9.3 Hz, H-5$_C$), 4.09 (d, 1H, J=15.6 Hz, CH$_2$Cl), 3.96 (d, 1H, CH$_2$Cl), 3.93 (pt, 1H, H-3$_E$), 3.83 (m, 1H, H-5$_E$), 3.77-3.68 (m, 2H, H-4$_E$, 6a$_E$), 3 65 (pt, 1H, H-4$_C$), 3.54 (m, 2H, H-6b$_E$, 2$_E$), 1.48 (d, 3H, J$_{5,6}$=6.2 Hz, H-6$_C$); $^{13}$C NMR δ 167.0, 166.0 (2C, CO), 139.1-127.9 (Ph), 99.5 (C-1$_E$), 92.3 (C-1$_C$), 81.9 (C-3$_E$), 81.0 (C-2$_E$), 79.9 (C-4$_C$), 77.6 (C-4$_E$), 76.0, 75.6, 74.2, 74.1 (4C, OCH$_2$), 72.1 (C-3$_C$), 71.7 (C-5$_E$), 71.1 (C-2$_C$), 68.0 (C-6$_E$), 67.5 (C-5$_C$), 41.5 (CH$_2$Cl), 18.9 (C-6$_C$); FAB-MS for C$_{49}$H$_{51}$ClO$_{12}$ (M, 866.3) m/z 889.3 [M+Na]$^+$. Anal. Calcd for C$_{49}$H$_{51}$ClO$_{12}$: C, 67.85; H, 5.93%. Found: C, 67.72; H, 6.00%.

(2,3,4,6-tetra-O-benzyl-α-D-glucopyranosyl)-(1→4)-2-O-benzoyl-3-O-chloroacetyl-α-L-rhamnopyranosyl trichloroacetimidate (119). Trichloroacetonitrile (1.1 mL, 10.9 mmol) and DBU (17 µL) were added to a solution of the hemiacetal 123 (950 mg, 1.09 mmol) in dry CH$_2$Cl$_2$ (8 mL), and the mixture was stirred at 0° C. for 1.5 h. Toluene was added, and volatiles were evaporated. The residue was purified by flash chromatography (solvent B, 3:2 containing 0.1% Et$_3$N) to give 119 (930 mg, 84%) as a colourless foam. Further elution gave some remaining starting material 123 (136 mg, 14%). [α]$_D$+39.3 (c 1.0); $^1$H NMR δ 8.76 (s, 1H, NH), 8.12-7.17 (m, 25H, Ph), 6.34 (d, 1H, J$_{1,2}$=1.5 Hz, H-1$_C$), 5.67 (dd, 1H, H-2$_C$), 5.54 (dd, 1H, J$_{2,3}$=3.4, J$_{3,4}$=8.8 Hz, H-3$_C$), 4.98 (d, 1H, OCH$_2$), 4.88 (d, 1H, J$_{1,2}$=3.4 H-1$_E$), 4.84 (d, 1H, J=11.1 Hz, OCH$_2$), 4.82 (d, 1H, J=11.2 Hz, OCH$_2$), 4.65 (d, 1H, OCH$_2$), 4.62 (d, 1H, OCH$_2$), 4.44 (d, 1H, J=11.4 Hz, OCH$_2$), 4.41 (d, 1H, J=11.8 Hz, OCH$_2$), 4.14 (dq, 1H, J$_{4,5}$=9.5 Hz, H-5$_C$), 4.11 (d, 1H, J=15.5 Hz, CH$_2$Cl), 3.98 (d, 1H, CH$_2$Cl), 3.94 (pt, 1H, H-3$_E$), 3.83-3.71 (m, 4H, H-5$_E$, 6a$_E$, 4$_E$, 4$_C$), 3.56-3.51 (m, 2H, H-6b$_E$, 2$_E$), 1.51 (d, 3H, J$_{5,6}$=6.2 Hz, H-6$_C$); $^{13}$C NMR δ 167.1, 165.7, 160.6 (3C, CO), 139.0-127.9 (Ph), 99.9 (C-1$_E$), 95.2 (C-1$_C$), 82.1 (C-3$_E$), 80.9 (C-2$_E$), 79.0 (C-4$_C$), 77.6 (C-4$_E$), 76.0, 75.6, 74.2, 73.8 (4C, OCH$_2$), 73.0 (C-3$_C$), 71.9 (C-5$_E$), 70.7 (C-5$_C$), 69.2 (C-2$_C$), 68.0 (C-6$_E$), 67.7 (C-5$_C$), 41.4 (CH$_2$Cl), 18.6 (C-6$_C$). Anal. Calcd for C$_{51}$H$_{51}$Cl$_4$NO$_{12}$: C, 60.54; H, 5.08; N, 1.38%. Found: C, 60.49; H, 5.01; N, 1.34%.

Methyl (2,3,4,6-tetra-O-benzyl-α-D-glucopyranosyl)-(1→4)-(2-O-benzoyl-3-O-chloroacetyl-α-L-rhamnopyranosyl)-(1→3)-2-acetamido-2-2-deoxy-3,4-O-isopropylidene-β-D-glycopyranoside (124). The acceptor (L. A. Mulard, C. Costachel, P. J. Sansonetti, *J. Carbohydr. Chem.* 2000, 19, 849-877) 118 (500 mg, 1.82 mmol) was dissolved in CH$_2$Cl$_2$ (5.5 mL) and 4 Å-MS (300 mg) were added. The mixture was cooled to −60° C. and stirred for 15 min. TMSOTf (35 µL, mmol) and a solution of the disaccharide donor 119 (2.39 g, 2.36 mmol) in CH$_2$Cl$_2$ (7.5 mL) were added. The mixture was stirred for 45 min while the cooling bath was coming back to rt, and for more 3 h at rt. The mixture was then heated at 65° C. for 1 h 30 min. Et$_3$N was added and the mixture was stirred at rt for 20 min, then diluted with CH$_2$Cl$_2$ and filtered through a pad of Celite. The filtrate was concentrated and purified by column chromatography (solvent B, 85:15→1:1) to give 124 (1.64 g, 80%) as a while powder [α]$_D$+55.1 (c 1.0); $^1$H NMR δ 8.06-6.93 (m, 25H, Ph), 6.18 (d, 1H, J$_{NH,2}$=7.3 Hz, NH$_D$), 5.40 (dd, 1H, J$_{2,3}$=3.5 Hz, H-3$_C$), 5.38 (bs, 1H, H-2$_C$), 4.98 (d, 1H, J$_{1,2}$=8.3 Hz, H-1$_D$), 4.94 (bs, 1H, H-1$_C$), 4.94 (d, 1H, OCH$_2$), 4.93 (d, 1H, J$_{1,2}$=3.4 Hz, H-1$_E$), 4.83 (d, 2H, J=10.7 Hz, OCH$_2$), 4.81 (d, 1H, J=10.6 Hz, OCH$_2$), 4.67 (d, 1H, J=11.7 Hz, OCH$_2$), 4.62 (d, 1H, J=11.4 Hz, OCH$_2$), 4.47 (m, 3H, H-3$_D$, OCH$_2$), 4.22 (dq, 1H, J$_{4,5}$=9.4, J$_{5,6}$=6.2 Hz, H-5$_C$), 4.10 (d, 1H, J=15.5 Hz, CH$_2$Cl), 3.96 (m, 2H, H-6a$_C$, CH$_2$Cl), 3.91 (pt, 1H, H-3$_E$), 3.82 (m, 2H, H-5$_E$, 6b$_D$), 3.72 (m, 3H, H-6a$_E$, 4$_E$, 4$_C$), 3.62 (pt, 1H, J$_{3,4}$=J$_{4,5}$=9.4 Hz, H-4$_D$), 3.55 (m, 2H, H-6b$_E$, 2$_E$), 3.51 (s, 3H, OCH$_3$), 3.41 (m, 1H, H-5$_D$), 3.15 (m, 1H, H-2$_D$), 2.04 (s, 3H, C(O)CH$_3$), 1.51 (s, 3H, C(CH$_3$)$_2$), 1.42 (m, 6H, H-6$_C$, C(CH$_3$)$_2$), 1.51 (d, 3H, J$_{5,6}$=6.2 Hz, H-6$_C$); $^{13}$C NMR δ 171.8, 167.3, 166.1 (3C, CO), 139.0-128.0 (Ph), 101.1 (C-1$_D$, J$_{CH}$<164 Hz), 99.9 (C(CH$_3$)$_2$), 99.4 (C-1$_E$, J$_{CH}$>165 Hz), 98.2 (C-1$_C$, J$_{CH}$=172 Hz), 81.8 (C-3$_E$), 80.9 (C-2$_E$), 79.0 (C-4$_C$*), 77.7 (C-4$_E$*), 76.7 (C-3$_D$), 75.9, 75.3, 74.2, 73.9 (4C, OCH$_2$), 73.7 (C-4$_D$), 73.4 (C-3$_C$), 71.9 (C-5$_E$), 71.2 (C-2$_C$), 68.2 (C-6$_E$), 67.8 (C-5$_C$), 67.4 (C-5$_D$), 62.7 (C-6$_D$), 59.6 (C-2$_D$), 57.6 (OCH$_3$), 41.5 (CH$_2$Cl), 29.5

$(C(CH_3)_2)$, 27.3 $(C(O)CH_3)$, 19.7 $(C(CH_3)_2)$, 18.6 $(C-6_C)$; FAB-MS for $C_{61}H_{70}ClNO_{17}$ (M, 1123.4) m/z 1146.5 [M+Na]$^+$. Anal. Calcd for $C_{61}H_{70}ClNO_{17}$: C, 65.15; H, 6.27; N, 1.25%. Found: C, 65.13; H, 6.23; N, 1.22%.

Methyl (2,3,4,6-tetra-O-benzyl-α-D-glucopyranosyl)-(1→4)-(2-O-benzoyl-α-L-rhamnopyranosyl)-(1→3)-2-acetamido-2-deoxy-3,4-O-isopropylidene-β-D-glucopyranoside (125). To a solution of the fully protected 124 (1.40 g, 1.25 mmol) in a mixture of methanol (18 mL) and pyridine (18 mL) was added thiourea (951 mg, 12.5 mmol). The mixture was stirred at 65° C. for 5 h at which time no TLC (solvent C, 4:1) that no starting material remained. Evaporation of the volatiles and co-evaporation of petroleum ether form the residue resulted in a crude solid which was taken up in a minimum of methanol. A large excess of $CH_2Cl_2$ was added and the mixture was left to stand at 0° C. for 1 h. The precipitate was filtrated on a pad of Celite and the filtrated was concentrated. Column chromatography of the residue (solvent C, 4:1) gave the trisaccharide acceptor 125 (1.28 g, 97%) as a white powder. $[\alpha]_D$+33.5 (c 1.0); $^1$H NMR δ 8.10-6.96 (m, 25H, Ph), 6.09 (d, 1H, $J_{NH,2}$=7.9 Hz, $NH_D$), 5.26 (dd, 1H, $J_{1,2}$=1.6, $J_{2,3}$=3.4 Hz, H-$2_C$), 4.97 (m, 3H, H-$1_C$, $1_E$, $OCH_2$), 4.86 (m, 3H, H-$1_D$, $OCH_2$), 4.81 (d, 1H,$OCH_2$), 4.72 (d, 1H, $OCH_2$), 4.58 (d, 1H, J=12.2 Hz, $OCH_2$), 4.51 (d, 1H, J=10.9 Hz, $OCH_2$), 4.48 (d, 1H, J=12.2 Hz, $OCH_2$), 4.23 (pt, 1H, $J_{2,3}$=$J_{3,4}$=9.4 Hz, H-$3_D$), 4.18-4.10 (m, 2H, H-$5_C$, $5_E$), 4.06-3.95 (m, 3H, H-$3_C$, $3_E$, $6a_D$), 3.80 (pt, 1H, $J_{5,6b}$=$J_{6a,6b}$=10.4 Hz, H-$6b_D$), 3.66 (m, 2H, H-$6a_E$, $6b_E$), 3.62 (dd, 1H, $J_{2,3}$=9.8, $J_{1,2}$=4.1 Hz, H-$2_E$), 3.59 (pt, 1H, $J_{3,4}$=$J_{4,5}$=8.9 Hz, H-$4_E$), 3.55 (pt, 1H, $J_{3,4}$=$J_{4,5}$=9.2 Hz, H-$4_D$), 3.51 (pt, 1H, $J_{3,4}$=$J_{4,5}$=9.3 Hz, H-$4_C$), 3.49 (s, 3H, $OCH_3$), 2.22 (s, 3H, $C(O)CH_3$), 1.90 (bs, 1H, OH), 1.49 (s, 3H, $CMe_2$), 1.43 (s, 3H, $CMe_2$), 1.40 (s, 3H, $J_{5,6}$=6.2 Hz, H-$6_C$); $^{13}$C NMR δ 171.8, 166.6 (2C, CO), 138.9-128.1 (Ph), 101.6 (C-$1_D$), 99.8 $(C(CH_3)_2)$, 98.6 (C-$1_E$*), 98.3 (C-$1_C$*), 85.4 (C-$4_C$), 82.0 (C-$3_E$), 80.4 (C-$2_E$), 78.2 (C-$4_E$), 77.1 (C-$3_D$), 75.9, 75.5, 74.2, 73.9 (4C, $OCH_2$), 73.6 (C-$4_D$*), 73.5 (C-$2_C$*), 71.7 (C-$5_E$), 69.0 (C-$6_E$), 68.3 (C-$3_C$), 67.5 (C-$5_D$), 66.9 (C-$5_C$), 62.7 (C-$6_D$), 58.9 (C-$2_D$), 57.5 ($OCH_3$), 29.5 $(C(CH_3)_2)$, 24.0 $(C(O)CH_3)$, 19.7 $(C(CH_3)_2)$, 18.2 (C-$6_C$); FAB-MS for $C_{59}H_{69}NO_{16}$ (M, 1047.5) m/z 1070.4 [M+Na]$^+$. Anal. Calcd for $C_{70}H_{76}O_{16}$: C, 67.61; H, 6.64; N, 1.34%. Found: C, 67.46; H, 6.78; N, 1.24%.

Methyl (3,4-Di-O-benzyl-2-O-chloroacetyl-α-L-rhamnopyranosyl)-(1→3)-[(2,3,4,6-tetra-O-benzyl-α-D-glucopyranosyl-(1→4)]-(2-benzoyl-3-O-chloroacetyl-α-L-rhamnopyranosyl)-(1→3)-2-acetamido-2-deoxy-3,4-O-isopropylidene-β-D-glucopyranoside (129). (a) The trisaccharide acceptor 125 (615 mg, 0.58 mmol) was dissolved in $Et_2O$ (10 mL) and the solution was cooled to −60° C. TMSOTf (32 μL) and donor 120 (497 mg, 0.88 mmol) in $Et_2O$ (12 mL) were added, and the mixture was stirred for 1 h while the bath was slowly coming back to −20° C. The mixture was stirred for 4 h at this temperature, then at 0° C. overnight. More 120 (50 mg, 88 μmol) was added, and the mixture was stirred at rt for 3 h more at 0° C. $Et_3N$ was added, and the mixture was concentrated. Column chromatography of the residue (solvent B, 9:1→1:1) gave the orthoester 135 (44 mg, 5%) then the fully protected 129 (445 mg, 52%) contaminated with the trimethylsilyl side product 126 (129/126: 9/1) together with a mixture of 129 and 135 (65 mg, 8%), and the starting 125 (27 mg, 4%). An analytical sample of compound 129 had $[\alpha]_D$+17.9 (c 1.0); $^1$H NMR δ 8.07-7.12 (m, 35H, Ph), 5.96 (d, 1H, $J_{NH,2}$=7.9 Hz, $NH_D$), 5.82 (m, 1H, H-$2_B$), 5.33 (dd, 1H, $J_{1,2}$=1.8, $J_{2,3}$=3.2 Hz, H-$2_C$), 5.07 (d, 1H, $J_{1,2}$=3.2 Hz, H-$1_E$), 5.05 (d, 1H, $J_{1,2}$=1.7 Hz, H-$1_B$), 4.98 (d, 1H, $OCH_2$), 4.97 (bs, 1H, H-$1_C$), 4.91-4.78 (m, 5H, H-$1_D$, $OCH_2$), 4.64 (d, 1H, J=11.6 Hz, $OCH_2$), 4.60-4.45 (m, 5H, $OCH_2$), 4.36 (d, 1H, J=11.9 Hz, $OCH_2$), 4.26 (pt, 1H, $J_{2,3}$=$J_{3,4}$=9.5 Hz, H-$3_D$), 4.17 (dd, 1H, $J_{2,3}$=3.4 Hz, H-$3_C$), 4.16 (d, 1H, J=15.1 Hz, $CH_2Cl$), 4.11 (d, 1H, $CH_2Cl$), 4.10 (dq, 1H, $J_{4,5}$=9.1, $J_{5,6}$=6.3 Hz, H-$5_C$), 4.06 (m, 1H, H-$5_E$), 4.00 (pt, 1H, $J_{3,4}$=$J_{2,3}$=9.4 Hz, H-$3_E$), 3.97 (dd, 1H, $J_{5,6a}$=5.3, $J_{6a,6b}$=10.8 Hz, $6a_D$), 3.89 (m, 1H, H-$6a_E$), 3.88-3.68 (m, 4H, H-$6b_E$, $6b_D$, $4_C$, $3_B$), 3.67 (m, 1H, H-$5_B$), 3.58 (pt, 1H, $J_{3,4}$=$J_{4,5}$=9.4 Hz, H-$4_D$), 3.52 (dd, 1H, $J_{1,2}$=3.3, $J_{2,3}$=9.8 Hz, H-$2_E$), 3.49 (s, 3H, $OCH_3$), 3.39 (m, 1H, H-$5_D$), 3.30 (m, 2H, H-$2_D$, $4_B$), 2.12 (s, 3H, $C(O)CH_3$), 1.52 (s, 3H, $C(CH_3)_2$), 1.42 (s, 3H, $C(CH_3)_2$), 1.33, 0.96 (2d, 3H, $J_{5,6}$=6.2 Hz, H-$6_B$, $6_C$); $^{13}$C NMR δ 171.9, 167.0, 166.3 (3C, CO), 138.8-128.0 (Ph), 101.4 (C-$1_D$, $J_{CH}$=164 Hz), 99.9 $(C(CH_3)_2)$, 99.3 (C-$1_C$, $J_{CH}$=168 Hz), 98.3 (C-$1_E$, $J_{CH}$=168 Hz), 97.9 (C-$1_B$, $J_{CH}$=171 Hz), 82.1 (C-$3_E$), 81.8 (C-$2_E$), 80.4 (bs, C-$3_B$), 80.0 (C-$4_C$), 78.8 (bs, C-$4_E$*), 78.3 (C-$4_B$*), 77.7 (C-$3_C$*), 76.9 (C-$3_D$), 75.9, 75.5, 75.3, 74.3 (4C, $OCH_2$), 73.4 (C-$4_D$), 73.2 ($OCH_2$), 72.7 (C-$2_B$), 72.1 (C-$5_E$), 69.1 (C-$5_C$), 67.7 (C-$5_D$*), 67.6 (C-$5_B$*), 62.7 (C-$6_D$), 59.1 (C-$2_D$), 57.5 ($OCH_3$), 41.4 ($CH_2Cl$), 29.5 $(C(CH_3)_2)$, 24.0 $(C(O)CH_3)$, 19.7 $(C(CH_3)_2)$, 18.8, 18.2 (2C, C-$6_B$, $6_C$); FAB-MS for $C_{81}H_{92}NClO_{21}$ (M, 1449.5) m/z 1472.7 [M+Na]$^+$. Anal. Calcd for $C_{81}H_{92}NClO_{21}$: C, 67.05; H, 6.39; N, 0.97%. Found: C, 66.21; H, 6.46; 1.01%.

Compound 135 had $[\alpha]_D$+26.7 (c 0.8); $^1$H NMR δ 8.07-7.15 (m, 35H, Ph), 5.47 (d, 1H, $J_{NH,2}$=7.4 Hz, $NH_D$), 5.45 (bs, 1H, H-$2_C$), 5.42 (d, 1H, $J_{1,2}$=2.3 Hz, H-$1_B$), 5.24 (d, 1H, $J_{1,2}$=3.4 Hz, H-$1_E$), 4.94 (d, 1H, $J_{1,2}$=8.2 Hz, H-$1_D$), 4.91-4.82 (m, 7H, H-$1_C$, $OCH_2$), 4.80 (d, 1H, J=11 Hz, $OCH_2$), 4.75 (d, 1H, J=11.6 Hz, $OCH_2$), 4.68 (dd, 1H, $J_{1,2}$=2.4, $J_{2,3}$=4.0 Hz, H-$2_B$), 4.65-4.47 (m, 4H, $OCH_2$), 4.44-4.32 (m, 4H, H-$5_E$, $3_D$, $3_C$, $OCH_2$), 4.15 (m, 1H, H-5C), 4.05 (pt, 1H, $J_{2,3}$=$J_{3,4}$=9.5 Hz, H-$3_E$), 4.03 (pt, 1H, $J_{3,4}$=$J_{4,5}$=9.4 Hz, H-$4_C$), 3.94 (dd, 1H, $J_{5,6a}$=5.3, $J_{6a,6b}$=10.7 Hz, H-$6a_D$), 3.83-3.75 (m, 4H, H-$6a_E$, $6b_D$, $CH_2Cl$), 3.74-3.70 (m, 3H, H-$4_E$, $6_E$, $3_B$), 3.65 (dd, 1H, $J_{2,3}$=3.4, $J_{2,3}$=9.4 Hz, H-$2_E$), 3.48 (pt, 2H, H-$4_B$, $4_D$), 3.46 (s, 3H, $OCH_3$), 3.38 (m, 1H, H-$5_D$), 3.22 (dq, 1H, $J_{4,5}$=9.5, $J_{5,6}$=6.2 Hz, H-$5_B$), 2.88 (m, 1H, H-$2_D$), 1.90 (s, 3H, $C(O)CH_3$), 1.42 (s, 3H, $C(CH_3)_2$), 1.36 (s, 6H, $C(CH_3)_2$, H-$6_C$), 1.30 (s, 3H, $J_{5,6}$=6.3 Hz, H-$6_B$); $^{13}$C NMR δ 171.8, 166.4 (2C, CO), 139.1-122.5 (Ph), 101.0 (C-$1_D$, $J_{CH}$=165 Hz), 99.7 $(C(CH_3)_2)$, 98.3 (C-$1_C$, $J_{CH}$=172 Hz), 97.8 (bs, C-$1_E$, $J_{CH}$=170 Hz), 97.5 (C-$1_B$, $J_{CH}$=176 Hz), 82.2 (C-$3_E$), 80.7 (C-$2_E$), 79.3 (bs, C-$4_B$), 78.8 (C-$3_B$), 78.1 (bs, C-$4_E$), 77.3 (C-$2_B$), 76.2 (bs, C-$3_C$), 75.8, 75.6, 74.9, 74.6, 73.9 (6C, C-$4_C$, $OCH_2$), 73.5 (2C, C-$4_D$, $2_C$), 71.4 ($OCH_2$), 71.0 (C-$3_D$), 70.7 (2C, C-$5_E$, $5_B$), 69.0 (C-$5_C$), 68.8 (C-$6_E$), 67.2 (C-$5_D$), 62.5 (C-$6_D$), 60.0 (C-$2_D$), 57.6 ($OCH_3$), 46.9 ($CH_2Cl$), 29.5 $(C(CH_3)_2)$, 23.9 $(C(O)CH_3)$, 19.7 $(C(CH_3)_2)$, 19.0 (C-$6_B$), 18.4 (C-$6_C$); FAB-MS for $C_{81}H_{92}NClO_{21}$ (M. 1449.5) m/z 1472.7 [M+Na]$^+$. Anal. Calcd for $C_{81}H_{92}NClO_{21}·H_2O$: C, 66.23; H, 6.34; N, 0.96%. Found: C, 66.11; H, 6.62; N, 0.85%.

Methyl (2 O-acetyl-3,4-di-O-benzyl-α-L-rhamnopyranosyl)-(1→3)-[(2,3,4,6-tetra-O-benzyl-α-D-glucopyranosyl-(1→4)]-(2-O-benzoyl-α-L-rhamnopyranosyl)-(1→3)-2-acetamido-2-deoxy-3,4-O-isopropylidene-β-D-glucopyranoside (130). The trisaccharide acceptor 125 (500 mg, 0.47 mmol) was dissolved in $CH_2Cl_2$ (5 mL) and the solution was cooled to −40° C. TMSOTf (21 μL) and donor 105 (328 mg, 0.62 mmol) were added and the mixture was left under stirring while the bath was slowly coming back to rt. After 5 h, more 105 (50 mg, 94 μmol) was added and the mixture was stirred at rt for 1 h more at rt. $Et_3N$ was added and the mixture was concentrated. Column chromatography of the residue (solvent B, 4:1→1:1) gave the fully protected 130 (484 mg, 72%) slightly contaminated with the corresponding trimethylsilyl side-product 126 The 130:126 ratio was estimated to be 85:15 from the $^1$H NMR spectrum. Eluting next was some residual starting 125 (45 mg, 9%), thus based on the consumed acceptor, the estimated yield of contaminated 130 was 79%. An analytical sample of 130 had $[\alpha]_D$+15.9 (c 0.8). $^1$H NMR: δ 8.09-7.14 (m, 35H, Ph), 6.04 (bs, 1H, NH$_D$), 5.76 (m, 1H, H-2$_B$), 5.37 (dd, 1H, J$_{1,2}$=1.9, J$_{2,3}$=2.8 Hz, H-2$_C$), 5.11 (d, 1H, J$_{1,2}$=3.1 Hz, H-1$_E$), 5.06 (d, 1H, H-1$_B$), 4.96 (bs, 1H, H-1$_C$), 5.02-4.82 (m, 7H, H-1$_D$, OCH$_2$), 4.69-4.37 (m, 6H, OCH$_2$), 4.28 (pt, 1H, J$_{2,3}$=J$_{3,4}$=9.5 Hz, H-3$_D$), 4.15 (dd, 1H, J$_{2,3}$=3.3, J$_{3,4}$=9.4 Hz, H-3$_C$), 4.13-3.93 (m, 5H, H-5$_E$, 6a$_E$, 3$_E$, 5$_C$, 6a$_D$), 3.87-3.76 (m, 5H, H-4$_E$, 6b$_E$, 3$_B$, 4$_C$, 6b$_D$), 3.68 (dq, 1H, J$_{4,5}$=9.5 Hz, H-5$_B$), 3.57 (pt, 1H, J$_{3,4}$=J$_{4,5}$=9.4 Hz, H-4$_D$), 3.54 (dd, 1H, J$_{2,3}$=3.2 Hz, H-2$_E$), 3.48 (s, 3H, OCH$_3$), 3.40 (m, 1H, H-5$_D$), 3.34 (pt, 1H, J$_{3,4}$=9.7 Hz, H-4$_B$), 3.27 (m, 1H, H-2$_D$), 2.18, 2.13 (2s, 6H, C(O)CH$_3$), 1.51, 1.42 (2s, 6H, C(CH$_3$)$_2$), 1.33 (d, 3H, J$_{5,6}$=6.2 Hz, H-2$_C$), 0.98 (d, 3H, J$_{5,6}$=6.2 Hz, H-2$_B$); $^{13}$C NMR δ 171.9, 170.5, 166.3 (3C, CO), 139.3-127.7 (Ph), 101.3 (C-1$_D$), 99.9 (C(CH$_3$)$_2$), 99.6 (C-1$_B$), 98.4 (C-1$_E$), 98.0 (C-1$_C$), 82.1 (C-3$_E$), 81.8 (C-2$_E$), 80.3 (2C, C-3$_C$, 4$_B$), 78.7 (bs, C-4$_C$), 78.2 (C-3$_B$*), 77.7 (C-4$_E$*), 76.9 (bs, C-3$_D$), 75.9, 75.4, 75.3, 74.3 (4C, OCH$_2$), 73.4 (C-4$_D$), 73.3 (OCH$_2$), 72.7 (C-2$_C$), 72.1 (C-5$_E$), 70.9 (OCH$_2$), 69.0 (3C, C-2$_B$, 5$_B$, 6$_E$), 67.8 (C-5$_C$), 67.6 (C-5$_D$), 62.7 (C-6$_D$), 59.2 (C-2$_D$), 57.5 (OCH$_3$), 29.5 (C(CH$_3$)$_2$), 24.0, 21.6 (2C, C(O)CH$_3$), 19.7 (C(CH$_3$)$_2$), 18.9 (C-6$_C$), 18.2 (C-6$_B$). FAB-MS for C$_{81}$H$_{93}$NO$_{21}$ (M, 1415) m/z 1438.6 [M+Na]$^+$.

Methyl (3,4-di-O-benzyl-α-L-rhamnopyranosyl)-(1→3)-[(2,3,4,6-tetra-O-benzyl-α-D-glucopyranosyl-(1→4)]-(2-O-benzoyl-α-L-rhamnopyranosyl)-(1→3)-2-acetamido-2-deoxy-3,4-O-isopropylidene-β-D-glycopyranoside (131). (a) Thiourea (22 mg, 0.29 mmol) was added to the chloroacetylated 129 (83 mg, 57 μmol) in MeOH/pyridine (1/1, 2.8 mL), and the mixture was heated overnight at 65° C. Volatiles were evaporated, and the solid residue thus obtained was taken up in the minimum of MeOH, CH$_2$Cl$_2$ was added, and the suspension was left standing at 0° C. for 1 h. The precipitate was filtered on a pad of Celite, and the filtrate was concentrated. Column chromatography of the residue (solvent B,9:1→1:1) gave the tetrasaccharide acceptor 131 (74 mg, 94%).

(b) The monoacetylated 130 (52 mg, 37 μmol) was dissolved in a mixture of EtOH (10 mL) and CH$_2$Cl$_2$ (100 μL). A freshly prepared 0.4 M ethanolic solution of guanidine (92 μL, 37 μmol) was added and the mixture was stirred at rt overnight. Volatiles were evaporated, and the residue taken up in CH$_2$Cl$_2$ was washed with water. The organic phase was dried and concentrated. Column chromatography of the crude product gave 131 (42 mg, 83%) as a glassy solid. Compound 131 had $[\alpha]_D$+27.3 (c 1.0); $^1$H NMR δ 8.24-6.88 (m, 35H, Ph), 5.90 (bs, 1H, NH$_D$), 5.29 (bs, 1H, H-2$_C$), 5.14 (d, 1H, J$_{1,2}$=3.0 Hz, H-1$_E$), 5.06 (d, 1H, J$_{1,2}$=1.6 Hz, H-1$_B$), 5.00-4.95 (m, 3H, H-1$_D$, 1$_C$, OCH$_2$), 4.88-4.46 (m, 9H, OCH$_2$), 4.31 (pt, 1H, J$_{2,3}$=J$_{3,4}$=9.4 Hz, H-3$_D$), 4.24 (bs, 1H, H-2$_B$), 4.14-3.08 (m, 3H, H-3$_C$, 5$_C$, 5$_E$), 4.02 (pt, 1H, J$_{2,3}$=J$_{3,4}$=9.3 Hz, H-3$_E$), 3.97 (dd, 1H, J$_{5,6a}$=5.2, J$_{6a,6b}$=10.7 Hz, 6a$_D$), 3.80 (m, 2H, H-4$_C$, 6b$_D$), 3.71 (m, 2H, H-6a$_E$, 6b$_E$), 3.66 (pt, 1H, J$_{4,5}$=9.5 Hz, H-4$_E$), 3.61-3.55 (m, 4H, H-3$_B$, 2$_E$, 5$_B$, 4$_D$), 3.50 (s, 3H, OCH$_3$), 3.42-3.36 (m, 2H, H-5$_D$, 4$_B$), 3.20 (m, 1H, H-2$_D$), 2.85 (bs, 1H, OH), 2.10 (s, 3H, C(O)CH$_3$), 1.51, 1.41 (2s, 6H, C(CH$_3$)$_2$), 1.33 (d, 3H, J$_{5,6}$=6.2 Hz, H-6$_C$), 1.15 (s, 3H, J$_{5,6}$=6.2 Hz, H-6$_B$); $^{13}$C NMR δ 171.7, 166.3 (2C, CO), 139.0-127.8 (Ph), 103.1 (C-1$_B$), 101.2 (C-1$_D$), 99.8 (C(CH$_3$)$_2$), 98.2, 98.1 (2C, C-1$_E$, 1$_C$), 82.0 (C-3$_E$), 81.5 (C-3$_B$*), 80.6 (C-4$_B$), 79.4 (C-2$_E$*), 79.1 (2C, C-4$_C$, 3$_C$), 78.2 (C-4$_B$), 76.8 (C-3$_D$), 76.0, 75.5, 74.5, 74.2 (4C, OCH$_2$), 73.9 (C-2$_C$), 73.7 (OCH$_2$), 73.5 (C-4$_D$), 72.1 (OCH$_2$), 71.6 (C-5$_E$), 69.0 (C-6$_E$), 68.7 (2C, C-2$_B$, 5$_B$), 67.9 (C-5$_C$), 67.5 (C-5$_D$), 62.7 (C-6$_D$), 59.4 (C-2$_D$), 57.5 (OCH$_3$), 29.5 (C(CH$_3$)$_2$), 24.0 (C(O)CH$_3$), 19.7 (C(CH$_3$)$_2$), 19.0 (C-6$_C$), 18.3 (C-6$_B$); FAB-MS for C$_{79}$H$_{91}$NO$_{20}$ (M, 1373) m/z 1396.5 [M+Na]$^+$. Anal. Calcd for C$_{79}$H$_{91}$NO$_{20}$·0.5 H$_2$O: C, 68.56; H, 6.65; N, 1.01%. Found: C, 68.53; H, 6.71; N, 1.01%.

Methyl (2-O-Acetyl-3,4-di-O-benzyl-α-L-rhamnopyranosyl)-(1→2)-(3,4-di-O-benzyl-α-L-rhamnopyranosyl)-(1→3)-[(2,3,4,6-tetra-O-benzyl-α-D-glucopyranosyl-(1→4)]-(2-O-benzoyl-3-O-chloroacetyl-α-L-rhamnopyranosyl)-(1→3)-2-acetamido-2-deoxy-3,4-O-isopropylidene-β-D-glucopyranoside (132). Activated 4 Å molecular sieves and TMSOTf (16 μL) were added to a solution of the tetrasaccharide acceptor 131 (406 mg, 0.29 mmol) in Et$_2$O (10 mL), and the mixture was stirred at −60° C. for 30 min. The donor 105 (234 mg, 0.44 mmol) in CH$_2$Cl$_2$ (7 mL) was added, and the mixture was stirred for 1 h while the bath temperature was reaching rt. After a further 1 h at this temperature, more 105 (50 mg, 94 μmol) was added, and the mixture was stirred for 1 h before Et$_3$N was added. Filtration through a pad of Celite and evaporation of the volatiles gave a residue which was column chromatographed twice (solvent B, 4:1; then solvent A, 17:3) to give 132 (262 mg, 52%) as a white powder; $[\alpha]_D$+25.9 (c 1.0); $^1$H NMR δ 8.07-7.13 (m, 45H, Ph), 6.03 (bs, 1H, NH$_D$), 5.59 (bs, 1H, H-2$_A$), 5.35 (bs, 1H, H-2$_C$), 5.16 (bs, 1H, H-1$_E$), 5.13 (bs, 1H, H-1$_A$), 5.06 (bs, 1H, H-1$_B$), 5.02-4.97 (m, 4H, H-1$_D$, 1$_C$, OCH$_2$), 4.91-4.50 (m, 12H, OCH$_2$), 4.44-4.32 (m, 4H, H-2$_B$, 3$_D$, OCH$_2$), 4.20-3.96 (m, 7H, H-5$_E$, 5$_A$, 3$_C$, 3$_E$, 6a$_D$, 5$_C$, 3$_A$), 3.87-3.68 (m, 6H, H-4$_E$, 6a$_E$, 6b$_E$, 6b$_D$, 4$_C$, 3$_B$), 3.64-3.47 (m, 7H, H-5$_B$, 4$_D$, 2$_E$, 4$_A$, OCH$_3$), 3.42 (m, 1H, H-5$_D$), 3.34 (pt, 1H, J$_{3,4}$=J$_{4,5}$=9.3 Hz, H-4$_B$), 3.17 (m, 1H, H-2$_D$), 2.13 (s, 3H, C(O)CH$_3$), 1.49 (s, 3H, C(CH$_3$)$_2$), 1.43 (s, 6H, C(CH$_3$)$_2$, H-2$_C$), 1.33 (d, 3H, J$_{5,6}$=6.1 Hz, H-6$_A$), 1.01 (d, 3H, J$_{5,6}$=5.8 Hz, H-6$_B$); $^{13}$C NMR δ 171.9, 170.3, 166.3 (3C, CO), 139.2-127.6 (Ph), 101.5 (bs, C-1$_B$, J$_{CH}$=171 Hz), 101.2 (C-1$_D$, J$_{CH}$=163 Hz), 99.8 (C(CH$_3$)$_2$), 99.7 (C-1$_A$, J$_{CH}$=171 Hz), 97.9(2C, C-1$_E$, 1$_C$, J$_{CH}$=172, J$_{CH}$=169 Hz), 82.4 (C-3$_E$), 82.1 (C-2$_E$), 80.5 (C-4$_A$), 80.2 (bs, C-3$_C$), 80.1 (C-4$_B$), 79.4, 78.1, 78.0 (4C, C-3$_B$, 4$_E$, 3$_A$, 4$_C$), 76.6 (bs, C-3$_D$), 75.9, 75.8, 75.4 (3C, OCH$_2$), 74.8 (2C, C-2$_B$, OCH$_2$), 73.5 (C-4$_D$), 73.4 (OCH$_2$), 73.2 (C-2$_C$), 72.1 (OCH$_2$), 71.8 (C-5$_A$), 71.2 (OCH$_2$), 69.4 (C-2$_A$), 69.2 (C-5$_B$), 68.9 (C-6$_E$), 68.7 (C-5$_C$), 67.8 (C-5$_E$), 67.5 (C-5$_D$), 62.7 (C-6$_D$), 59.6 (bs, C-2$_D$), 57.6 (OCH$_3$), 29.5 (C(CH$_3$)$_2$), 24.0, 21.4 (2C, C(O)CH$_3$), 19.7 (C(CH$_3$)$_2$), 19.1 (C-6$_A$), 18.8 (C-6$_C$), 18.2 (C-6$_B$); FAB-MS for C$_{101}$H$_{115}$NO$_{25}$ (M, 1741.7) m/z 1765.9 [M+Na]$^+$. Anal. Calcd for C$_{101}$H$_{115}$NO$_{25}$: C, 69.60; H, 6.65; N, 0.80%. Found: C, 69.56; H, 6.75; N, 0.73%.

Methyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (102). 50% aq TFA (1 mL) was added at 0° C. to a solution of the fully protected pentasaccharide 132 (155 mg, 89 μmol) dissolved in CH$_2$Cl$_2$ (4 mL). After 1 h at this temperature, volatiles were evaporated. The residue (crude 133) was taken up in 0.5M methanolic sodium methoxide (8 mL) and the mixture was heated overnight at 55° C. Neutralisation with Dowex X8 (H$^+$), evaporation of the volatiles, and column chromatography of the residue gave 134 (121 mg, 98%). Compound 134 (111 mg, 81 μmol) was dissolved in a mixture of ethanol (13 mL) and ethyl acetate (2.6 mL) containing 1N aq HCl (130 μL). Palladium on charcoal (130 mg) was added and the suspension was stirred under a hydrogen atmosphere for 2 h. Filtration of the catalyst and reverse phase chromatography gave the target pentasaccharide (60 mg, 88%) as a slightly yellow foam. RP-HPLC purification followed by freeze-drying gave pure 102 (36 mg). Compound 102 had Rt: 9.63 min (solvent F, 100: 0→80:20 over 20 min); $[\alpha]_D$–18.6 (c 1.0, methanol); $^1$H NMR δ 5.13 (d, 1H, $J_{1,2}$=3.7 Hz, H-1$_E$), 4.98 (bs, 1H, H-1$_B$), 4.90 (d, 1H, $J_{1,2}$=1.4 Hz, H-1$_A$), 4.72 (d, 1H, 1.4 Hz, H-1$_C$), 4.39 (d, 1H, $J_{1,2}$=8.6 Hz, H-1$_D$), 4.09 (dq, 1H, $J_{4,5}$=9.2 Hz, H-5$_C$), 4.00 (m, 2H, H-2$_B$, 2$_A$), 3.94-3.79 (m, 7H, H-5$_E$, 2$_C$, 3$_C$, 6a$_E$, 6a$_D$, 2$_D$, 3$_A$), 3.76-3.65 (m, 7H, H-4$_C$, 3$_E$, 6b$_E$, 6b$_D$, 5$_A$, 5$_B$, 3$_B$), 3.52 (pt, 1H, $J_{3,4}$=8.8 Hz, H-3$_D$), 3.49-3.33 (m, 9H, H-4$_D$, 2$_E$, 4$_A$, 4$_B$, 5$_D$, 4$_E$, OCH$_3$), 1.98 (s, 3H, C(O)CH$_3$), 1.27 (d, 3H, $J_{5,6}$=6.3 Hz, H-6$_C$), 1.24, 1.23 (d, 3H, H-6$_A$, 6$_B$); $^{13}$C NMR δ 172.3 (CO), 100.7 (C-1$_A$, $J_{CH}$=171 Hz), 99.6 (2C, C-1$_D$, 1$_B$, $J_{CH}$=163, $J_{CH}$=170 Hz), 99.2 (C-1$_C$, $J_{CH}$=170 Hz), 95.7 (bs, C-1$_E$, $J_{CH}$=170 Hz), 82.0 (C-3$_D$), 79.1 (C-2$_B$), 79.4 (bs, C-3$_C$), 76.4 (C-5$_D$*), 75.4 (bs, C-4$_C$), 73.0 (C-3$_E$), 72.4 (2C, C-4$_A$, 4$_B$), 72.2 (C-5$_E$), 71.7 (C-2$_E$), 71.1 (C-2$_C$), 70.4, 70.1, 70.0 (4C, C-2$_A$, 3$_A$, 3$_B$, 4$_E$), 69.7, 69.6, 69.3 (3C, C-5$_A$, 5$_B$, 5$_C$), 68.8 (C-4$_D$), 61.2, 61.0 (2C, C-6$_D$, 6$_E$), 57.4 (OCH$_3$), 55.4 (C-2$_D$), 22.6 (C(O)CH$_3$), 18.2 (C-6$_C$), 17.2, 17.0 (C-6$_A$, 6$_B$); HRMS (MALDI) Calcd for C$_{33}$H$_{57}$NO$_{23}$+ Na: 858.3219. Found: 858.3089.

Methyl (2-O-Acetyl-3,4-di-O-benzyl-α-L-rhamnopyranosyl)-(1→3)-[(2,3,4,6-tetra-O-benzyl-α-D-glucopyranosyl-(1→4)]-(2-O-benzoyl-α-L-rhamnopyranosyl)-(1→3)-2-acetamido-2-deoxy-β-D-glucopyranoside (136). 50% aq TFA (400μL) was added to a solution of the fully protected tetrasaccharide 130 (57 mg, 40 μmol) in CH$_2$Cl$_2$ (1 mL) at 0° C., and the mixture was stirred overnight at this temperature. Volatiles were evaporated and the residue was purified by column chromatography (solvent B, 1:1) to give diol 136 (47 mg, 85%). $[\alpha]_D$+19.5 (c 0.9); $^1$H NMR δ 8.10-7.16 (m, 35H, Ph), 5.80 (d, 1H, J=8.8 Hz, NH$_D$), 5.66 (m, 1H, H-2$_B$), 5.39 (pt, 1H, $J_{1,2}$=2.8 Hz, H-2$_C$), 5.01 (m, 2H, H-1$_B$, 1$_E$), 4.96 (m, 2H, H-1$_C$, OCH$_2$), 4.90-4.81 (m, 5H, H-1$_D$, OCH$_2$), 4.66-4.41 (m, 7H, OCH$_2$), 4.18 (dd, 1H, $J_{2,3}$=2.9, $J_{3,4}$=7.4 Hz, H-3$_C$), 4.10 (pt, 1H, H-3$_D$), 4.08-3.95 (m, 5H, H-5$_E$, 3$_E$, 5$_C$), 3.89-3.64 (m, 8H, H-6a$_D$, 6b$_D$, 6a$_E$, 6b$_E$, 3$_B$, 4$_C$, 4$_E$, 5$_B$), 3.54-3.49 (m, 5H, H-2$_E$, 4$_D$, OCH$_3$), 3.45 (m, 1H, H-5$_D$), 3.33 (pt, 1H, $J_{3,4}$=$J_{4,5}$=9.4 Hz, H-4$_B$), 3.27 (m, 1H, H-2$_D$), 2.26 (bs, 1H, OH), 2.17 (s, 6H, C(O)CH$_3$), 1.99 (bs, 1H, OH), 1.39 (d, 3H, $J_{5,6}$=6.2 Hz, H-6$_C$), 0.95 (d, 3H, $J_{5,6}$=6.1 Hz, H-6$_B$); $^{13}$C NMR δ 171.5, 170.4, 166.1 (3C, CO), 139.1-127.8 (Ph), 100.9 (C-1$_D$), 99.7 (2C, C-1$_B$*, 1$_C$), 99.2 (bs, C-1$_E$), 85.0 (C-3$_D$), 82.1 (C-3$_E$), 81.3 (bs, C-3$_C$), 80.1 (C-4$_B$), 78.0, 77.8 (4C, C-3$_C$, 4$_C$, 3$_B$, 4$_E$), 76.0 (OCH$_2$), 75.6 (C-5$_D$), 75.3, 75.2, 74.4, 73.4 (4C, OCH$_2$), 72.3 (C-2$_C$), 72.1 (C-5$_C$*), 71.3 (C-4$_D$), 71.2 (OCH$_2$), 69.2 (C-5$_B$), 69.0 (C-5$_E$, 2$_B$), 68.4 (C-6$_E$), 63.2 (C-6$_D$), 57.4 (2C, C-2$_D$, OCH$_3$), 23.9, 21.0 (2C, C(O)CH$_3$), 19.1 (C-6$_C$), 18.0 (C-6$_B$). FAB-MS for C$_{78}$H$_{89}$NO$_{21}$ (M, 1375.59) m/z 1398.6 [M+Na]$^+$. Anal. Calcd for C$_{78}$H$_{89}$NO$_{21}$: C, 68.06; H, 6.52; N, 1.02%. Found: C, 68.10; H, 6.62; N, 0.98%.

Methyl α-L-rhamnopyranosyl-(1→3)-[α-D-glucopyranosyl-(1→4)]-α-L-rhamnopyranosyl-(1→3)-2-acetamido-2-deoxy-β-D-glucopyranoside (103). 1% methanolic sodium methoxide (255 μL) was added to a suspension of diol 136 (68 mg, 49 μmol) in MeOH (2 mL) and the mixture was healed overnight at 55° C. TLC (solvent A, 19:1) showed that the starting material had been converted to a more polar product. Neutralisation with Dowex X8 (H$^+$), evaporation of the volatiles, and column chromatography (solvent A, 24:1) gave tetraol 137 (52 mg, 85%). The latter (48 mg, 39 μmol) was dissolved in a mixture of ethanol (5 mL) and ethyl acetate (2 mL) containing 1N aq HCl (50 μL). Palladium on charcoal (50 mg) was added and the suspension was stirred under a hydrogen atmosphere overnight. TLC (solvent E, 4:1:2) showed the presence of a single product. Filtration of the catalyst and reverse phase chromatography, followed by RP-HPLC purification and freeze-drying gave pure 103 (19 mg, 71%). Rt: 9.35 min (solvent F, 100:0→80:20 over 20 min); $[\alpha]_D$+12.5 (c 0.8, methanol); $^1$H NMR δ 5.09 (d, 1H, $J_{1,2}$=3.7 Hz, H-1$_E$), 4.89 (bs, 1H, H-1$_B$), 4.71 (d, 1H, $J_{1,2}$=1.1 Hz, H-1$_C$), 4.39 (d, 1H, $J_{1,2}$=8.6Hz, H-1$_D$), 4.08 (dq, 1H, $J_{4,5}$=9.3 Hz, H-5$_C$), 3.96 (dd, 1H, $J_{1,2}$=1.4, $J_{2,3}$=3.2 Hz, H-2$_B$), 3.88-3.80 (m, 4H, H-2$_C$, 3$_C$, 6a$_E$, 6b$_E$, 5$_D$), 3.77-3.62 (m, 6H, H-6a$_D$, 6b$_D$, 3$_B$, 5$_B$, 2$_D$, 4$_C$), 3.59 (pt, 1H, $J_{3,4}$=$J_{4,5}$=9.4 Hz, H-3$_E$), 3.50 (pt, 1H, $J_{3,4}$=$J_{4,5}$=9.4 Hz, H-3$_E$), 3.50 (pt, 1H, $J_{3,4}$=$J_{4,5}$=8.7 Hz, H-3$_D$), 3.47-3.34 (m, 8H, H-2$_E$, 4$_E$, 4$_B$, 4$_D$, 5$_E$, OCH$_3$), 1.98 (s, 3H, C(O)CH$_3$), 1.27 (d, 3H, $J_{5,6}$=6.3 Hz, H-6$_C$), 1.21 (d, 3H, $J_{5,6}$=6.3 Hz, H-6$_B$); $^{13}$C NMR δ 174.5 (CO), 103.2 (bs, C-1$_B$, $J_{CH}$=172 Hz), 101.8 (C-1$_D$, $J_{CH}$=160 Hz), 101.5 (C-1$_C$, $J_{CH}$=170 Hz), 98.0 (C-1$_E$, $J_{CH}$=170 Hz), 82.2 (C-3$_D$), 79.1 (bs, C-3$_C$), 76.6 (bs, C-4$_C$), 76.4 (C-4$_B$*), 72.9 (C-3$_E$), 72.3, 72.2 (2C, C-4$_D$, C-5$_D$), 71.87 (C-2$_E$), 71.1 (bs, C-2$_C$), 70.6 (2C, C-2$_B$, 3$_B$), 69.7, 69.6 (2C, C-5$_E$, 5$_B$), 69.2, 68.9 (2C, C-6$_D$, 6$_E$), 57.4 (OCH$_3$), 55.4 (C-2$_D$), 22.6 (C(O)CH$_3$), 18.0 (C-6$_C$), 17.0 (C-6$_B$). HRMS (MALDI) Calcd for C$_{27}$H$_{47}$NO$_{19}$NA: 712.2635. Found: 712.2635.

B—Synthesis of a Pentasaccharide Building Block of the O-specific Polysaccharide of Shigella flexneri Serotype 2a: DAB(E)C Dodecyl 3,4,6-tri-O-acetyl-2-deoxy-1-thio-2-trichloroacetamido-β-D-glucopyranoside (205). A mixture of the peracetylated 204 (G. Blatter, J.-M. Beau, J.-C. Jacquinet, Carbohydr. Res. 1994, 260, 189-202) (6.2 g, 12.5 mmol) and dodecanthiol (2.5 mL, 94 mmol), 4 Å molecular sieves and dry 1,2-DCE (90 mL) was stirred for 1 h, then cooled to 0° C. BF$_3$.Et$_2$O (1.57 mL, 12.5 mmol) was added. The stirred mixture was allowed to reach rt in 2 h 30. Et$_3$N was added until neutral pH and the mixture filtered. After evaporation, the residue was eluted from a column of silica gel with 2:1 cyclohexane-EtOAc to give 205 as a white solid (7.5 g, 93%); $[\alpha]_D$–20° (c 1, CHCl$_3$). $^1$H NMR: δ 6.82 (d, 1H, $J_{2,NH}$=9.2 Hz, NH), 5.31 (dd, 1H, $J_{2,3}$=9.9, $J_{3,4}$=9.6 Hz, H-3), 5.15 (dd, 1H, $J_{4,5}$=9.6 Hz, H-4), 4.68 (d, 1H, $J_{1,2}$=10.3 Hz, H-1), 4.28 (dd, 1H, $J_{5,6a}$=5.0, $J_{6a,6b}$=12.3 Hz, H-6a), 4.17 (dd, 1H, $J_{5,6b}$=2.3 Hz, H-6b), 4.11 (dd, 1H, H-2), 3.75 (m, 1H, H-5), 2.70 (m, 2H, SCH$_2$), 2.10, 2.05, 2.04 (3s, 9H, OAc), 1.65-1.20 (m, 20H, (CH$_2$)$_{10}$CH$_3$), 0.90 (t, 3H, (CH$_2$)$_{10}$CH$_3$). $^{13}$C NMR: δ 171.0, 170.7, 169.3 (C=O), 161.9 (C=OCCl$_3$), 92.3 (CCl$_3$), 84.2 (C-1), 76.5 (C-5), 73.4 (C-3), 68.6 (C-4), 62.6 (C-6), 55.2 (C-2), 32.3, 30.6, 30.0-29.1, 14.5 (S(CH$_2$)$_{11}$CH$_3$), 21.1, 21.0, 20.9 (OAc). FAB-MS for C$_{26}$H$_{42}$Cl$_3$NO$_8$S (M, 635.0) m/z 658.1 [M+Na]$^+$. Anal. Calcd for C$_{26}$H$_{42}$Cl$_3$NO$_8$S: C, 49.17; H, 6.67; N, 2.21%. Found: C, 49.16; H, 6.71; N, 2.13%.

Dodecyl 2-deoxy-4,6-O-isopropylidene-1-thio-2-trichloroacetamido-β-D-glucopyranoside (207). A mixture of 205 (5.0 g, 7.87 mmol) in MeOH (15 mL) was deacetylated by catalytic MeONa overnight. The solution was neutralized by IR 120 (H$^+$) and filtered. After concentration in vacuo, the residue 206 was treated by 2,2-dimethoxypropane (70 mL) and APTS (148 mg, 0.94 mmol) in DMF (20 mL). After stirring overnight, the mixture was neutralized with Et$_3$N and concentrated. The residue was eluted from a column of silica gel with 3:1 cyclohexane-EtOAc to give 207 as a white solid (3.45 g, 80%); $[\alpha]_D$–35° (c 1, ChCl$_3$). $^1$H NMR: δ 6.92 (d, 1H, $J_{2,NH}$=8.0 Hz, NH), 4.77 (d, 1H, $J_{1,2}$=10.4 Hz, H-1), 3.98 (m, 1H, $J_{2,3}$=$J_{3,4}$=9.2 Hz, H-3), 3.88 (dd, 1H, $J_{5,6a}$=5.4, $J_{6a,6b}$=10.8 Hz, H-6a), 3.70 (dd, 1H, $J_{5,6b}$=0.5 Hz, H-6b), 3.63 (m, 1H, H-2), 3.53 (pt, 1H, $J_{4,5}$=9.2 Hz, H-4), 3.29 (m, 1H, H-5), 2.98 (s, 1H, OH), 2.60 (m, 2H, SCH$_2$), 1.60-1.10 (m, 20H, (CH$_2$)$_{10}$CH$_3$), 1.45, 1.35 (2s, 6H, C(CH$_3$)$_2$), 0.80 (t, 3H, CH$_3$); $^{13}$C NMR: δ 162.5 (C=OCCl$_3$), 100.3 (C(CH$_3$)$_2$), 92.8 (CCl$_3$), 84.0 (C-1), 74.6 (C-4), 72.3 (C-3), 71.7 (C-5), 62.2 (C-6), 58.3 (C-2), 29.3, 19.5 (C(CH$_3$)$_2$), 32.3, 30.8, 30.1-29.5, 29.1, 14.5 (SCH$_2$(CH$_2$)$_{10}$CH$_3$). FAB-MS for C$_{23}$H$_{40}$Cl$_3$NO$_5$S (M, 548.9) m/z 572.2 [M+Na]$^+$. Anal. Calcd for C$_{23}$H$_{40}$Cl$_3$NO$_5$S: C, 50.32; H, 7.34; N, 2.55%. Found: C, 50.30; H, 7.40; N, 2.36%.

Dodecyl 3-O-acetyl-2-deoxy-4,6-O-isopropylidene-1-thio-2-trichloroacetamido-β-D-glucopyranoside (208). A mixture of 207 (1.07 g, 1.94 mmol) in pyridine (10 mL) was cooled to 0° C. Ac$_2$O (5 mL) was added and the solution was allowed to reach rt in 2 h. The mixture was then concentrated and pyridine was coevaporated with toluene. The residue was eluted from a column of silica gel with 6:1 cyclohexane-EtOAc with 0.2% of Et$_3$N to give 208 as a white solid (1.12 g, 97%): [α]$_D$ −62° (c 1, CHCl$_3$); $^1$H NMR: δ 7.51 (d, 1H, $J_{2,NH}$=9.7 Hz, NH), 5.40 (dd, 1H, $J_{2,3}$=$J_{3,4}$=10.0 Hz, H-3), 4.62 (d, 1H, $J_{1,2}$=10.4 Hz, H-1), 4.20 (m, 1H, H-2), 4.01 (dd, 1H, $J_{5,6a}$=5.2, $J_{6a,6b}$=10.7 Hz, H-6a), 3.84 (dd, 1H, $J_{4,5}$=9.7 Hz, H-4), 3.70 (m, 2H, H-5, H-6b), 2.68 (m, 2H, SCH$_2$), 2.09 (s, 3H, OAc), 1.60-1.20 (m, 20H, (CH$_2$)$_{10}$CH$_3$), 1.52, 1.38 (2s, 6H, C(CH$_3$)$_2$), 0.90 (t, 3H, SCH$_2$(CH$_2$)$_{10}$CH$_3$). $^{13}$C NMR: δ 171.4 (C=O), 161.8 (C=OCCl$_3$), 99.5 (C(CH$_3$)$_2$), 92.3 (CCl$_3$), 84.6 (C-1), 73.6 (C-3), 72.0 (C-4), 71.9 (C-5), 62.2 (C-6), 55.0 (C-2), 29.1, 19.3 (C(CH$_3$)$_2$), 32.3, 30.7, 30.0-29.0, 14.5 (SCH$_2$(CH$_2$)$_{10}$CH$_3$). FAB-MS for C$_{25}$H$_{42}$Cl$_3$NO$_6$S (M, 591.0) m/z 614.1 [M+Na]$^+$. Anal. Calcd for C$_{25}$H$_{42}$Cl$_3$NO$_6$S: C, 50.80; H, 7.16; N, 2.37%. Found: C, 50.67; H, 7.32; N, 2.24%.

Allyl 3,4-di-O-benzyl-2-O-levulinoyl-α-L-rhamnopyranoside (210). DCC (5.76 g, 28.0 mmol), levulinic acid (2.65 g, 22.8 mmol)) and DMAP (115 mg) were added to a solution of alcohol 209 (1.65 g, 4.29 mmol) in THF (70 mL). The suspension was stirred at rt overnight. Et$_2$O was added and solids were filtered. The filtrate was concentrated, and the residue was purified twice from a column of silica gel, eluting first with 99.5:0.5 to 98:2 DCM-EtOAc, then with 9:1 cyclohexane-acetone. The target 210 (2.00 g 97%)) as a colourless oil slightly contaminated by a less polar product. $^1$H NMR: δ 7.40-7.30 (m, 10H, Ph), 5.90 (m, 1H, All), 5.40 (dq, 1H, $J_{1,2}$=1.8, $J_{2,3}$=3.4 Hz, H-2), 5.28 (m, 1H, All), 5.20 (m, 1H, All), 4.93 (d, 1H, J=10.8 Hz, CH$_2$Ph), 4.78 (d, 1H, $J_{1,2}$=1.6 Hz, H-1), 4.78 (d, 1H, J=11.2 Hz, CH$_2$Ph), 4.63 (d, 1H, CH$_2$Ph), 4.51 (d, 1H, CH$_2$Ph), 4.17 (m, 2H, All, H-3), 3.78 (dq, 1H, $J_{4,5}$=9.5, $J_{5,6}$=6.2 Hz, H-5), 3.43 (pt, 1H, $J_{3,4}$=9.5 Hz, H-4), 2.80 (m, 4H, Lev), 2.19 (s, 3H, Ac), 1.37 (d, 3H, H-6). $^{13}$C NMR: δ 124.0-125.1 (Ph), 118.0 (All), 97.0 (C-1), 80.2 (C-4), 78.5 (C-3), 75.2 (CH$_2$Ph), 72.0 (CH$_2$Ph), 70.2 (C-2), 68.5 (All), 68.3 (C-5), 38.5 (Lev), 31.5 (Ac), 28.5 (Lev), 20.1 (C-6). Anal. Calcd for C$_{25}$H$_{30}$O$_7$: C, 69.69; H, 7.10. Found: C, 69.61; H, 7.10.

3,4-Di-O-benzyl-2-O-levulinoyl-α-L-rhamnopyranose (211). 1,5-Cyclooctadiene-bis(methyldiphenylphosphine) iridium hexafluorophosphate (25 mg, 20 µmol) was dissolved THF and the resulting red solution was degassed in an argon stream. Hydrogen was then bubbled through the solution, causing the colour to change to yellow. The solution was then degassed again in an argon stream. A solution of 210(1.4 g, 3.12 mmol) in THF was degassed and added. The mixture was stirred at rt overnight, then concentrated to dryness. The residue was dissolved in a solution of I$_2$ (1.37 g, 5.4 mmol) in 30 mL of THF/H$_2$O (15:4). The mixture was stirred at rt for 1 h, and THF was evaporated. The resulting suspension was taken up in DCM, washed twice with water, satd aq NaHSO$_3$, water, satd aq NaHCO$_3$, water and said aq NaCl, successively. The organic layer was dried and concentrated. The residue was eluted from a column of silica gel with 7:3 to 6:4 Cyclohexane-EtOAc to give the corresponding hemiacetal 211 (1.3 g, 93%). $^1$H NMR: δ 7.40-7.30 (m, 10H, Ph), 5.40 (dq, 1H, $J_{1,2}$=1.8, $J_{2,3}$=3.4 Hz, H-2), 4.93 (d, 1H, J=10.8 Hz, CH$_2$Ph), 4.78 (d, 1H, $J_{1,2}$=16 Hz, H-1), 4.78 (d, 1H, J=11.2 Hz, CH$_2$Ph), 4.63 (d, 1H, CH$_2$Ph), 4.51 (d, 1H, CH$_2$Ph), 3.99 (m, 1H, $J_{3,4}$=9.5 Hz, H-3), 3.78 (dq, 1H, $J_{4,5}$=9.5, $J_{5,6}$=6.2 Hz, H-5), 3.43 (pt, 1H, H-4), 2.80 (m, 4H, Lev), 2.19 (s, 3H, Ac), 1.37 (d, 3H, H-6). Anal. Calcd for C$_{28}$H$_{34}$O$_7$: C, 67.86; H, 6.83. Found: C. 67.94; H, 6.87.

3,4-Di-O-benzyl-2-O-levulinoyl-α-L-rhamnopyranosyl trichloroacetimidate (212). Trichloroacetonitrile (1.3 mL, 13 mmol) and DBU (51 µL, 0.3 mmol) were added to a solution of the residue 211 (1.0 g, 2.3 mmol) in anhydrous DCM (6 mL) at 0° C. After 2 h, the mixture was concentrated. The residue was eluted from a column of silica gel with 3:1 cyclohexane-EtOAc and 0.2% Et$_3$N to give 212 as a white foam (1.0 g, 95%); $^1$H NMR: δ 8.67 (s, 1H, NH), 7.40-7.30 (m, 10H, Ph), 6.19 (d, 1H, $J_{1,2}$=1.9 Hz, H-1), 5.48 (dd, 1H, $J_{1,2}$=2.0, $J_{2,3}$=3.3 Hz, H-2), 4.95 (d, 1H, CH$_2$Ph), 4.73 (d, 1H, CH$_2$Ph), 4.66 (d, 1H, CH$_2$Ph), 4.58 (d, 1H, CH$_2$Ph), 4.51 (d, 1H, CH$_2$Ph), 4.00 (dd, 1H, $J_{3,4}$=9.5 Hz, H-3), 3.95 (dq, 1H, $J_{4,5}$=9.6, $J_{5,6}$=6.3 Hz, H-5), 3.52 (pt, 1H, H-4), 2.80 (m, 4H, Lev), 2.20 (s, 3H, Ac), 1.36 (d, 3H, H-6). Anal. Calcd for C$_{27}$H$_{30}$Cl3NO$_7$.0.5H$_2$O: C, 54.42; H, 5.24; N, 2.35. Found: C, 54.06; H, 5.06; 2.05.

Allyl (2-O-levulinoyl-3,4-di-O-benzyl-α-L-rhamnopyranosyl)-(1→3)-[2,3,4,6-tetra-O-benzyl-α-D-glucopyranasyl-(1→4)]-2-O-benzoyl-α-L-rhamnopyranoside (215). A mixture of alcohol 214 (F. Segat, L. A. Mulard, *Tetrahedron: Asymmetry* 2002, 13, 2211-2222) (300 mg, 0.36 mmol) and imidate 212 (320 mg, 0.54 mmol) in anhydrous Et$_2$O (20 mL) was stirred for 15 min under dry Ar. After cooling at −75° C., Me$_3$SiOTf (13 µL, 70 µmol) was added dropwise and the mixture was stirred 3 h. Et$_3$N (60 µL) was added and the mixture was concentrated. The residue was eluted from a column of silica gel with 9:1 cyclohexane-EtOAc to give 215 (440 mg, 92%) as a colourless foam. $^1$H NMR: δ 8.10-7.10 (m, 35H, Ph), 5.95 (m, 1H, All), 5.73 (dd, 1H, $J_{1,2}$=2.2, $J_{2,3}$=2.3 Hz, H-2$_B$), 5.43 (dd, 1H, $J_{1,2}$=2.0, $J_{2,3}$=3.0 Hz, H-2$_C$), 5.30 (m, 2H, All), 5.08 (d, 1H, $J_{1,2}$=3.2 Hz, H-1$_E$), 5.03 (d, 1H, $J_{1,2}$=1.7 Hz, H-1$_B$), 4.97 (d, 1H, $J_{1,2}$=1.9 Hz, H-1$_C$), 4.30-5.00 (m, 12H, CH$_2$Ph), 4.20 (m, 2H, All, H-3$_C$), 4.05 (m, 3H, All, H-3$_E$, 5$_E$), 3.98 (m, 1H, H-6a$_E$), 3.81 (m, 5H, H-3$_B$, 4$_C$, 4$_E$, 5$_C$, 6$_E$), 3.69 (dq, 1H, $J_{4,5}$=9.3, $J_{5,6}$=6.0 Hz, H-5$_B$), 3.52 (dd, 1H, $J_{2,3}$=9.7 Hz, H-2$_E$), 3.29 (dd, 1H, $J_{3,4}$=$J_{4,5}$=9.4 Hz, H-4$_B$), 2.71 (m, 4H, CH$_2$CH$_2$), 2.15 (s, 3H, Ac), 1.40 (d, 3H, H-6$_C$), 1.01 (d, 3H, H-6$_B$).

Allyl (3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (216). The trisaccharide 215 (200 mg, 0.16 mmol) was treated with 0.4 mL of a solution 1 M of hydrazine (100 mg) diluted in a mixture of pyridine (1.6 mL) and acetic acid (0.4 mL) at rt. The solution was stirred during 20 min. Acetone (1.2 mL) was added and the solution was concentrated. The residue was eluted from a column of silica gel with 98.5:1.5 DCM-EtOAc to give 216 (174 mg) as a foam. Although, contaminated with hydrazine salts, the $^1$H NMR spectrum showed that compound 216 had NMR data identical to that of a reference compound. (F. Bélot, K. Wright, C. Costachel, A. Phalipon, L. A. Mulard, *J. Org. Chem.* 2004, 69, 1060-1074)

Allyl (2-O-levulinoyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (217). Triflic acid (3.5 µL, 40 µmol) was added to a mixture of the donor 212 (88 mg, 265 µmol), the acceptor 216 (F. Bélot, K. Wright, C. Costachel, A. Phalipon, L. A. Mulard, *J. Org. Chem.* 2004, 69, 1060-1074) (197 mg, 176 µmol), and 4 Å molecular sieves in dry DCM (2.5 mL) kept under stirring at −30° C. The suspension was stirred for 1 h at this temperature, then at rt for 2 h. More 212 (40 mg, 120 mmol) was added and the mixture was kept at 4° C. for 40 h. After addition of more triflic acid (1 µL, 11 µmol) and stirring for 2 h at rt, Et$_3$N was added to the reaction mixture. Filtration through a pad of Celite, and evaporation of the volatiles resulted in a oily residue which was purified by flash chromatography with 7:3 cyclohexane-EtOAc to give 217 (123 mg, 54%).

$^1$H NMR: δ 8.10-7.00 (m, 45H, Ph), 5.82 (m, 1H, All), 5.61 (bs, 1H, H-2$_A$), 5.48 (bs, 1H, H-2$_C$), 5.34 (m, 2H, All), 4.97 (bs, 2H, H-1$_B$, 1$_E$), 5.10 (bs, 1H, H-1$_C$), 5.02 (bs, 1H, H-1$_A$), 5.06-4.37 (m, 16H, CH$_2$Ph), 4.45 (bs, 1H, H-2$_B$), 4.28-3.83 (m, 8H, H-3$_E$, 5$_E$, 3$_A$, 5$_A$, 3$_C$, 5$_C$), 3.83 (m, 3H, H-6a$_E$, 6b$_E$, 4$_C$), 3.80 (m, 1H, H-4$_E$), 3.72 (dd, 1H, H-3$_B$), 3.66 (m, 1H, H-5$_B$), 3.57 (dd, 1H, H-2$_E$), 3.51 (dd, 1H, H-4$_A$), 3.39 (dd, 1H, H-4$_B$), 2.66 (m, 4H, CH$_2$CH$_2$), 2.13 (s, 3H, CH$_3$), 1.45 (2d, 6H, H-6$_A$, 6$_C$), 1.07 (d, 3H, H-6$_B$); $^{13}$C NMR: δ 206.4, 172.1, 166.2 (3C, C=O), 139.2-127.6 (Ph), 118.1 (All), 101.4 (C-1$_B$), 99.7 (C-1$_A$), 98.3 (C-1$_E$), 96.5 (C-1$_C$), 82.3 (C-3$_E$), 81.5 (C-2$_E$), 80.5 (C-3$_C$), 80.2 (2C, C-4$_A$, 4$_B$), 79.3 (C-3$_B$), 78.6 (C-3$_A$), 78.0 (2C, C-4$_C$, 4$_E$), 76.0, 75.8, 75.6 (3C, CH$_2$Ph), 75.2 (C-2$_B$), 75.0, 74.4, 73.4 (3C, CH$_2$Ph), 72.9 (C-2$_C$), 72.0 (CH$_2$Ph), 71.8 (C-5$_E$), 71.1 (CH$_2$Ph), 69.8 (C-2$_A$), 69.3 (C-5$_B$), 68.9, 68.8 (All, C-6$_E$), 68.7 (C-5$_A$), 68.0 (C-5$_C$), 38.5, 28.5 (2C, CH$_2$CO), 30.2 (CH$_3$), 19.2, 18.8, 18.2 (3C, C-6$_A$, 6$_B$, 6$_C$).

Allyl (3,4-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (218). The tetrasaccharide 217 (121 mg, 0.09 mmol) was treated with 235 µL of a 1 M solution of hydrazine hydrate (100 mg) in a mixture of pyridine (1.6 mL) and acetic acid (0.4 mL) at rt. The solution was stirred during 15 min. Acetone (3 mL) was added and the solution was concentrated. The residue was eluted from a column of silica gel with 9:1 cyclohexane-acetone to give alcohol 218 (70 mg). Compound 218 had NMR data identical to that of a reference compound. (F. Bélot, K. Wright, C. Costachel, A. Phalipon, L. A. Mulard, *J. Org. Chem* 2004, 69, 1060-1074)

Allyl (3-O-acetyl-4,6-O-isopropylidene-2-trichloroacetamido-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (219). A mixture of the donor 208 (294 mg, 357 µmol), the acceptor 218 (F. Bélot, K. Wright, C Costachel, A. Phalipon. L. A. Mulard, *J. Org. Chem.* 2004, 69, 1060-1074) (313 mg, 211 µmol), and 4 Å molecular sieves in dry DCM (4 mL) was stirred for 1.5 h then cooled to −15° C. NIS (94 mg, 0.42 mmol) and triflic acid (8 µL, 0.1 mmol) were successively added. The stirred mixture was allowed to reach 0° C. in 1.5 h. Et$_3$N (25 µL) was added and the mixture filtered. After evaporation, the residue was eluted from a column of silica gel with 6:1 cyclohexane-EtOAc and 0.5% of Et$_3$N to give 219 as a white foam (232 mg, 58%); [α]$_D$−2° (c 1, CHCl$_3$); $^1$H NMR: δ 7.00-8.00 (m, 45H, Ph), 6.81 (d, 1H, J$_{2,NH}$=9.0 Hz, NH$_D$), 5.82 (m, 1H, All), 5.30 (dd, 1H, J$_{1,2}$=1.0, J$_{2,3}$=3.0 Hz, H-2$_C$), 5.10-5.23 (m, 2H, All), 4.96 (bs, 1H, H-1$_A$), 4.91 (d, 1H, J$_{1,2}$=3.1 Hz, H-1$_E$), 4.87 (d, 1H, J$_{1,2}$=1.6 Hz, H-1$_B$), 4.84 (bs, 1H, H-1$_C$), 4.79 (dd, 1H, J$_{2,3}$=J$_{3,4}$=10.0 Hz, H-3$_D$), 4.35 (d, 1H, H-1$_D$), 4.34 (dd, 1H, H-2$_B$), 4.20-4.80 (m, 16H, CH$_2$Ph), 4.00 (dd, 1H, H-2$_A$), 3.90 (dd, 1H, H-2$_D$), 2.90-4.10 (m, 22H, All, H-2$_E$, 3$_A$, 3$_B$, 3$_C$, 3$_E$, 4$_A$, 4$_B$, 4$_C$, 4$_D$, 4$_E$, 5$_A$, 5$_B$, 5$_C$, 5$_D$, 5$_E$, 6a$_D$, 6b$_D$, 6a$_E$, 6b$_E$), 1.93 (s, 3H, OAc), 1.2-0.9 (m, 15H, C(CH$_3$)$_2$, H-6$_A$, 6$_B$, 6$_C$). $^{13}$C NMR: δ 170.7, 165.5, 161.7 (C=O), 138.4-117.3 (Ph, All), 101.7 (C-1$_D$), 100.8 (C-1$_B$), 100.6 (C-1$_A$), 99.5 (C(CH$_3$)$_2$), 97.9 (C-1$_E$), 95.7 (C-1$_C$), 92.0 (CCl$_3$), 82.2, 81.7, 81.6, 80.3, 79.9, 78.8, 77.9, 77.9, 76.6, 76.0, 75.8, 75.4, 75.1, 74.7, 74.3, 74.1, 73.3, 72.8, 72.6, 71.9, 71.5, 70.8, 69.0, 68.8, 68.5, 68.0, 67.8, 62.0, 56.7 (C-2$_D$), 28.6 (C(CH$_3$)$_2$), 21.3 (OAc), 19.4 (C(CH$_3$)$_2$), 19.0, 18.5, 18.4 (3C, C-6$_A$, 6$_B$, 6$_C$).

Allyl (2-acetamido-3-O-acetyl-4,6-O-isopropylidene-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (201). A mixture of 219 (144 mg, 0.06 mmol), Bu$_3$SnH (0.1 mL, 0.37 mmol) and AIBN (10 mg) in dry toluene (3 mL) was stirred for 1 h at rt under a stream of dry Ar, then was heated for 1.5 h at 90° C., cooled and concentrated. The residue was eluted from a column of silica gel with 2:1 cyclohexane-EtOAc and 0.2% of Et$_3$N to give 201 (100 mg, 74%). $^1$H NMR: δ 6.95-8.00 (m, 45H, Ph), 5.82 (m, 1H, All), 5.46 (d, 1H, J$_{2,NH}$=8.0 Hz, NH$_D$), 5.29 (dd, 1H, J$_{1,2}$=1.0, J$_{2,3}$=3.0 Hz, H-2$_C$), 5.11-5.25 (m, 2H, All), 5.00 (bs, 1H, H-1$_A$), 4.90 (d, 1H, J$_{1,2}$=3.1 Hz, H-1$_E$), 4.85 (d, 1H, J$_{1,2}$=1.6 Hz, H-1$_B$), 4.83 (bs, 1H, H-1$_C$), 4.70 (dd, 1H, J$_{2,3}$=J$_{3,4}$=10.0 Hz, H-3$_D$), 4.44 (d, 1H, H-1$_D$), 4.34 (dd, 1H, H-2$_B$), 4.20-4.80 (m, 16H, CH$_2$Ph), 4.02 (dd, 1H, H-2$_A$), 3.37 (dd, 1H, H-2$_E$), 2.90-4.10 (m, 21H, All, H-2$_D$, 3$_A$, 3$_B$, 3$_C$, 3$_E$, 4$_A$, 4$_B$, 4$_C$, 4$_D$, 4$_E$, 5$_A$, 5$_B$, 5$_C$, 5$_D$, 5$_E$, 6a$_D$, 6b$_D$, 6a$_E$, 6b$_E$), 1.92 (s, 3H, OAc), 1.57 (s, 3H, AcNH), 1.27-0.90 (m, 15H, C(CH$_3$)$_2$, H-6$_A$, 6$_B$, 6$_C$). $^{13}$C NMR: δ 171.3, 170.3, 166.2 (C=O), 138.7-117.9 (Ph, All), 103.9 (C-1$_D$), 101.5 (C-1$_B$), 101.4 (C-1$_A$), 99.9 (C(CH$_3$)$_2$), 98.5 (C-1$_E$), 96.3 (C-1$_C$), 82.1, 81.7, 81.6, 80.3, 80.1, 78.8, 78.1, 77.8, 76.0, 75.8, 75.3, 75.1, 74.7, 74.2, 73.6, 73.3, 72.7, 71.9, 71.4, 70.8, 69.0, 68.8, 68.7, 68.4, 68.1, 67.8, 62.1, 55.0 (C-2$_D$), 30.0 (C(CH$_3$)$_2$), 23.5 (AcNH), 21.6 (OAc), 19.2 (C(CH$_3$)$_2$), 19.0, 18.3, 18.2 (3C, C-6$_A$, 6$_B$, 6$_C$). FAB-MS for C$_{103}$H$_{117}$NO$_{25}$ (M, 1769.0) m/z 1791.9 [M+Na]$^+$. Anal. Calcd. for C$_{103}$H$_{117}$NO$_{25}$: C, 69.93; H, 6.67; N, 0.79. Found: C, 69.77; H, 6.84; N, 0.72.

(2-Acetamido-3-O-acetyl-4,6-O-isopropylidene-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranosyl trichloroacetimidate (203). 1,5-Cyclooctadiene-bis(methyldiphenylphosphine)iridium hexafluorophosphate (50 mg, 58 µmol) was dissolved THF (10 mL), and the resulting red solution was degassed in an argon stream. Hydrogen was then bubbled through the solution, causing the colour to change to yellow. The solution was then degassed again in an argon stream. A solution of 201 (1.8 g, 1.02 mmol) in THF (20 mL) was degassed and added. The mixture was stirred at rt overnight then concentrated to dryness. The residue was dissolved in acetone (9 mL), then water (2 mL), mercuric chloride (236 mg) and mercuric oxide (200 mg) were added successively. The mixture protected from light was stirred at rt for 2 h and acetone was evaporated. The resulting suspension was taken up in DCM, washed twice with 50% aq KI, water and satd aq NaCl, dried and concentrated. The residue was eluted from a column of silica gel with 3:2 Cyclohexane-EtOAc and 0.2% Et$_3$N to give the corresponding hemiacetal 220. Trichloroacetonitrile (2.4 mL) and DBU (72 µL) were added to a solution of the residue in anhydrous DCM (24 mL) at 0° C. After 1 h, the mixture was concentrated. The residue was eluted from a column of silica gel with 3:2 cyclohexane-EtOAc and 0.2% Et$_3$N to give 203 as a colourless oil (1.58 g, 82%); [α]$_D$+2° (c 1, CHCl$_3$). $^1$H NMR: δ 8.62 (s, 1H, C═NH), 6.95-8.00 (m, 45H, Ph), 6.24 (d, 1H, J$_{1,2}$=2.6 Hz, H-1$_C$), 5.48 (dd, 1H, J$_{2,3}$=3.0 Hz, H-2$_C$), 5.41 (d, 1H, J$_{2,NH}$=8.4 Hz, NH$_D$), 4.99 (bs, 1H, H-1$_A$), 4.92 (d, 1H, J$_{1,2}$=3.2 Hz, H-1$_E$), 4.88 (d, 1H, J$_{1,2}$=1.6 Hz, H-1$_B$), 4.69 (dd, 1H, J$_{2,3}$=J$_{3,4}$=10.0 Hz, H-3$_D$), 4.44 (d, 1H, H-1$_D$), 4.34 (dd, 1H, H-2$_B$), 4.20-4.80 (m, 16H, CH$_2$Ph), 4.02 (dd, 1H, H-2$_A$), 3.38 (dd, 1H, H-2$_E$), 2.90-4.10 (m, 19H, H-2$_D$, 3$_A$, 3$_B$, 3$_C$, 3$_E$, 4$_A$, 4$_B$, 4$_C$, 4$_D$, 4$_E$, 5$_A$, 5$_B$, 5$_C$, 5$_D$, 5$_E$, 6a$_D$, 6b$_D$, 6a$_E$, 6b$_E$), 1.95 (s, 3H, OAc), 1.55 (s, 3H, AcNH), 1.30-0.85 (m, 15H, C(CH$_3$)$_2$, H-6$_A$, 6$_B$, 6$_C$). $^{13}$C NMR: δ 172.4, 171.4, 166.9 (C═O), 140.2-128.9 (Ph), 104.2 (C-1$_D$), 101.4 (2C, C-1$_A$, 1$_B$), 101.1 (C(CH$_3$)$_2$), 98.0 (C-1$_E$), 94.8 (C-1$_C$), 92.4 (CCl$_3$), 82.1, 81.5, 80.2, 80.1, 78.6, 78.1, 77.8, 77.6, 76.0, 75.8, 75.5, 75.0, 74.3, 74.2, 73.5 (C-3$_D$), 73.4, 71.9, 71.4, 71.0, 70.5, 69.2, 68.8, 68.3, 68.1, 62.1, 54.9 (C-2$_D$), 29.3 (C(CH$_3$)$_2$), 23.4 (AcNH), 21.4 (OAc), 19.2 (C(CH$_3$)$_2$), 19.0, 18.2, 18.1 (3C, C-6$_A$, 6$_B$, 6$_C$). FAB-MS for C$_{102}$H$_{113}$Cl$_3$N$_2$O$_{25}$ (M, 1873.3) m/z 1896.3 [M+Na]$^+$. Anal. Calcd. for C$_{102}$H$_{113}$Cl$_3$N$_2$O$_{25}$: C, 65.40; H, 6.08; N, 1.50. Found: C, 65.26; H, 6.02; N, 1.31.

C. Convergent Synthesis of the Decasaccharide D'A'B'(E')C'DAB(E)C as its Methyl Glycoside Phenyl (3,4,6-tri-O-acetyl-2-deoxy-2-trichloroacetamido-β-D-glucopyranosyl)-(1→2)-3,4-di-O-benzyl-1-thio-α-L-rhamnopyranoside (308). A mixture of alcohol 315 (0.12 g, 0.27 mmol) and imidate 316 (0.245 g, 0.41 mmol) in anhydrous DCM (10 mL) was stirred for 15 min under dry argon. After cooling at 0° C., Me$_3$SiOTf (28 µL) was added dropwise and the mixture was stirred for 0.5 h. Triethylamine (60 µL) was added and the mixture was concentrated. The residue was eluted from a column of silica gel with 4:1 cyclohexane-EtOAc to give 308 (227 mg, 97%) as a colourless foam; [α]$_D$−63° (c 1, CHCl$_3$). $^1$H NMR: δ 7.40-7.10 (m, 15H, Ph), 6.73 (d, 1H, J$_{2,NH}$=8.5 Hz, NH$_D$), 5.47 (d, 1H, J$_{1,2}$=1.2 Hz, H-1$_A$), 5.07 (pt, 1H, J$_{2,3}$=J$_{3,4}$=10.0 Hz, H-3$_D$), 4.99 (pt, 1H, J$_{4,5}$=10.0 Hz, H-4$_D$), 4.80-4.55 (m, 4H, CH$_2$Ph), 4.52 (d, 1H, J$_{1,2}$=8.2 Hz, H-1$_D$), 4.13-3.95 (m, 2H, J$_{5,6}$=5.3, J$_{6a,6b}$=12.2 Hz, H-6a$_D$, 6b$_D$), 4.10 (dq, 1H, J$_{4,5}$=9.5, J$_{5,6}$=6.1 Hz, H-5$_A$), 4.00 (dd, 1H, J$_{2,3}$=3.0 Hz, H-2$_A$), 3.99 (m, 1H, H-2$_D$), 3.77 (dd, 1H, J$_{3,4}$=9.4 Hz, H-3$_A$) 3.50 (m, 1H, H-5$_D$), 3.39 (dd, 1H, H-4$_A$), 1.95, 1.93, 1.90 (3s, 9H, OAc), 1.23 (d, 3H, H-6$_A$); $^{13}$C NMR (CDCl$_3$) δ 171.1, 170.9, 169.6, 162.1 (C═O), 138-127 (Ph), 102.1 (C-1$_D$), 92.7 (CCl$_3$), 87.4 (C-1$_A$), 81.3 (C-4$_A$), 80.5 (C-3$_A$), 79.1 (C-2$_A$), 76.4, 74.1 (2C, CH$_2$Ph), 72.4 (C-5$_D$), 72.4 (C-3$_D$), 69.8 (C-5$_A$), 68.7 (C-4$_D$), 62.3 (C-6$_D$), 56.2 (C-2$_D$), 21.0, 20.9, 20.8 (3C, OAc), 18.1 (C-6$_A$). FAB-MS for C$_{40}$H$_{44}$Cl$_3$NO$_{12}$S (M, 867), m/z 890 [M+Na]$^+$. Anal. Calcd for C$_{40}$H$_{44}$Cl$_3$NO$_{12}$S: C, 55.27; H, 5.10; N, 1.61. Found: C, 55.16; H, 5.18; N, 1.68.

Allyl (3,4,6-tri-O-acetyl-2-deoxy-2-trichloroacetamido-β-D-glucopyranosyl)-(1→2)-3,4-di-O-benzyl-α-L-rhamnopyranoside (317). A mixture of alcohol 314 (1.86 g, 4.86 mmol) and imidate 316 (3.85 g, 6.47 mmol) in anhydrous CH$_3$CN (80 mL) was stirred for 15 min under dry Ar. After cooling at 0° C. Me$_3$SiOTf (46 µL) was added dropwise and the mixture was stirred for 0.5 h. Triethylamine (150 µL) was added and the mixture was concentrated. The residue was eluted from a column of silica gel with 7:3 cyclohexane-EtOAc to give 317 (4.0 g, 99%) as a white solid; [α]$_D$−3° (c 1, CHCl$_3$). $^1$H NMR:δ 7.32-7.18 (m, 10H, Ph), 6.70 (d, 1H, J$_{2,NH}$=8.4 Hz, NH$_D$), 5.82-5.78 (m, 1H, All), 5.20-5.05 (m, 2H, All), 5.00 (m, 2H, H-3$_D$, 4$_D$), 4.75-4.45 (m, 4H, CH$_2$Ph), 4.76 (d, 1H, J$_{1,2}$=1.1 Hz, H-1$_A$), 4.60 (d, 1H, J$_{1,2}$=8.5 Hz, H-1$_D$), 4.15-4.05 (m, 2H, J$_{5,6}$=4.8, J$_{6a,6b}$=12.2 Hz, H-6a$_D$, 6b$_D$), 3.98 (m, 1H, H-2$_D$), 3.90 (m, 2H, All), 3.86 (dd, 1H, J$_{2,3}$=3.2 Hz, H-2$_A$), 3.81 (dd, 1H, J$_{3,4}$=9.5 Hz, H-3$_A$), 3.62 (dq, 1H, J$_{4,5}$=9.5, J$_{5,6}$=6.1 Hz, H-5$_A$), 3.50 (m, 1H, H-5$_D$), 3.32 (pt, 1H, H-4$_A$), 2.02, 1.97, 1.93 (3 s, 9H, OAc), 1.24 (d, 3H, H-6$_A$); $^{13}$C NMR: δ 171.0, 170.9, 169.6, 162.1 (C═O), 138.5-117.1 (Ph, All), 101.8 (C-1$_D$), 98.5 (C-1$_A$), 92.6 (CCl$_3$), 81.4 (C-4$_A$), 80.4 (C-3$_A$), 77.1 (C-2$_A$), 75.9, 74.1 (2C, CH$_2$Ph), 72.7 (C-3$_D$), 72.5 (C-5$_D$), 68.6 (C-4$_D$), 68.3 (C-5$_A$), 68.1 (All), 62.3 (C-6$_D$), 56.1 (C-2$_D$), 21.1, 20.9, 20.9 (3C, OAc), 18.2 (C-6$_A$). FAB-MS for C$_{37}$H$_{44}$Cl$_3$NO$_{13}$ (M, 815), m/z 838 [M+Na]$^+$. Anal. Calcd for C$_{37}$H$_{44}$Cl$_3$NO$_{13}$: C, 54.39; H, 5.43; N, 1.71%. Found: C, 54.29; H, 5.45; N, 1.72%.

(3,4,6-tri-O-acetyl-2-deoxy-2-trichloroacetamido-β-D-glucopyranosyl)-(1→2)-3,4-di-O-benzyl-α-L-rhamnopyranose (318). 1,5-Cyclooctadiene-bis(methyldiphenylphosphine)iridium hexafluorophosphate (120 mg, 140 µmol) was dissolved tetrahydrofuran (10 mL), and the resulting red solution was degassed in an argon stream. Hydrogen was then bubbled through the solution, causing the colour to change to yellow. The solution was then degassed again in an argon stream. A solution of 317 (1.46 g, 1.75 mmol) in tetrahydrofuran (20 mL) was degassed and added. The mixture was stirred at rt overnight. The mixture was concentrated. The residue was taken up in acetone (27 mL), and water (3 mL) was added. Mercuric bromide (949 mg, 2.63 mmol) and mercuric oxide (761 mg, 3.5 mmol) were added to the mixture, protected from light. The mixture was stirred for 2 h at rt, then concentrated. The residue was taken up in CH$_2$Cl$_2$ and washed three limes with sat. aq. KI, then with brine. The organic phase was dried and concentrated. The residue was purified by column chromatography (cyclohexane-EtOAc 4:1) to give 318 (1.13 g, 81%) as a white foam. [α]$_D$+4° (c 1, CHCl$_3$). $^1$H NMR: δ 7.35-7.05 (m, 10H, Ph), 6.74 (d, 1H, J$_{2,NH}$=8.5 Hz, NH$_D$), 5.10 (d, 1H, J$_{1,2}$=1.1 Hz, H-1$_A$), 5.02 (m, 2H, H-3$_D$, 4$_D$), 4.80-4.50 (m, 4H, CH$_2$Ph), 4.61 (d, 1H, J$_{1,2}$=8.5 Hz, H-1$_D$), 4.15-4.08 (m, 2H, J$_{5,6}$=4.5, J$_{6a,6b}$=12.3 Hz, H-6a$_D$, 6b$_D$), 4.00 (m, 1H, H-2$_D$), 3.90 (dd, 1H, J$_{2,3}$=3.3, H-2$_A$), 3.86 (dd, 1H, J$_{3,4}$=9.5 Hz, H-3$_A$), 3.85 (dq, 1H, J$_{4,5}$=9.5, J$_{5,6}$=6.2 Hz, H-5$_A$), 3.50 (m, 1H, H-5$_D$), 3.30 (pt, 1H, H-4$_A$), 2.85 (d, 1H, J$_{1,OH}$=3.5 Hz, OH), 2.02, 1.97, 1.94 (3s, 9H, OAc), 1.23 (d, 3H, H-6$_A$); $^{13}$C NMR: δ 171.1, 170.0, 169.6, 162.1 (C═O), 138.5-127.1 (Ph), 101.7 (C-1$_D$), 94.1 (C-1$_A$), 92.6 (CCl$_3$), 81.4 (C-4$_A$), 79.9 (C-2$_A$), 77.3 (C-3$_A$), 75.9, 74.1 (2C, CH$_2$Ph), 72.7 (C-3$_D$), 72.5 (C-5$_D$), 68.6 (C-4$_D$), 68.4 (C-5$_A$), 62.2 (C-6$_D$), 56.1 (C-2$_D$), 21.1, 21.0, 20.9 (3C, OAc), 18.3 (C-6$_A$). FAB-MS for C$_{34}$H$_{40}$Cl$_3$NO$_{13}$ (M, 775), m/z 789 [M+Na]$^+$. Anal. Calcd for C$_{34}$H$_{40}$Cl$_3$NO$_{13}$: C, 52.55; H, 5.19; N, 1.80%. Found: C, 52.48; H, 5.37; N, 1.67%.

(3,4,6-tri-O-acetyl-2-deoxy-2-trichloroacetamido-β-D-glucopyranosyl)-(1→2)-3,4-di-O-benzyl-α-L-rhamnopyranose trichloroacetimidate (306). The hemiacetal 318 (539 mg, 0.68 mmol) was dissolved in CH$_2$Cl$_2$ (50 mL), placed under argon and cooled to 0° C. Trichloroacetonitrile (0.6 mL, 6.8 mmol), then DBU (10 µL, 70 µmol) were added. The mixture was stirred at 0° C. for 30 min. The mixture was concentrated and toluene was co-evaporated from the residue. The residue was eluted from a column of silica gel with 7:3 cyclohexane-EtOAc and 0.2% of Et$_3$N to give 306 (498 mg, 78%) as a colourless foam; $[\alpha]_D$ −18° (c 1, CHCl$_3$). $^1$H NMR: δ 8.48 (s, 1H, NH), 7.40-7.15 (m, 10H, Ph), 6.75 (d, 1H, $J_{2,NH}$=8.5 Hz, NH$_D$), 6.18 (d, 1H, $J_{1,2}$=1.1 Hz, H-1$_A$), 5.15 (pt, 1H, $J_{2,3}$=$J_{3,4}$=9.5 Hz, H-3$_D$), 5.07 (pt, 1H, $J_{4,5}$=9.5 Hz, H-4$_D$), 4.82-4.50 (m, 4H, CH$_2$Ph), 4.62 (d, 1H, $J_{1,2}$=8.5 Hz, H-1$_D$), 4.20-4.03 (m, 2H, $J_{5,6}$=4.5, $J_{6a,6b}$=12.3 Hz, H-6a$_D$, 6b$_D$), 3.98 (m, 1H, H-2$_D$), 3.85 (dq, 1H, $J_{4,5}$=9.5, $J_{5,6}$=6.2 Hz, H-5$_A$), 3.84 (dd, 1H, $J_{2,3}$=3.3 Hz, H-2$_A$), 3.83 (dd, 1H, $J_{3,4}$=9.5 Hz, H-3$_A$), 3.55 (m, 1H, H-5$_D$), 3.45 (pt, 1H, H-4$_A$), 1.98, 1.96, 1.93 (3s, 9H, OAc), 1.23 (d, 3H, H-6$_A$); $^{13}$C NMR: δ 171.1, 170.0, 169.6, 162.1 (C=O), 138.4-127.2 (Ph), 101.7 (C-1$_D$), 97.2 (C-1$_A$), 92.6 (CCl$_3$), 80.5 (C-4$_A$), 79.1 (C-3$_A$), 76.2 (C-2$_A$), 76.2, 74.1 (2C, CH$_2$Ph), 74.4 (C-3$_D$), 74.1 (C-5$_D$), 71.3 (C-5$_A$), 68.6 (C-4$_D$), 62.3 (C-6$_D$), 56.3 (C-2$_D$), 21.1, 21.0, 20.9 (3C, OAc), 18.2 (C-6$_A$). Anal. Calcd for C$_{36}$H$_{40}$Cl$_6$N$_2$O$_{13}$: C, 46.93; H, 4.38; N, 3.04%. Found: C, 46.93; H, 4.52; N, 2.85%.

Allyl (2-acetamido-3,4,6-tri-O-acetyl-2-deoxy-β-D-glucopyranosyl)-(1→2)-3,4-di-O-benzyl-α-L-rhamnopyranoside (319). A mixture of the protected disaccharide 317 (3.0 g, 3.61 mmol) in MeOH (50 mL) was cold to 0° C. and treated by NH$_3$ gaz overnight. The solution was concentrated and the residue (2.02 g) was dissolved again in MeOH (50 mL) and treated by Ac$_2$O (3.98 mL, 36.1 mol). The solution was stirred for 2 h and then concentrated. The residue was eluted from a column of silica gel with 95:5 DCM-EtOAC to give the intermediate triol which was dissolved in Pyridine (5 mL), cold to 0° C. and treated by Ac$_2$O (2.4 mL). The mixture was stirred overnight and concentrated. The residue was eluted from a column of silica gel with 3:2 cyclohexane-EtOAc to give 319 (2.3 g, 90%) was obtained as a colourless foam. $[\alpha]_D$ −12° (c 1, CHCl$_3$). $^1$H NMR: δ 7.32-7.18 (m, 10H, Ph), 5.80-5.70 (m, 1H, All), 5.40 (d, 1H, $J_{2,NH}$=8.1 Hz, NH), 5.20-5.10 (m, 2H, All), 4.96 (pt, 1H, $J_{3,4}$=$J_{4,5}$=9.5 Hz, H-4$_D$), 4 90 (pt, 1H, $J_{2,3}$=9.5 Hz, H-3$_D$), 4.80 (d, 1H, $J_{1,2}$=1.2 Hz, H-1$_A$), 4.76-4.52 (m, 4H, CH$_2$Ph), 4.46 (d, 1H, $J_{1,2}$=8.5 Hz, H-1$_D$), 4.10-4.02 (m, 2H, $J_{5,6}$=4.7, $J_{6a,6b}$=11.2 Hz, H-6a$_D$, 6b$_D$), 3.92 (m, 1H, H-2$_D$), 3.87 (m, 2H, All), 3.86 (dd, 1H, $J_{2,3}$=3.5 Hz, H-2$_A$), 3.82 (dd, 1H, $J_{3,4}$=9.5 Hz, H-3$_A$), 3.62 (dq, 1H, $J_{4,5}$=9.5, $J_{5,6}$=6.2 Hz, H-5$_A$), 3.52 (m, 1H, H-5$_D$), 3.30 (pt, 1H, H-4$_A$), 1.98, 1.94, 1.92 (3 s, 9H, OAc), 1.26 (d, 3H, H-6$_A$); $^{13}$C NMR: δ 171.1, 171.0, 170.3, 169.6 (C=O), 138-117 (Ph, All), 103.4 (C-1$_D$), 98.5 (C-1$_A$), 81.3 (C-4$_A$), 80.4 (C-3$_A$), 78.5 (C-2$_A$), 75.9, 73.9 (2C, CH$_2$Ph), 73.6 (C-3$_D$), 72.4 (C-5$_D$), 68.7 (C-4$_D$), 68.2 (C-5$_A$), 68.1 (All), 62.5 (C-6$_D$), 54.5 (C-2$_D$), 23.4 (NHAc), 21.2, 21.1, 21.0 (3C, OAc), 18.1 (C-6$_A$). FAB-MS for C$_{37}$H$_{47}$NO$_{13}$ (M, 713.3) m/z 736.2 [M+Na]$^+$. Anal. Calcd for C$_{37}$H$_{47}$NO$_{13}$: C, 62.26; H, 6.64; N, 1.96. Found: C, 62.12; H, 6.79; N, 1.87.

(2-acetamido-3,4,6-tri-O-acetyl-2-deoxy-β-D-glucopyranosyl)-(1→2)-3,4-di-O-benzyl-α-L-rhamnopyranose (320). 1,5-Cyclooctadiene-bis(methyldiphenylphosphine)iridium hexafluorophosphate (10 mg, 12 µmol) was dissolved THF (10 mL), and the resulting red solution was degassed in an argon stream. Hydrogen was then bubbled through the solution, causing the colour to change to yellow. The solution was then degassed again in an argon stream. A solution of 319 (830 mg, 1.16 mmol) in THF (40 mL) was degassed and added. The mixture was stirred at rt overnight. The mixture was concentrated. The residue was taken up in acetone (90 mL), and water (10 mL) was added. Mercuric chloride (475 mg, 1.75 mmol) and mercuric oxide (504 mg, 2.32 mmol) were added to the mixture, protected from light. The mixture was stirred for 2 h at rt, then concentrated. The residue was taken up in CH$_2$Cl$_2$ and washed three times with sat. aq. KI, then with brine. The organic phase was dried and concentrated. The residue was purified by column chromatography (cyclohexane-EtOAc 3:7) to give 320 (541 mg, 69%) as a white foam; $[\alpha]_D$+16° (c 1.0, CHCl$_3$): $^1$H NMR: δ 7.35-7.05 (m, 10H, Ph), 5.50 (d, 1H, $J_{2,NH}$=8.2 Hz, NH$_D$), 5.22 (d, 1H, $J_{1,2}$=1.1 Hz, H-1$_A$), 5.06 (pt, 1H, $J_{3,4}$=$J_{4,5}$=9.5 Hz, H-4$_D$), 5.00 (pt, 1H, $J_{2,3}$=9.5 Hz, H-3$_D$), 4.85-4.60 (m, 4H, CH$_2$Ph), 4.56 (d, 1H, $J_{1,2}$=7.0 Hz, H-1$_D$), 4.22-4.13 (m, 2H, $J_{5,6}$=4.5, $J_{6a,6b}$=12.3 Hz, H-6a$_D$, 6b$_D$), 4.03 (m, 1H, H-2$_D$), 4.00 (dq, 1H, $J_{4,5}$=9.5, $J_{5,6}$=6.2 Hz, H-5$_A$), 3.96 (dd, 1H, $J_{2,3}$=3.3 Hz, H-2$_A$), 3.90 (dd, 1H, $J_{3,4}$=9.5 Hz, H-3$_A$), 3.60 (m, 1H, H-5$_D$), 3.48 (d, 1H, $J_{1,OH}$=3.5 Hz, OH), 3.40 (pt, 1H, H-4$_A$), 2.08, 2.03, 2.01 (3s, 9H, OAc), 1.65 (s, 3H, NHAc), 1.30 (d, 3H, H-6$_A$); $^{13}$C NMR: δ 171.2, 171.0, 170.4, 169.6 (C=O), 138.2-128.0 (Ph), 103.3 (C-1$_D$), 94.1 (C-1$_A$), 81.4 (C-4$_A$), 79.9 (C-2$_A$), 78.7 (C-3$_A$), 75.8, 73.9 (2C, CH$_2$Ph), 73.6 (C-3$_D$), 72.4 (C-5$_D$), 68.7 (C-4$_D$), 68.2 (C-5$_A$), 62.4 (C-6$_D$), 54.5 (C-2$_D$), 23.3 (NHAc), 21.1, 21.0, 21.0 (3C, OAc), 18.3 (C-6$_A$). FAB-MS for C$_{34}$H$_{43}$NO$_{13}$ (M, 673.2), m/z 696.3 [M+Na]$^+$. Anal. Calcd for C$_{34}$H$_{43}$NO$_{13}$: C, 60.61; H, 6.43; N, 2.08. Found: C, 60.46; H, 6.61; N, 1.95.

(2-acetamido-3,4,6-tri-O-acetyl-2-deoxy-β-D-glucopyranosyl)-(1→2)-3,4-di-O-benzyl-α-L-rhamnopyranose trichloroacetimidate (307). The hemiacetal 320 (541 mg, 0.80 mmol) was dissolved in CH$_2$Cl$_2$ (20 mL), placed under argon and cooled to 0° C. Trichloroacetonitrile (0.810 mL, 8 mmol), then DBU (10 µL, 80 µmol) were added. The mixture was stirred at 0° C. for 1 h. The mixture was concentrated and toluene was co-evaporated from the residue. The residue was eluted from a column of silica gel with 1:1 cyclohexane-EtOAc and 0.2% of Et$_3$N to give 307 (560 mg, 86%) as a colourless foam; $[\alpha]_D$+2° (c 1, CHCl$_3$). $^1$H NMR: δ 8.56 (s, 1H, NH), 7.50-7.20 (m, 10H, Ph), 6.29 (d, 1H, $J_{1,2}$=1.3 Hz, H-1$_A$), 5.50 (d, 1H, $J_{2,NH}$=8.3 Hz, NH$_D$), 5.17 (pt, 1H, $J_{2,3}$=$J_{3,4}$=9.5 Hz, H-3$_D$), 5.09 (dd, 1H, $J_{4,5}$=9.5 Hz, H-4$_D$), 4.85-4.60 (m, 4H, CH$_2$Ph), 4.68 (d, 1H, $J_{1,2}$=8.0 Hz, H-1$_D$), 4.22-4.10 (m, 2H, $J_{5,6}$=5.0, $J_{6a,6b}$=12.2 Hz, H-6a$_D$, 6b$_D$), 4.00 (m, 1H, H-2$_D$), 3.99 (dd, 1H, $J_{2,3}$=3.5 Hz, H-2$_A$), 3.90 (dq, 1H, $J_{4,5}$=9.6, $J_{5,6}$=6.2 Hz, H-5$_A$), 3.89 (dd, 1H, $J_{3,4}$=9.5 Hz, H-3$_A$), 3.62 (m, 1H, H-5$_D$), 3.50 (dd, 1H, H-4$_A$), 2.02, 2.00, 1.98 (3s, 9H, OAc), 1.65 (s, 3H, NHAc), 1.32 (d, 3H, H-6$_A$); $^{13}$C NMR: δ 171.2, 171.0, 170.4, 169.6 (C=O), 160.5 (C=NH), 138.2-128.0 (Ph), 103.3 (C-1$_D$), 97.3 (C-1$_A$), 91.4 (CCl$_3$), 80.3 (C-4$_A$), 79.9 (C-3$_A$), 77.5 (C-2$_A$), 76.0, 73.8 (2C, CH$_2$Ph), 73.1 (C-3$_D$), 72.2 (C-5$_D$), 71.1 (C-5$_A$), 68.8 (C-4$_D$), 62.5 (C-6$_D$), 54.8 (C-2$_D$), 23.3 (NHAc), 21.4, 21.1, 21.0 (3C, OAc), 18.4 (C-6$_A$) Anal. Calcd for C$_{36}$H$_{43}$Cl$_3$N$_2$O$_{13}$: C, 52.85; H, 5.30; N, 3.42. Found: C, 52.85; H, 5.22; N, 3.47.

Allyl (2-O-acetyl-3,4-di-O-benzyl-α-L-rhamnopyranosyl)-(1→2)-3,4-di-O-benzyl-α-L-rhamnopyranoside (322). The acceptor 314 (1.78 g, 4.65 mmol) and the trichloroacetimidate donor 321 (2.96 g, 5.58 mmol) were dissolved in anhydrous ether (100 mL). The mixture was placed under argon and cooled to −55° C. TMSOTf (335 µL, 1.86 mmol) was added dropwise. The mixture was stirred at −55° C. to −20° C. over 3 h. Triethylamine (0.75 mL) was added, and the mixture was allowed to warm to rt. The mixture was concentrated. The residue was purified by column chromatography (cyclohexane:EtOAc, 7:3) to give 322 as a colourless syrup (3.21 g, 92%); $[\alpha]_D$−16° (c 0.55, CHCl$_3$ lit. Zhang, J.; Mao, J. M.; Chen, H, M.; Cai, M. S. *Tetrahedron: Asymmetry* 1994, 5, 2283-2290) $[\alpha]_D$−19.3° (c, 1.2, CHCl$_3$); $^1$H NMR: δ 7.42-7.30 (m, 20H, Ph), 5.92-5.82 (m, 1H, All), 5.62 (dd, 1H, $J_{1,2}$=1.6, $J_{2,3}$=3.2 Hz, H-2$_A$), 5.32-5.20 (m, 2H, All), 5.07 (d, 1H, H-1$_A$), 4.82 (d, 1H, $J_{1,2}$=1.0 Hz, H-1$_B$), 4.95-4.60 (m, 8H, CH$_2$Ph), 4.20-4.15 (m, 1H, All), 4.09 (d, 1H, J$_{2,3}$=3.0 Hz, H-2$_B$), 4.05 (dd, 1H, J$_{3,4}$=9.4 Hz, H-3$_A$), 4.05-3.95 (m, 1H, All), 3.96 (dd, 1H, J$_{3,4}$=9.5 Hz, H-3$_B$), 3.89 (dq, 1H, J$_{4,5}$=9.5, J$_{5,6}$=6.3 Hz, H-5$_A$), 3.76 (dq, 1H, J$_{4,5}$=9.5, J$_{5,6}$=6.2 Hz, H-5$_B$), 3.52 (m, 1H, H-4$_B$), 3.50 (m, 1H, H-4$_A$), 2.18 (s, 3H, OAc), 1.39 (d, 3H, H-6$_A$), 1.36 (d, 3H, H-6$_B$); $^{13}$C NMR: δ 170.8 (C=O), 138.4-117.1 (Ph, All), 99.5 (C-1$_A$), 98.4 (C-1$_B$), 80.5 (2C, C-4$_A$, 4$_B$), 80.0 (C-3$_B$), 78.1 (C-3$_A$), 75.8, 75.7 (2C, CH$_2$Ph), 74.9 (C-2$_B$), 72.5, 72.2 (2C, CH$_2$Ph), 69.3 (C-2$_A$), 68.6 (C-5$_A$), 68.4 (C-5$_B$), 68.0 (All), 21.5 (OAc), 18.4, 18.2 (2C, C-6$_A$, 6$_B$). CI-MS for C$_{45}$H$_{52}$O$_{10}$ (M, 752) m/z 770 [M+NH$_4$]$^+$. Anal. Calcd. for C$_{45}$H$_{52}$O$_{10}$: C, 71.79; H, 6.96. Found: C, 70.95; H, 7.01.

Allyl (3,4-di-O-benzyl-α-L-rhamnopyranosyl)-(1→2)-3,4-di-O-benzyl-α-L-rhamnopyranoside (323). A 1M solution of sodium methoxide in methanol (1.1 mL) was added to a solution of 322 (3.10 g, 4.13 mmol) in methanol. The mixture was stirred at rt for 3 h. The mixture was neutralised with Amberlite IR-120 (H$^+$) resin, filtered and concentrated to give 323 (2.72 g, 93%) as a colourless syrup which crystallised on standing; mp 98-99° C.; lit. (Pinto, B. M.; Reimer, K. B.; Morissette, D. G.; Bundle, D. R. *J. Org. Chem.* 1989, 54, 2650-2656) mp 100° C. (hexane); [α]$_D$–30° (c 0.5, CHCl$_3$), lit. (Pinto, B. M.; Reimer, K. B.; Morissette, D. G.; Bundle, D. R. *J. Org. Chem.* 1989, 54, 2650-2656) [α]$_D$–32.5° (c, 0.4, CHCl$_3$); $^1$H NMR: δ 7.42-7.30 (m, 20H, Ph), 5.90-5.80 (m, 1H, All), 5.32-5.20 (m, 2H, All), 5.13 (d, 1H, J$_{1,2}$=1.4 Hz, H-1$_A$), 4.82 (d, 1H, J$_{1,2}$=1.6 Hz, H-1$_B$), 4.95-4.60 (m, 8H, CH$_2$Ph), 4.20-4.12 (m, 1H, All), 4.19 (m, 1H, J$_{2,3}$=3.2, J$_{2,OH}$=1.8 Hz, H-2$_A$), 4.09 (d, 1H, J$_{2,3}$=3.2 Hz, H-2$_B$), 4.00-3.95 (m, 1H, All), 3.95 (dd, 1H, J$_{3,4}$=9.4 Hz, H-3$_A$), 3.93 (dd, 1H, J$_{3,4}$=9.4 Hz, H-3$_B$), 3.87 (dq, 1H, J$_{4,5}$=9.4, J$_{5,6}$=6.2 Hz, H-5$_A$), 3.74 (dq, 1H, J$_{4,5}$=9.4, J$_{5,6}$=6.2 Hz, H-5$_B$), 3.53 (pt, 1H, H-4$_A$), 3.46 (pt, 1H, H-4$_B$), 2.52 (d, 1H, OH), 1.35 (m, 6H, H-6$_A$, 6$_B$); $^{13}$C NMR: δ 138.4-117.1 (Ph, All), 101.2 (C-1$_A$), 98.4 (C-1$_B$), 80.8, 80.4 (2C, C-4$_A$, 4$_B$), 80.3 (C-3$_B$), 80.0 (C-3$_A$), 75.8, 75.7 (2C, CH$_2$Ph), 75.0 (C-2$_B$), 72.7, 72.6 (2C, CH$_2$Ph), 69.1 (C-2$_A$), 68.4 (C-5$_B$), 68.3 (C-5$_A$), 68.1 (All), 18.4, 18.3 (2C, C-6$_A$, 6$_B$). CI-MS for C$_{43}$H$_{50}$O$_9$ (M, 710) m/z 728 [M+NH$_4$]$^+$.

3,4,6-Tri-O-acetyl-2-deoxy-2-tetrachlorophtalimido-β-D-glucopyranosyl Trichloroacetimidate (324) (Castro-Palomino, J. C; Schmidt, R. R. *Tetrahedron Lett.* 1995, 36, 5343-5346). Trichloroacetonitrile (2.5 mL) and anhydrous potassium carbonate were added to a suspension of 3,4,6-tri-O-acetyl-2-deoxy-2-tetrachlorophtalimido-α/β-D-glucopyranose (7.88 g, 13.75 mmol) in 1,2-DCE (120 mL). The mixture was stirred at rt overnight. TLC (cyclohexane:EtOAc, 3:2) showed that no starting material remained. The mixture was filtered through a pad of Celite, and the filtrate was concentrated to give the target 324 as a slightly brownish solid (9.08 g, 92%).

Allyl (3,4,6-Tri-O-acetyl-2-deoxy-2-trichloroacetamido-β-D-glucopyranosyl)-(1→2)-(3,4-di-O-benzyl-α-L-rhamnopyranosyl)-(1→2)-3,4-di-O-benzyl-α-L-rhamnopyranoside (325). 1,2-DCE (35 mL) was added to the trichloroacetimidate donor 316 (2.49 g, 4.20 mmol), the acceptor 323 (2.48 g, 3.50 mmol) and 4 Å powdered molecular sieves (4 g). The mixture was stirred for 1.5 h at rt under Argon. The mixture was cooled to –20° C. and TMSOTf (230 µL, 1.26 mmol) was added. The temperature was allowed to reach 0° C. over 1 h, and the mixture was stirred for an additional 2 h at this temperature. Triethylamine (0.5 mL) was added and the mixture was allowed to warm to rt. The mixture was diluted with DCM and filtered. The filtrate was concentrated. The residue was purified by column chromatography with 3:1 cyclohexane-EtOAc to give 325 (3.83 g, 96%) as a colourless amorphous solid: [α]$_D$–6° (c 0.5, CHCl$_3$); $^1$H NMR: δ 7.52-7.28 (m, 20H, Ph), 6.83 (d, 1H, J$_{2,NH}$=8.4 Hz, NH), 5.85 (m, 1H, All), 5.26-5.09 (m, 4H, H-3$_D$, 4$_D$, All), 4.98 (d, 1H, J$_{1,2}$=1.4 Hz, H-1$_A$), 4.98-4.58 (m, 10H, H-1$_B$, 1$_D$, CH$_2$Ph), 4.08 (m, 4H, H-2$_A$, 2$_D$, 6a$_D$, All), 3.91 (m, 5H, H-2$_B$, 3$_A$, 3$_B$, 6b$_D$, All), 3.79 (m, 2H, H-5$_A$, 5$_D$), 3.45 (m, 3H, H-4$_A$, 4$_B$, 5$_D$), 2.04, 2.02, 1.97 (3s, 9H, OAc), 1.30 (m, 6H, H-6$_A$, 6$_B$); $^{13}$C NMR: δ 170.6, 170.3, 169.1, 161.6 (C=O), 138.4-117.1 (Ph, All), 101.3 (C-1$_D$), 100.9 (C-1$_A$), 97.6 (C-1$_B$), 92.0 (CCl$_3$), 80.9, 80.4 (2C, C-4$_A$, 4$_B$), 79.1, 79.0 (2C, C-3$_A$, 3$_B$), 77.3 (C-2$_A$), 76.5 (C-2$_B$), 75.4, 75.2, 73.6 (3C, CH$_2$Ph), 72.2 (C-3$_D$), 71.9 (C-5$_D$), 71.6 (CH$_2$Ph), 68.2 (C-5$_B$*), 67.8 (C-4$_D$), 67.5 (C-5$_A$*), 67.5 (CH$_2$O), 61.3 (C-6$_D$), 55.7 (C-2$_D$), 20.5, 20.4 (3C, OAc), 17.9, 17.7 (2C, C-6$_A$, 6$_B$). FAB-MS for C$_{57}$H$_{66}$Cl$_3$NO$_{17}$ (M, 1141.3) m/z 1164.3 [M+Na]$^+$. Anal. Calcd. for C$_{57}$H$_{66}$Cl$_3$NO$_{17}$: C, 59.87; H, 5.82; N, 1.22%. Found: C, 59.87; H, 5.92; N, 1.16%.

Allyl (3,4,6-Tri-O-acetyl-2-deoxy-2-tetrachlorophthalimido-β-D-glucopyranosyl)-(1→2)-(3,4-di-O-benzyl-α-L-rhamnopyranosyl)-(1→2)-3,4-di-O-benzyl-α-L-rhamnopyranoside (328). Anhydrous Et$_2$O (30 mL) and DCM (15 mL) were added to the trichloroacetimidate donor 324 (3.34 g, 4.66 mmol), the acceptor 323 (2.20 g, 3.10 mmol). The mixture was cooled to 0° C. and TMSOTf (85 µL, 0.466 mmol) was added dropwise. The mixture was stirred at 0° C. for 1 h, then at rt for 3 h. Triethylamine (1 mL) was added and the mixture was stirred for 10 min, then concentrated. The mixture was taken up in Et$_2$O and the resulting precipitate was filtered off. The filtrate was concentrated. The residue was purified by column chromatography with 7:3 cyclohexane-EtOAc to give 328 (2.57 g, 65%) as a colourless amorphous solid: [α]$_D$+22° (c 1.0, CHCl$_3$); $^1$H NMR (300 MHz): δ 7.42-7.16 (m, 20H, Ph), 5.91 (dd, 1H, H-3$_D$), 5.81 (m, 1H, All), 5.24-5.10 (m, 4H, H-1$_D$, 4$_D$, All), 4.93 (s, 1H, H-1$_A$), 4.81-4.53 (m, 5H, H-1$_B$, CH$_2$Ph), 4.45-4.23 (m, 5H, H-2$_D$, CH$_2$Ph), 4.05 (m, 2H, H-6a$_D$, All), 3.91-3.58 (m, 8H, H-2$_A$, 2$_B$, 3$_A$, 3$_B$, 5$_A$, 5$_B$, 6b$_D$, All), 3.38 (m, 1H, H-5$_D$), 3.21-3.13 (m, 2H, H-4$_A$, 4$_B$), 2.05, 2.02, 2.00 (3s, 9H, OAc), 1.24 (m, 6H, H-6$_A$, 6$_B$); $^{13}$C NMR (75 MHz): δ 170.5, 170.4, 169.3 (C=O), 138.4-117.1 (Ph, All), 101.1 (C-1$_A$), 99.9 (C-1$_D$), 97.7 (C-1$_B$), 80.6 (2C, C-4$_A$, 4$_B$), 79.7, 78.9 (2C, C-3$_A$, 3$_B$), 78.2 (C-2$_A$), 76.3 (C-2$_B$), 75.2, 75.1, 72.6, 71.3 (4C, CH$_2$Ph), 71.2 (C-5$_D$), 70.1 (C-3$_D$), 68.4 (C-5$_B$*), 68.4 (C-4$_D$), 67.6 (C-5$_A$*), 67.6 (All), 61.3 (C-6$_D$), 55.4 (C-2$_D$), 20.6, 20.5 (3C, OAc), 18.0, 17.6 (2C, C-6$_A$, 6$_B$). FAB-MS for C$_{63}$H$_{65}$Cl$_4$NO$_{18}$ (M, 1263.3) m/z 1288.4, 1286.4 [M+Na]$^+$. Anal. Calcd. for C$_{63}$H$_{65}$Cl$_4$NO$_{18}$: C, 59.77; H, 5.17; N, 1.11%. Found: C, 60.19; H, 5.53; N, 1.18%.

Allyl (2-Acetamido-2-deoxy-β-D-glucopyranosyl)-(1→2)-(3,4-di-O-benzyl-α-L-rhamnopyranosyl)-(1→2)-3,4-di-O-benzyl-α-L-rhamnopyranoside (326). The trisaccharide 325 (1.71 g, 1.50 mmol) was dissolved in MeOH (20 mL). A 1 M solution of sodium methoxide in methanol (9 mL) and triethylamine (5 mL) were added, and the mixture was stirred at rt for 18 h. The mixture was cooled to 0° C. and acetic anhydride was added dropwise until the pH reached 6. A further portion of acetic anhydride (0.4 mL) was added, and the mixture was stirred at rt for 30 min. The mixture was concentrated, and toluene was co-evaporated from the residue. The residue was purified by column chromatography with 95:5 DCM-MeOH to give 326 (623 mg, 45%) as a colourless amorphous solid: [α]$_D$–16° (c 0.5. CHCl$_3$); $^1$H NMR (300 MHz): δ 7.48-7.24 (m, 20H, Ph), 6.79 (d, 1H, NH), 5.73 (m, 1H, All), 5.12 (m, 3H, H-1$_A$, All), 4.86-4.52 (m, 9H, H-1$_B$, CH$_2$Ph), 4.34 (d, 1H, H-1$_D$), 4.08-3.79 (m, 6H, H-2$_A$, 2$_B$, 3$_A$, 3$_B$, All), 3.74-3.53 (m, 3H, H-5$_A$, 5$_B$, 6a$_D$), 3.45-3.24 (m, 6H, H-2$_D$, 3$_D$, 4$_A$, 4$_B$, 4$_D$, 6b$_D$), 3.20 (m, 1H, H-5$_D$), 1.46 (s, 3H, NHAc), 1.24 (m, 6H, H-6$_A$, 6$_B$); $^{13}$C NMR (75 MHz): δ 173.6 (C=O), 137.4-117.3 (Ph, All), 103.2 (C-1$_D$), 100.3 (C-1$_A$), 97.9 (C-1$_B$), 81.3, 80.4 (2C, C-4$_A$, 4$_B$), 79.9 (2C, C-3$_A$, 3$_B$), 79.9 (C-2$_B$*), 78.9 (C-3$_D$), 75.7 (C-5$_D$), 75.6, 75.3, 74.5 (3C, CH$_2$Ph), 73.6 (C-2$_A$*), 72.5 (CH$_2$Ph), 71.9 (C-4$_D$), 68.2, 68.0 (2C, C-5$_A$, 5$_B$), 67.7 (CH$_2$O), 62.5 (C-6$_D$), 58.8 (C-2$_D$), 22.3 (NHAc), 18.0, 17.8 (2C, C-6$_A$, 6$_B$). FAB-MS for C$_{51}$H$_{63}$NO$_{14}$ (M, 913.4) m/z 936.6 [M+Na]$^+$. Anal. Calcd. for C$_{51}$H$_{63}$NO$_{14}$.H$_2$O: C, 65.72; H, 7.03; N, 1.50%. Found: C, 65.34; H, 7.03; N, 1.55%.

Allyl (2-Acetamido-3,4,6-tri-O-acetyl-2-deoxy-β-O-glucopyranosyl)-(1→2)-(3,4-di-O-benzyl-α-L-rhamnopyranosyl)-(1→2)-3,4-di-O-benzyl-α-L-rhamnopyranoside (327). (a) Pyridine (5 mL) was added to 326 (502 mg, 0.55 mmol) and the mixture was cooled to 0° C. Acetic anhydride (3 mL) was added. The mixture was stirred at rt for 18 h. The mixture was concentrated and toluene was co-evaporated from the residue. The residue was taken up in DCM and washed successively with 5% aq HCl and saturated aq NaHCO$_3$. The organic phase was dried and concentrated to give 327 (538 mg, 94%) as a colourless foam.

(b) THF (3 mL) and ethanol (3.3 mL) were added to 328 (384 mg, 0.30 mmol). Ethylenediamine (90 μL, 1.36 mmol) was added and the mixture was heated at 55° C. for 4 h. The mixture was allowed to cool to rt. Acetic anhydride (1.0 mL) was added, and the mixture was stirred at rt for 1.5 h. The mixture was concentrated. The residue was taken up in pyridine (5 mL) and the mixture was cooled to 0° C. Acetic anhydride (2.5 mL) was added. The mixture was stirred at rt for 18 h. The mixture was concentrated and toluene was co-evaporated from the residue. The residue was taken up in DCM, which caused the formation of a white precipitate. The mixture was filtered through a plug of silica gel, eluting with 7:3 cyclohexane-acetone. The filtrate was concentrated lo give 327 (215 mg, 68%) as a colourless foam: [α]$_D$–7° (c 0.5, CHCl$_3$): $^1$H NMR (300 MHz): δ 7.48-7.24 (m, 20H, Ph), 5.84 (m, 1H, All), 5.53 (d, 1H, NH), 5.19 (m, 2H, All), 5.03 (dd, 1H, H-4$_D$), 4.98 (m, 2H, H-1$_A$, 3$_D$), 4.95-4.54 (m, 10H, H-1$_B$, 1$_D$, CH$_2$Ph), 4.07 (m, 4H, H-2$_A$, 2$_D$, 6a$_D$, All), 3.88 (m, 5H, H-2$_B$, 3$_A$, 3$_B$, 6b$_D$, All), 3.79, 3.68 (2m, 2H, H-5$_A$, 5$_B$), 3.42 (m, 3H, H-4$_A$, 4$_B$, 5$_D$), 2.02, 2.01, 1.97, 1.64 (4s, 12H, OAc, NHAc), 1.30 (m, 6H, H-6$_A$, 6$_B$); $^{13}$C NMR (75 MHz): δ 170.7, 170.4, 169.9, 169.1 (C=O), 138.5-117.1 (Ph, All), 102.9 (C-1$_A$), 101.2 (C-1$_A$), 97.7 (C-1$_B$), 81.0, 80.5 (2C, C-4$_A$, 4$_B$), 79.5, 79.1 (2C, C-3$_A$, 3$_B$), 78.2 (C-2$_A$), 76.1 (C-2$_B$), 75.5, 75.2, 73.6 (CH$_2$Ph), 73.3 (C-3$_D$), 71.9 (C-5$_D$), 71.7 (CH$_2$Ph), 68.3 (C-5$_A$*), 68.0 (C-4$_D$), 67.6 (C-5$_B$*), 67.6 (CH$_2$O), 61.6 (C-6$_D$), 54.1 (C-2$_D$), 22.9 (NHAc), 20.7, 20.6 (3C, OAc), 18.0, 17.7 (2C, C-6$_A$, 6$_B$). FAD-MS for C$_{57}$H$_{69}$NO$_{17}$ (M, 1039.5) m/z 1062.4 [M+Na]$^+$. Anal. Calcd. for C$_{57}$H$_{69}$NO$_{17}$: C, 65.82; H, 6.69; N, 1.35%. Found: C, 65.29; H, 6.82; N, 1.29%.

(2-Acetamido-3,4,6-tri-O-acetyl-2-deoxy-β-D-glucopyranosyl)-(1→2)-(3,4-di-O-benzyl-α-L-rhamnopyranosyl)-(1→2)-3,4-di-O-benzyl-α/β-L-rhamnopyranose (329). 1,5-Cyclooctadiene-bis(methyldiphenylphosphine)iridium hexafluorophosphate (30 mg, 35 μmol) was dissolved THF (5 mL), and the resulting red solution was processed as described for the preparation of 318. A solution of 327 (805 mg, 0.775 mmol) in THF (10 mL) was degassed and added. The mixture was stirred at rt overnight, then concentrated. The residue was taken up in acetone (15 mL) and water (1.5 mL). Mercuric chloride (315 mg, 1.16 mmol) and mercuric oxide (335 mg, 1.55 mmol) were added. The mixture, protected from light, was stirred for 1 h at rt, then concentrated. The residue was taken up in DCM and washed three times with satd aqueous KI, then with brine. The organic phase was dried and concentrated. The residue was purified by column chromatography with 2:3 EtOAc-cyclohexane to give 329 (645 mg, 83%) as a white foam. The $^1$H NMR spectra showed the α:β ratio to be 3.3:1; [α]$_D$+3° (c 0.5, CHCl$_3$); $^1$H NMR (300 MHz) α-anomer: δ 7.47-7.30 (m, 20H, Ph), 5.53 (d, 1H, NH), 5.17 (d, 1H, J$_{1,2}$=1.9 Hz, H-1$_B$), 5.08 (m, 1H, H-4$_D$), 5.03 (d, 1H, J$_{1,2}$=1.5 Hz, H-1$_A$), 4.99 (m, 1H, H-3$_D$), 4.92-4.62 (m, 8H, CH$_2$Ph), 4.60 (d, 1H, J$_{1,2}$=8.4 Hz, H-1$_D$), 4.18-4.01 (m, 3H, H-2$_A$, 2$_D$, 6a$_D$), 3.97-3.90 (m, 5H, H-2$_B$, 3$_A$, 3$_B$, 5$_A$*, 6b$_D$), 3.83 (m, 1H, H-5$_B$*), 3.45-3.37 (m, 3H, H-4$_A$, 4$_B$, 5$_D$), 2.04, 2.03, 1.99, 1.68 (4s, 12H, OAc, NHAc), 1.32 (m, 6H, H-6$_A$, 6$_B$); $^{13}$C NMR (75 MHz) α-anomer: δ 170.7, 170.4, 169.9, 169.1 (C=O), 138.5-129.3 (Ph), 103.3 (C-1$_D$), 101.6 (C-1$_A$), 93.9 (C-1$_B$), 81.5, 80.8 (2C, C-4$_A$, 4$_B$), 79.9, 78.9 (2C, C-3$_A$, 3$_B$), 78.6 (C-2$_A$), 76.8 (C-2$_B$), 76.0, 75.5, 74.0 (3C, CH$_2$Ph), 73.7 (C-3$_D$), 72.4 (C-5$_D$), 72.2 (CH$_2$Ph), 68.7 (C-5$_A$*), 68.5 (C-4$_D$), 68.2 (C-5$_B$*), 62.0 (C-6$_D$), 54.6 (C-2$_D$), 23.4 (NHAc), 21.1, 21.0 (3C, OAc), 18.5, 18.1 (2C, C-6$_A$, 6$_B$). FAB-MS for C$_{54}$H$_{65}$NO$_{17}$ (M, 999.4) m/z 1022.5 [M+Na]$^+$. Anal. Calcd. for C$_{54}$H$_{65}$NO$_{17}$: C, 64.85; H, 6.55; N, 1.40%. Found: C, 64.55; H, 7.16; N, 1.15%.

(2-Acetamido-3,4,6-tri-O-acetyl-2-deoxy-β-D-glucopyranosyl)-(1→2)-(3,4-di-O-benzyl-α-L-rhamnopyranosyl)-(1→2)-3,4-di-O-benzyl-α/β-L-rhamnopyranosyl Trichloroacetimidate (313). The hemiacetal 329 (595 mg, 0.59 mmol) was dissolved in DCM (10 mL), placed under Argon and cooled to 0° C. Trichloroacetonitrile (0.6 mL, 6 mmol), then DBU (10 μL, 59 μmol) were added. The mixture was stirred at 0° C. for 20 min, then at rt for 20 min. The mixture was concentrated and toluene was co-evaporated from the residue. The residue was purified by flash chromatography with 1:1 cyclohexane-EtOAc and 0.2% of Et$_3$N to give 313 (634 mg, 94%) as a colorless foam. The $^1$H NMR spectra showed the α:β ratio to be 10:1: [α]$_D$–20° (c 1, CHCl$_3$); $^1$H NMR (300 MHz) α-anomer: δ 8.47 (s, 1H, C=NH), 7.38-7.20 (m, 20H, Ph), 610 (d, 1H, J$_{1,2}$=1.3 Hz, H-1$_B$), 5.40 (d, 1H, NH), 5.01 (m, 1H, H-4$_D$), 4.95 (d, 1H, J$_{1,2}$=1.2 Hz, H-1$_A$), 4.89 (m, 1H, H-3$_D$), 4.85-4.55 (m, 9H, H-1$_D$, CH$_2$Ph), 4.07 (dd, 1H, H-6a$_D$), 4.03 (m, 1H, H-2$_A$), 3.97 (m, 1H, H-2$_D$), 3.91 (dd, 1H, H-6b$_D$), 3.85-3.71 (m, 5H, H-2$_B$, 3$_A$, 3$_B$, 5$_A$, 5$_B$), 3.45-3.31 (m, 3H, H-4$_A$, 4$_B$, 5$_D$), 1.99, 1.96, 1.91, 1.58 (4s, 12H, OAc, NHAc), 1.26 (m, 6H, H-6$_A$, 6$_B$); $^{13}$C NMR (75 MHz): δ 171.1, 170.9, 170.3, 169.6 (C=O), 160.6 (C=NH), 138.6-128.1 (Ph), 103.3 (C-1$_D$), 101.6 (C-1$_A$), 96.9 (C-1$_B$), 91.3 (CCl$_3$), 81.4, 80.2 (2C, C-4$_A$, 4$_B$), 79.9, 78.5 (2C, C-3$_A$, 3$_B$), 78.3 (C-2$_A$), 75.9 (2C, CH$_2$Ph), 75.0 (C-2$_B$), 73.7 (CH$_2$Ph), 73.7 (C-3$_D$), 72.4 (CH$_2$Ph), 72.4 (C-5$_D$), 71.0, 69.0 (2C, C-5$_A$, 5$_B$), 68.5 (C-4$_D$), 62.1 (C-6$_D$), 54.6 (C-2$_D$), 23.4 (NHAc), 21.1, 21.0 (3C, OAc), 18.5, 18.0 (2C, C-6$_A$, 6$_B$). Anal. Calcd. for C$_{56}$H$_{65}$Cl$_3$N$_2$O$_{17}$: C, 58.77; H, 5.72; N, 2.45%. Found: C, 58.78; H, 5.83; N, 2.45%.

Allyl (2-Acetamido-3,4,6-tri-O-acetyl-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (305). Anhydrous Et$_2$O (5 mL) was added to the donor- 313 (500 mg, 0.44 mmol) and the acceptor 311 (Segat, F.; Mulard, L. A. *Tetrahedron: Asymmetry* 2002, 13, 2211-2222) (242 mg, 0.29 mmol) and powdered 4 Å molecular sieves. The mixture was placed under Argon and cooled to 0° C. Boron trifluoride etherate (415 μL, 3.27 mmol) was added. The mixture was stirred at 0° C. for 1 h, then at rt for 18 h. The mixture was diluted with DCM and triethylamine (1 mL) was added. The mixture was filtered through a pad of Celite and the filtrate was concentrated. The residue was purified by column chromatography with 3:2 cyclohexane-EtOAc to give, in order, the acceptor 311 (132 mg, 54%), 305 (231 mg, 44%) and the hemiacetal 329 (129 mg, 29%). The desired pentasaccharide 305 was obtained as a colourless foam: $[\alpha]_D+10°$ (c 1.0, CHCl$_3$); $^1$H NMR: δ 8.02-7.09 (m, 45H, Ph), 5.92 (m, 1H, All), 5.65 (d, 1H, NH), 5.37 (m, 1H, H-2$_C$), 5.19 (m, 2H, All), 5.13 (bs, 1H, H-1$_A$), 4.96-4.35 (m, 15H, J-1$_B$, 1$_C$, 1$_D$, 1$_E$, 2$_B$, 3$_D$, 4$_D$, CH$_2$Ph), 4.17 (m, 2H, H-2$_A$, All), 4.04-3.87 (m, 8H, H-2$_D$, 3$_A$, 3$_C$, 3$_E$, 5$_A$, 5$_E$, 6a$_D$, All), 3.81-3.63 (m, 7H, H-3$_B$, 4$_C$, 4$_E$, 5$_C$, 6a$_E$, 6b$_E$, 6b$_D$), 3.59 (m, 1H, H-5$_B$), 3.43 (m, 3H, H-2$_C$, 4$_A$, 5$_D$), 3.28 (pt, 1H, H-4$_B$), 2.01, 1.99, 1.71, 1.66 (4s, 12H, OAc, NHAc), 1.34 (m, 6H, H-6$_A$, 6$_C$), 1.00 (d, 3H, H-6$_B$); $^{13}$C NMR: δ 170.5, 170.0, 169.3, 165.8, 163.5 (C=O), 138.7-117.6 (Ph, All), 102.7 (C-1$_D$), 100.8 (2C, C-1$_A$, 1$_B$), 98.1 (C-1$_E$), 95.9 (C-1$_C$), 81.8 (C-3$_E$), 81.2 (2C, C-2$_E$, 4$_A$), 80.0 (C-4$_B$), 79.7 (2C, C-3$_A$, 3$_C$), 78.2 (C-3$_B$), 77.7 (C-2$_A$), 77.3 (2C, C-4$_C$, 4$_E$), 75.6, 75.4, 74.9 (CH$_2$Ph), 74.3 (C-2$_B$), 73.8 (CH$_2$Ph), 73.7 (C-3$_D$)r 72,8 (CH$_2$Ph), 72.3 (C-2$_C$), 72.1 (C-5$_D$), 71.5 (C-5$_E$), 70.2 (CH$_2$Ph), 68.5 (C-5$_B$), 68.4 (C-5$_A$, CH$_2$O), 68.2 (C-4$_D$), 67.9 (C-6$_E$), 67.4 (C-5$_C$), 61.8 (C-6$_D$), 54.3 (C-2$_D$), 23.1 (NHAc), 20.7, 20.6, 20.4 (3C, OAc), 18.6 (C-6$_A$), 18.0 (C-6$_C$), 17.8 (C-6$_B$). FAB-MS for C$_{104}$H$_{117}$NO$_{27}$ (M, 1812.1) m/z 1836.2, 1835.2 [M+Na]$^+$. Anal. Calcd. for C$_{104}$H$_{117}$NO$_{27}$: C, 68.90; H, 6.50; N, 0.77%. Found: C, 68.64; H, 6.66; N, 1.05%.

Allyl (3,4-Di-O-benzyl-2-O-chloroacetyl-α-L-rhamnopyranosyl)-(1→2)-3,4-di-O-benzyl-α-L-rhamnopyranoside (332). To a mixture of 323 (3.8 g, 5.35 mmol) in pyridine (40 mL) was added chloroacetic anhydride (1.83 g, 10.7 mmol) at 0° C. The solution was stirred overnight at 0° C. MeOH (10 mL) was added and the mixture was concentrated. The residue was eluted from a column of silica gel with 95:5 cyclohexane-acetone to give 332 (2.4 g, 57%) as a colorless syrup: $[\alpha]_D-15°$ (c 1.0. CHCl$_3$); $^1$H NMR: δ 7.30-7.15 (m, 20H, Ph), 5.81-5.71 (m, 1H, All), 5.49 (dd, 1H, J$_{1,2}$=1.7, J$_{2,3}$=3.2 Hz, H-2$_A$), 5.20-5.08 (m, 2H, All), 4.90 (d, 1H, H-1$_A$), 4.84-4.50 (m, 8H, PhCH$_2$), 4.65 (d, 1H, J$_{1,2}$<1.0 Hz, H-1$_B$), 4.04-3.85 (m, 2H, All), 4.02 (m, 2H, CH$_2$Cl), 3.93 (dd, 1H, J$_{2,3}$=3.0 Hz, H-2$_B$), 3.88 (dd, 1H, J$_{3,4}$=9.5 Hz, H-3$_A$), 3.81 (pt, 1H, J$_{3,4}$=9.5 Hz, H-3$_B$), 3.73 (dq, 1H, J$_{4,5}$=9.5, J$_{5,6}$=6.2 Hz, H-5$_A$), 3.62 (dq, 1H, J$_{4,5}$=9.0, J$_{5,6}$=6.1 Hz, H-5$_B$), 3.34 (dd, 1H, H-4$_B$), 3.30 (dd, 1H, H-4$_A$), 1.22 (d, 3H, H-6$_A$), 1.21 (d, 3H, H-6$_B$); $^{13}$C NMR: δ 166.9 (C=O), 138.5-117.2 (Ph, All), 99.2 (C-1$_A$), 98.2 (C-1$_B$), 80.4 (C-4$_A$), 80.3 (C-3$_B$), 80.2 (C-4$_B$), 77.9 (C-3$_A$), 75.8, 75.7, 72.6, 72.4 (4C, PhCH$_2$), 74.9 (C-2$_B$), 71.2 (C-2$_A$), 68.6 (C-5$_A$), 68.4 (C-5$_B$), 68.0 (All), 41.3 (CH$_2$Cl), 18.3 (2C, C-6$_A$, 6$_B$). FAB-MS for C$_{45}$H$_{52}$ClO$_{10}$ (M, 786.3) m/z 809.3 [M+Na]$^+$. Anal. Calcd for C$_{45}$H$_{51}$ClO$_{10}$: C, 68.65; H, 6.53%. Found: C, 68.51; H, 6.67%.

(3,4-Di-O-benzyl-2-O-chloroacetyl-α-L-rhamnopyranosyl)-(1→2)-3,4-di-O-benzyl-α/β-L-rhamnopyranose (333). 1,5-Cyclooctadiene-bis(methyldiphenylphosphine)iridium hexafluorophosphate (40 mg, 46 μmol) was dissolved THF (7 mL), and the resulting red solution was processed us described for the preparation of 318. A solution of 332 (2.39 g, 3.04 mmol) in THF (18 mL) was degassed and added. The mixture was stirred at rt overnight. The mixture was concentrated. The residue was taken up in acetone (30 mL) and water (5 mL). Mercuric chloride (1.24 g, 4.56 mmol) and mercuric oxide (1.3 g, 6.08 mmol) were added. The mixture, protected from light, was stirred for 2 h at rt, then concentrated. The residue was taken up in DCM and washed three times with satd aqueous KI, then with brine. The organic phase was dried and concentrated. The residue was purified by column chromatography (cyclohexane-EtOAc, 4:1) to give 333 (1.91 g, 84%) as a white foam: $[\alpha]_D-2°$ (c 1.0, CHCl$_3$); $^1$H NMR: δ 7.40-7.10 (m, 20H, Ph), 5.49 (dd, 1H, J$_{1,2}$=1.7, J$_{2,3}$=3.2 Hz, H-2$_A$), 4.99 (d, 1H, J$_{1,2}$<1.0 Hz, H-1$_B$), 4.90 (d, 1H, H-1$_A$), 4.85-4.45 (m, 8H, PhCH$_2$), 4.01 (m, 2H, CH$_2$Cl), 3.93 (dd, 1H, J$_{2,3}$=3.0 Hz, H-2$_B$), 3.90 (dd, 1H, J$_{3,4}$=9.3 Hz, H-3$_A$), 3.84 (dd, 1H, J$_{3,4}$=9.0 Hz, H-3$_B$), 3.81 (dq, 1H, J$_{4,5}$=9.0 Hz, J$_{5,6}$=6.2 Hz, H-5$_B$), 3.72 (dq, 1H, J$_{4,5}$=9.5, J$_{5,6}$=6.2 Hz, H-5$_A$), 3.33 (pt, 1H, H-4$_B$), 3.30 (dd, 1H, H-4$_A$), 2.81 (d, 1H, J$_{2,OH}$=3.4 Hz, OH), 1.22 (d, 3H, H-6$_A$), 1.20 (d, 3H, H-6$_B$); $^{13}$C NMR: δ 167.0 (C=O), 138.5-127.2 (Ph), 99.1 (C-1$_A$), 93.9 (C-1$_B$), 80.3 (C-4$_B$), 80.2 (C-4$_A$), 79.7 (C-3$_B$), 77.8 (C-3$_A$), 75.8, 75.7, 72.6, 72.4 (4C, PhCH$_2$), 75.0 (C-2$_B$), 71.1 (C-2$_A$), 68.6 (C-5$_A$), 68.4 (C-5$_B$), 41.3 (CH$_2$Cl), 18.1 (2C, C-6$_A$, 6$_B$). FAB-MS for C$_{42}$H$_{47}$ClO$_{10}$ (M, 746.3) m/z 769.3 [M+Na]$^+$. Anal. Calcd for C$_{42}$H$_{47}$ClO$_{10}$: C, 67.51; H, 6.34%. Found: C, 67.46; H, 6.39%.

(3,4-Di-O-benzyl-2-O-chloroacetyl-α-L-rhamnopyranosyl)-(1→2)-3,4-di-O-benzyl-α-L-rhamnopyranosyl Trichloroacetimidate (334). The hemiacetal 333 (1.80 g, 2.41 mmol) was dissolved in DCM (25 mL), placed under Argon and cooled to 0° C. Trichloroacetonitrile (2.4 mL, 24 mmol), then DBU (35 μL, 0.24 mmol) were added. The mixture was stirred at 0° C. for 40 min. The mixture was concentrated and toluene was co-evaporated from the residue. The residue was eluted from a column of silica gel with 4:1 cyclohexane-EtOAc and 0.2% Et$_3$N to give 334 (1.78 g, 83%) as a colorless foam: $[\alpha]_D-12°$ (c 1.0, CHCl$_3$); $^1$H NMR: δ 8.60 (s, 1H, NH), 7.50-7.30 (m, 20H, Ph), 6.21 (d, 1H, J$_{1,2}$=1.8 Hz, H-1$_B$), 5.63 (dd, 1H, J$_{1,2}$=1.5, J$_{2,3}$=3.2 Hz, H-2$_A$), 5.07 (d, 1H, H-1$_A$), 5.00-4.65 (m, 8H, PhCH$_2$), 4.19 (m, 2H, CH$_2$Cl), 4.09 (dd, 1H, J$_{2,3}$=3.2 Hz, H-2$_B$), 4.04 (dd, 1H, J$_{3,4}$=9.0 Hz, H-3$_B$), 3.95 (m, 3H, H-3$_A$, 5$_A$, 5$_B$), 3.58 (dd, 1H, H-4$_A$), 3.48 (dd, 1H, H-4$_B$), 1.39 (m, 6H, H-6$_A$, 6$_B$); $^{13}$C NMR: δ 167.1 (C=O), 160.7 (C=N), 138.3-127.0 (Ph), 99.4 (C-1$_A$), 97.5 (C-1$_B$), 91.4 (CCl$_3$), 80.1 (C-4$_B$), 80.0 (C-4$_A$), 79.2 (C-3$_A$), 77.9 (C-3$_B$), 75.9, 75.8, 73.0, 72.6 (4C, PhCH$_2$), 73.7 (C-2$_B$), 71.4 (C-2$_A$), 71.2, 68.9 (2C, C-5$_A$, 5$_B$), 41.3 (CH$_2$Cl), 18.4, 18.2 (2C, C-6$_A$, 6$_B$). Anal. Calcd for C$_{44}$H$_{47}$Cl$_4$NO$_{10}$: C, 59.27; H, 5.31; N, 1.57%. Found: C, 59.09; H, 5.49; N, 1.53%.

Allyl (3,4-Di-O-benzyl-2-O-pmethoxybenzyl-α-L-rhamnopyranosyl)-(1→2)-3,4-di-O-benzyl-α-L-rhamnopyranoside (335). The alcool 323 (3.8 g, 5.35 mmol) was dissolved in DMF (25 mL). The mixture was cold to 0° C. and NaH (320 mg, 8.02 mmol) was added in 3 parts each 10 min. Then pMeOBnCl (1.8 mL, 13.34 mmol) was added and the mixture was stirred overnight at rt. MeOH (5 mL) was added and the solution stirred for 10 min. The solution was concentrated and the residue was eluted from a column of silica gel with 95:5 cyclohexane-acetone to give 335 (4.34 g, 97%) as a colorless syrup: $[\alpha]_D-8°$ (c 1.0, CHCl$_3$); $^1$H NMR (300 MHz): δ 7.20-6.80 (m, 24H, Ph), 5.90-5.80 (m, 1H, All), 5.30-5.15 (m, 2H, All), 5.12 (d, 1H, J$_{1,2}$<1.0 Hz, H-1$_A$), 4.73 (d, 1H, J$_{1,2}$<1.0 Hz, H-1$_B$), 4.70-4.40 (m, 10H, PhCH$_2$), 4.20-4.08 (m, 1H, All), 4.10 (dd, 1H, J$_{2,3}$=3.0 Hz, H-2$_B$), 3.95-3.88 (m, 3H, H-3$_A$, 3$_B$, All), 3.80-3.78 (m, 2H, J$_{4,5}$=9.4, J$_{5,6}$=6.1 Hz, H-2$_A$, 5$_A$), 3.72 (s, 3H, OCH$_3$), 3.70 (m, 1H, J$_{4,5}$=9.4, J$_{5,6}$=6.1 Hz, H-5$_B$), 3.61 (dd, 1H, H-4$_A$), 3.32 (dd, 1H, H-4$_B$), 1.18 (d, 3H, H-6$_A$), 1.10 (d, 3H, H-6$_B$); $^{13}$C NMR (75 MHz): δ 133.9-113.8 (Ph, All), 99.0 (C-1$_A$), 97.8 (C-1$_B$), 80.4 (C-4$_B$), 80.2 (C-4$_A$), 80.0 (C-3$_B$), 79.0 (C-3$_A$), 75.2, 72.3, 71.8, 71.5, 71.3, 67.5 (5C, PhCH$_2$, All), 74.1 (C-2$_A$), 73 8 (C-2$_B$), 68.3 (C-5$_A$), 67.8 (C-5$_B$), 55.0

(OCH$_2$), 17.8, 17.9 (2C, C-6$_A$, 6$_B$). FAB-MS for C$_{51}$H$_{58}$O$_{10}$ (M, 830.4) m/z 853.5 [M+Na]$^+$. Anal. Calcd. for C$_{51}$H$_{58}$O$_{10}$: C, 73.71; H, 7.03%. Found: C, 73.57; H, 7.21%.

(3,4-Di-O-benzyl-2-O-pmethoxybenzyl-α-L-rhamnopyranosyl)-(1→2)-3,4-di-O-benzyl-α-L-rhamnopyranose (336). 1,5-Cyclooctadiene-bis(methyldiphenylphosphine) iridium hexafluorophosphate (50 mg, 60 μmol) was dissolved THF (6 mL), and the resulting red solution was processed as described for the preparation of 318. A solution of 335 (4.23 g, 5.09 mmol) in THF (24 mL) was degassed and added. The mixture was stirred at rt overnight, then concentrated. The residue was taken up in acetone (45 mL), and water (5 mL) was added. Mercuric chloride (2.07 g, 7.63 mmol) and mercuric oxide (2.2 g, 10.2 mmol) were added. The mixture, protected from light, was stirred for 2 h at rt, then concentrated. The residue was taken up in DCM and washed three times with satd aqueous KI, then with brine. The organic phase was dried and concentrated. The residue was purified by column chromatography (cyclohexane-EtOAc, 4:1) to give 336 (2.97 g, 73%) as a white foam: [α]$_D$+8° (c 1.0, CHCl$_3$); $^1$H NMR (300 MHz): δ 7.40-7.25 (m, 20H, Ph), 7.18-6.73 (m, 4H, Ph), 5.12 (d, 1H, J$_{1,2}$<1.0 Hz, H-1$_A$), 5.05 (d, 1H, J$_{1,2}$<1.0 Hz, H-1$_B$), 4.80-4.40 (m, 10H, PhCH$_2$), 4.08 (dd, 1H, J$_{2,3}$=3.0 Hz, H-2$_B$), 3.90-3.80 (m, 2H, J$_{3,4}$=J$_{4,5}$=9.5, J$_{5,6}$=6.1 Hz, H-3$_B$, 5$_B$), 3.80-3.78 (m, 2H, J$_{2,3}$=3.1, J$_{4,5}$=9.4, J$_{5,6}$=6.1 Hz, H-2$_A$, 5$_A$), 3.73 (m, 1H, J$_{3,4}$=9.4 Hz, H-3$_A$), 3.72 (s, 3H, OCH$_3$), 3.60 (pt, 1H, H-4$_A$), 3.33 (pt, 1H, H-4$_B$), 1.34 (d, 3H, H-6$_A$), 1.24 (d, 3H, H-6$_B$); $^{13}$C NMR (75 MHz): δ 113.2-129.8 (Ph), 99.1 (C-1$_A$), 93.8 (C-1$_B$), 80.7 (C-4$_A$), 80.3 (C-4$_B$), 79.7 (C-3$_B$), 79.2 (C-3$_A$), 75.5, 75.4, 72.6, 72.5, 72.4 (5C, PhCH$_2$), 74.2 (C-2$_A$), 74.1 (C-2$_B$), 68.5 (C-5$_A$), 68.1 (C-5$_B$), 55.3 (OCH$_3$), 18.1 (2C, C-6$_A$, 6$_B$). FAB-MS for C$_{48}$H$_{54}$O$_{10}$ (M, 790.4) m/z 813.4 [M+Na]$^+$. Anal. Calcd. for C$_{48}$H$_{54}$O$_{10}$: C, 72.89; H, 6.88%. Found: C, 72.86; H, 6.98%.

(3,4-Di-O-benzyl-2-O-pmethoxybenzyl-α-L-rhamnopyranosyl)-(1→2)-3,4-di-O-benzyl-α/β-L-rhamnopyranosyl Trichloroacetimidate (337). The hemiacetal 336 (2.1 g, 2.66 mmol) was dissolved in DCM (20 mL), placed under Argon and cooled to 0° C. Trichloroacetonitrile (2.7 mL, 26 mmol), then DBU (40 μL, 0.26 mmol) were added. The mixture was stirred at 0° C. for 30 min. The mixture was concentrated and toluene was co-evaporated from the residue. The residue was eluted from a column of silica gel with 8:2 cyclohexane-EtOAC and 0.2% Et$_3$N to give 337 (2.03 g, 82%) as a colorless foam: [α]$_D$−10° (c 1.0, CHCl$_3$); $^1$H NMR (300 MHz): δ 8.50 (s, 1H, NH), 7.25-7.05 (m, 20H, Ph), 7.05-6.62 (m, 4H, Ph), 6.08 (d, 1H, J$_{1,2}$<1.0 Hz, H-1$_B$), 5.10 (d, 1H, J$_{1,2}$<1.0 Hz, H-1$_A$), 4.80-4.40 (m, 10H, PhCH$_2$), 4.10 (dd, 1H, J$_{2,3}$=3.0 Hz, H-2$_B$), 3.90-3 80 (m, 4H, H-3$_B$, 2$_A$, 3$_A$, 5$_A$), 3.80-3.72 (m, 1H, H-5$_B$), 3.72 (s, 3H, OCH$_3$), 3.63 (pt, 1H, J$_{3,4}$=J$_{4,5}$=9.5 Hz, H-4$_A$), 3.42 (pt, 1H, J$_{3,4}$=J$_{4,5}$=9.5 Hz, H-4$_B$), 1.30 (d, 3H, H-6$_B$), 1.25 (d, 3H, H-6$_A$). $^{13}$C NMR (75 MHz): δ 161.1 (C=NH), 129.5-113.4 (Ph), 99.6 (C-1$_A$), 97.0 (C-1$_B$), 80.6 (C-4$_A$), 79.6 (C-4$_B$), 79.3 (2C, C-3$_A$, 3$_B$), 75.7, 75.5, 72.8, 72.3, 72.0 (5C, PhCH$_2$), 74.4 (C-2$_A$), 72.6 (C-2$_B$), 71.1 (C-5$_A$), 68.9 (C-5$_B$), 55.3 (OCH$_3$), 18.1 (2C, C-6$_A$, 6$_B$). Anal. Calcd. for C$_{50}$H$_{54}$Cl$_3$NO$_{10}$: C, 64.21; H, 5.82; N, 1.50%. Found: C, 64.67; H, 6.01; N, 1.28%.

Allyl (3,4-Di-O-benzyl-2-O-chloroacetyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (338). A mixture of alcohol 311 (212 mg, 0.255 mmol) and imidate 334 (270 mg, 0.33 mmol) in anhydrous Et$_2$O (4 mL) was stirred for 15 min under dry Argon. After cooling at −60° C., TMSOTf (30 μL, 0.166 mmol) was added dropwise and the mixture was stirred overnight and allowed to reach rt. Triethylamine (120 μL) was added and the mixture was concentrated. The residue was eluted from a column of silica gel with 7:1 cyclohexane-EtOAc to give 338 (86 mg, 22%) as a foam: [α]$_D$+5° (c 1.0, CHCl$_3$); $^1$H NMR (300 MHz) δ 8.00-6.95 (m, 45H, Ph), 6.00-5.80 (m, 1H, All), 5.56 (dd, 1H, H-2$_A$), 5.40 (dd, 1H, J$_{1,2}$<1.0, J$_{2,3}$=3.0 Hz, H-2$_C$), 5.37-5.20 (m, 2H, All), 5.08 (d, 1H, J$_{1,2}$=3.2 Hz, H-1$_E$), 5.04 (d, 1H, J$_{1,2}$<1.0 Hz, H-1$_A$), 5.00 (d, 1H, J$_{1,2}$<1.0 Hz, H-1$_B$), 4.99 (d, 1H, H-1$_C$), 4.90-4.30 (m, 16H, CH$_2$Ph), 4.35 (dd, 1H, J$_{2,3}$=3.0 Hz, H-2$_B$), 4.14 (dd, 1H, J$_{3,4}$=9.5 Hz, H-3$_C$), 4.03 (pt, 1H, J$_{2,3}$=J$_{3,4}$=10.0 Hz, H-3$_E$), 4.20-3.90 (m, 2H, All), 4.00-3.75 (m, 4H, CH$_2$Cl, H-6a$_E$, 6b$_E$), 3.96 (dd, 1H, H-3$_A$), 3.95 (m, 1H, H-5$_A$), 3.95 (m, 1H, H-5$_E$), 3.83 (dd, 1H, H-4$_C$), 3.80 (m, 1H, H-5$_C$), 3.72 (dd, 1H, H-4$_E$), 3.64 (dd, 1H, H-3$_B$), 3.60 (m, 1H, H-5$_B$), 3.52 (dd, 1H, H-2$_E$), 3.39 (dd, 1H, H-4$_A$), 3.30 (dd, 1H, H-4$_B$), 1.35 (d, 1H, H-6$_A$), 1.30 (d, 1H, H-6$_C$), 1.00 (d, 1H, H-6$_B$); $^{13}$C NMR (75 MHz) δ 166.1, 165.7 (C=O), 133.4-117.0 (Ph), 100.9 (C-1$_B$), 98.9 (C-1$_A$), 97.8 (C-1$_E$), 96.0 (C-1$_C$), 81.8 (C-3$_E$), 80.9 (C-2$_E$), 79.9 (C-4$_A$), 79.6 (C-4$_B$), 79.6 (C-3$_C$), 78.9 (C-3$_B$), 78.0 (C-4$_C$), 77.5 (C-4$_E$), 77.3 (C-3$_A$), 75.6, 75.3, 75.0, 74.7, 73.9, 73.5, 72.8, 70.9 (9C, CH$_2$Ph, All), 74.9 (C-2$_B$), 72.5 (C-2$_C$), 71.2 (C-5$_E$), 70.9 (C-2$_A$), 68.8 (C-5$_B$), 68.5 (C-6$_E$), 68.3 (C-5$_A$), 67.5 (C-5$_C$), 40.9 (CH$_2$Cl), 18.8 (C-6$_A$), 18.2 (C-6$_C$), 17.8 (C-6$_B$). FAB-MS for C$_{92}$H$_{99}$ClO$_{20}$ (M, 1558.6) m/z 1581.7 [M+Na]$^+$. Anal. Calcd. for C$_{92}$H$_{99}$ClO$_{20}$: C, 70.82; H, 6.40%. Found: C, 70.67; H, 6.58%.

Allyl (3,4-Di-O-benzyl-2-O-pmethoxybenzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (339). A mixture of alcohol 311 (125 mg, 0.15 mmol) and 4 Å molecular sieves in anhydrous Et$_2$O (3 mL) was stirred for 45 min under dry Argon. After cooling at −40° C., Me$_3$SiOTf (20 μL, 0.112 mmol) was added dropwise. A solution of the donor 337 (210 mg, 0.225 mmol) in anhydrous Et$_2$O (2 mL) was added dropwise to the solution of the acceptor during 1 h. The mixture was stirred for 3 h at −40° C. Triethylamine (100 μL) was added and the mixture was filtered and concentrated. The residue was eluted from a column of silica gel with 85:15 cyclohexane-EtOAc to give 339 (107 mg, 44%) as a foam: [α]$_D$+12° (c 1.0, CHCl$_3$); $^1$H NMR: δ 8.10-7.10 (m, 45H, Ph), 7.00-6.50 (m, 4H, CH$_2$PhOMe), 5.90-5.70 (m, 1H, All), 5.32 (dd, 1H, J$_{1,2}$=1.6, J$_{2,3}$=3.1 Hz, H-2$_C$), 5.25-5.10 (m, 2H, All), 5.05 (d, 1H, H-1$_B$), 4.98 (d, 1H, J$_{1,2}$=3.2 Hz, H-1$_E$), 4.85 (m, 2H, H-1$_A$, 1$_C$), 4.80-4.20 (m, 18H, CH$_2$Ph), 4.20-3.90 (m, 2H, All), 4.20-3.00 (m, 20H, H-2$_A$, 2$_B$, 2$_E$, 3$_A$, 3$_B$, 3$_C$, 3$_E$, 4$_A$, 4$_B$, 4$_C$, 4$_E$, 5$_A$, 5$_B$, 5$_C$, 5$_E$, 6a$_E$, 6b$_E$, OCH$_2$), 1.30-0.82 (3d, 9H, H-6$_A$, 6$_B$, 6$_C$); $^{13}$C NMR: δ 166.3 (C=O), 138.5-118.2 (Ph, All), 99.5, 99.3 (2C, C-1$_A$, 1$_B$), 98.4 (C-1$_E$), 96.4 (C-1$_C$), 82.3, 81.4, 81.1, 80.5, 80.3, 79.5, 78.2, 77.6 (8C, C-2$_E$, 3$_A$, 3$_B$, 3$_C$, 3$_E$, 4$_A$, 4$_B$, 4$_C$), 76.0, 75.5, 75.3, 74.9, 74.3, 73.3, 72.3, 71.8, 71.6 (9C, CH$_2$Ph), 74.1, 73.8 (2C, C-2$_A$, 2$_B$), 72.5 (C-2$_C$), 72.0 (C-4$_E$), 69.2, 69.0, 68.9 (3C, C-5$_A$, 5$_B$, 5$_C$), 68.8, 68.6 (All, C-6$_E$), 67.8 (C-5$_E$), 55.5 (OCH$_3$), 19.0, 18.8, 18.4 (3C, C-6$_A$, 6$_B$, 6$_C$). FAB-MS for C$_{98}$H$_{106}$ O$_{20}$ (M, 1603.8) m/z 1626.6 [M+Na]$^+$.

Allyl (3,4-Di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (310). A solution of the trisaccharide 342 (Segat, F.; Mulard, L. A. Tetrahedron: Asymmetry 2002, 13, 2211-2222) (8.0 g, 6.5 mmol) in MeOH (128 mL) was treated with 5.7 mL of HBF$_4$/Et$_2$O at rt. The solution was stirred during 4 days. Et$_3$N was added until neutralization and concentrated. The residue was diluted with DCM, washed with satd aq NaHCO$_3$ and water. The organic layer was dried on MgSO$_4$, filtered and concentrated. The residue was eluted from a column of silica gel with 15:1 toluene-EtOAc to give 310 (6.31 g, 84%) as a foam: [α]$_D$+14° (c 1.0, CHCl$_3$); $^1$H NMR: δ 8.10-7.05 (m, 35H, Ph), 5.82 (m, 1H, All), 5.25 (dd, 1H, J$_{1,2}$=1.7, J$_{2,3}$=3.1 Hz, H-2$_C$), 5.19 (m, 2H, All), 5.00 (d, 1H, J$_{1,2}$=3.1 Hz, H-1$_E$), 4.87 (d, 1H, J$_{1,2}$=1.8 Hz, H-1$_B$), 4.81 (d, 1H, H-1$_C$), 4.90-4.35 (m, 12H, CH$_2$Ph), 4.20-4.00 (m, 2H, All), 4.10 (dd, 1H, J$_{3,4}$=8.5 Hz, H-3$_C$), 4.09 (dd, 1H, J$_{2,3}$=3.2 Hz, H-2$_B$), 3.95 (m, 1H, J$_{4,5}$=9.5 Hz, H-5$_E$), 3.92 (pt, 1H, J$_{2,3}$=9.5=J$_{3,4}$=9.5 Hz, H-3$_E$), 3.78 (dq, 1H, J$_{5,6}$=6.0 Hz, H-5$_C$), 3.70 (m, 1H, H-4$_C$), 3.62-3.58 (m, 2H, H-6a$_E$, 6b$_E$), 3.59 (m, 1H, J$_{4,5}$=9.0, J$_{5,6}$=6.2 Hz, H-5$_B$), 3.54 (dd, 1H, H-4$_E$), 3.48 (dd, 1H, J$_{3,4}$=8.5 Hz, H-3$_B$), 3.45 (dd, 1H, H-2$_E$), 3.31 (dd, 1H, H-4$_B$), 2.68 (d, 1H, J$_{2,OH}$=2.3 Hz, OH), 1.29 (d, 3H, H-6$_C$), 1.09 (d, 3H, H-6$_B$); $^{13}$C NMR: δ 166.2 (C=O), 137.5-118.2 (Ph, All), 103.1 (C-1$_B$), 98.5 (C-1$_E$), 96.6 (C-1$_C$), 82.1 (C-3$_E$), 81.4 (C-2$_E$), 80.4 (C-4$_B$), 79.7 (C-3$_B$), 79.4 (C-4$_C$), 78.9 (C-3$_C$), 78.1 (C-4$_E$), 76.0, 75.5, 74.5, 74.2, 73.6, 72.1 (6C, CH$_2$Ph), 73.7 (C-2$_C$), 71.6 (C-2$_B$), 68.9 (C-6$_E$), 68.8 (C-5$_B$), 68.7 (All, C-5$_E$), 68.1 (C-5$_C$), 19.1 (C-6$_C$), 18.2 (C-6$_B$). FAB-MS for C$_{70}$H$_{76}$O$_{15}$ (M, 1156.5) m/z 1179.5 [M+Na]$^+$. Anal. Calcd for C$_{70}$H$_{76}$O$_{15}$: C, 72.64; H, 6.62%. Found: C, 72.49; H, 6.80%.

Allyl (2-O-Acetyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (344). A mixture of alcohol 310 (5.2 g, 4.49 mmol), imidate 321 (3.58 g, 6.74 mmol) and 4 Å molecular sieves in anhydrous Et$_2$O (117 mL) was stirred for 1 h under dry Argon. After cooling at −30° C., Me$_3$SiOTf (580 μL, 3.2 mmol) was added dropwise and the mixture was stirred and allowed to rt overnight. Triethylamine (1.2 mL) was added and the mixture was filtered and concentrated. The residue was eluted from a column of silica gel with 9:1 cyclohexane-EtOAc to give 344 (6.16 g, 90%) as a white foam; [α]$_D$+13° (c 1.0, CHCl$_3$); $^1$H NMR: δ 8.10-7.00 (m, 45H, Ph), 5.82 (m, 1H, All), 5.45 (dd, 1H, J$_{1,2}$=1.5, J$_{2,3}$=2.5 Hz, H-2$_A$), 5.29 (dd, 1H, J$_{1,2}$=1.5, J$_{2,3}$=2.5 Hz, H-2$_C$), 5.19 (m, 2H, All), 4.97 (d, 1H, J$_{1,2}$=3.2 Hz, H-1$_E$), 4.95 (d, 1H, H-1$_A$), 4.91 (d, 1H, J$_{1,2}$=1.6 Hz, H-1$_B$), 4.84 (d, 1H, H-1$_C$), 4.90-4.35 (m, 16H, CH$_2$Ph), 4.29 (dd, 1H, J$_{2,3}$=2.6 Hz, H-2$_B$), 4.10-4.00 (m, 2H, All), 4.02 (dd, 1H, J$_{3,4}$=8.5 Hz, H-3$_C$), 3.90 (m, 2H, J$_{2,3}$=J$_{3,4}$=J$_{4,5}$=9.5 Hz, H-3$_E$, 5$_E$), 3.85 (m, 2H, J$_{3,4}$=9.3, J$_{4,5}$=9.5 Hz, H-3$_A$, 5$_A$), 3.72 (m, 2H, J$_{5,6}$=6.0 Hz, H-4$_C$, 5$_C$), 3.66-3.62 (m, 2H, H-6a$_E$, 6b$_E$), 3.61 (dd, 1H, H-4$_E$), 3.54 (dd, 1H, J$_{3,4}$=9.4 Hz, H-3$_B$), 3.45 (dd, 1H, J$_{4,5}$=9.5, J$_{5,6}$=6.1 Hz, H-5$_B$), 3.39 (dd, 1H, H-2$_E$), 3.34 (dd, 1H, H-4$_A$), 3.21 (dd, 1H, H-4$_B$), 1.89 (s, 3H, OAc), 1.26 (2d, 6H, H-6$_A$, 6$_C$), 0.89 (d, 3H, H-6$_B$); $^{13}$C NMR: δ 170.2, 166.1 (C=O), 138.4-118.1 (Ph, All), 101.3 (C-1$_B$), 99.8 (C-1$_A$), 98.2 (C-1$_E$), 96.4 (C-1$_C$), 82.2 (C-3$_E$), 81.4 (C-2$_E$), 80.6 (C-4$_A$), 80.5 (C-3$_C$), 80.1 (C-4$_B$), 79.3 (C-3$_E$), 78.5 (C-4$_C$), 78.1 (C-3$_A$), 78.0 (C-4$_E$), 76.0, 75.9, 75.7, 75.2, 74.3, 73.3, 72.1, 71.1 (8C, CH$_2$Ph), 75.2 (C-2$_B$), 72.9 (C-2$_C$), 71.7 (C-5$_E$), 69.5 (C-2$_A$), 69.2 (2C, C-5$_A$, 5$_B$), 68.9 (All), 68.9 (C-6$_E$), 67.9 (C-5$_C$), 21.4 (OAc), 19.1 (C-6$_A$), 18.7 (C-6$_C$), 18.1 (C-6$_B$). FAB-MS for C$_{92}$H$_{100}$O$_{20}$ (M, 1524.7) m/z 1547.8 [M+Na]$^+$. Anal. Calcd for C$_{92}$H$_{100}$O$_{20}$: C, 72.42; H, 6.61%. Found: C, 72.31; H, 6.75%.

Allyl (3,4-Di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (340). A mixture of 344 (6.0 g, 3.93 mmol) in MeOH (200 mL) was treated with 10 mL of HBF$_4$/Et$_2$O at rt. The solution was stirred during 5 days. Et$_3$N was added until neutralization and concentrated. The residue was diluted with DCM, washed with satd aq NaHCO$_3$ and water. The organic layer was dried on MgSO$_4$, filtered and concentrated. The residue was eluted from a column of silica gel with 6:1 cyclohexane-EtOAc to give 340 (5.0 g, 84%) as a colourless foam: [α]$_D$+12° (c 1.0, CHCl$_3$); $^1$H NMR: δ 8.00-7.00 (m, 45H, Ph), 5.83 (m, 1H, All), 5.29 (dd, 1H, J$_{1,2}$=1.8, J$_{2,3}$=2.9 Hz, H-2$_C$), 5.19 (m, 2H, All), 4.99 (d, 1H, J$_{1,2}$=1.4 Hz, H-1$_A$), 4.97 (d, 1H, J$_{1,2}$=3.3 Hz, H-1$_E$), 4.94 (d, 1H, J$_{1,2}$=1.7 Hz, H-1$_B$), 4.83 (d, 1H, H-1$_C$), 4.90-4.35 (m, 16H, CH$_2$Ph), 4.30 (dd, 1H, J$_{2,3}$=2.7 Hz, H-2$_B$), 4.10-4.00 (m, 2H, All), 4.02 (dd, 1H, J$_{2,3}$=3.5, J$_{3,4}$=8.5 Hz, H-3$_C$), 3.98 (m, 1H, H-2$_A$), 3.95-3.91 (m, 3H, H-5$_E$, 6a$_E$, 6a$_E$), 3.90 (dd, 1H, J$_{2,3}$=9.5, J$_{3,4}$=9.4 Hz, H-3$_E$), 3.82-3.73 (m, 4H, H-3$_A$, 5$_A$, 4$_C$, 5$_C$), 3.66 (dd, 1H, J$_{4,5}$=9.6 Hz, H-4$_E$), 3.53 (dd, 1H, J$_{3,4}$=9.5 Hz, H-3$_B$), 3.48 (m, 1H, J$_{4,5}$=9.5 Hz, H-5$_B$), 3.44-3.40 (m, 2H, H-4$_A$, 2$_E$), 3.17 (pt, 1H, H-4$_B$), 2.18 (d, 1H, J$_{2,OH}$=2.0 Hz, OH), 1.26 (d, 3H, J$_{5,6}$=5.5 Hz, H-2$_C$), 1.25 (d, 3H, J$_{5,6}$=6.2 Hz, H-6$_A$), 0.90 (d, 3H, J$_{5,6}$=6.2 Hz, H-6$_B$); $^{13}$C NMR: δ 166.2 (C=O), 138.3-118.0 (Ph, All), 101.5 (C-1$_B$), 101.4 (C-1$_A$), 98.2 (C-1$_E$), 96.4 (C-1$_C$), 82.2 (C-3$_E$), 81.4 (C-2$_E$), 80.6 (C-4$_A$), 80.3 (C-4$_B$), 79.9 (2C, C-3$_C$, 3$_A$), 79.2 (C-3$_B$), 78.3 (C-4$_C$), 78.0 (C-4$_E$), 7.59, 75.6, 75.5, 74.8, 74.2, 73.5, 72.4, 71.0 (8C, CH$_2$Ph), 75.3 (C-2$_B$), 72.9 (C-2$_C$), 71.6 (C-2$_A$), 69.2, 69.1, 68.3, 67.9 (4C, C-5$_A$, 5$_B$, 5$_C$, 5$_E$), 68.9, 68.7 (3C, C-6$_D$, 6$_E$, All), 19.1 (C-6$_C$), 18.6 (C-6$_A$), 18.1 (C-6$_B$). FAB-MS for C$_{90}$H$_{98}$O$_{19}$ (M, 1482.7) m/z 1505.8 [M+Na]$^+$. Anal. Calcd for C$_{90}$H$_{98}$O$_{19}$.2H$_2$O: C, 71.12; H, 6.77%. Found: C, 71.21; H, 6.78%.

Allyl (3,4,6-Tri-O-acetyl-2-deoxy-2-trichloroacetamido-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-)-benzyl-α-D-glucopyranosyl-(1→4)]-2-O-benzoyl-α-L-rhamnopyranoside (304). (a) A mixture of the donor 308 (200 mg, 230 μmol) and the acceptor 310 (188 mg, 144 μmol), 4 Å molecular sieves and dry Et$_2$O:1,2-DCE (1:1, 5 mL) was stirred for 1.5 h then cooled to 0° C. NIS (104 mg, 0.46 mmol) and triflic acid (4 μL, 0.05 mmol) were successively added. The stirred mixture was allowed to reach rt in 1 h. Et$_3$N (25 μL) was added and the mixture filtered. After evaporation, the residue was eluted from a column of silica gel with 4:1 to 2:1 cyclohexane-EtOAc to give 304 (28 mg, 10%).

(b) A mixture of alcohol 310 (5.0 g, 3.37 mmol), imidate 316 (3.0 g, 5.04 mmol) and 4 Å molecular sieves in anhydrous DCM (120 mL) was stirred for 1 h under dry Argon. After cooling at 0° C., TMSOTf (240 μL, 1.32 mmol) was added dropwise and the mixture was stirred for 2.5 h while coming back to rt. Et$_3$N (800 μL) was added, and the mixture was filtered and concentrated. The residue was eluted from a column of silica gel with 4:1 to 2:1 cyclohexane-EtOAc to give 304 (6.27 g, 98%) as a colourless foam: [α]$_D$+1.5° (c 1.0, CHCl$_3$); $^1$H NMR: δ 8.00-7.00 (m, 45H, Ph), 6.68 (d, 1H, J$_{2,NH}$=8.5 Hz, NH$_D$), 5.82 (m, 1H, All), 5.29 (dd, 1H, J$_{1,2}$=1.0, J$_{2,3}$=2.3 Hz, H-2$_C$), 5.19 (m, 2H, All), 5.00 (d, 1H, J$_{1,2}$=1.0 Hz, H-1$_A$), 4.96 (dd, 1H, J$_{2,3}$=10.5, J$_{3,4}$=10.5 Hz, H-3$_D$), 4.88 (d, 1H, J$_{1,2}$=3.3 Hz, H-1$_E$), 4.85 (d, 1H, H-1$_C$), 4.82 (d, 1H, J$_{1,2}$=1.7 Hz, H-1$_B$), 4.81 (dd, 1H, J$_{4,5}$=10.0 Hz, H-4$_D$), 4.72 (d, 1H, J$_{1,2}$=8.6 Hz, H-1$_D$), 4.90-4.35 (m, 16H, CH$_2$Ph), 4.38 (m, 1H, H-2$_B$), 4.10-4.00 (m, 2H, All), 4.05 (dd, 1H, J$_{2,3}$=2.7 Hz, H-2$_A$), 3.95 (dd, 1H, J$_{2,3}$=3.5, J$_{3,4}$=8.5 Hz, H-3$_C$), 3.90 (m, 2H, H-5$_E$, 4$_E$), 3.86-3.82 (m, 2H, H-6a$_D$, 6b$_D$), 3.84-3.70 (m, 6H, H-3$_E$, 6a$_E$, 6b$_E$, 3$_A$, 5$_A$, 2$_D$), 3.68 (m, 1H, H-5$_D$), 3.61 (dd, 1H, J$_{4,5}$=9.0 Hz, H-4$_C$), 3.56 (dd, 1H, J$_{3,4}$=9.5 Hz, H-3$_B$), 3.47 (m, 1H, $J_{4,5}$=9.5, $J_{5,6}$=6.1 Hz, H-$5_B$), 3.35-3.33 (m, 3H, H-$4_A$, $5_D$, $2_C$), 3.17 (dd, 1H, H-$4_B$), 2.02, 2.00, 1.98 (3s, 9H, OAc), 1.24 (d, 3H, $J_{5,6}$=6.0 Hz, H-$6_A$), 1.23 (d, 3H, $J_{5,6}$=5.9 Hz, H-$6_C$), 0.90 (d, 3H, H-$6_B$); $^{13}$C NMR: δ 170.9, 170.7, 169.6, 166.1, 162.1 (C=O), 138.3-118.1 (Ph, All), 101.5 (C-$1_D$), 101.4 (C-$1_B$), 101.1 (C-$1_A$), 98.5 (C-$1_E$), 96.4 (C-$1_C$), 92.6 (CCl$_3$), 82.1 (C-$3_E$), 81.7 (C-$3_C$), 81.6 (C-$2_E$), 80.4 (C-$4_B$), 80.1 (C-$3_A$), 79.1 (bs, C-$4_C$), 78.5 (C-$3_B$), 77.9 (C-$4_A$), 77.6 (C-$4_E$), 76.4 (C-$2_A$), 76.1, 75.8, 75.4, 74.7, 74.3, 74.2, 73.2, 70.4 (8C, CH$_2$Ph), 74.9 (C-$2_B$), 72.9 (C-$3_D$), 72.7 (C-$2_C$), 72.5 (C-$5_D$), 71.9 (C-$5_E$), 68.4 (C-$6_E$), 68.8 (All), 68.9, 68.7, 68.5, 67.7 (4C, C-$4_D$, $5_A$, $5_B$, $5_C$), 62.1 (C-$6_D$), 56.2 (C-$2_D$), 20.9, 20.7 (3C, OAc), 19.0 (C-$6_A$), 18.5 (C-$6_C$), 18.2 (C-$6_B$). FAB-MS of C$_{104}$H$_{114}$Cl$_3$NO$_{27}$ (M, 1916.4) m/z 1938.9 [M+Na]$^+$. Anal. Calcd for C$_{104}$H$_{114}$Cl$_3$NO$_{27}$: C, 65.18; H, 6.00; N, 0.73%. Found: C, 64.95; H, 6.17; N, 0.76%.

(2,3,4-Tri-O-acetyl-2-deoxy-2-trichloroacetamido-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranosyl trichloroacetimidate (346). Compound 304 (3.5 g, 1.8 mmol) was dissolved in anhydrous THF (35 mL). The solution was degassed and placed under Argon. 1,5-Cyclooctadiene-bis(methyldiphenylphosphine)iridium hexafluorophosphate (81 mg) was added, and the solution was degassed again. The catalyst was activated by passing over a stream of hydrogen until the solution has turned yellow. The reaction mixture was degassed again and stirred under an Argon atmosphere, then concentrated to dryness. The residue was dissolved in acetone (15 mL), then water (3 mL), mercuric chloride (490 mg) and mercuric oxide (420 mg) were added successively. The mixture, protected from light, was stirred at rt for 2 h and acetone was evaporated. The resulting suspension was taken up in DCM, washed twice with 50% aq KI, water and brine, dried and concentrated. The residue was eluted from a column of silica gel with 2:1 petroleum ether-EtOAc to give the corresponding hemiacetal 345. Trichloroacetonitrile (6.5 mL) and DBU (97 μL) were added to a solution of the residue in anhydrous DCM (33 mL) at 0° C. After 1 h, the mixture was concentrated. The residue was eluted from a column of silica gel with 5:2 cyclohexane-EtOAc and 0.2% Et$_3$N to give 346 (2.48 g, 66%) as a colourless foam; [α]$_D$+4° (c 1.0, CHCl$_3$); $^1$H NMR: δ 8.71 (s, 1H, NH), 8.00-7.00 (m, 45H, Ph), 6.80 (d, 1H, $J_{2,NH}$=8.6 Hz, NH$_D$), 6.37 (d, 1H, $J_{1,2}$=2.7 Hz, H-$1_C$), 5.59 (dd, 1H, $J_{2,3}$=2.9 Hz, H-$2_C$), 5.10 (bs, 1H, H-$1_A$), 5.05 (pt, 1H, $J_{2,3}$=9.8 Hz, H-$3_D$), 5.02-4.96 (m, 4H, H-$1_E$, $1_B$, $4_D$, CH$_2$Ph), 5.00-4.42 (m, 17H, 15 CH$_2$Ph, H-$1_D$, $3_C$), 4.14 (bs, 1H, H-$2_A$), 4.05-3.68 (m, 14H, H-$3_E$, $4_E$, $5_E$, $6a_E$, $6b_E$, $4_C$, $5_C$, $2_B$, $3_B$, $3_A$, $5_A$, $2_D$, $6a_D$, $6b_D$), 3.61 (dq, 1H, $J_{5,6}$=6.2, $J_{4,5}$=9.3 Hz, H-$5_B$), 3.51-3.41 (m, 3H, H-$2_E$, $4_A$, $5_D$), 3.30 (pt, 1H, $J_{3,4}$=$J_{4,5}$=9.4 Hz, H-$4_B$), 2.03, 2.02, 1.80 (3s, 9H, OAc), 1.39, 1.32 (2d, 6H, H-$6_A$, $6_C$), 1.00 (bd, 3H, H-$6_B$). $^{13}$C NMR: δ 169.7, 169.5, 168.3, 164.5, 160.9 (C=O, C=N), 137.5-126.2 (Ph), 101.6 (C-$1_D$), 101.3 (2C, C-$1_A$, $1_B$), 98.7 (C-$1_E$), 94.8 (C-$1_C$), 91.3 (CCl$_3$), 82.1, 81.5, 80.4, 80.1, 78.4, 77.9, 77.6, 76.5 (10C, C-$2_A$, $2_E$, $3_A$, $3_B$, $3_C$, $3_E$, $4_A$, $4_B$, $4_C$, $4_E$), 76.0, 75.9, 75.5, 74.9, 74.3, 73.3 (8C, CH$_2$Ph), 72.9, 72.6, 71.9, 70.9, 70.6, 69.1, 68.8, 68.5 (9C, C-$2_B$, $2_C$, $3_D$, $4_D$, $5_A$, $5_B$, $5_C$, $5_D$, $5_E$), 68.3 (C-$6_E$), 62.1 (C-$6_D$), 56.2 (C-$2_D$), 21.0, 20.9, 20.8 (3C, OAc), 19.1, 18.3, 18.1 (3C, C-$6_A$, $6_B$, $6_C$). Anal. Calcd for C$_{103}$H$_{110}$Cl$_6$N$_2$O$_{27}$: C, 61.22; H, 5.49; N, 1.39%. Found: C, 61.24; H, 5.50; N, 1.21%.

Methyl (2-Deoxy-4,6-O-isopropylidene-2-trichloroacetamido-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranosiden (348). The pentasaccharide 302 (578 mg, 0.321 mmol) was dissolved in MeOH (10 mL). MeONa was added until pH reach 10. The mixture was stirred for 25 min then treated by IR 120 (H$^+$) until neutral pH. The solution was filtered and concentrated. The residue was eluted from a column of silica gel with 9:1 DCM-MeOH to give the expected triol 347 (505 mg, 89%). To a mixture of 347 (505 mg, 0.286 mmol) in dry DMF (2 mL) was added 2-methoxypropane (60 μL, 2.5 eq) and CSA (14 mg, cat). The mixture was stirred 1 h and Et$_3$N (200 μL) was added. After evaporation, the residue was eluted from a column of silica gel with 5:2 cyclohexane-EtOAc with 0.3% of Et$_3$N to give 348 (420 mg, 81%) as a colorless foam: $^1$H NMR: δ 8.00-7.00 (m, 45H, Ph), 7.17 (d, 1H, NH$_D$), 5.39 (dd, 1H, $J_{1,2}$=1.2, $J_{2,3}$=3.0 Hz, H-$2_C$), 5.13 (d, 1H, $J_{1,2}$=1.1 Hz, H-$1_A$), 5.01 (d, 1H, $J_{1,2}$=3.2 Hz, H-$1_E$), 4.99 (d, 1H, $J_{1,2}$=1.7 Hz, H-$1_B$), 4.80 (d, 1H, H-$1_C$), 4.70 (d, 1H, H-$1_D$), 4.90-4.35 (m, 16H, CH$_2$Ph), 4.40 (m, 1H, H-$2_B$), 4.10 (dd, 1H, H-$2_A$), 4.05 (dd, 1H, H-$3_C$), 4.00-3.00 (m, 20H, H-$4_C$, $5_C$, $3_B$, $4_B$, $5_B$, $3_A$, $4_A$, $5_A$, $2_D$, $4_D$, $5_D$, $6a_D$, $6b_D$, $2_E$, $3_E$, $4_E$, $5_E$, $6a_E$, $6b_E$), 3.40 (s, 3H, OCH$_3$), 1.40-1.00 (m, 15H, C(CH$_3$)$_2$, H-$6_A$, $6_B$, $6_C$); $^{13}$C NMR partial: δ 166.2, 164.4 (C=O), 137.5-126.5 (Ph), 101.8 (C-$1_D$), 101.4 (C-$1_B$), 101.2 (C-$1_A$), 100.2 (C(CH$_3$)$_2$), 98.4 (C-$1_E$), 98.2 (C-$1_C$), 92.4 (CCl$_3$), 68.5 (C-$6_E$), 61.8 (C-$6_D$), 60.1 (C-$2_D$), 55.5 (OCH$_3$), 29.3, 19.4 (C(CH$_3$)$_2$), 19.1, 18.6, 18.2 (C-$6_A$, $6_B$, $6_C$). FAB-MS of C$_{99}$H$_{110}$Cl$_3$N$_1$O$_{24}$ (M, 1804.1), m/z 1827.0 [M+Na]$^+$. Anal. Calcd for C$_{99}$H$_{110}$Cl$_3$N$_1$O$_{24}$: C, 65.90; H, 6.15; N, 0.78%. Found: C, 65.89; H, 6.29; N, 0.68%.

Methyl (3,4,6-Tri-O-acetyl-2-deoxy-2-trichloroacetamido-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-deoxy-2-trichloroacetamido-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (350). A mixture of 346 (154 mg, 76 μmol) and 348 (92 mg, 51 μmol), 4 Å molecular sieves and dry 1,2-DCE (3 mL), was stirred for 1 h, then cooled to −35° C. Triflic acid (6 μL) was added. The stirred mixture was allowed to reach 10° C. in 2.5 h. Et$_3$N (25 μL) was added and the mixture was filtered. After evaporation, the residue was eluted from a column of silica gel with 2:1 cyclohexane-EtOAc and 0.5% of Et$_3$N to give 349 (186 mg) as a contaminated material. To a solution of the isolated contaminated 349 (186 mg) in DCM (3 mL) was added dropwise, at 0° C., a solution of TFA (0.5 mL) and water (0.5 mL). The mixture was stirred for 3 h, then concentrated by co-evaporation with water then toluene. The residue was eluted from a column of silica gel with 2:1 to 1:1 petroleum ether-EtOAc to give 350 (134 mg, 72%, 2 steps) as a white solid: [α]$_D$+6° (c 1.0, CHCl$_3$); $^1$H NMR: δ 8.05-7.10 (m, 90H, Ph), 6.86-6.82 (2d, 2H, $J_{2,NH}$=8.0, $J_{2,NH}$=8.5 Hz, NH$_D$, NH$_{D'}$), 5.35-5.19 (m, 2H, H-$2_C$, $2_{C'}$), 5.20, 5.08 (2s, 2H, H-$1_A$, $1_{A'}$), 5.05 (dd, 1H, H-$3_{D'}$), 4.99-4.80 (m, 9H, H-1, $1_{B'}$, $1_C$, $1_{C'}$, $1_D$, $1_{D'}$, $1_E$, $1_{E'}$, $4_{D'}$), 4.80-4.30 (m, 32H, OCH$_2$Ph), 4.10-3.15 (m, 44H, H-$2_A$, $2_{A'}$, $2_B$, $2_{B'}$, $2_D$, $2_{D'}$, $2_E$, $2_{E'}$, $3_A$, $3_{A'}$, $3_B$, $3_{B'}$, $3_C$, $3_{C'}$, $3_D$, $3_E$, $3_{E'}$, $4_A$, $4_{A'}$, $4_B$, $4_{B'}$, $4_C$, $4_{C'}$, $4_D$, $4_E$, $4_{E'}$, $5_A$, $5_{A'}$, $5_B$, $5_{B'}$, $5_C$, $5_{C'}$, $5_D$, $5_{D'}$, $5_E$, $5_{E'}$, $6a_D$, $6b_D$, $6a_{D'}$, 6b$_{D'}$, 6a$_E$, 6b$_E$, 6a$_{E'}$, 6b$_{E'}$), 3.42 (3H, s, OMe), 2.08, 2.04. 2.02 (9H, 3s, OAc), 1.40-0.96 (18H, m, H-6$_A$, 6$_{A'}$, 6$_b$, 6$_{B'}$, 6$_C$, 6$_{C'}$); $^{13}$C NMR: δ 171.5, 170.9, 170.8, 169.6, 166.2, 162.4, 162.1 (C=O), 139.5-127.2 (Ph), 101.9, 101.6, 101.5, 101.3, 99.2, 98.8, 98.2 (10C, C-1$_A$, 1$_{A'}$, 1$_B$, 1$_{B'}$, 1$_C$, 1$_{C'}$, 1$_D$, 1$_{D'}$, 1$_E$, 1$_{E'}$), 92.7, 92.6 (2C, CCl$_3$), 82.1, 81.8, 81.7, 80.5, 80.3, 80.1, 79.3, 77.9, 77.8, 73.0, 72.6, 72.5, 72.0, 69.4, 69.0, 68.9, 67.4 (39C, C-2$_A$, 2$_{A'}$, 2$_B$, 2$_{B'}$, 2$_C$, 2$_{C'}$, 2$_E$, 2$_{E'}$, 3$_A$, 3$_{A'}$, 3$_B$, 3$_{B'}$, 3$_C$, 3$_{C'}$, 3$_D$, 3$_{D'}$, 3$_E$, 3$_{E'}$, 4$_A$, 4$_{A'}$, 4$_B$, 4$_{B'}$, 4$_C$, 4$_{C'}$, 4$_D$, 4$_{D'}$, 4$_E$, 4$_{E'}$, 5$_A$, 5$_{A'}$, 5$_B$, 5$_{B'}$, 5$_C$, 5$_{C'}$, 5$_D$, 5$_{D'}$, 5$_E$, 5$_{E'}$, 6$_{D'}$), 76.0, 75.9, 74.8, 74.3, 73.6, 73.2, 68.6 (CH$_2$Ph), 62.3, 62.2, 60.7 (3C, C-6$_D$, 6$_E$, 6$_{E'}$), 55.5, 56.2 (3C, C-2$_D$, 2$_{D'}$, OCH$_2$), 21.0, 20.9, 20.8 (OAc), 19.0, 18.7, 18.6, 18.2, 17.9 (6C, C-6$_A$, 6$_{A'}$, 6$_B$, 6$_{B'}$, 6$_C$, 6$_{C'}$). FAB-MS for C$_{197}$H$_{214}$Cl$_6$N$_2$O$_{50}$ (M, 3622.5) m/z 3645.3 [M+Na]$^+$. Anal. Calcd for C$_{197}$H$_{214}$Cl$_6$N$_2$O$_{50}$: C, 65.32; H, 5.95; N, 0.77%. Found: C, 65.20; H, 6.03; N, 0.78%.

Methyl (2-acetamido-2-deoxy-β-D-glucopyranosyl)-(1→2)-(α-L-rhamnopyranosyl)-(1→2)-(α-L-rhamnopyranosyl)-(1→3)-[α-D-glucopyranosyl-(1→4)]-(α-L-rhamnopyranosyl)-(1→3)-(2-acetamido-2-deoxy-β-D-glucopyranosyl)-(1→2)-(α-L-rhamnopyranosyl)-(1→2)-(α-L-rhamnopyranosyl)-(1→3)-[α-D-glucopyranosyl-(1→4)]-α-L-rhamnopyranoside (301). A solution of 350 (183 mg, 50 μmol), in EtOH (3 mL), EtOAc (0.3 mL), 1 M HCl (100 μL) was hydrogenated in the presence of Pd/C (250 mg) for 72 h at rt. The mixture was filtered and concentrated. A solution of the residue in MeOH (4 mL) and Et$_3$N (200 μL) was hydrogenated in the presence of Pd/C (200 mg) for 24 h at rt. The mixture was filtered and concentrated. A solution of the residue (50 mg, 25 μmol) in MeOH (3 mL) and DCM (0.5 mL) was treated by MeONa until pH reached 10. The mixture was stirred overnight at 55° C. After cooling at rt, IR 120 (H$^+$) was added until neutral pH, and the solution was filtered and concentrated, then was eluted from a column of C-18 with water/CH$_3$CN and freeze-dried to afford amorphous 301 (30 mg, 37%): [α]$_D$−1° (c 1.0, water); $^1$H NMR (D$_2$O): δ 5.13 (2d, 2H, J$_{1,2}$=3.5 Hz, H-1$_E$, 1$_{E'}$), 5.05, 4.95, 4.75 (m, 5H, H-1$_A$, 1$_B$, 1$_{A'}$, 1$_{B'}$, 1$_{C'}$), 4.64-4.62 (2d, 2H, J$_{1,2}$=8.0 Hz, H-1$_D$, 1$_{D'}$), 4.58 (d, 1H, J$_{1,2}$=2.2 Hz, H-1$_C$), 4.10-3.20 (m, 51H, H-2$_A$, 2A', 2$_B$, 2$_{B'}$, 2$_C$, 2$_{C'}$, 2$_D$, 2$_{D'}$, 2$_E$, 2$_{E'}$, 3$_A$, 3$_{A'}$, 3$_B$, 3$_{B'}$, 3$_C$, 3$_{C'}$, 3$_D$, 3$_{D'}$, 3$_E$, 3$_{E'}$, 4$_A$, 4$_{A'}$, 4$_B$, 4$_{B'}$, 4$_C$, 4$_{C'}$, 4$_D$, 4$_{D'}$, 4$_E$, 4$_{E'}$, 5$_A$, 5$_{A'}$, 5$_B$, 5$_{B'}$, 5$_C$, 5$_{C'}$, 5$_D$, 5$_{D'}$, 5$_E$, 5$_{E'}$, 6a$_E$, 6b$_E$, 6a$_{D'}$, 6b$_{D'}$, 6a$_E$, 6b$_E$, 6a$_{E'}$, 6b$_{E'}$, OCH$_3$), 19.9, 1.97 (2s, 6H, 2 NHAc), 1.33-1.15 (6d, 18H, J$_{5,6}$=6.3 Hz, H-6$_A$, 6$_B$, 6$_C$, 6$_{A'}$, 6$_{B'}$, 6$_{C'}$); $^{13}$C NMR (D$_2$O): δ 175.2, 174.7 (C=O), 103.1 (2C, C-1$_{D'}$, 1$_D$), 102.6, 101.7, 101.3, 100.8 (6C, C-1$_B$, 1$_C$, 1$_A$, 1$_{B'}$, 1$_{C'}$), 98.0 (2C, C-1$_E$, 1$_{E'}$), 81.6, 79.7, 79.6, 79.1, 76.2, 76.1, 73.9, 73.0, 72.7, 72.6, 72.5, 72.2, 72.1, 71.6, 70.1, 70.0, 69.7, 69.0, 68.5 (38C, , C-2$_A$, 2A', 2$_B$, 2$_{B'}$, 2$_C$, 2$_{C'}$, 2$_E$, 2$_{E'}$, 3$_A$, 3$_{A'}$, 3$_B$, 3$_{B'}$, 3$_C$, 3$_{C'}$, 3$_D$, 3$_{D'}$, 3$_E$, 3$_{E'}$, 4$_A$, 4$_{A'}$, 4$_B$, 4$_{B'}$, 4$_C$, 4$_{C'}$, 4$_D$, 4$_{D'}$, 4$_E$, 4$_{E'}$, 5$_A$, 5$_{A'}$, 5$_B$, 5$_{B'}$, 5$_C$, 5$_{C'}$, 5$_D$, 5$_{D'}$, 5$_E$, 5$_{E'}$), 60.9 (4C, C-6$_E$, 6$_{E'}$, 6$_D$, 6$_{D'}$), 56.2, 56.0, 55.3 (3C, C-2$_D$, 2$_{D'}$, OCH$_2$), 22.7, 22.6 (2C, NHAc), 18.3, 18.1, 17.2, 17.1, 17.0, 16.9 (6C, C-6$_A$, 6$_B$, 6$_C$, 6$_{A'}$, 6$_{B'}$, 6$_{C'}$). HRMS (MALDI) calcd for [C$_{65}$H$_{110}$N$_2$O$_{45}$+Na]$^+$: 1661.6278. Found: 1661.6277.

D—Synthesis of the 2-amionoethyl Glycoside of a Hapten Representative of the O-specific Polysaccharide of *Shigella flexneri* Serotype 2a and of a Corresponding PADRE-conjugate (2-acetamido-3,4,6-tri-O-acetyl-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranosyl trichloroacetimidate (406). 1,5-Cyclooctadiene-bis(methyldiphenylphosphine)iridium hexafluorophosphate (25 mg, 29 μmol) was dissolved THF (5 mL), and the resulting red solution was degassed in an argon stream. Hydrogen was then bubbled through the solution, causing the colour to change to yellow. The solution was then degassed again in an argon stream. A solution of 407 (1.0 g, 0.55 mmol) in THF (10 mL) was degassed and added. The mixture was stirred at rt overnight, then concentrated to dryness. The residue was dissolved in acetone (5 mL), then water (1 mL), mercuric chloride (140 mg) and mercuric oxide (120 mg) were added successively. The mixture protected from light was stirred at rt for 2 h and acetone was evaporated. The resulting suspension was taken up in DCM, washed twice with 50% aq KI, water and satd aq NaCl, dried and concentrated. The residue was eluted from a column of silica gel with 2:1 petroleum ether-EtOAc to give the corresponding hemiacetal 408. Trichloroacetonitrile (2.5 mL) and DBU (37 μL) were added to a solution of the crude 408 in anhydrous DCM (12.5 mL) at 0° C. After 1 h, the mixture was concentrated. The residue was eluted from a column of silica gel with 5:4 cyclohexane-EtOAc and 0.2% Et$_3$N to give 406 as a white foam (0.9 g, 85%); [α]$_D$+10° (c 1, CHCl$_3$). $^1$H NMR:δ 8.70 (s, 1H, C=NH), 8.00-7.00 (m, 45H, Ph), 6.36 (d, 1H, J$_{1,2}$=2.6 Hz, H-1$_C$), 5.59 (m, 2H, N-H$_D$, H-2$_C$), 5.13 (d, 1H, J$_{1,2}$=1.0 Hz, H-1$_A$), 5.01-4.98 (m, 2H, H-1$_E$, 1$_B$), 4.92 (dd, 1H, H-3$_D$), 4.90 (dd, 1H, H-4$_D$), 4.68 (d, 1H, H-1$_D$), 5.00-4.02 (m, 19H, 8 CH$_2$Ph, H-3$_C$, 2$_A$, 2$_B$), 4.01 (dd, 1H, H-2$_E$), 4.00-3.20 (m, 16H, H-3$_E$, 4$_E$, 5$_E$, 6a$_E$, 6b$_E$, 4$_C$, 5$_C$, 3$_B$, 4$_B$, 5$_B$, 3$_A$, 4$_A$, 5$_A$, 5$_D$, 6a$_D$, 6b$_D$), 2.02, 2.00, 1.75, 1.65 (4s, 12H, C=OCH$_3$), 1.40, 1.32 and 1.00 (3d, 9H, H-6$_A$, 6$_B$, 6$_C$). $^{13}$C NMR (partial): δ 170.2, 169.9, 169.3, 168.7, 164.9 (6C, C=O, C=N), 103.2 (C-1$_D$), 101.4 (2C, C-1$_A$, 1$_B$), 99.0 (C-1$_E$), 94.8 (C-1$_C$), 21.1, 20.9, 20.8 (3C, CH$_3$C=O), 19.1, 18.2 (3C, C-6$_A$, 6$_B$, 6$_C$). Anal. Calcd for C$_{103}$H$_{113}$Cl$_3$N$_2$O$_{27}$: C, 64.52; H, 5.94; N, 1.46%. Found: C, 64.47; H, 5.99; N, 1.45%.

2-Azidoethyl (2-acetamido-3,4,6-tri-O-acetyl-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-4,6-O-isopropylidene-β-D-glucopyranoside (409). A mixture of alcohol 405 (110 mg, 330 μmol), trichloroacetimidate 406 (720 mg, 376 μmol) and 4 Å molecular sieves in anhydrous 1,2-DCE (6 mL) was stirred for 1 h under dry argon. After cooling at 0° C., TfOH (16 μL, 180 μmol) was added dropwise and the mixture was stirred at 80° C. for 2.5 h. Triethylamine (60 μL) was added and the mixture was filtered, and concentrated. The residue was eluted from a column of silica gel with 3:4 cyclohexane-EtOAc and Et$_3$N (0.2%) to give 409 as a colourless oil (540 mg, 78%); [α]$_D$+6.5° (c 1, CHCl$_3$). $^1$H NMR: δ 8.00-7.00 (m, 45H, Ph), 5.95 (d, 1H, J$_{2,NH}$=7.1 Hz, NH$_D$), 5.51 (d, 1H, J$_{2,NH}$=8.1 Hz, NH$_{D'}$), 5.20 (dd, 1H, J$_{1,2}$=1.7, J$_{2,3}$=3.0 Hz, H-2$_C$), 5.08 (d, 1H, J$_{1,2}$=1.0 Hz, H-1$_A$), 5.05 (d, 1H, J$_{1,2}$=8.3 Hz, H-1$_D$), 4.93 (d, 1H, J$_{1,2}$=3.1 Hz, H-1$_E$), 4.87 (d, 1H, J$_{1,2}$=1.0 Hz, H-1$_B$), 4.82 (d, 1H, J$_{1,2}$=1.7 Hz, H-1$_C$), 4.80 (dd, 1H, J$_{3,4}$=J$_{4,5}$=10.0 Hz, H-4$_D$), 4.76 (dd, 1H, J$_{2,3}$=9.5 Hz, H-3$_{D'}$), 4.75-4.30 (m, 16H, CH$_2$Ph), 4.57 (d, 1H, J$_{1,2}$=7.8 Hz, H-1$_{D'}$), 4.35 (dd, 1H, H-2$_B$), 4.30 (dd, 1H, J$_{2,3}$=10.0, J$_{3,4}$=9.6 Hz, H-3$_D$), 4.02 (dd, 1H, J$_{2,3}$=2.0 Hz, H-2$_A$), 4.00-3.60 (m, 16H, H-6a$_D$, 6b$_D$, 3$_E$, 4$_E$, 5$_E$, 6a$_E$, 6b$_E$, 3$_C$, 4$_C$, 5$_C$, 3$_B$, 3$_A$, 5$_A$, 2$_{D'}$, 6a$_D$, 6b$_D$), 3.48 (m, 1H, J$_{4,5}$=9.5 Hz, H-5$_B$), 3.46 (dd, 1H, H-4$_D$), 3.40 (m, 1H, H-5$_D$), 3.36 (dd, 1H, H-2$_E$), 3.35, 3.19 (m, 4H, OCH$_2$CH$_2$N$_3$), 3.30 (dd, 1H, H-4$_A$), 3.19 (dd, 1H, J$_{3,4}$=9.5 Hz, H-4$_B$), 3.17 (m, 1H, H-5$_D$), 3.02 (m, 1H, H-2$_D$), 1.90-1.60 (6s, 18H, CH$_3$C=O), 1.33, 1.26 (2s, 6H, C(CH$_3$)$_2$), 1.27 (d, 1H, J$_{5,6}$=6.2 Hz, H-6$_A$), 1.18 (d, 3H, J$_{5,6}$=6.1 Hz, H-6$_C$), 0.90 (d, 3H, J$_{5,6}$=6.1 Hz, H-6$_B$). $^{13}$C NMR: δ 172.1, 171.1, 170.8, 170.1, 169.6, 166.2 (6C, C=O), 139.2-127.1 (Ph), 103.1A (C-1$_{D'}$), 101.6 (C-1$_B$), 101.0 (C-1$_A$), 100.0 (C-1$_D$), 98.1 (C-1$_E$), 97.8 (C-1$_C$), 82.0 (C-2$_E$), 81.7, 81.5, 80.2, 78.6, 78.4, 77.9, 77.9 (8C, C-3$_E$, 4$_E$, 3$_C$, 4$_C$, 3$_B$, 4$_B$, 3$_A$, 4$_A$), 77.8 (C-2$_A$), 76.0, 74.6 (2C, C-3$_D$, 3$_{D'}$), 74.0 (C-2$_B$), 73.4 (C-4D), 73.3 (C-2$_C$), 72.2, 71.9 (2C, C-5$_D$, 5$_{D'}$), 68.9, 68.8, 67.7 (3C, C-5$_A$, 5$_B$, 5$_E$), 68.6 (C-4$_{D'}$), 68.5 (C-6$_E$), 67.5 (C-5$_C$), 62.6, 62.2 (2C, C-6$_D$, 6$_{D'}$), 59.7 (C-2$_{D'}$), 54.6 (C-2$_{D'}$), 51.0 (CH$_2$N$_3$), 29.5 (C(CH$_3$)$_2$), 23.9, 23.5, 21.1, 20.9, 20.7 (5C, C=OCH$_3$), 19.6 (C(CH$_3$)$_2$), 18.9 (C-6$_C$), 18.4 (C-6$_A$), 18.2 (C-6$_B$). FABMS of C$_{114}$H$_{133}$N$_5$O$_{32}$ (M, 2085.3) m/z 2107.9 [M+Na]$^+$ 2-Azidoethyl (2,3,4-tri-O-acetyl-2-deoxy-2-acetamido-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-β-D-glucopyranoside (410). To a solution of 409 (503 mg, 241 μmol) in AcOH (6 mL) was added water (1.5 mL) dropwise at rt. The mixture was stirred for 1 h at 60° C. then concentrated by successive co-evaporation with water and toluene. The residue was eluted from a column of silica gel with 1:4 Cyclohexane-EtOAc to give 410 as a while foam (463 mg, 94%); [α]$_D$+9° (c 1, CHCl$_3$). $^1$H NMR: δ 8.00-7.00 (m, 45H, Ph), 5.70 (d, 1H, NH$_D$), 5.46 (d, 1H, J$_{2,NH}$=8.0 Hz, NH$_{D'}$), 5.25 (dd, 1H, H-2$_C$), 5.05 (d, 1H, J$_{1,2}$=8.4 Hz, H-1$_D$), 5.00 (d, 1H, J$_{1,2}$=1.0 Hz, H-1$_A$), 4.86 (m, 3H, H-1$_C$, 3$_{D'}$, 4$_{D'}$), 4.84 (m, 2H, H-1$_B$, 1$_E$), 4.56 (d, 1H, H-1$_{D'}$), 4.40 (dd, 1H, H-3$_E$), 4.35 (dd, 1H, H-2$_B$), 4.15 (dd, 1H, H-3$_D$), 4.80-4.00 (m, 16H, CH$_2$Ph), 4.03 (dd, 1H, H-2$_A$), 4.00-3.00 (m, 26H, H-4$_D$, 5$_D$, 6a$_D$, 6b$_D$, 2$_E$, 4$_E$, 5$_E$, 6a$_E$, 6b$_E$, 3$_C$, 4$_C$, 5$_C$, 3$_B$, 4$_B$, 5$_B$, 3$_A$, 4$_A$, 5$_A$, 2$_{D'}$, 5$_{D'}$, 6a$_{D'}$, 6b$_{D'}$, OCH$_2$CH$_2$N$_3$), 2.99 (m, 1H, H-2$_D$), 1.85-1.60 (5s, 15H, CH$_3$C=O), 1.25 and 0.85 (3d, 9H, H-6$_A$, 6$_B$, 6$_C$). $^{13}$C NMR (partial): δ 171.6, 171.4, 170.8, 170.1, 169.6 (C=O), 140.0-127.1 (Ph), 103.1 (C-1$_{D'}$), 101.2 (C-1$_A$), 99.6 (2C, C-1$_E$, 1$_B$), 99.4 (C-1$_D$), 99.0 (C-1$_C$), 23.8, 23.5 (2C, NHAc), 21.1, 20.9, 20.8 (3C, OAc), 19.1, 18.5, 18.2 (C-6$_A$, 6$_B$, 6$_C$). FABMS of C$_{111}$H$_{129}$N$_5$O$_{32}$ (M, 2045.2), m/z 2067.9 [M+Na]$^+$. Anal. Calcd for C$_{111}$H$_{129}$N$_5$O$_{32}$: C, 65.19; H, 6.36; N, 3.42%. Found: C, 65.12; H, 6.51; N, 3.41%.

2-Aminoethyl (2-deoxy-2-aectamido-β-D-glucopyranosyl)-(1→2)-(α-L-rhamnopyranosyl)-(1→2)-(α-L-rhamnopyranosyl)-(1→3)-[α-D-glucopyranosyl-(1→4)]-(α-L-rhamnopyranosyl)-(1→3)-2-acetamido-2-deoxy-β-D-glucopyranoside (402). A solution of 410 (207 mg, 101 μmol) in MeOH (5 mL) was treated by MeONa until pH 9. The mixture was stirred 1 week at rt. IR 120 (H$^+$) was added until neutral pH and the solution was filtered, and concentrated. The residue was eluted from a column of silica gel with 20:1 to 15:1 DCM-MeOH to give amorphous 411. A solution of crude 411 in EtOH (2.2 mL), EtOAc (220 μL), 1 M HCl (172 μL, 2 eq) was hydrogenated in the presence of Pd/C (180 mg) for 72 h at rt. The mixture was filtered and concentrated. Elution of the residue from a column of C18 with water and freeze-drying of appropriate fractions resulted in amorphous 402 (81 mg, 77%); [α]$_D$−10° (c 1, water). $^1$H NMR partial (D$_2$O): δ 5.12 (d, 1H, J$_{1,2}$=3.4 Hz, H-1$_E$), 5.07 (d, 1H, J$_{1,2}$=1.0 Hz, H-1$_{Rha}$), 4.94 (d, 1H, J$_{1,2}$=1.0 Hz, H-1$_{Rha}$), 4.75 (d, 1H, J$_{1,2}$=1.0 Hz, H-1$_{Rha}$), 4.63 (d, 1H, J$_{1,2}$=8.35 Hz, H-1$_{GlcNac}$), 4.54 (d, 1H, J$_{1,2}$=8.3 Hz, H-1$_{GlcNac}$), 1.98 and 1.96 (2s, 6H, 2 CH$_3$C=ONH), 1.28-1.20 (m, 9H, H-6$_A$, 6$_B$, 6$_C$). $^{13}$C NMR partial (D$_2$O): δ 175.2, 174.8 (2C, C=O), 103.1 (C-1$_{D'}$), 101.6, 101.4 (3C, C-$_A$, 1$_B$, 1$_C$), 100.8 (C-1$_D$), 97.9 (C-1$_E$), 56.2, 55.4 (2C, C-2$_D$, 2$_{D'}$), 22.7. 22.6 (2 NHAc), 18.2, 17.2, 17.0 (3C, C-6$_A$, 6$_B$, 6$_C$). HRMS (MALDI) Calcd for C$_{42}$H$_{73}$N$_3$O$_{28}$Na: 1090.4278. Found 1090.4286.

(S-Acetylthiomethyl)carbonylaminoethyl 2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (412). A solution of 404 (3.4 mg, 11.4 μmol) in CH$_3$CN (50 μL) was added to the aminoethyl hexasaccharide 402 (4.1 mg, 3.84 μmol) in 0.1 M phosphate buffer (pH 7.4, 500 μL). The mixture was stirred at rt for 1 h and purified by RP-HPLC to give 412 (2.7 mg, 59%). HPLC (230 nm): Rt 14.27 min (99.9% pure, Kromasil 5 μm C18 100 Å 4.6×250 mm analytical column, using a 0-20% linear gradient over 20 min of CH$_3$CN in 0.01 M aq TFA at 1 mL/min flow rate). ES-MS for C$_{46}$H$_{77}$N$_3$O$_{30}$S (M, 1184.19) m/z 1184.08.

PADRE (thiomethyl)carbonylaminoethyl 2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (401). Compound 412 (4.9 mg, 4.12 μmol) was dissolved in water (350 μL) and added to a solution of 403 (9.1 mg, 5.2 μmol) in a mixture of water (750 μL), CH$_3$CN (150 μL) and 0.5 M phosphate buffer (pH 5.6, 900 μL). 89 μL of a solution of hydroxylamine hydrochloride (139 mg/mL) in 0.5 M phosphate buffer (pH 5.6) was added and the mixture was stirred for 2 h. RP-HPLC purification gave the pure target 401 (6.3 mg, 53%). HPLC (230 nm): Rt 9.70 min (100% pure, Kromasil 5 μm C18 100 Å 4.6×250 mm analytical column, using a 20-50% linear gradient over 20 min of CH$_3$CN in 0.01 M aq TFA at 1 mL/min flow rate). ES-MS Calcd for C$_{153}$H$_{254}$N$_{24}$O$_{65}$S (M, 2901.34) m/z 2901.20.

F—Preparation of Chemically Defined Glycopeptides as Potential Synthetic Conjugate Vaccines Against *Shigella flexneri* Serotype 2a Disease Solvent mixtures of appropriately adjusted polarity used for chromatography consisted of A, dichloromethane-methanol; B, cyclohexane-ethyl acetate, C, cyclohexane-acetone, D, toluene-ethyl acetate.

2-Azidoethyl 2-acetamido-2-deoxy-4,6-O-isopropylidene-β-D-glucopyranoside (507). Camphorsulfonic acid (200 mg, 0.9 mmol) was added to a solution of triol 514 (1.31 g, 4.52 mmol) in a mixture of DMF (4 mL) and 2,2-dimethoxypropane (4 mL). After 3 h at rt, low boiling point solvents were evaporated under reduced pressure and more 2,2-dimethoxypropane (2 mL, 15.8 mmol) was added. The mixture was stirred for 2 h at rt, Et$_3$N was added, and the mixture was concentrated. The crude product was purified by column chromatography (solvent A, 19:1) to give 507 as a white solid (1.21 g, 81%), [α]$_D$−89.8; $^1$H NMR: δ 6.15 (d, 1H, J=5.9 Hz, NH), 4.70 (d, 1H, J$_{1,2}$=8.3 Hz, H-1), 4.05 (m, 1H, OCH$_2$), 3.97-3.89 (m, 2H, H-6a, 3), 3.79 (pt, 1H, J$_{5,6b}$=J$_{6a,6b}$=10.5 Hz, H-6b), 3.70 (m, 1H, OCH$_2$), 3.62-3.46 (m, 3H, H-2, 4, OCH$_2$), 3.35-3.26 (m, 2H, H-5, CH$_2$N$_3$), 2.05 (s, 3H, Ac), 1.52 (s, 3H, C(CH$_3$)$_2$), 1.44 (s, 3H, C(CH$_3$)$_2$); $^{13}$C NMR: δ 100.9 (C-1), 74.3 (C-4), 81.8 (C-3), 68.6 (OCH$_2$), 67.5 (C-5), 62.0 (C-6), 58.7 (C-2), 50.7 (CH$_2$N$_3$), 29.0 (C(CH$_3$)$_2$), 23.6 (CH$_3$CO), 19.1 (C(CH$_3$)$_2$). CIMS for C$_{13}$H$_{22}$N$_4$O$_6$ (330) m/z 331 [M+H]$^+$. Anal. Calcd. for C$_{67}$H$_{74}$N$_4$O$_{17}$.0.5H$_2$O: C, 46.01; H, 6.83; N, 16.51%. Found C, 46.37; H, 6.69; N, 16.46%.

2-Azidoethyl (2,3,4-Tetra-O-benzyl-α-D-glucopyranosyl)-(1→4)-(2,3-di-O-benzoyl-α-L-rhamnopyranosyl)-(1→3)-2-acetamido-2-deoxy-4,6-O-isopropylidene-β-D-glucopyranoside (515) and 2-Azidoethyl (2,3,4,6-tetra-O- benzyl-α-D-glucopyranosyl)-(1→4)-(2,3-di-O-benzoyl-α-L-rhamnopyranosyl)-(1→3)-2-acetamido-2-deoxy-β-D-glucopyranoside (516). (a) The disaccharide donor 504 (1.425 g, 1.37 mmol) and the acceptor 507 (377 mg, 1.14 mmol) with 4 Å-MS (2 g) were placed under argon and $CH_2Cl_2$ (15 mL) was added. The mixture was stirred for 1 h at rt, then cooled to −40° C. A solution of $BF_3.OEt_2$ (0.5 mL, 4.11 mmol) in $CH_2Cl_2$ (5 mL) was added dropwise. The mixture was stirred at −40° C. to −15° C. over 3 h. Triethylamine (2.5 mL) was added and the mixture stirred for 20 min. The mixture was filtered through a pad of Celite, and the filtrate was concentrated. The mixture was purified by column chromatography (solvent B, 2:3) to give 515 (803 mg, 58%) as a colourless foam. Further elution (solvent A, 9:1) gave 516 (395 mg, 30%) as a colourless foam. Compound 516 had $[\alpha]_D$+91.5 (c 0.18); $^1$H NMR: δ 6.99-8.02 (m, 30H, Ph), 6.10 (d, 1H, $J_{NH,2}$=6.9 Hz, NH), 5.60 (dd, 1H, $J_{2,3}$=3.4, $J_{3,4}$=9.1 Hz, H-$3_C$), 5.52 (dd, 1H, H-$2_C$), 5.20 (d, 1H, $J_{1,2}$=8.3 Hz, H-$1_D$), 5.00 (d, 1H, $J_{1,2}$=1.9 Hz, H-$1_C$), 4.95 (d, 1H, $J_{1,2}$=3.4 Hz, H-$1_E$), 4.89-4.63 (m, 5H, $CH_2$Ph), 4.47 (dd, 1H, $J_{2,3}$=8.3, $J_{3,4}$=10.3 Hz, H-$3_D$), 4.25 (d, 1H, J=10.9 Hz, $CH_2$Ph), 4.19 (m, 2H, H-$5_C$, $CH_2$Ph), 4.06 (m, 1H, $CH_2$O), 3.87 (m, 5H, H-$3_E$, $4_C$, $6a_{Df}$, $6b_D$, $CH_2$Ph), 3.74-3.58 (m, 4H, H-$4_E$, $5_D$, $5_E$, $CH_2$O), 3.50 (m, 3H, H-$2_E$, $4_D$, $CH_2N_3$), 3.32 (d, 1H, $J_{6a,6b}$=9.6 Hz, H-$6a_E$), 3.26 (m, 1H, $CH_2N_3$), 3.04 (d, 2H, H-$2_D$, $6b_E$), 2.02 (s, 3H, $CH_3$CO), 1.51 (d, 3H, $J_{5,6}$=6.2 Hz, H-$6_C$); $^{13}$C NMR: δ 171.5, 165.6, 165.2 (3C, C=O), 138.6-127.3 (Ph), 99.6 (C-$1_C$), 99.5 (C-$1_E$), 99.0 (C-$1_D$), 83.4 (C-$3_D$), 81.6 (C-$3_E$), 80.1 (C-$2_E$), 79.2 (C-$4_C$), 77.2 (C-$4_E$), 75.5 ($CH_2$Ph), 75.1 (C-$4_D$), 74.7, 74.0, 73.2 (3C, $CH_2$Ph), 71.3 (C-$5_D$*), 70.9 (C-$5_E$*), 70.8 (C-$3_C$), 70.4 (C-$2_C$), 69.0 (C-$5_C$), 68.8 ($CH_2$O), 67.5 (C-$6_E$), 62.6 (C-$6_D$), 57.9 (C-$2_D$), 50.5 ($CH_2N_3$), 23.4 ($CH_3$CO), 18.2 (C-$6_C$). FAB-MS for $C_{64}H_{70}N_4O_{17}$ (M, 1166) m/z 1185 [M+Na]$^+$. Anal. Calcd. for $C_{64}H_{70}N_4O_{17}.H_2O$: C, 64.85; H, 6.12; N, 4.73%. Found: C, 64.71; H, 6.01; N, 4.83%.

(b) 4 Å Molecular sieves (560 mg) were added to a solution of donor 504 (565 mg, 0.54 mmol) and acceptor 507 (150 mg, 0.45 mmol) in DCM (3 mL) and the suspension was stirred for 15 min −40° C. Triflic acid (16 μL) was added and the mixture was stirred for 3h at rt once the cooling bath had reached rt. $Et_3$N was added and after 15 min, the mixture was filtered through a pad of Celite. Volatiles were evaporated and the residue was column chromatographed (solvent B, 9:1) to give 515 (475 mg, 87%). $[\alpha]_D$+87.7 (c 0.32); $^1$H NMR: δ 8.07-6.99 (m, 30H, Ph), 6.21 (d, 1H, NH), 5.58 (dd, 1H, H-$3_C$), 5.44 (m, 1H, H-$2_C$), 5.13 (d, 1H, $J_{1,2}$=8.3 Hz, H-$1_D$), 5.02 (d, 1H, $J_{1,2}$=3.4 Hz, H-$1_E$), 4.97 (d, 1H, $J_{1,2}$=1.5 Hz, H-$1_C$), 4.64-4.90 (m, 5H, $CH_2$Ph), 4.45 (t, 1H, H-$3_D$), 4.27 (m, 3H, H-$5_C$, $CH_2$Ph), 4.05-3.79 (m, 7H, H-$3_E$, $4_C$, $5_D$, $6a_D$, $6b_D$, $CH_2$O, $CH_2$Ph), 3.60-3.76 (m, 4H, H-$4_D$, $4_E$, $5_E$, $CH_2$O), 3.37-3.51 (m, 3H, H-$2_E$, $5_D$, $CH_2N_3$), 3.34-3.16 (m, 3H, H-$2_D$, $6a_E$, $CH_2N_3$), 3.04 (d, 1H, H-$6b_E$), 2.01 (s, 3H, $CH_E$C=O), 1.43 (s, 6H, $(CH_3)_2$C), 1.36 (d, 3H, H-$6_C$); $^{13}$C NMR: δ 171.7, 165.6, 163.4 (C=O), 138.6-127.3 (Ph), 99.6 (C-$1_D$), 99.1 (C-$1_E$), 97.7 (C-$1_C$), 91.9 (($CH_3)_2$C), 81.4 (C-$3_E$), 80.3 (C-$2_E$), 79.4 (C-$4_C$), 77.1 (C-$4_D$), 76.0 (C-$3_D$), 75.3, 74.6, 73.9, 73.2 (4C, $CH_2$Ph), 73.1 (C-$4_E$), 71.2 (2C, C-$2_C$, $3_C$), 71.1 (C-$5_E$), 68.6 ($CH_2$O), 67.5 (C-$5_C$), 67.4 (C-$6_E$), 67.1 (C-$5_D$), 62.1 (C-$6_D$), 59.0 (C-$2_D$), 50.5 ($CH_2N_3$), 28.9 (($CH_3)_2$C), 23.4 ($CH_3$CO), 19.2 (($CH_3)_2$C), 18.1 (C-$6_C$). FAB-MS for $C_{67}H_{74}N_4O_{17}$ (1206) m/z 1229 [M+Na]$^+$. Anal. Calcd. for $C_{67}H_{74}N_4O_{17}$: C, 60.41; H, 5.66; N, 4.82%. Found: C, 60.36; H, 5.69; N, 4.78%.

2-Azidoethyl (2,3,4,6-Tetra-O-benzyl-α-D-glucopyranosyl)-(1→4)-α-L-rhamnopyranosyl-(1→3)-2-acetamido-2-deoxy-β-D-glucopyranoside (517). An ice cold solution of 95% aq TFA (1.5 mL) in $CH_2Cl_2$ (13.5 mL) was added to the trisaccharide 515 (730 mg, 0.60 mmol). The mixture was kept at 0° C. for 15 min, then diluted with toluene and concentrated. Toluene was co-evaporated from the residue. The residue was dissolved in MeOH (20 mL), and a 1M solution of sodium methoxide in MeOH (1.5 mL) was added. The mixture was left to stand at rt for 3 h. The mixture was neutralised with Amberlite IR-120 (H$^+$) resin and filtered. The filtrate was concentrated. The mixture was purified by column chromatography (solvent A, 9:1) to give 517 (548 mg, 94%) as a colourless foam. $[\alpha]_D$+9.7 (c 0.48, MeOH); $^1$H NMR: δ 7.13-7.31 (m, 8H, Ph), 5.99 (d, 1H, $J_{NH,2}$=7.8 Hz, NH), 4.97-4.79 (m, 7H, H-$1_C$, $1_D$, $1_E$, $CH_2$Ph), 4.374-4.35 (m, 4H, $CH_2$Ph), 4.10-3.91 (m, 7H, H-$2_C$, $3_D$, $3_E$, $5_C$, $5_E$, $6a_D$, $CH_2$O), 3.80 (m, 2H, H-$3_E$, $6b_D$), 3.73 (m, 1H, $CH_2$O), 3.40-3.63 (m, 8H, H-$2_E$, $4_C$, $4_D$, $4_E$, $5_D$, $6a_E$, $6b_E$, $CH_2N_3$), 3.27 (m, 2H, H-$2_D$, $CH_2N_3$), 1.99 (s, 3H, $CH_3$CO), 1.41 (d, 3H, $J_{5,6}$=6.2 Hz, H-$6_C$); $^{13}$C NMR: δ 170.7 (C=O), 138.4-127.6 (Ph), 101.2 (C-$1_C$), 99.7 (C-$1_E$), 99.0 (C-$1_D$), 84.7 (C-$4_C$), 84.3 (C-$3_D$), 81.5 (C-$3_E$), 79.6 (C-$2_E$), 77.6 (C-$4_D$*), 75.6 ($CH_2$Ph), 75.3 (C-$4_E$*), 74.9, 73.5, 73.4 (3C, $CH_2$Ph), 71.2 (C-$5_E$), 70.8 (C-$5_C$), 70.8 (C-$5_D$), 69.4 (C-$3_C$), 68.6 (C-$6_E$), 68.4 ($CH_2$O), 67.6 (C-$2_C$), 62.6 (C-$6_D$), 56.4 (C-$2_D$), 50.5 ($CH_2N_3$), 23.5 ($CH_3$CO), 17.6 (C-$6_C$). FAB-MS for $C_{50}H_{62}N_4O_{15}$ (958) m/z 981 [M+Na]$^+$. Anal. Calcd. for $C_{50}H_{62}N_4O_{15}.H_2O$: C, 61.46; H, 6.60; N, 5.73%. Found: C, 61.41; H, 6.61; N, 5.97%.

2-Aminoethyl α-D-glucopyranosyl-(1→4)-α-L-rhamnopyranosyl-(1→3)-2-acetamido-2-deoxy-β-D-glucopyranoside (518). The trisaccharide 517 (368 mg, 0.38 mmol) was dissolved in a mixture of EtOH (10 mL) and EtOAc (1 mL). A 1N solution of aqueous HCl (0.77 mL) was added. The mixture was stirred under hydrogen in the presence of 10% Pd/C (400 mg) for 24 h. The mixture was diluted with water and filtered. The filtrate was concentrated, then lyophilised. The residue was dissolved in a solution of $NaHCO_3$ (75 mg) in water (1 mL) and purified by passing first through a column of $C_{18}$ silica (eluting with water), then through a column of Sephadex $G_{10}$ (eluting with water) to give, after lyophilisation, 518 (151 mg, 69%). HPLC (215 nm): Rt 4.09 min (Kromasil 5 μm C18 100 Å 4.6×250 mm analytical column, using a 0-20% linear gradient over 20 min of $CH_3$CN in 0.01M aq TFA at 1 mL/min flow rate). $^1$H NMR (D$_2$O): δ 4.97 (d, 1H, $J_{1,2}$=3.8 Hz, H-$1_E$), 4.78 (d, 1H, $J_{1,2}$=1.2 Hz, H-$1_C$), 4.54 (d, 1H, $J_{1,2}$=8.6 Hz, H-$1_D$), 4.02 (m, 1H, H-$5_C$), 5.00-3.90 (m, 3H, H-$5_E$, $6a_D$, $CH_2$O), 3.88-3.67 (m, 7H, H-$2_C$, $2_D$, $3_C$, $6a_E$, $6b_E$, $6b_D$, $CH_2$O), 3.61 (dd, 1H, J=9.8, J=9.1 Hz, H-$3_E$), 3.60-3.42 (m, 5H, H-$2_E$, $4_C$, $4_D$, $4_E$, $5_D$), 3.54 (m, 1H, H-$3_D$), 3.03 (m, 2H, $CH_2NH_2$), 2.00 (s, 3H, $CH_3$CO), 1.31 (d, 3H, $J_{5,6}$=6.3 Hz, H-$2_C$); $^{13}$C NMR (D$_2$O): δ 175.2 (C=O), 101.6 (C-$1_C$), 100.7 (C-$1_D$), 100.0 (C-$1_E$), 82.1 (C-$3_D$), 81.4 (C-$4_C$), 76.3 (C-$2_E$), 73.1 (C-$3_E$), 72.2 (C-$5_E$), 71.9 (C-$4_D$), 71.3 (C-$2_C$), 69.7 (C-$4_E$), 69.3 (C-$3_C$), 68.8 (C-$5_D$), 68.5 (C-$5_C$), 66.0 ($CH_2$O), 60.9 (C-$6_D$), 60.5 (C-$6_E$), 55.5 (C-$2_D$), 39.8 ($CH_2NH_2$), 22.57 ($CH_3$CO), 17.1 (C-$6_C$). ES-MS for $C_{22}H_{40}N_2O_{15}$ (572) m/z 573 [M+H]$^+$. HRMS (MALDI) Calcd for $C_{22}H_{40}N_2O_{15}$Na: 595.2326. Found: 595.2341.

Allyl (2,3,4-tri-O-acetyl-α-L-rhamnopyranosyl)-(1→3)-[(2,3,4,6-tetra-O-benzyl-α-D-glucopyranosyl)-(1→4)]-2-O-benzoyl-α-L-rhamnopyranoside (521). TMSOTf (100 μL) was added to a solution of donor 520 (2.5 g, 5.78 mmol) and acceptor 519 (4.0 g, 4.80 mmol) in Et$_2$O (40 mL) at −50° C. The mixture was stirred for 2.5 h, at which time the cooling bath had reached rt. Et$_3$N was added and after 15 min, volatiles were evaporated. Column chromatography (solvent C, 4:1) of the crude product gave the fully protected 521

(4.74 g, 89%) as a white solid. $^1$H NMR: δ 8.00-6 90 (m, 25H, Ph), 5.92 (m, 1H, CH=), 5.53 (dd, 1H, H-2$_B$), 5.40-5.20 (m, 4H, H-1$_E$, 2$_C$, CH$_2$=), 5.18 (dd, 1H, J$_{2,3}$=3.4, J$_{3,4}$=10.0 Hz, H-3$_B$), 5.10 (d, 1H, J$_{1,2}$=1.6 Hz, H-1$_B$), 5.00-4.40 (m, 10H, H-4$_B$, 1$_C$, OCH$_2$), 4.30-4.00 (m, 5H, H-3$_E$, 3$_C$, 5$_E$, OCH$_2$), 4.00-3.50 (m, 7H, H-2$_E$, 4$_E$, 6a$_E$, 6b$_E$, 5$_B$, 5$_C$, 4$_C$), 1.90 (s, 3H, Ac), 1.60 (s, 3H, Ac), 1.22 (s, 3H, Ac), 1.20 (d, 3H, J$_{5,6}$=6.2 Hz Hz, H-6$_C$), 0.80 (d, 3H, J$_{5,6}$=6.2 Hz, H-6$_B$); $^{13}$C NMR: δ 169.9, 169.7, 169.5, 166.1 (4C, C=O), 133.4-127.3 (Ph), 117.5 (=CH$_2$), 9.8 (C-1$_B$), 96.9 (C-1$_E$), 95.7 (C-1$_C$), 81.4 (C-3$_E$), 80.7 (C-2$_E$), 7.3 (C-3$_C$), 77.7 (C-4$_E$), 77.5 (brs, C-4$_C$), 75.3, 74.6, 73.6 (3C, OCH$_2$Ph), 72.8 (C-2$_C$), 72.6 (CH$_2$Ph), 70.9 (2C, C-5$_E$, 4$_B$), 69.6 (C-2$_B$), 68.7 (C-6$_E$), 68.6 (C-3$_B$), 68.2 (OCH$_2$), 67.2 (C-5$_C$), 66.8 (C-5$_B$), 20.7, 20.3, 20.2 (3C, C(O)CH$_3$), 18.5 (C-6$_C$), 16.8 (C-6$_B$). CI-MS for C$_{62}$H$_{70}$O$_{18}$ (1102) m/z 1125 [M+Na]$^+$. Anal. Calcd. for C$_{62}$H$_{70}$O$_{18}$: C, 67.50; H, 6.40%. Found: C, 67.51; H, 6.52%.

(2,3,4-Tri-O-acetyl-α-L-rhamnopyranosyl)-(1→3)-[(2,3,4,6-tetra-O-benzyl-α-D-glucopyranosyl)-(1→4)]-2-O-benzoyl-α-L-rhamnopyranose (522). 1,5-Cyclooctadiene-bis(methyldiphenylphosphine)iridium hexafluorophosphate (33 mg) was dissolved in THF (10 mL) and the resulting red solution was degassed in an argon stream. Hydrogen was then bubbled through the solution, until the colour had changed to yellow. The solution was then degassed again in an argon stream. A solution of 521 (4.59 g, 4.16 mmol) in THF (30 mL) was degassed and added. The mixture was stirred at rt overnight, then concentrated. The residue was taken up in a mixture of acetone (10:1, 44 mL). Mercuric bromide (1.78 g, 8.32 mmol) and mercuric oxide (1.69 g, 6.24 mmol) were added to the mixture, which was protected from light. The suspension was stirred at rt for 1 h, then concentrated. The residue was taken up in CH$_2$Cl$_2$ and washed three times with sat aq KI, then with brine. The organic phase was dried and concentrated. The residue was purified by column chromatography (solvent B, 3:1) to give 522 (3.52 g, 80%) as a colourless foam; $^1$H NMR: δ 7.15 (m, 25H, Ph), 5.50 (dd, 1H, H-2$_B$), 5.30-5.27 (m, 2H, H-1$_C$, H-2$_C$), 5.23 (d, 1H, J$_{1,2}$=3.3 Hz, H-1$_E$), 5.18 (dd, 1H, J$_{2,3}$=3.2, J$_{3,4}$=10.0 Hz, H-3$_B$), 5.10 (d, 1H, J$_{1,2}$=1.2 Hz, H-1$_B$), 5.00-4.35 (m, 9H, H-4$_B$, OCH$_2$), 4.28 (dd, 1H, J$_{2,3}$=3.2, J$_{3,4}$=8.6 Hz, H-3$_C$), 4.20-4.00 (m, 3H, H-3$_E$, 5$_E$, 5$_C$), 3.80-3.50 (m, 6H, H-2$_E$, 6a$_E$, 6b$_E$, 5$_B$, 4$_E$, 4$_C$), 3.05 (d, 1H, J$_{H,1}$=4.0 Hz, OH), 2.09, 1.81, 1.44 (3s, 9H, CH$_3$C=O), 1.37 (d, 3H, J$_{5,6}$=6.2 Hz, H-6$_C$), 0.95 (d, 3H, J$_{5,6}$=6.2 Hz, H-6$_B$); $^{13}$C NMR: δ 169.9, 169.8, 169.6, 166.2 (4C, C=O), 138.9-127.5 (Ph), 99.8 (C-1$_B$), 97.3 (C-1$_E$), 91.3 (C-1$_C$), 81.7 (C-3$_E$), 80.7 (C-2$_E$), 78.8 (C-3$_C$), 78.1, 78.0 (2C, C-4$_E$, 4$_C$), 76.6, 75.5 (2C, CH$_2$Ph), 74.9 (2C, C-2$_E$, CH$_2$Ph), 73.8 (CH$_2$Ph), 73.3 (2C, C-4$_B$, 5$_E$), 72.9 (C-2$_B$), 71.2 (2C, C-3$_B$, 6$_E$), 67.5 (C-5$_C$), 67.1 (C-5$_B$), 21.0, −20.6, 20.5 (3C, CH$_3$C=O), 18.9 (C-6$_C$), 17.1 (C-6$_B$). FAB-MS for C$_{59}$H$_{66}$O$_{18}$ (1062) m/z 1085 [M+Na]$^+$. Anal. Calcd. for C$_{59}$H$_{66}$O$_{18}$·H$_2$O: C, 65.54; H, 6.34%. Found: C, 65.68; H, 6.41%.

(2,3,4-Tri-O-acetyl-α-L-rhamnopyranosyl)-(1→3)-[(2,3,4,6-tetra-O-benzyl-α-D-glucopyranosyl)-(1→4)]-2-O-benzoyl-α-L-rhamnopyranose trichloroacetimidate (505). DBU (100 μL) was added at 0° C. to a solution of the hemiacetal 522 (3.8 g, 3.58 mmol) in DCM (40 mL) containing trichloroacetonitrile (4 mL). The mixture was stirred for 30 min at 0° C., and volatiles were evaporated. Flash chromatography (solvent B, 7:3+0.2% Et$_3$N) of the crude material gave the donor 505 (3.9 g, 90%) as a while solid; $^1$H NMR (α anomer): δ 8.75 (s, 1H, NH), 8.13-7.12 (m, 25H, Ph), 6.40 (d, 1H, J$_{1,2}$=2.4 Hz, H-1$_C$), 5.54 (br s, 1H, H-2$_B$), 5.49 (dd, 1H, J$_{2,3}$=2.9 Hz, H-2$_C$), 5.26 (d, 1H, J$_{1,2}$=2.8 Hz, H-1$_E$), 5.20 (dd, 1H, J$_{2,3}$=J$_{3,4}$=10.0 Hz, H-3$_B$), 5.17 (br s, 1H, H-1$_B$), 4.96 (dd, 1H, H-4$_B$), 4.99-4.41 (m, 8H, OCH$_2$), 4.34 (m, 1H, H-3$_C$), 4.14-4.02 (m, 3H, H-3$_E$, 5$_E$, 5$_C$), 3.87 (m, 1H, H-4$_C$), 3.78 (dq, 1H, J$_{4,5}$=9.5, J$_{5,6}$=6.1 Hz, H-5$_B$), 3.70 (m, 2H, H-6a$_E$, 6b$_E$), 3.65 (dd, 1H, J$_{2,3}$=3.4, J$_{3,4}$=9.8 Hz, H-2$_E$), 3.57 (pt, 1H, J$_{2,3}$=J$_{3,4}$=9.4 Hz, H-4$_E$), 1.86, 1.83 (2s, 9H, CH$_3$CO), 1.42 (d, 3H, J$_{5,6}$=6.2 Hz, H-2$_C$), 0.98 (d, 3H, H-6$_B$); $^{13}$C NMR (α anomer): δ 170.3, 170.1, 169.9, 166.1 (4C, C=O), 160.7 (C=NH), 139.2-127.8 (Ph), 100.2 (C-1$_B$), 98.1 (C-1$_E$), 94.8 (C-1$_C$), 91.2 (CCl$_3$), 82.4 (C-4$_C$), 82.0 (C-3$_E$), 81.2 (br s, C-2$_E$), 78.5 (br s, C-3$_C$), 78.3 (C-4$_E$), 75.9, 75.4, 74.3, 73.3 (4C, CH$_2$Ph), 71.8 (C-5$_E$), 71.7 (C-2$_C$), 71.3 (C-4$_B$), 70.8 (br s, C-5$_C$), 70.0 (C-2$_B$), 69.3 (C-3$_B$), 69.2 (C-6$_E$), 67.6 (C-5$_B$), 21.3, 21.0, 20.9 (3C, CH$_3$CO), 18.9 (C-6$_C$), 17.1 (C-6$_B$). Anal. Calcd. for C$_{61}$H$_{66}$Cl$_3$NO$_{18}$: C, 60.67; H, 5.51; N, 1.16%. Found: C, 60.53; H, 5.48; N, 1.38%.

2-Azidoethyl (2,3,4-tri-O-acetyl-α-L-rhamnopyranosyl)-(1→3)-[(2,3,4,6-tetra-O-benzyl-α-D-glucopyranosyl)-(1→4)]-(2-O-benzoyl-α-L-rhamnopyranosyl)-(1→3)-2-acetamido-2-deoxy-4,6-O-isopropylidene-β-D-glucopyranoside (523). The trisaccharide donor 505 (1.86 g, 1.54 mmol) and the acceptor 507 (712 mg, 2.16 mmol) were dissolved in 1,2-dichloroethane (15 mL) and 4 Å-MS (2 g) were added. The mixture was stirred at rt for 1 h. The mixture was cooled to 0° C. and triflic acid (34 μL, 0.385 mmol) was added. The mixture was stirred at 0° C. for 30 min, then at rt for 30 min. The mixture was then heated at 65° C. for 1 h. The mixture was allowed to cool, Et$_3$N (0.5 mL) was added, and the mixture was stirred at rt for 20 min. The mixture was diluted with CH$_2$Cl$_3$ and filtered through a pad of Celite. The filtrate was concentrated and purified by column chromatography (solvent B, 1:1) to give 523 (1.61 g, 76%). $^1$H NMR: δ 7.90-6.90 (m, 25H, Ph), 5.92 (d, 1H, J'7.5 Hz, NH), 5.53 (dd, 1H, J$_{1,2}$=1.8 Hz, H-2$_B$), 5.29 (d, 1H, H-1$_E$), 5.19 (m, 2H, H-2$_C$, 3$_B$), 5.09 (m, 2H, H-1$_C$, 1$_D$), 4.97 (bs, 1H, H-1$_B$), 4.96-4.70 (m, 9H, CH$_2$Ph, H-4$_B$), 4.54-4.41 (m, H, CH$_2$Ph), 4.34 (pt, 1H, J$_{3,4}$=J$_{4,5}$=9.3 Hz, H-3$_D$), 4.19-3.89 (m, 6H, H-3$_C$, 5$_C$, 5$_E$, 3$_E$, 6a$_D$, OCH$_2$), 3.79-3.60 (m, 5H, H-6b$_D$, 4$_C$, 5$_B$, 2$_E$, OCH$_2$), 3.56-3.33 (m, 4H, H-5$_D$, 4$_E$, 4$_D$, CH$_2$N$_3$), 3.27-3.12 (m, 2H, CH$_2$N$_3$, H-2$_D$), 2.10, 2.09 (2s, 6H, C(CH$_3$)$_2$), 1.78 (s, 3H, OAc), 1.73 (s, 3H, NHAc), 1.42, 1.35 (2s, 6H, OAc), 1.30 (d, 3H, J$_{5,6}$=6.2 Hz, H-2$_C$), 0.90 (d, 3H, J$_{5,6}$=6.2 Hz, H-6$_B$); $^{13}$C NMR: δ 171.4, 169.7, 169.6, 169.5, 166.0 (5C, C=O), 138.7-127.2 (Ph), 99.8, 99.7 (C-1$_D$, 1$_C$), 97.1 (C-1$_B$), 96.4 (C-1$_E$), 81.5 (C-3$_E$), 81.1 (C-2$_E$), 79.5 (bs, C-3$_C$), 77.9 (C-4$_E$), 77.0 (bs, C-4$_C$), 75.4 (C-3$_D$), 75.3, 74.7, 73.6 (3C, CH$_2$Ph), 73.0, 72.9 (2C, C-2$_C$, 4$_E$), 72.9 (CH$_2$Ph), 71.2 (C-5$_E$), 71.1 (C-4$_B$), 69.9 (C-2$_B$), 69.2 (C-6$_E$), 68.8 (C-3$_B$), 68.7 (OCH$_2$), 67.2, 67.1 (3C, C-5$_C$, 5$_B$, 5$_D$), 62.2 (C-6$_D$), 59.0 (C-2$_D$), 50.6 (CH$_2$N$_3$), 29.0, 23.4 (2C, C(CH$_3$)$_2$), 20.9, 20.4 (3C, OAc), 19.0 (NHAc), 18.4 (C-6$_C$), 17.0 (C-6$_B$). FAB-MS for C$_{72}$H$_{86}$N$_4$O$_{23}$ (1374) m/z 1397 [M+Na]$^+$. Anal. Calcd. for C$_{72}$H$_{86}$N$_4$O$_{23}$: C, 62.87; H, 6.30; N, 4.07%. Found: C, 63.51; H, 6.66; N, 3.77%.

2-Azidoethyl (2,3,4-tri-O-acetyl-α-L-rhamnopyranosyl)-(1→3)-[(2,3,4,6-tetra-O-benzyl-α-D-glucopyranosyl)-(1→4)]-(2-O-benzoyl-α-L-rhamnopyranosyl)-(1→3)-2-acetamido-2-deoxy-β-D-glucopyranoside (524). 50% aq TFA (1.3 mL) was added to a solution of the fully protected tetrasaccharide 523 (210 mg, 111 μmol) in DCM (6 ml). The mixture was stirred at 0° C. for 1 h. Volatiles were evaporated and toluene was co-evaporated from the residue. Column chromatography (solvent B, 7:3→1:1) of the crude product gave 524 (195 mg, 95%). [α]$_D$−6.9 (c 0.5, MeOH);

$^1$H NMR: δ 8.08-7.14 (m, 25H, Ph), 5.78 (d, 1H, $J_{2,NH}$=7.4 Hz, NH), 5.51 (br s, 1H, H-$2_B$), 5.27 (d, 1H, $J_{1,2}$=$J_{2,3}$=2.9 Hz, H-$2_C$), 5.18 (m, 2H, H-$1_E$, $3_B$), 5.12 (br s, 1H, H-$1_B$), 5.08 (d, 1H, $J_{1,2}$=8.3 Hz, H-$1_D$), 5.00 (d, 1H, $J_{1,2}$=2.4 Hz, H-$1_C$), 4.97 (d, 1H, J=11.0 Hz, CH$_2$Ph), 4.94 (pt, 1H, $J_{3,4}$=$J_{4,5}$=9.9 Hz, H-$4_B$), 4.87-4.24 (m, 7H, CH$_2$Ph), 4.21 (dd, 1H, $J_{2,3}$=8.0, $J_{3,4}$=10.2 Hz, H-$3_D$), 4.19 (dd, 1H, $J_{2,3}$=3.2, $J_{3,4}$=7.9 Hz, H-$3_C$), 4.10-4.04 (m, 2H, H-$5_C5_E$), 4.03 (pt, 1H, $J_{2,3}$=$J_{3,4}$=9.4 Hz, H-$3_E$), 3.96 (dd, 1H, $J_{5,6a}$=3.5, $J_{6a,6b}$=12.5 Hz, H-$6a_D$), 3.85 (dd, 1H, $J_{5,6b}$=4.0 Hz, H-$6b_D$), 3.77-3.70 (m, 5H, H-$4_C$, $6a_E$, $6b_E$, OCH$_2$), 3.68 (m, 1H, $J_{4,5}$=9.8 Hz, H-$5_B$), 3.63 (dd, 1H, $J_{1,2}$=3.4, $J_{2,3}$=9.8 Hz, H-$2_E$), 3.60 (dd, 1H, $J_{4,5}$=9.6 Hz, H-$4_E$), 3.55-3.44 (m, 3H, H-$4_D$, $5_D$, CH$_2$N$_3$), 3.29 (m, 1H, CH$_2$N$_3$), 3.14 (m, 1H, H-$2_D$), 2.13, 2.01, 1.82, 1.80 (4s, 12H, CH$_3$CO), 1.39 (d, 3H, $J_{5,6}$=6.2 Hz, H-$6_C$), 0.93 (d, 3H, $J_{5,6}$=6.1 Hz, H-$6_B$); $^{13}$C NMR: δ 171.5, 170.2, 170.1, 170.0, 166.3 (C=O), 139.2-127.9 (Ph), 99.8 (2C, C-$1_B$, $1_D$), 99.5 (C-$1_C$), 98.0 (br s, C-$1_E$), 84.3 (C-$3_D$), 82.0 (C-$3_E$), 81.1 (C-$2_E$), 78.8 (br s, C-$3_C$), 78.2 (2C, C-$4_C$, $4_E$), 75.9 (CH$_2$Ph), 75.6 (C-$4_D$), 75.2, 74.2, 73.4 (3C, CH$_2$Ph), 73.0 (C-$2_C$), 71.7 (C-$5_E$), 71.4 (C-$5_D$), 71.3 (C-$4_B$), 70.1 (C-$2_B$), 69.4 (C-$6_E$), 69.2, 69.1 (C-$3_B$, $5_C$), 68.9 (OCH$_2$), 67.5 (C-$5_B$), 63.2 (C-$6_D$), 57.7 (C-$2_D$), 51.1 (CH$_2$N$_3$), 23.8, 21.3, 21.0, 20.9 (4C, CH$_3$CO), 19.1 (C-$6_C$), 17.4 (C-$6_B$). FAB-MS for C$_{69}$H$_{82}$N$_4$O$_{23}$ (1334) m/z 1357.5 [M+Na]$^+$. Anal. Calcd. for C$_{69}$H$_{82}$N$_4$O$_{23}$.H$_2$O: C, 60.43; H, 6.32; N, 4.09% Found: C, 60.56; 6.22, 3.92%.

2-Aminoethyl α-L-rhamnopyranosyl-(1→3)-[α-D-glucopyranosyl-(1→4)]-α-L-rhamnopyranosyl-(1→3)-2-acetamido-2-deoxy-β-D-glucopyranoside (525). An ice cold solution of 95% aqueous trifluoroacetic acid (2.4 mL) in CH$_3$Cl$_3$ (21.6 mL) was added to the tetrasaccharide 523 (1.93 g, 1.40 mmol). The mixture was kept at 0° C. for 5 min., then diluted with toluene and concentrated. Toluene was co-evaporated from the residue. The residue was dissolved in MeOH (65 mL), and a 1M solution of sodium methoxide in MeOH (3 mL) was added. The mixture was left to stand at rt for 18 h, then neutralised with Amberlite IR-120 (H$^+$) resin, and filtered. The filtrate was concentrated, and the residue was purified by column chromatography (solvent B, 9:1) to give 524 (1.38 g, 89%) as a colourless foam. The tetrasaccharide 524 (1.38 g, 1.25 mmol) was dissolved in a mixture of EHtOH (35 mL) and EtOAc (3.5 mL). A 1N solution of aq HCl (2.5 mL) was added. The mixture was stirred under hydrogen in the presence of 10% Pd/C (1.5 g) for 72 h, then diluted with water and filtered. The filtrate was concentrated, then lyophilized. The residue was dissolved in a solution of 5% aq NaHCO$_3$ and purified by passing first through a column of C$_{18}$ silica (eluting with water), then through a column of Sephadex G$_{10}$ (eluting with water) to give, after lyophilization, 525 (693 mg, 77%). Further RP-HPLC purification of 373 mg of the latter gave 351 mg of RP-HPLC pure 525. HPLC (215 nm): Rt 4.78 min (Kromasil 5 μm C18 100 Å 4.6×250 mm analytical column, using a 0-20% linear gradient over 20 min of CH$_3$CN in 0.01 M aq TFA at 1 mL/min flow rate). $^1$H NMR (D$_2$O): δ 5.10 (d, 1H, $J_{1,2}$=3.7 Hz, H-$1_E$), 4.89 (d, 1H, $J_{1,2}$=1.1 Hz, H-$1_B$), 4.73 (d, 1H, $J_{1,2}$=1.0 Hz, H-$1_C$), 4.50 (d, 1H, $J_{1,2}$=8.6 Hz, H-$1_D$), 4.08 (m, 1H, H-$5_C$), 3.96 (m, 1H, H-$2_B$), 3.91 (m, 2H, H-$6a_D$, CH$_2$O), 3.68-3.88 (m, 12H, H-$2_C$, $2_D$, $3_B$, $3_C$, $4_B$, $4_C$, $5_B$, $5_E$, $6b_D$, $6a_E$, $6b_E$, CH$_2$O), 3.59 (pt, 1H, H-$3_E$), 3.52 (pt, 1H, H-$3_D$), 3.33-3.48 (m, 4H, H-$2_E$, $4_D$, $4_E$, $5_D$), 3.01 (m, 2H, CH$_2$NH$_2$), 1.99 (s, 3H, CH$_3$CO), 1.28 (d, 3H, H-$6_C$), 1.18 (d, 3H, H-$6_B$); $^{13}$C NMR (D$_2$O): δ 174.8 (C=O), 103.2 (C-$1_B$), 101.4 (C-$1_C$), 100.9 (C-$1_D$), 98.6 (C-$1_E$), 81.9 (C-$3_D$), 79.0 (C-$4_B$), 76.6 (C-$4_C$), 76.3 (C-$2_E$), 72.9 (C-$3_E$), 72.3 (C-$5_E$), 72.3 (C-$4_D$), 71.8 (C-$3_C$), 71.1 (C-$2_C$), 70.5 (C-$2_B$, $3_B$), 69.7 (C-$4_B$), 69.5 (C-$4_E$), 69.2 (C-$5_D$), 68.8 (2C, C-$5_B$, $5_C$), 67.9 (CH$_2$O), 61.0 (C-$6_D$), 60.8 (C-$6_E$), 55.5 (C-$2_D$), 40.0 (CH$_2$NH$_2$), 22.6 (CH$_3$C=O), 18.0 (C-$6_C$), 17.0 (C-$6_B$). FAB-MS for C$_{28}$H$_{50}$N$_2$O$_{19}$ (718) m/z 741 [M+Na]$^+$. HRMS (MALDI) Calcd for C$_{28}$H$_{50}$N$_2$O$_{19}$Na: 741.2905. Found: 741.2939.

Allyl (2,3,4-Tri-O-benzoyl-α-L-rhamnopyranosyl)-(→2)-3,4-di-O-benzyl-α-L-rhamnopyranoside (528). TMSOTf (11 μL, 59 μmol) was added to a solution of the rhamnoside 526 (2.26 g, 5.88 mmol) and the trichloroacetimidate 527 (4.23 g, 6.82 mmol) in anhydrous Et$_2$O (60 mL) at −70° C. The reaction mixture was stirred for 8 h while the cooling bath was slowly coming back to rt. Et$_3$N (100 μL) was added, and the mixture was stirred at rt for 15 min. Solvents were evaporated, and the crude material was purified by column chromatography (solvent B, 49:1→9:1), to give 528 as a while foam (4.78 g, 96%). $^1$H NMR: δ 8.17-7.12 (m, 25H, Ph), 5.97-5.85 (m, 3H, H-$2_A$, $3_A$, CH=), 5.67 (pt, 1H, $J_{3,4}$=9.6 Hz, H-$4_A$), 5.34-5.19 (m, 3H, $1_A$, CH$_2$=), 5.01 (d, 1H, J=9.0 Hz, CH$_2$Ph), 4.92 (d, 1H, $J_{1,2}$=1.3 Hz, H-$1_B$), 4.82-4.74 (m, 2H, CH$_2$Ph), 4.71 (d, 1H, J=11.8 Hz, OCH$_2$), 4.31 (dq, 1H, $J_{4,5}$=9.7 Hz, H-$5_A$), 4.21 (m, 1H, OCH$_2$), 4.10 (dd, 1H, H-$2_B$), 4.02 (m, 1H, OCH$_2$), 3.97 (dd, 1H, $J_{2,3}$=3.0, $J_{3,4}$=9.2 Hz, H-$3_B$), 3.82 (dq, 1H, $J_{4,5}$=9.4 Hz, H-$5_B$), 3.71 (pt, 1H, H-$4_B$), 1.43 (d, 3H, $J_{5,6}$=6.1 Hz, H-$6_B$), 1.37 (d, 3H, $J_{5,6}$=6.2 Hz, H-$6_A$); $^{13}$C NMR: δ 166.3, 165.9, 165.7 (3C, C=O), 139.0-127.9 (CH=, Ph), 117.8 (CH$_2$=), 99.9 (C-$1_A$), 98.3 (C-$1_B$), 80.6 (C-$4_B$), 80.2 (C-$3_B$), 76.5 (C-$2_B$), 76.0, 72.9 (2C, CH$_2$Ph), 72.3 (C-$4_A$), 71.0 (C-$2_A$*), 70.4 (C-$3_A$*), 68.7 (C-$5_B$), 68.1 (OCH$_2$), 67.5 (C-$5_A$), 18.4 (C-$6_B$), 18.1 (C-$6_A$). FAB-MS for C$_{50}$H$_{50}$O$_{12}$ (M, 842.3) m/z 865.1 [M+Na]$^+$. Anal. Calcd. for C$_{50}$H$_{50}$O$_{12}$: C, 71.24; H, 5.98%. Found C, 71.21; H, 5.99%.

(2,3,4-tri-O-Benzoyl-α-L-rhamnopyranosyl)-(1→2)-3,4-di-O-benzyl-α-L-rhamnopyranose (529). 1,5-Cyclooctadiene-bis(methyldiphenylphosphine)iridium hexafluorophosphate (25 mg) was dissolved in THF (10 mL) and the resulting red solution was degassed in an argon stream. Hydrogen was then bubbled through the solution, until the colour had changed to yellow. The solution was then degassed again in an argon stream. A solution of 528 (4.71 g, 5.59 mmol) in THF (40 mL) was degassed and added. The mixture was stirred at rt overnight, then concentrated. The residue was taken up in acetone (350 mL) and water (82 mL). Mercuric bromide (3.23 g, 8.96 mmol) and mercuric oxide (2.64 g, 12.3 mmol) were added to the mixture, which was protected from light. The suspension was stirred at rt for 1 h, then concentrated. The residue was taken up in CH$_2$Cl$_2$ and washed three times with sat aq KI, then with brine. The organic phase was dried and concentrated. The residue was purified by column chromatography (solvent B, 3:1) to give 529 (3.87 g, 84%) as a colourless foam. $^1$H NMR: δ 8.15-7.12 (m, 25H, Ph), 5.94-5.88 (m, 3H, H-$2_A$, $3_A$, CH=), 5.70 (pt, 1H, $J_{3,4}$=9.7 Hz, H-$4_A$), 5.31 (dd, 1H, $J_{1,OH}$=3.0 Hz, H-$1_B$), 5.28 (bs, 1H, H-$1_A$), 4.98 (d, 1H, J=11.0 Hz, CH$_2$Ph), 4.82-4.68 (m, 3H, CH$_2$Ph), 4.31 (dq, 1H, $J_{4,5}$=9.8 Hz, H-$5_A$), 4.13 (dd, 1H, $J_{1,2}$=2.1 Hz, H-$2_B$), 4.06-3.99 (m, 2H, H-$3_B$, $5_B$), 3.72 (pt, 1H, $J_{3,4}$=$J_{4,5}$=9.4 Hz, H-$4_B$), 2.79 (bs, 1H, OH-$1_B$), 1.41 (d, 3H, $J_{5,6}$=6.2 Hz, H-$6_B$), 1.37 (d, 3H, $J_{5,6}$=6.3 Hz, H-$6_A$); $^{13}$C NMR: δ 166.2, 165.9, 165.7 (3C, C=O), 138.9-127.9 (Ph), 99.7 (C-$1_A$), 94.2 (C-$1_B$), 80.5 (C-$4_B$), 79.6 (C-$3_B$), 77.6 (C-$2_B$), 76.5, 72.5 (2C, CH$_2$Ph), 72.3 (C-$4_A$), 71.0 (C-$2_A$*), 70.4 (C-$3_A$*), 68.8 (C-$5_B$), 67.6 (C-$5_A$), 18.5 (C-$6_B$*), 18.1 (C-$6_A$). FAB-MS for C$_{47}$H$_{46}$O$_{12}$ (M, 802.3) m/z 825.1 [M+Na]⁺. Anal. Calcd. for $C_{47}H_{46}O_{12}$.0.5$H_2O$: C, 69.53; H, 5.84%. Found C, 69.55; H, 5.76%.

(2,3,4-Tri-O-benzoyl-α-L-rhamnopyranosyl)-(1→2)-3,4-di-O-benzyl-α/β-L-rhamnopyranosyl trichloroacetimidate (530). The hemiacetal 529 (3.77 g, 4.71 mmol) was dissolved in $CH_2Cl_2$ (15 mL) and the solution was cooled to 0° C. Trichloroacetonitrile (2.5 mL) was added, then DBU (200 μL). The mixture was stirred at rt for 2 h. Toluene was added, and co-evaporated twice from the residue. The crude material was purified by flash chromatography (solvent B, 4:1+0.1% $Et_3N$) to give 530 as a white foam (4.29 g, 96%). Some hydrolyzed material 529 (121 mg, 3%) was eluted next. The trichloroacetimidate 530, isolated as an α/β mixture had ¹H NMR (α anomer): δ 8.62 (s, 1H, NH), 8.20-7.18 (m, 25H, Ph), 6.31 (s, 1H, H-1$_B$), 5.94 (dd, 1H, $J_{1,2}$=1.6 Hz, H-2$_A$), 5.89 (dd, 1H, $J_{2,3}$=3.4, $J_{3,4}$=9.9 Hz, H-3$_A$), 5.71 (pt, 1H, H-4$_A$), 5.27 (bs, 1H, H-1$_A$), 5.02 (d, 1H, J=10.8 Hz, $CH_2Ph$), 4.84 (d, 1H, J=11.9 Hz, $CH_2Ph$), 4.79 (d, 1H, $CH_2Ph$), 4.72 (d, 1H, $CH_2Ph$), 4.36 (dq, 1H, $J_{4,5}$=9.8 Hz, H-5$_A$), 4.13 (dd, 1H, H-2$_B$), 4.03-3.97 (m, 2H, H-3$_B$, 5$_B$), 3.80 (pt, 1H, $J_{3,4}$=9.5 Hz, H-4$_B$), 1.45 (d, 3H, $J_{5,6}$=6.1 Hz, H-6$_B$), 1.40 (d, 3H, $J_{5,6}$=6.2 Hz, H-6$_A$); ¹³C NMR (α anomer): δ 166.2, 165.9, 165.7 (3C, C=O), 160.8 (C=NH), 138.6-128.2 (Ph), 99.9 (C-1$_A$), 97.2 (C-1$_B$), 91.4 ($CCl_3$), 79.9 (C-4$_B$), 79.1 (C-3$_B$), 76.2 ($CH_2Ph$), 74.9 (C-2$_B$), 73.3 ($CH_2Ph$), 72.1 (C-4$_B$), 71.7 (C-5$_B$), 71.0 (C-2$_A$), 70.2 (C-3$_A$), 67.8 (C-5$_A$), 18.4 (C-6$_B$), 18.0 (C-6$_A$). Anal. Calcd. for $C_{49}H_{46}Cl_3NO_{12}$: C, 62.13; H, 4.89; N, 1.48%. Found C, 61.81; H, 4.86; N, 1.36%.

Allyl (2,3,4 Tri-O-benzoyl-α-L-rhamnopyranosyl)-(1→2)-(3,4-di-O-benzyl-α-L-rhamnopyranosyl)-(1→3)-[(2,3,4,6-tetra-O-benzyl-α-D-glucopyranosyl)-(1→4)]-2-O-benzoyl-α-L-rhamnopyranoside (533). (a) The acceptor 519 (465 mg, 0.56 mmol) was dissolved in $Et_2O$ (3 mL). The solution was cooled to −60° C. and TMSOTf (65 μL, 0.36 mmol) was added. The donor 530 (690 mg, 0.73 mmol) was dissolved in $Et_2O$ (6 mL) and added to the acceptor solution in two portions with an interval of 30 min. The mixture was stirred at −60° C. to −30° C. over 2 h. $Et_3N$ (100 μL) was added. The mixture was concentrated and the residue was purified by column chromatography (solvent B, 7:1) to give 533 (501 mg, 55%).

(b) A solution of the donor 527 (1.41 g, 2.25 mmol) and the acceptor 532 (1.07 g, 1.79 mmol) in anhydrous $Et_2O$ (88 mL) was cooled to −60° C. TMSOTf (63 μL) was added, and the mixture was stirred at −60° C. to −20° C. over 2.5 h. $Et_3N$ was added (100 μL). The mixture was concentrated and the residue was purified by column chromatography (solvent D, 49:1) to give 533 (2.66 g, 92%); [α]$_D$+74.1 (c 0.5); ¹H NMR: δ 7.06-8.11 (m, 50H, Ph), 5.88-6.05 (m, 3H, H-2$_A$, 3$_A$, CH=), 5.71 (t, 1H, H-4$_A$), 5.51 (dd, 1H, H-2$_C$), 5.22-5.41 (m, 3H, H-1$_A$, $CH_2$=), 5.14 (d, 1H, $J_{1,2}$=0.9 Hz, H-1$_B$), 5.10 (d, 1H, $J_{1,2}$=3.2 Hz, H-1$_E$), 4.97 (bs, 1H, H-1$_C$), 4.35-5.00 (m, 14H, H-2$_B$, 5$_A$, 12×$CH_2Ph$), 3.98-4.19 (m, 5H, H-3$_C$, 3$_E$, 5$_E$, $OCH_2$), 3.43-3.87 (m, 9H, H-2$_E$, 3$_B$, 4$_B$, 4$_C$, 4$_E$, 5$_B$, 5$_C$, 6$_E$, 6'$_E$), 1.44 (d, 3H, H-6$_A$), 1.40 (d, 3H, H-6$_C$), 1.13 (d, 3H, H-6$_B$); ¹³C NMR: δ 165.9, 165.4, 165.1 (C=O), 127.1-138.7 (CH=, Ph), 117.8 ($CH_2$=), 101.3 (C-1$_B$), 99.6 (C-1$_A$), 97.9 (C-1$_E$), 96.1 (C-1$_C$), 81.9 (C-3$_E$), 81.0 (C-2$_E$), 80.1 (C-3$_C$), 79.8 (C-4$_B$), 78.9 (C-3$_B$), 77.9 (C-4$_C$), 77.4 (C-4$_E$), 75.9 (C-2$_B$), 75.6, 75.0, 74.9, 73.9, 72.9 ($CH_2Ph$), 72.4 (C-2$_C$), 71.9 (C-4$_A$), 71.2 (C-5$_E$), 70.9 ($CH_2Ph$), 70.7 (C-2$_A$*), 70.0 (C-3$_A$*), 69.2 (C-5$_B$), 68.5 ($OCH_2$), 68.1 (C-6$_E$), 67.6 (C-5$_C$), 67.2 (C-5$_A$), 18.8 (C-6$_A$), 18.1 (C-6$_C$), 17.8 (C-6$_B$). FAB-MS for $C_{97}H_{98}O_{22}$ (1614) m/z 1637 [M+Na]⁺. Anal. Calcd. for $C_{97}H_{98}O_{22}$: C, 72.10; H, 6.11%. Found: C, 71.75; H, 6.27%.

(2,3,4-Tri-O-benzoyl-α-L-rhamnopyranosyl)-(1→2)-(3,4-di-O-benzyl-α-L-rhamnopyranosyl)-(1→3)-[(2,3,4,6-tetra-O-benzyl-α-D-glucopyranosyl)-(1→4)]-(2-O-benzoyl-α/β-L-rhamnopyranose (534). 1,5-Cyclooctadiene-bis(methyldiphenylphosphine)iridium hexafluorophosphate (12.5 mg) was dissolved in THF (5 mL) and the resulting red solution was degassed in an argon stream. Hydrogen was then bubbled through the solution, causing the colour to change to yellow. The solution was then degassed again in an argon stream. A solution of 533 (1.138 g, 0.70 mmol) in THF (15 mL) was degassed and added. The mixture was stirred at rt overnight. The mixture was concentrated. The residue was taken up in acetone (7 mL) and water (0.7 mL). Mercuric chloride (285 mg, 1.05 mmol) and mercuric oxide (303 mg, 1.4 mmol) were added to the mixture, which was protected from light. The mixture was stirred at rt for 1 h, then concentrated. The residue was taken up in $CH_2Cl_2$ and washed three times with sat. aq. KI, then with brine. The organic phase was dried and concentrated. The residue was purified by column chromatography (solvent B, 7:3) to give 534 (992 mg, 90%) as a colourless foam. ¹H NMR: δ 7.05-8.16 (m, 50H, Ph), 5.88-5.93 (m, 2H, H-2$_A$, 3$_A$), 5.73 (pt, 1H, H-4$_A$), 5.55 (m, 1H, H-2$_C$), 5.37 (bs, 1H, H-1$_A$), 5.28 (bs, 1H, H-1$_C$), 5.14 (bs, 1H, H-1$_B$), 5.07 (d, 1H, $J_{1,2}$=3.1 Hz, H-1$_E$), 4.78-4.99 (m, 6H, $CH_2Ph$), 4.31-4.68 (m, 8H, H-2$_B$, 5$_A$, $CH_2Ph$), 4.24 (dd, 1H, H-3$_C$), 3.99-4.09 (m, 3H, H-3$_E$, 5$_C$, 5$_E$), 3.82 (pt, 1H, H-4$_C$), 3.57-3.76 (m, 5H, H-3$_B$, 4$_E$, 5$_B$, 6a$_E$, 6b$_E$), 3.48 (dd, 1H, H-2$_E$), 3.17 (d, 1H, OH), 1.43 (d, 6H, H-6$_A$, 6$_C$), 1.14 (d, 3H, H-6$_B$); ¹³C NMR: δ 166.0, 165.6, 165.2 (4C, C=O), 127.2-138.9 (Ph), 101.1 (C-1$_B$), 99.7 (C-1$_A$), 98.1 (C-1$_E$), 91.6 (C-1$_C$), 81.9 (C-3$_E$), 81.1 (C-2$_E$), 79.9 (C-4$_B$), 79.4 (C-3$_C$), 78.9 (C-3$_B$), 78.3 (C-4$_C$), 77.6 (C-4$_E$), 76.1 (C-2$_B$), 75.8, 75.3, 75.1, 74.0, 73.1 (5C, $CH_2Ph$), 72.7 (C-2$_C$), 72.1 (C-4$_A$), 71.4 (C-5$_E$), 71.1 ($CH_2Ph$), 70.8 (C-2$_A$*), 70.2 (C-3$_A$*), 69.4 (C-5$_B$), 68.3 (C-6$_E$), 67.7 (C-5$_C$), 67.3 (C-5$_A$), 19.0 (C-6$_A$), 18.2 (C-6$_C$), 17.9 (C-6$_B$). FAB-MS for $C_{94}H_{94}O_{22}$ (1574) m/z 1597 [M+Na]⁺. Anal. Calcd. for $C_{94}H_{94}O_{22}$: C, 71.65; H, 6.01%. Found: C, 71.48; H, 6.17%.

(2,3,4-Tri-O-benzoyl-α-L-rhamnopyranosyl)-(1→2)-(3,4-di-O-benzyl-α-L-rhamnopyranosyl)-(→3)-[(2,3,4,6-tetra-O-benzyl-α-D-glucopyranosyl)-(1→4)]-(2-O-benzoyl-α/β-L-rhamnopyranosyl trichloroacetimidate (506). The hemiacetal 534 (412 mg, 0.26 mmol) was dissolved in $CH_2Cl_2$ (5 mL) and the solution was cooled to 0° C. Trichloroacetonitrile (0.26 mL) was added, then DBU (4 μL). The mixture was stirred at 0° C. for 1 h. The mixture was concentrated and toluene was co-evaporated from the residue. The residue was purified by flash chromatography (solvent B, 4:1+0.1% $Et_3N$) to give 506 (393 mg, 88%). ¹H NMR (α-anomer): δ 8.74 (s, 1H, NH), 7.03-8.10 (m, 50H, Ph), 6.42 (d, 1H, $J_{1,2}$=2.3 Hz, H-1$_C$), 5.87 (m, 2H, H-2$_A$, 3$_A$), 5.67 (m, 2H, H-2$_C$, 4$_A$), 5.30 (bs, 1H, H-1$_1$), 5.14 (bs, 1H, H-1$_B$), 5.08 (d, 1H, $J_{1,2}$=3.1 Hz, H-1$_E$E), 4.74-4.98 (m, 6H, $CH_2Ph$), 4.23-4.69 (m, 9H, H-2$_B$, 3$_C$, 5$_A$, $CH_2Ph$), 3.88-4.07 (m, 3H, H-3$_E$, 5$_B$, 5$_E$), 3.57-3.74 (m, 7H, H-2$_E$, 4$_B$, 4$_C$, 4$_E$, 5$_C$, 6a$_E$, 6b$_E$), 3.50 (dd, 1H, H-3$_B$), 1.38 (d, 6H, H-6$_A$, 6$_B$), 1.07 (d, 3H, H-6$_C$); ¹³C NMR (α-anomer): δ 165.9, 165.5, 165.4, 165.1 (4C, C=O), 160.1 (C=NH), 127.2-138.7 (Ph), 101.2 (C-1$_B$), 99.7 (C-1$_A$), 98.3 (C-1$_E$), 94.3 (C-1$_C$), 90.9 ($CCl_3$), 81.7 (C-3$_E$), 80.9 (C-2$_E$), 79.6 (C-3$_C$, 4$_B$), 78.5 (C-3$_B$), 77.2 (C-4$_C$), 77.5 (C-4$_E$), 75.9 (C-2$_B$), 75.6, 75.1, 75.0, 74.0, 72.9 ($CH_2Ph$), 71.8 (C-2$_C$), 71.3 (C-4$_A$), 71.0 ($CH_2Ph$), 70.7 (C-5$_E$), 70.5 (C-2$_A$*), 70.3 (C-3$_A$*), 70.0

(C-5$_B$), 69.5 (C-5$_C$), 67.9 (C-6$_E$), 67.2 (C-5$_A$), 18.7 (C-6$_A$), 17.8 (C-6$_C$), 17.7 (C-6$_B$). Anal. Calcd. for C$_{96}$H$_{94}$Cl$_3$NO$_{22}$.H$_2$O: C, 66.34; H, 5.57; N, 0.81%. Found: C, 66.26; H, 5.72; N, 0.94%.

2-Azidoethyl (2,3,4-tri-O-benzoyl-α-L-rhamnopyranosyl)-(1→2)-(3,4-di-O-benzyl-α-L-rhamnopyranosyl)-(1→3)-[(2,3,4,6-tetra-O-benzyl-α-D-glucopyranosyl)-(1→4)]-(2-O-benzoyl-α-L-rhamnopyranosyl)-(1→3)-2-acetamido-2-deoxy-4,6-O-isopropylidene-β-D-glucopyranoside (535). (a) The tetrasaccharide donor 506 (500 mg, 0.29 mmol) and the acceptor 507 (140 mg, 0.42 mmol) were dissolved in 1,2-dichloroethane (5 mL) and 4 Å-MS (400 mg) were added. The mixture was stirred at rt for 2 h. The mixture was cooled to 0° C. and triflic acid (7 μL, 0.072 mmol) was added. The mixture was stirred at 0° C. to rt over 1 h 30 min. The mixture was then heated at 65° C. for 1 h 30 min. The mixture was allowed to cool, Et$_3$N (0.5 mL) was added, and the mixture was stirred at rt for 20 min. The mixture was diluted with CH$_2$Cl$_2$ and filtered through a pad of Celite. The filtrate was concentrated and purified by column chromatography (solvent B, 4:3) to give 535 (340 mg, 62%).

(b) The tetrasaccharide donor 506 (250 mg, 145 μmol) and the acceptor 507 (67 mg, 204 μmol) were dissolved in DCM (1.5 mL) and 4 Å-MS (200 mg) were added. The mixture was stirred at −40° C. for 30 min and triflic acid (5 μL) was added. The mixture was stirred at rt over 3 h, triethylamine was added, and the mixture was stirred at rt for 15 min. The mixture was diluted with CH$_2$Cl$_2$ and filtered through a pad of Celite. The filtrate was concentrated and purified by column chromatography (solvent B, 9:1→1:1) to give 535 (219 mg, 80%). [α]$_D$+64.0 (c 0.1); $^1$H NMR: δ 7.04-8.06 (m, 50H, Ph), 6.24 (d, 1H, NH), 5.90 (m, 2H, H-2$_A$, 3$_A$), 5.70 (t, 1H, H-4$_A$), 5.42 (m, 1H, H-2$_C$), 5.35 (bs, 1H, H-1$_A$), 5.13 (m, 3H, H-1$_B$, 1$_D$, 1$_E$), 4.77-5.00 (m, 5H, H-1$_C$, CH$_2$Ph), 4.29-4.66 (m, 11H, H-2$_B$, 3$_D$, 5$_A$, CH$_2$Ph), 3.80-4.11 (m, 6H, H-3$_C$, 3$_E$, 5$_C$, 5$_E$, 6a$_D$, CH$_2$O), 3.45-3.78 (m, 12H, H-2$_E$, 3$_B$, 4$_B$, 4$_C$, 4$_D$, 4$_E$, 5$_B$, 5$_D$, 6b$_D$, 6a$_E$, 6b$_E$, CH$_2$O), 3.39 (m, 1H, CH$_2$N$_3$), 3.23 (m, 2H, H-2$_D$, CH$_2$N$_3$), 2.13 (s, 3H, CH$_3$CO), 1.43 (d, 9H, H-6$_A$, (CH$_3$)2C), 1.29 (d, 3H, H-6$_C$), 1.11 (d, 3H, H-6$_B$); $^{13}$C NMR: δ 171.8, 165.9, 165.5, 165.0, 163.5 (5C, C═O), 127.1-138.7 (Ph), 101.3 (C-1$_B$), 99.8 (C-1$_D$), 99.3 (C-1$_A$), 97.7 (C-1$_C$), 96.6 (C-1$_E$), 91.8 (C(CH$_3$)$_2$), 81.6 (C-3$_E$), 81.0 (C-2$_E$), 80.0 (C-3$_C$), 79.7 (C-4$_D$), 78.9 (C-4$_E$), 77.5 (C-3$_B$, 4$_C$), 76.4 (C-3$_D$), 75.6 (C-2$_B$), 75.5, 74.9, 74.8, 73.8, 73.0 (5C, CH$_2$Ph), 72.9 (C-4$_E$), 72.7 (C-2$_C$), 71.8 (C-4$_A$), 71.3 (C-5$_E$), 71.0 (CH$_2$Ph), 70.6 (C-2$_A$*), 70.0 (C-3$_A$*), 69.3 (C-5$_B$), 68.6 (OCH$_2$), 68.3 (C-6$_E$), 67.5 (C-5$_C$), 67.3 (C-5$_A$), 67.1 (C-5$_D$), 62.2 (C-6$_D$), 58.9 (C-2$_D$), 50.6 (CH$_2$N$_3$), 29.1 (CH$_3$C), 23.6 (CH$_3$C═O), 19.2 (CH$_3$C), 18.6(C-6$_A$), 18.0 (C-6$_C$), 17.6 (C-6$_B$). FAB-MS for C$_{107}$H$_{114}$N$_4$O$_{27}$ (1886) m/z 1909 [M+Na]$^+$. Anal. Calcd. for C$_{107}$H$_{114}$N$_4$O$_{27}$: C, 68.07; H, 6.09; N, 2.97%. Found: C, 68.18; H, 6.07; N, 2.79%.

2-Aminoethyl α-L-rhamnopyranosyl-(1→2)-α-L-rhamnopyranosyl-(1→3)-[α-D-glucopyranosyl)-(1→4)]-α-L-rhamnopyranosyl-(1→3)-2-acetamido-2-deoxy-β-D-glucopyranoside (537). An ice cold solution of 95% aq TFA (2.1 mL) in CH$_2$Cl$_2$ (8 mL) was added to the pentasaccharide 535 (283 mg, 0.15 mmol). The mixture was kept at 0° C. for 2 h, then diluted with toluene and concentrated. Toluene was co-evaporated from the residue. Chromatography of the residue (solvent B, 7:3→1:1) gave the intermediate diol (265 mg, 96%). The latter (265 mg) was dissolved in MeOH (6 mL), and a 1% solution of methanolic sodium methoxide (4.0 mL) was added. The mixture was stirred at 55° C. for 2 h, then neutralised with Dowex X8 (H$^+$) resin and filtered. The filtrate was concentrated. The mixture was purified by column chromatography (solvent A, 100:0→95:5) to give 536 (195 mg, 87%) as a colourless foam, whose structure was confirmed from mass spectrometry analysis (FAB-MS for C$_{76}$H$_{94}$N$_4$O$_{23}$ (M, 1430) m/z 1453 [M+Na]$^+$). Pentasaccharide 536 (171 mg, 0.11 mmol) was dissolved in EHtOH (18 mL). A 1 M solution of aq HCl (210 μL) was added. The mixture was stirred under hydrogen in the presence of 10% Pd/C (96 mg) for 2 h. The mixture was diluted with EtOH and water, then filtered through a pad of Celite. The filtrate was concentrated, and preliminary purified by passing first through a column of C$_{18}$ silica (eluting with water). The residue was purified by RP-HPLC to give, after lyophilization, 537 (50 mg, 53%). HPLC (215 nm): Rt 5.87 min (Kromasil 5 μm C18 100 Å 4.6×250 mm analytical column, using a 0-20% linear gradient over 20 min of CH$_3$CN in 0.01M aq TFA at 1 mL/min flow rate). $^1$H NMR (D$_2$O): δ 5.15 (d, 1H, J$_{1,2}$=3.7Hz, H-1$_E$), 5.00 (bs, 1H, H-1$_A$), 4.92 (d, 1H, J$_{1,2}$=1.1 Hz, H-1$_B$), 4.76 (bs, 1H, H-1$_C$), 4.53 (d, 1H, J$_{1,2}$=8.6 Hz, H-1$_D$), 4.10 (m, 1H, H-5$_C$), 4.03 (m, 2H, H-2$_A$, 2$_B$), 4.01 (m, 3H, H-4$_A$, 4$_B$, CH$_2$O), 3.83-3.88 (m, 7H, H-2$_C$, 2$_D$, 3$_A$, 6a$_D$, 6b$_D$, 6a$_E$, CH$_2$O), 3.69-3.76 (m, 7H, H-3$_B$, 3$_C$, 3$_E$, 4$_C$, 5$_A$, 5$_B$, 6b$_E$), 3.52 (pt, 1H, H-3$_D$), 3.33-3.54 (m, 5H, H-2$_E$, 4$_D$, 4$_E$, 5$_D$, 5$_E$), 3.09 (m, 2H, CH$_2$NH$_2$), 1.98 (s, 3H, CH$_3$C═O), 1.28 (d, 3H, H-6$_C$), 1.22 (m, 6H, H-6$_A$, 6$_B$); $^{13}$C NMR (D$_2$O): δ 175.3 (C═O), 103.4 (C-1$_B$), 101.9 (C-1$_A$), 101.4 (C-1$_C$, 1$_D$), 98.4 (C-1$_E$), 82.3 (C-3$_D$), 80.2 (C-2$_B$), 79.9, 76.7 (C-2$_E$), 72.9, 72.4, 72.4, 72.2, 71.8, 71.6, 70.5, 70.4, 70.1, 70.0, 69.7, 69.6, 69.4, 68.7, 66.7 (CH$_2$O), 61.0 (2C, C-6$_D$, 6$_E$), 55.5 (C-2$_D$), 39.9 (CH$_2$NH$_2$), 22.6 (CH$_3$C═O), 18.2 (C-6$_C$), 17.2 (C-6$_A$), 17.0 (C-6$_B$). HRMS (MALDI) Calcd for C$_{34}$H$_{60}$N$_2$O$_{23}$+H: 865.3665. Found: 865.3499.

Maleimido activated PADRE Lys (508).

Starting from 0.1 mmol of Fmoc Pal Peg Ps resin, amino acids (0.4 mmol) were incorporated using HATU/DIEA (0.4 mmol) activation. The N-terminal D-Ala was incorporated as Boc-D-Ala-OH. After completion of the chain elongation, the resin was treated three times with hydrazine monohydrate (2% solution in DMF, 25 mL/g of peptide resin) for 3 min, which allowed the selective deblocking of the Dde protecting group. To a solution of maleimide butyric acid (183 mg, 1.0 mmol) in DCM (2 mL) was added DCC (103 mg, 0.5 mmol). After stirring for 10 min, the suspension was filtered, and the filtrate was added to the drained peptide resin. DIEA (17 μL, 0.5 mmol) was added. After 30 min, the peptide resin was washed with DMF (100 mL), MeOH (100 mL), and dried under vacuum. After TFA/TIS/H$_2$O (95/2.5/2.5) cleavage (10 mL/g of resin, 1.5 h), the crude peptide (157 mg) was dissolved in 16 mL of 15% CH$_3$CN in 0.08% aq TFA, and purified by reverse phase Medium Pressure Liquid Chromatography (MPLC) on a Nucleoprep 20 μm C18 100 Å column, using a 15-75% linear gradient of CH$_3$CN in 0.08% aq TFA over 60 min at 25 mL/min flow rate (214 nm detection) to give 508 (107 mg, 61%). HPLC (214 nm): Rt 13.4 min (94% pure, Nucleosil 5 μm C18 300 Å analytical column, using a 15-45% linear gradient over 20 min of CH$_3$CN in 0.08% aq TFA at 25 mL/min flow rate). Positive ion ES-MS Calcd for C$_{85}$H$_{139}$N$_{21}$O$_{19}$: 1759.18. Found; 1758.83 (SD: 0.40).

(S-Acetylthiomethyl)carbonylaminoethyl α-D-glucopyranosyl-(1→4)-α-L-rhamnopyranosyl-(1→3)-2-acetamido-2-deoxy-β-D-glucopyranoside (538). The trisaccharide 518 (58 mg, 0.1 mmol) was dissolved in DMF (1 mL). SAMA-Pfp (33 mg, 0.11 mmol) was added, and the mixture was left to stand at rt for 40 min. Toluene was added and the mixture was concentrated. Ether was added to the residue. The resulting precipitate was collected and purified by passing through a column of $C_{18}$ silica (water-acetonitrile, gradient) to give 538 (36 mg, 53%). HPLC (230 nm): Rt 13.74 min (99% pure, Kromasil 5 μm C18 100 Å 4.6×250 mm analytical column, using a 0-20% linear gradient over 20 min of $CH_3CN$ in 0.01M aq TFA at 1 mL/min flow rate). $^{13}C$ NMR ($D_2O$): δ 200.3 (SC=O), 175.2, 171.9 (NC=O), 102.1 ($C-1_C$), 101.2 ($C-1_D$), 100.5($C-1_E$), 82.7 ($C-3_D$), 81.8 ($C-4_C$), 76.8 ($C-2_E$), 73.6 ($C-3_E$), 72.6 ($C-5_E$), 72.4 ($C-4_D$), 71.8 ($C-2_C$), 70.2 ($C-4_E$), 69.7 ($C-3_C$), 69.4 ($C-5_D$), 68.9 ($C-5_C$), 68.9 ($CH_2O$), 61.6 ($C-6_D$), 60.9 ($C-6_E$), 56.1 ($C-2_D$), 40.6 ($CH_2NH$), 33.7 ($CH_2S$), 30.4 ($CH_3C(O)S$), 23.0 ($CH_3C(O)N$), 17.5 ($C-6_C$). ES-MS for $C_{26}H_{44}N_2O_{17}S$ (688) m/z 689 [M+H]$^+$. HRMS (MALDI) Calcd for $C_{22}H_{44}N_2O_{17}SNa$: 711.2258. Found: 711.2294.

(5-Acetylthiomethyl)carbonylaminoethyl α-L-rhamnopyranosyl-(1→3)-[α-D-glucopyranosyl-(1→4)]-α-L-rhamnopyranosyl-(1→3)-2-acetamido-2-deoxy-β-D-glucopyranoside (539). A solution of SAMA-Pfp (16.7 mg, 40 μmol) in $CH_3CN$ (150 μL) was added to the tetrasaccharide 525 (20 mg, 28.8 μmol) in 0.1 M phosphate buffer (pH 7.4, 600 μL). The mixture was stirred at rt for 45 min and purified by RP-HPLC to give 539 (17 mg, 74%). HPLC (230 nm): Rt 13.63 min (98% pure, Kromasil 5 μm C18 100 Å 4.6×250 mm analytical column, using a 0-20% linear gradient over 20 min of $CH_3CN$ in 0.01 M aq TFA at 1 mL/min flow rate). $^1H$ NMR ($D_2O$): δ 5.10 (d, 1H, $J_{1,2}$=3.7 Hz, $H-1_E$), 4.91 (d, 1H, $J_{1,2}$=0.8 Hz, $H-1_B$), 4.73 (bs, 1H, $H-1_C$), 4.45 (d, 1H, $J_{1,2}$=8.5 Hz, $H-1_D$), 4.09 (m, 1H, $H-5_C$), 3.97 (m, 1H, $H-2_B$), 3.87 (m, 4H, $H-2_C$, $3_C$, $6a_D$, $CH_2O$), 3.62-3.78 (m, 8H, $H-2_D$, $3_B$, $4_C$, $5_B$, $6b_D$, $6a_E$, $6b_E$, 1×$CH_2O$), 3.60 (m, 3H, $H-3_E$, $CH_2S$), 3.48 (pt, 1H, $H-3_D$), 3.39-3.46 (m, 6H, $H-2_E$, $4_B$, $4_D$, $4_E$, $5_D$, $5_E$), 3.33 (m, 2H, $CH_2NH_2$), 2.35 (s, 3H, $CH_3C(O)S$), 1.98 (s, 3H, $CH_3C(O)N$), 1.27 (d, 3H, $H-6_C$), 1.23 (d, 3H, $H-6_B$); $^{13}C$ NMR ($D_2O$): δ 199.8 (SC=O), 174.5, 171.3 (NC(O)), 103.2 ($C-1_B$), 101.4 ($C-1_C$), 100.9 ($C-1_D$), 98.6 ($C-1_E$), 82.0 ($C-3_D$), 79.0 ($C-4_B$), 76.6 ($C-4_C$), 76.3 ($C-2_E$), 72.9 ($C-3_E$), 72.3 ($C-5_E$), 72.2 ($C-4_D$), 71.8 ($C-3_C$), 71.0 ($C-2_C$), 70.5 ($C-2_B$, $3_B$), 69.7 ($C-4_B$), 69.5 ($C-4_E$), 69.1 ($C-5_C$, $5_D$), 68.8 ($C-5_B$), 68.7 ($CH_2O$), 61.1 ($C-6_D$), 60.7 ($C-6_E$), 55.5 ($C-2_D$), 40.1 ($CH_2NH$), 33.2 ($CH_2S$), 29.9 ($CH_3C(O)S$), 22.6 ($CH_3C(O)N$), 17.9 ($C-6_C$), 16.9 ($C-6_B$). MS for $C_{32}H_{54}N_2O_{21}S$ (834) m/z 857 [M+Na]$^+$. HRMS-MALDI Calcd for $C_{32}H_{54}N_2O_{21}S$+Na: 857.2838. Found: 857.2576.

(S-Acetylthiomethyl)carbonylaminoethyl α-L-rhamnopyranosyl-(1→2)-α-L-rhamnopyranosyl-(1→3)-[α-D-glucopyranosyl)-(1→4)]-α-L-rhamnopyranosyl-(1→3)-2-acetamido-2-deoxy-β-D-glucopyranoside (540). The pentasaccharide 537 (6.4 mg, 7.4 μmol) was dissolved in 0.1 M phosphate buffer (pH 7.4, 1.0 mL). SAMA-Pfp (6.6 mg, 22 μmol) was added, and the mixture was stirred at rt for 5 h. More SAMA-Pfp (6.6 mg, 22 μmol) was added and the mixture was stirred for 1 h more at rt. RP-HPLC of the mixture gave 540 (5.4 mg, 75%). HPLC (230 nm): Rt 13.86 min (100% pure, Kromasil 5 μm C18 100 Å 4.6×250 mm analytical column, using a 0-20% linear gradient over 20 min of $CH_3CN$ in 0.01M aq TFA at 1 mL/min flow rate). $^1H$ NMR ($D_2O$): δ 5.13 (d, 1H, $J_{1,2}$=3.7 Hz, $H-1_E$), 4.98 (bs, 1H, $H-1_A$), 4.90 (bs, 1H, $H-1_B$), 4.74 (bs, 1H, $H-1_C$), 4.47 (d, 1H, $J_{1,2}$=8.5 Hz, $H-1_D$), 4.09 (m, 1H, $H-5_C$), 4.00 (m, 2H, $H-2_A$, $2_B$), 3.79-3.85 (m, 8H, $H-2_C$, $2_D$, $3_A$, $4_A$, $4_B$, $6a_D$, $6b_D$, $CH_2O$), 3.65-3.74 (m, 9H, $H-3_B$, $3_C$, $3_E$, $4_C$, $5_A$, $5_B$, $6a_E$, $6b_E$, $CH_2O$), 3.60 (m, 2H, $CH_2S$), 3.53 (pt, 1H, $H-3_D$), 3.13-3.49 (m, 7H, $H-2_E$, $4_D$, $4_E$, $5_D$, $5_E$, $CH_2NH$), 2.35 (s, 3H, $CH_3C=OS$), 1.99 (s, 3H, $CH_3C=ON$), 1.28 (d, 3H, $H-6_C$), 1.20 (m, 6H, $H-6_A$, $6_B$); $^{13}C$ NMR ($D_2O$): δ 199.9 (SC=O), 174.5, 171.4 (NC=O), 102.8 ($C-1_B$), 101.7 ($C-1_A$), 101.4 ($C-1_C$), 100.9 ($C-1_D$), 97.9 ($C-1_E$), 82.0 ($C-3_D$), 79.7 ($C-2_B$), 79.0, 76.3, 72.9, 72.4, 72.2, 71.8, 71.0, 70.5, 69.7, 69.5, 69.1, 68.8, 68.5 ($CH_2O$), 61.2, 61.0 (2C, $C-6_D$, $6_E$), 55.6 ($C-2_D$), 40.1 ($CH_2NH$), 33.2 ($CH_2S$), 29.9 ($CH_3C=OS$), 22.7 ($CH_3C=ON$), 18.2 ($C-6_C$), 17.2 ($C-6_A$), 17.0 ($C-6_B$). HRMS (MALDI) Calcd for $C_{38}H_{64}N_2O_{25}SNa$: 1003.3417. Found: 1003.3426.

PADRE-Lys-(thiomethyl)carbonylaminoethyl α-D-glucopyranosyl-(1→4)-α-L-rhamnopyranosyl-(1→3)-2-acetamido-2-deoxy-β-D-glucopyranoside (501). Compound 538 (5.0 mg, 7.3 μmol) was dissolved in water (500 μL) and added to a solution of 508 (10 mg, 5.68 μmol) in a mixture of water (900 μL), acetonitrile (100 μL) and 0.1M phosphate buffer (pH 6.0, 1 mL). 117 μL of a solution of hydroxylamine hydrochloride (139 mg/mL) in 0.1M phosphate buffer (pH 6.0) was added and the mixture was stirred for 1 h. RP-HPLC purification gave the pure glycopeptide 501 (8.5 mg, 62%). HPLC (230 nm): Rt 10.40 min (100% pure, Kromasil 5 μm C18 100 Å 4.6×250 mm analytical column, using a 0-20% linear gradient over 20 min of $CH_3CN$ in 0.01 M aq TFA at 1 mL/min flow rate). ES-MS Calcd for $C_{109}H_{181}N_{23}O_{35}S$: 2405.85. Found: 2405.52.

PADRE-Lys-(thiomethyl)carbonylaminoethyl α-L-rhamnopyranosyl-(1→3)-[α-D-glucopyranosyl)-(1→4)]-α-L-rhamnopyranosyl-(1→3)-2-acetamido-2-deoxy-β-D-glucopyranoside (502). Compound 539 (4.9 mg, 5.8 μmol) was dissolved in water (500 μL) and added to a solution of 508 (13 mg, 7.4 μmol) in a mixture of water (1 mL), acetonitrile (200 μL) and 0.5 M phosphate buffer (pH 5.7, 1.2 mL). 117 μL of a solution of hydroxylamine hydrochloride (139 mg/mL) in 0.5M phosphate buffer (pH 5.7) was added, and the mixture was stirred for 1 h. RP-HPLC purification gave the pure glycopeptide 502 (6.7 mg, 48%). HPLC (230 nm): Rt 11.60 min (100% pure, Kromasil 5 μm C18 100 Å 4.6×250 mm analytical column, using a 20-50% linear gradient over 20 min of $CH_3CN$ in 0.01M aq TFA at 1 mL/min flow rate). ES-MS Calcd for $C_{125}H_{191}N_{23}O_{39}S$: 2552.99. Found: 2551.90.

PADRE-Lys-(thiomethyl)carbonylaminoethyl α-L-rhamnopyranosyl-(1→2)-α-L-rhamnopyranosyl-(1→3)-[α-D-glucopyranosyl)-(1→4)]-α-L-rhamnopyranosyl-(1→3)-2-acetamido-2-deoxy-β-D-glucopyranoside (503). Compound 540 (5.59 mg, 5.7 μmol) was dissolved in water (500 μL) and added to a solution of 508 (12.6 mg, 7.2 μmol) in a mixture of water (1 mL), acetonitrile (200 μL), which had been previously diluted with 0.5 M phosphate buffer (pH 5.7. 1.2 mL). A solution of hydroxylamine hydrochloride (139 mg/mL) in 0.5M phosphate buffer (pH 5.7, 117 μL) was added and the mixture was stirred for 1 h. RP-HPLC purification gave the pure glycopeptide 503 (7.1 mg, 46%). HPLC (230 nm): Rt 10.33 min (100% pure, Kromasil 5 μm C18 100 Å 4.6×250 mm analytical column, using a 20-50% linear gradient over 20 mm of $CH_3CN$ in 0.01 M aq TFA at 1 mL/min flow rate). ES-MS Calcd for $C_{121}H_{201}N_{23}O_{43}S$: 2698.14. Found: 2698.09.

F—Synthesis of Two Linear PADRE-conjugates Hearing a Deca- or a Pentasaccharide B Epitope as Potential Synthetic Vaccine Against *Shigella flexneri* Serotype 2a Infection Allyl (2-acetamido-3,4,6-tri-O-acetyl-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (611). A mixture of 610 (3.14 g, 1.6 mmol), $Bu_3SnH$ (2.5 mL, 9.3 mmol) and AIBN (240 mg) in dry toluene (40 mL) was stirred for 30 min at rt under a stream of dry Argon, then was heated for 1 h at 100° C. cooled and concentrated. The residue was eluted from a column of silica gel with 3:2 petroleum ether-EtOAc to give 611 as a white foam (2.0 g, 68%); $[\alpha]_D$+3° (c 1, CHCl$_3$). $^{13}$H NMR (CDCl$_3$): δ 8.00-7.00 (m, 45H, Ph), 5.82 (m, 1H, All), 5.58 (d, 1H, $J_{2,NH}$=8.0 Hz, N-H$_D$), 5.35 (dd, 1H, $J_{1,2}$=1.0, $J_{2,3}$=2.3 Hz, H-2$_C$), 5.19 (m, 2H, All), 5.10 (d, 1H, $J_{1,2}$=1.0 Hz, H-1$_A$), 4.92 (dd, 1H, $J_{2,3}$=10.5, $J_{3,4}$=10.5 Hz, H-3$_D$), 4.92 (d, 1H, $J_{1,2}$=3.3 Hz, H-1$_E$), 4.90 (d, 1H, $J_{1,2}$=1.7 Hz, H-1$_B$), 4.89 (d, 1H, H-1$_C$), 4.88 (dd, 1H, $J_{4,5}$=10.0 Hz, H-4$_D$), 4.62 (d, 1H, $J_{1,2}$=8.5 Hz, H-1$_D$), 4.90-4.35 (m, 16H, CH$_2$Ph), 4.40 (m, 1H, H-2$_B$), 4.10-4.00 (m, 2H, All), 4.08 (dd, 1H, $J_{2,3}$=2.4 Hz, H-2$_A$), 4.02 (dd, 1H, H-3$_C$), 3.91 (m, 1H, H-2$_D$), 3.90-3.70 (m, 11H, H-4$_C$, 5$_C$, 3$_A$, 5$_A$, 6a$_D$, 6b$_D$, 3$_E$, 4$_E$, 5$_E$, 6a$_E$, 6b$_E$), 3.61 (dd, 1H, $J_{3,4}$=9.5 Hz, H-3$_B$), 3.55 (m, 1H, H-5$_B$), 3.41-3.40 (m, 3H, H-4$_A$, 5$_D$, 2$_E$), 3.47 (m, 1H, $J_{4,5}$9.5, $J_{5,6}$=6.1 Hz, H-5$_B$), 3.35-3.33 (m, 3H, H-4$_A$, 5$_D$, 2$_E$), 3.25 (dd, 1H, H-4$_B$), 1.95, 1.70 (3s, 9H, OAc), 1.65 (s, 3H, NHAc), 1.32 (d, 3H, $J_{5,6}$=6.1 Hz, H-6$_A$), 1.30 (d, 3H, $J_{5,6}$=6.0 Hz, H-6$_C$), 0.97 (d, 3H, $J_{5,6}$=6.0 Hz, H-6$_B$), $^{13}$C NMR: δ 171.1, 170.8, 170.2, 169.6, 166.2 (5C, C=O), 138.2-118.5 (Ph, All), 103.1 (C-1$_D$), 101.4 (C-1$_B$), 101.2 (C-1$_A$), 98.5 (C-1$_E$), 96.4 (C-1$_C$), 82.2 (C-3$_E$), 81.7 (C-2$_E$), 81.7 (C-4$_A$), 80.4 (C-4$_B$), 80.2 (C-3$_C$), 79.0 (C-3$_A$), 78.6 (C-3$_E$), 78.1 (C-2$_A$), 77.8 (C-4$_C$), 77.6 (C-4$_E$), 76.0, 75.8, 75.4, 74.7, 74.3, 74.2, 73.3, 70.5 (8C, CH$_2$Ph), 74.9 (C-2$_B$), 72.7 (C-2$_C$), 72.6 (C-3$_D$), 71.9 (2C, C-5$_E$, 5$_D$), 69.1 (C-5$_B$), 68.9 (2C, All, C-5$_A$), 68.3 (C-6$_E$), 67.8 (C-5$_C$), 62.3 (C-6$_D$), 54.6 (C-2$_D$), 23.5 (NHAc), 21.1, 21.0, 20.8 (3C, OAc), 19.0 (C-6$_C$), 18.4 (C-6$_A$), 18.2 (C-6B). FAB-MS of C$_{104}$H$_{117}$NO$_{27}$ (M, 1913.1), m/z 1936.2 [M+Na]$^+$. Anal. Calcd. for C$_{104}$H$_{117}$NO$_{27}$: C, 68.90; H, 6.50; N, 0.77. Found: C, 68.64; H, 6.66; N, 1.05.

Allyl (2-acetamido-4,6-O-isopropylidene-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranoside (613). The pentasaccharide 611 (2.65 g, 1.47 mmol) was dissolved in MeOH (20 mL). MeONa was added until pH 10. The mixture was stirred for 25 min then treated by IR 120 (H$^+$) until neutral pH. The solution was filtered and concentrated. The residue was eluted from a column of silica gel with 9:1 DCM-MeOH to give the expected triol 612 which was then treated overnight at rt by 2,2-dimethoxypropane (11 mL, 0.1 mol) and PTSA (20 mg, 0.17 mmol) in DMF (20 mL). Et$_3$N was added and the solution evaporated. The residue was eluted from a column of silica gel with 1:1 cyclohexane-EtOAc and 0.2% of Et$_3$N to give 613 as a white foam (2.05 g, 81% from 611); $[\alpha]_D$+3° (c 1, CHCl$_3$). $^1$H NMR: δ 6.98-8.00 (m, 45H, Ph), 6.17 (bs, 1H, NH$_D$), 5.82 (m, 1H, All), 5.30 (dd, 1H, $J_{1,2}$=1.0, $J_{2,3}$=3.0 Hz, H-2$_C$), 5.11-5.25 (m, 2H, All), 5.06 (bs, 1H, H-1$_A$), 4.92 (d, 1H, $J_{1,2}$=3.1 Hz, H-1$_E$), 4.88 (d, 1H, $J_{1,2}$=1.6 Hz, H-1$_B$), 4.84 (bs, 1H, H-1$_C$), 4.35 (d, 1H, H-1$_D$), 4.34 (dd, 1H, H-2$_B$), 4.20-4.80 (m, 16H, CH$_2$Ph), 4.05 (dd, 1H, H-2$_A$), 3.36 (dd, 1H, H-2$_E$), 2.90-4.10 (m, 22H, All, H-2$_D$, 3$_A$, 3$_B$, 3$_C$, 3$_D$, 3$_E$, 4$_A$, 4$_B$, 4$_C$, 4$_D$, 4$_E$, 5$_A$, 5$_B$, 5$_C$, 5$_D$, 5$_E$, 6a$_D$, 6b$_D$, 6a$_E$, 6b$_E$), 1.5 (s, 3H, NHAc), 1.2-0.9 (m, 15H, C(CH$_3$)$_2$, H-6$_A$, 6$_B$, 6$_C$). $^{13}$C NMR: δ 172.7, 164.9 (2C, C=O), 137.7-116.7 (Ph, All), 102.3 (C-1$_D$), 100.2 (C-1$_B$), 100.0 (C-1$_A$), 98.9 (C(CH$_3$)$_2$), 97.2 (C-1$_E$), 95.1 (C-1$_C$), 82.1, 82.0, 81.8, 81.6, 80.6, 80.3, 79.0, 78.8, 78.3, 77.8, 77.6, 75.7, 75.6, 75.0, 74.3, 72.8, 71.8, 71.6, 70.8, 70.3, 69.0, 68.5, 67.8, 67.4, 61.9, 60.8, 60.5, 29.4 (C(CH$_3$)$_2$), 22.7 (NHAc), 19.0 (C(CH$_3$)$_2$), 18.9, 18.4, 18.2 (3C, C-6$_A$, 6$_B$, 6$_C$). FAB-MS for C$_{101}$H$_{115}$NO$_{24}$ (M, 1726.9) m/z 1749.7 [M+Na]$^+$. Anal. Calcd. for C$_{101}$H$_{115}$NO$_{24}$.H$_2$O: C, 69.52; H, 6.76; N, 0.80. Found: C, 69.59; H 6.71; N, 0.57.

Allyl (2-acetamido-3-O-acetyl-4,6-O-isopropylidene-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)-]-2-O-benzoyl-α-L-rhamnopyranoside (614). A mixture of 613 (2.05 g, 1.19 mmol) in pyridine (60 mL) was cooled to 0° C. Acetic anhydride (20 mL) was added and the solution was stirred 2.5 h. The solution was concentrated and coevaporated with toluene. The residue was eluted from a column of silica gel with 2:1 Cyclohexane-EtOAc and 0.2% of Et$_3$N to give 614 as a white foam (1.99 g, 94%); $[\alpha]_D$+1° (c 1, CHCl$_3$). $^1$H NMR: δ 6.95-8.00 (m, 45H, Ph), 5.82 (m, 1H, All), 5.46 (d, JH, $J_{2,NH}$=8.0 Hz, NH$_D$), 5.29 (dd, 1H, $J_{1,2}$=1.0, $J_{2,3}$=3.0 Hz, H-2$_C$), 5.11-5.25 (m, 2H, All), 5.00 (bs, 1H, H-1$_A$), 4.90 (d, 1H, $J_{1,2}$=3.1 Hz, H-1$_E$), 4.85 (d, 1H, $J_{1,2}$=1.6 Hz, H-1$_B$), 4.83 (bs, 1H, H-1$_C$), 4.70 (dd, 1H, $J_{2,3}$=$J_{3,4}$=10.0 Hz, H-3$_D$), 4.44 (d, 1H, H-1$_D$), 4.34 (dd, 1H, H-2$_B$), 4.20-4.80 (m, 16H, CH$_2$Ph), 4.02 (dd, 1H, H-2$_A$), 3.37 (dd, 1H, H-2$_E$), 2.90-4.10 (m, 21H, All, H-2$_D$, 3$_A$, 3$_B$, 3$_C$, 3$_E$, 4$_A$, 4$_B$, 4$_C$, 4$_D$, 4$_E$, 5$_A$, 5$_B$, 5$_C$, 5$_D$, 5$_E$, 6a$_D$, 6b$_D$, 6a$_E$, 6b$_E$), 1.92 (s, 3H, OAc), 1.57 (s, 3H, NHAc), 1.27-0.90 (m, 15H, C(CH$_3$)$_2$, H-6$_A$, 6$_B$, 6$_C$). $^{13}$C NMR: δ 171.3, 170.3, 166.2 (3C, C=O), 138.7-117.9 (Ph, All), 103.9 (C-1$_D$), 101.5 (C-1$_B$), 101.4 (C-1$_A$), 99.9 (C(CH$_3$)$_2$), 98.5 (C-1$_E$), 96.3 (C-1$_C$), 82.1, 81.7, 81.6, 80.3, 80.1, 78.8, 78.1, 77.8, 76.0, 75.8, 75.3, 75.1, 74.7, 74.2, 73.6, 73.3, 72.7, 71.9, 71.4, 70.8, 69.0, 68.8, 68.7, 68.4, 68.1, 67.8, 62.1, 55.0 (C-2$_D$), 30.0 (C(CH$_3$)$_2$), 23.5 (NHAc), 21.6 (OAc), 19.2 (C(CH$_3$)$_2$), 19.0, 18.3, 18.2 (3C, C-6$_A$, 6$_B$, 6$_C$). FAB-MS for C$_{103}$H$_{117}$NO$_{25}$ (M, 1769.0) m/z 1791.9 [M+Na]$^+$. Anal. Calcd. for C$_{103}$H$_{117}$NO$_{25}$: C, 69.93; H, 6.67; N, 0.79. Found: C, 69.77; H, 6.84; N, 0.72.

(2-Acetamido-3-O-acetyl-4,6-O-isopropylidene-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6tetra-O-benzyl-α-D-glucopyranosyl-(1→4)-]-2-O-benzoyl-α-L-rhamnopyranosyl trichloroacetimidate (607). 1,5-Cyclooctadiene-bis(methyldiphenylphosphine)iridium hexafluorophosphate (50 mg, 58 μmol) was dissolved THF (10 mL), and the resulting red solution was degassed in an argon stream. Hydrogen was then bubbled through the solution, causing the color to change to yellow. The solution was then degassed again in an argon stream. A solution of 614 (1.8 g, 1.02 mmol) in THF (20 mL) was degassed and added. The mixture was stirred at rt overnight, then concentrated to dryness. The residue was dissolved in acetone (9 mL), then water (2 mL), mercuric chloride (236 mg) and mercuric oxide (200 mg) were added successively. The mixture protected from light was stirred at rt for 2 h, and acetone was evaporated. The resulting suspension was taken up in DCM, washed twice with 50% aq KI, water and satd aq NaCl, dried and concentrated. The residue was eluted from a column of silica gel with 3:2 Cyclohexane-EtOAc and 0.2% Et$_3$N to give the corresponding hemiacetal 615. Trichloroacetonitrile (2.4 mL) and DBU (72 μL) were added to a solution of the residue in anhydrous DCM (24 mL) at 0° C. After 1 h, the mixture was concentrated. The residue was eluted from a column of silica gel with 3:2 cyclohexane-EtOAc and 0.2% Et$_3$N to give 607 as a colourless oil (1.58 g, 82% from 614); $[\alpha]_D$+2° (c 1, CHCl$_3$). $^1$H NMR: δ 8.62 (s, 1H, NH), 6.95-8.00 (m, 45H, Ph), 6.24 (d, 1H, $J_{1,2}$=2.6 Hz, H-1$_C$), 5.48 (dd, 1H, $J_{2,3}$=3.0 Hz, H-2$_C$), 5.41 (d, 1H, $J_{2,NH}$=8.4 Hz, NH$_D$), 4.99 (bs, 1H, H-1$_A$), 4.92 (d, 1H, $J_{1,2}$=3.2 Hz, H-1$_E$), 4.88 (d, 1H, $J_{1,2}$=1.6 Hz, H-1$_B$), 4.69

(dd, 1H, $J_{2,3}=J_{3,4}=10.0$ Hz, H-3$_D$), 4.44 (d, 1H, H-1$_D$), 4.34 (dd, 1H, H-2$_B$), 4.20-4.80 (m, 16H, CH$_2$Ph), 4.02 (dd, 1H, H-2$_A$), 3.38 (dd, 1H, H-2$_E$), 2.90-4.10 (m, 19H, H-2$_D$, 3$_A$, 3$_B$, 3$_C$, 3$_E$, 4$_A$, 4$_B$, 4$_C$, 4$_D$, 4$_E$, 5$_A$, 5$_B$, 5$_C$, 5$_D$, 5$_E$, 6a$_D$, 6b$_D$, 6a$_E$, 6b$_E$), 1.95 (s, 3H, OAc), 1.55 (s, 3H, NHAc), 1.30-0.85 (m, 15H, C(CH$_3$)$_2$, H-6$_A$, 6$_B$, 6$_C$). $^{13}$C NMR: δ 172.4, 171.4, 166.9 (3C, C=O), 140.2-128.9 (Ph), 104.2 (C-1$_D$), 101.4 (2C, C-1$_A$, 1$_B$), 101.1 (C(CH$_3$)$_2$), 98.0 (C-1$_E$), 94.8 (C-1$_C$), 92.4 (CCl$_3$), 82.1, 81.5, 80.2, 80.1, 78.6, 78.1, 77.8, 77.6, 76.0, 75.8, 75.5, 75.0, 74.3, 74.2, 73.5 (C-3$_D$), 73.4, 71.9, 71.4, 71.0, 70.5, 69.2, 68.8, 68.3, 68.1, 62.1, 54.9 (C-2$_D$), 29.3 (C(CH$_3$)$_2$), 23.4 (NHAc), 21.4 (OAc), 19.2 (C(CH$_3$)$_2$), 19.0, 18.2, 18.1 (3C, C-6$_A$, 6$_B$, 6$_C$). FAB-MS for C$_{102}$H$_{113}$Cl$_3$N$_2$O$_{25}$ (M, 1873.3) m/z 1896.5 [M+Na]$^+$. Anal. Calcd. for C$_{102}$H$_{113}$Cl$_3$N$_2$O$_{25}$: C, 65.40; H, 6.08; N, 1.50. Found: C, 65.26; H, 6.02; N, 1.31.

2-Azidoethyl (2-acetamido-3-O-acetyl-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-4,6-O-isopropylidene-β-D-glucopyranoside (616). A mixture of donor 607 (745 mg, 0.4 mmol) and acceptor 608 (170 mg, 0.51 mmol), 4 Å molecular sieves and dry 1,2-DCE (12 mL), was stirred for 1 h then cooled to 0° C. Triflic acid (25 μL) was added. The stirred mixture was allowed to reach rt in 10 min then stirred again for 2.5 h at 75° C. After cooling to rt, Et$_3$N (100 μL) was added and the mixture filtered. After evaporation, the residue was eluted from a column of silica gel with 1:2 cyclohexane-EtOAc and 0.2% Et$_3$N to give 616 as a white foam (615 mg, 76%); [α]$_D$+0° (c 1, CHCl$_3$). $^1$H NMR: δ 6.95-7.90 (m, 45H, Ph), 6.02 (d, 1H, $J_{2,NH}$=7.1 Hz, NH$_D$), 5.46 (d, 1H, $J_{2,NH}$=8.6 Hz, NH$_{D'}$), 5.20 (dd, 1H, $J_{1,2}$=1.0, $J_{2,3}$=3.0 Hz, H-2$_C$), 5.03 (d, 1H, $J_{1,2}$=8.1 Hz, H-1$_D$), 5.02 (bs, 1H, H-1$_A$), 4.92 (d, 1H, $J_{1,2}$=3.1 Hz, H-1$_E$), 4.85 (d, 1H, $J_{1,2}$=1.6 Hz, H-1$_B$), 4.82 (bs, 1H, H-1$_C$), 4.70 (dd, 1H, H-3$_{D'}$), 4.44 (d, 1H, H-1$_{D'}$), 4.30 (dd, 1H, H-2$_B$), 4.20-4.80 (m, 16H, CH$_2$Ph), 3.99 (dd, 1H, H-2$_A$), 3.37 (dd, 1H, H-2$_E$), 2.90-3.95 (m, 29H, H-2$_D$, 2$_{D'}$, 3$_A$, 3$_B$, 3$_C$, 3$_D$, 3$_E$, 4$_A$, 4$_B$, 4$_C$, 4$_D$, 4$_{D'}$, 4$_E$, 5$_A$, 5$_B$, 5$_C$, 5$_D$, 5$_{D'}$, 5$_E$, 6a$_D$, 6b$_D$, 6a$_{D'}$, 6b$_{D'}$, 6a$_E$, 6b$_E$, OCH$_2$CH$_2$N$_3$), 2.00 (s, 3H, NHAc), 1.92 (s, 3H, OAc), 1.57 (s, 3H, NHAc), 1.27-0.90 (m, 21H, 2 C(CH$_3$)$_2$, H-6$_A$, 6$_B$, 6$_C$). $^{13}$C NMR: δ 172.1, 171.5, 170.3, 166.2 (4C, C=O), 139.0-127.7 (Ph), 103.9 (C-1$_{D'}$), 101.7 (C-1$_B$), 101.2 (C-1$_A$), 100.0 (C-1$_D$), 99.9, 99.8 (2C, C(CH$_3$)$_2$), 98.3 (C-1$_E$), 97.8 (C-1$_C$), 82.0, 81.7, 81.5, 80.8, 80.2, 80.1, 78.9, 78.6, 78.0, 77.9, 76.0, 75.9, 75.8, 75.3, 74.8, 74.6, 74.2, 74.0, 73.6, 73.5, 73.4, 73.0, 71.9, 71.4, 70.8, 69.1, 69.0, 68.8, 68.6, 68.0, 67.7, 67.6, 62.6, 62.1, 60.8. 59.7 (C-2$_D$), 55.0 (C-2$_D$), 51.1 (CH$_2$N$_3$), 29.5 (C(CH$_3$)$_2$), 29.3 (C(CH$_3$)$_2$), 23.9 (NHAc), 23.5 (NHAc), 21.3 (OAc), 19.7 (C(CH$_3$)$_2$), 19.2 (C(CH$_3$)$_2$), 18.8, 18.4, 18.2 (3C, C-6$_A$, 6$_B$, 6$_C$). FAB-MS for C$_{113}$H$_{133}$N$_5$O$_{30}$ (M, 2041.3) m/z 2064.2 [M+Na]$^+$. Anal. Calcd. for C$_{113}$H$_{133}$N$_5$O$_{30}$: C, 66.49; H, 6.57; N, 3.43. Found: C, 65.93; H, 6.57; N, 2.61.

2-Azidoethyl (2-acetamido-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-4,6-O-isopropylidene-β-D-glucopyranoside (617). The hexasaccharide 616 (615 mg, 0.30 mmol) was dissolved in MeOH (8 mL). MeONa was added until pH 9. The mixture was stirred for 3 h, then treated by IR 120 (H$^+$) until neutral pH. The solution was filtered and concentrated. The residue was eluted from a column of silica gel with 25:1 DCM-MeOH and 0.2% of Et$_3$N to give 617 as a white foam (590 mg, 97%); [α]$_D$+1° (c 1, CHCl$_3$). $^1$H NMR: δ 8.00-7.00 (m, 45H, Ph), 6.10 (d, 1H, NH$_D$), 6.05 (d, 1H, $J_{2,NH}$=7.4 Hz, NH$_{D'}$), 5.20 (dd, 1H, $J_{1,2}$=1.7, $J_{2,3}$=3.0 Hz, H-2$_C$), 5.10 (d, 1H, $J_{1,2}$=1.0 Hz, H-1$_A$), 4.99 (d, 1H, $J_{1,2}$=8.3 Hz, H-1$_D$), 4.96 (d, 1H, $J_{1,2}$=3.2 Hz, H-1$_E$), 4.90 (d, 1H, $J_{1,2}$=1.0 Hz, H-1$_B$), 4.86 (d, 1H, $J_{1,2}$=1.0 Hz, H-1$_C$), 4.52 (d, 1H, $J_{1,2}$=7.5 Hz, H-1$_{D'}$), 4.37 (dd, 1H, H-2$_B$), 4.22 (dd, 1H, H-3$_D$), 4.02 (dd, 1H, H-2$_A$), 4.80-4.00 (m, 16H, CH$_2$Ph), 4.00-2.95 (m, 30H, H-2$_D$, 4$_D$, 5$_D$, 6a$_D$, 6b$_D$, 2$_E$, 3$_E$, 4$_E$, 5$_E$, 6a$_E$, 6b$_E$, 3$_C$, 4$_C$, 5$_C$, 3$_B$, 4$_B$, 5$_B$, 3$_A$, 4$_A$, 5$_A$, 2$_{D'}$, 3$_{D'}$, 4$_{D'}$, 5$_{D'}$, 6a$_{D'}$, 6b$_{D'}$, OCH$_2$CH$_2$N$_3$), 2.00-0.92 (6s, 3d, 27H, NHAc, C(CH$_3$)$_2$, H-6$_A$, 6$_B$, 6$_C$). $^{13}$C NMR partial: δ 173.9, 172.1, 166.3 (3C, C=O), 140.0-125.0 (Ph), 103.6 (C-1$_{D'}$), 101.7 (C-1$_B$), 101.2 (C-1$_A$), 100.2 (C(CH$_3$)$_2$), 100.2 (C-1$_D$), 99.9 (C(CH$_3$)$_2$), 98.2 (C-1$_E$), 97.8 (C-1$_C$), 51.1 (CH$_2$N$_3$), 29.4, 29.3, 23.9, 22.8, 19.6, 19.2, 18.9, 18.4, 18.2 (C-6$_A$, 6$_B$, 6$_C$, NHAc, C(CH$_3$)$_2$). FAB-MS for C$_{111}$H$_{131}$N$_5$O$_{29}$ (M, 1999.2) m/z 2021.8 [M+Na]$^+$. Anal. Calcd. for C$_{111}$H$_{131}$N$_5$O$_{29}$: C, 66.68; H, 6.60; N, 3.50. Found: C, 66.63; H, 6.78; N, 3.32.

(2-O-Acetyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-2-O-benzoyl-α-L-rhamnopyranosyl trichloroacetimidate (606). 1,5-Cyclooctadiene-bis(methyldiphenylphosphine)iridium hexafluorophosphate (80 mg, 93 μmol) was dissolved THF (10 mL), and the resulting red solution was degassed in an argon stream. Hydrogen was then bubbled through the solution, causing the colour to change to yellow. The solution was then degassed again in an argon stream. A solution of 609 (2.55 g, 1.67 mmol) in THF (20 mL) was degassed and added. The mixture was stirred at rt overnight, then concentrated to dryness. The residue was dissolved in acetone (15 mL), then water (3 mL), mercuric chloride (380 mg) and mercuric oxide (320 mg) were added successively. The mixture protected from light was stirred at rt for 2 h, and acetone was evaporated. The resulting suspension was taken up in DCM, washed twice with 50% aq KI, water and said aq NaCl, dried and concentrated. The residue was eluted from a column of silica gel with 3:1 petroleum ether-EtOAc to give the corresponding hemiacetal. Trichloroacetonitrile (2.0 mL) and DBU (25 μL) were added to a solution of the residue in anhydrous DCM (15 mL) at 0° C. After 1 h, the mixture was concentrated. The residue was eluted from a column of silica gel with 3:1 petroleum ether-EtOAc and 0.2% Et$_3$N to give 606 as a white foam (1.5 g, 56%); [α]$_D$+22° (c 1, CHCl$_3$). $^1$H NMR: δ 8.72 (s, 1H, C=NH), 8.00-7.00 (m, 45H, Ph), 6.39 (d, 1H, $J_{1,2}$=2.5 Hz, H-1$_C$), 5.60 (dd, 1H, $J_{2,3}$=3.0 Hz, H-2$_C$), 5.58 (dd, 1H, $J_{1,2}$=1.7 Hz, $J_{2,3}$=3.0 Hz, H-2$_A$), 5.12 (d, 1H, $J_{1,2}$=3.2 Hz, H-1$_E$), 5.08 (m, 2H, H-1$_A$, 1$_B$), 5.00-4.00 (m, 16H, CH$_2$Ph), 4.20 (dd, 1H, H-3$_C$), 405 (dd, 1H, H-3$_E$), 4.00-3.35 (m, 14H, H-2$_E$, 4$_E$, 5$_E$, 6a$_E$, 6b$_E$, 4$_C$, 5$_C$, 2$_B$, 3$_B$, 4$_B$, 5$_B$, 3$_A$, 4$_A$, 5$_A$), 2.05 (s, 3H, OAc), 1.42, 1.36 and 1.00 (3d, 9H, H-6$_A$, 6$_B$, 6$_C$). $^{13}$C NMR: δ 170.3, 165.8 (2C, C=O), 138-127 (Ph), 99.9 (2C, C-1$_A$, 1$_B$), 98.5 (C-1$_E$), 94.7 (C-1$_C$), 82.1, 81.2, 80.4, 80.0, 79.1, 78.1, 78.0, 75.2, 71.7, 71.2, 70,7, 69.5, 69.4, 68.7 (16C, C-2$_A$, 3$_A$, 4$_A$, 5$_A$, 2$_B$, 3$_B$, 4$_B$, 5$_B$, 2$_C$, 3$_C$, 4$_C$, 5$_C$, 2$_E$, 3$_E$, 4$_E$, 5$_E$), 76.0, 75.7, 75.5, 75.1, 74.3, 73.3, 72.2, 71.2 (8C, PhCH$_2$), 68.5 (C-6$_E$), 21.4 (OAc), 19.2, 18.5, 18.1 (C-6$_A$, 6$_B$, 6$_C$). Anal. Calcd. for C$_{91}$H$_{96}$Cl$_3$NO$_{20}$: C, 67.05; H, 5.94; N, 0.86. Found: C, 66.44; H, 6.21; N, 0.93.

2-Azidoethyl (2-O-acetyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-4,6-O-isopropylidene-β-D-glucopyranoside (618). A mixture of alcohol 617 (110 mg, 55 μmol), trichloroacetimidate 606 (179 mg, 110 μmol) and 4 Å molecular sieves in anhydrous 1,2-DCE (2.5 mL) was stirred for 1 h under dry Ar. After cooling at −35° C., triflic acid (5 μL, 50 μmol) was added dropwise and the mixture was stirred for 2.5 h, while allowed to reach 10° C. Et$_3$N (25 μL) was added, and the mixture was filtered and concentrated. The residue was eluted from a column of silica gel with 4:1 to 3:1 toluene-EtOAc and Et$_3$N (0.2%) to give 618 as a white foam (158 mg, 82%); [α]$_D$+18° (c 1, CHCl$_3$). $^1$H NMR: δ 8.00-6.90 (90H, m, Ph), 5.90 (d, 1H, J$_{2,NH}$=7.0 Hz, NH$_D$), 5.58 (d, 1H, J$_{2,NH}$=7.5 Hz, NH$_{D'}$), 5.45, 5.22 (m, 2H, J$_{1,2}$=1.0, J$_{2,3}$=2.0 Hz, H-2$_C$, 2$_{C'}$), 5.12 (dd, 1H, H-2$_{A'}$), 5.11 (d, 1H, J$_{1,2}$=8.3 Hz, H-1$_D$), 5.05 (d, 1H, J$_{1,2}$=1.0 Hz, H-1$_A$), 5.01 (d, 1H, J$_{1,2}$=3.2 Hz, H-1$_E$), 4.96 (d, 1H, J$_{1,2}$=1.0 Hz, H-1$_C$), 4.94 (m, 2H, H-1$_{E'}$, 1$_B$), 4.86 (d, 1H, H-1$_{B'}$), 4.82 (d, 1H, H-1$_{C'}$), 4.72 (d, 1H, H-1$_{D'}$), 4.70 (d, 1H, H-1$_{A'}$), 4.90-4.20 (m, 36H, 16 OCH$_2$Ph, H-2$_B$, 2$_{B'}$, 3$_D$, 3$_{D'}$), 4.00-2.90 (m, 45H, H-2$_A$, 4$_D$, 5$_D$, 6a$_D$, 6b$_D$, 3$_C$, 4$_C$, 5$_C$, 2$_E$, 3$_E$, 4$_E$, 5$_E$, 6a$_E$, 6b$_E$, 3$_B$, 4$_B$, 5$_B$, 2$_A$, 3$_A$, 4$_A$, 5$_A$, 2$_{D'}$, 4$_{D'}$, 5$_{D'}$, 6a$_{D'}$, 6b$_{D'}$, 3$_{C'}$, 4$_{C'}$, 5$_{C'}$, 2$_{E'}$, 3$_{E'}$, 4$_{E'}$, 5$_{E'}$, 6a$_{E'}$, 6b$_{E'}$, 3$_{B'}$, 4$_{B'}$, 5$_{B'}$, 3$_{A'}$, 4$_{A'}$, 5$_{A'}$, OCH$_2$CH$_2$N$_3$)( 2.00 (s, 3H, NHAc), 1.88 (s, 3H, OAc), 1.86 (s, 3H, NHAc), 1.40-0.82 (m, 30H, H-6$_A$, 6$_B$, 6$_C$, 6$_{A'}$ 6$_{B'}$, 6$_{C'}$, C(CH$_3$)$_2$). $^{13}$C NMR partial: δ 172.1, 171.4, 170.2, 166.2, 165.9 (5C, C=O), 102.7 (C-1$_{D'}$), 101.6, 101.2 (2C, C-1$_B$, 1$_{B'}$), 101.1 (C-1$_A$), 99.8 (C-1$_D$), 99.7 (C-1$_C$), 98.2 (2C, C-1$_E$, 1$_{A'}$), 97.2 (2C, C-1$_{C'}$, 1$_{E'}$), 63.3, 62.6 (2C, C-6$_E$, 6$_{E'}$), 60.0, 57.8 (2C, C-2$_D$, 2$_{D'}$), 51.0 (CH$_2$N$_3$), 29.5, 29.4 (2C, C(CH$_3$)$_2$), 24.0 (2C, NHAc), 21.3 (OAc), 19.6, 19.5 (2C, C(CH$_3$)$_2$), 19.1, 18.9, 18.8, 18.5, 18.2, 18.1 (6C, C-6$_A$, 6$_B$, 6$_C$, 6$_{A'}$, 6$_{B'}$, 6$_{C'}$). FAB-MS of C$_{200}$H$_{225}$N$_5$O$_{48}$ (M, 3446.9), m/z 3489.5 ([M+Na]$^+$).

2-Azidoethyl (2-O-acetyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido--2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-β-D-glucopyranoside (619).

To a solution of 618 (630 mg, 181 μmol) in DCM (12 mL) was added dropwise, at 0° C., a solution of TFA (2 mL) and water (2 mL). The mixture was stirred for 3 h at this temperature, then concentrated by coevaporation first with water, then with toluene. The residue was eluted from a column of silica gel with 1:1 toluene-EtOAc to give 619 as a white foam (460 mg, 75%); [α]$_D$+9° (c 1, CHCl$_3$). FAB-MS of C$_{194}$H$_{217}$N$_5$O$_{48}$ (M, 3386.8), m/z 3409.2 ([M+Na]$^+$). Anal. Calcd for C$_{194}$H$_{217}$N$_5$O$_{48}$·H$_2$O: C, 68.43; H, 6.45; N, 2.06. Found: C, 68.40; H, 7.02; N, 1.61.

2-Aminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (603). A mixture of 619 (130 mg, 38 μmol) in MeOH (4 mL) was treated by MeONa until pH 9. The mixture was stirred for 1 h at rt, then heated at 55° C. overnight. After cooling to rt, IR 120 (H$^+$) was added until neutral pH, and the solution was filtered and concentrated. The residue was eluted from a column of silica gel with 25:1 to 20:1 DCM-MeOH to give an amorphous residue. A solution of this residue in EtOH (1.5 mL), EtOAc (150 μL), 1M HCl (66 μL, 2 eq) was hydrogenated in the presence of Pd/C (100 mg) for 72 h at rt. The mixture was filtered and concentrated into a residue which was eluted from a column of C-18 with water, liophilized to afford amorphous 603 as a white foam (41 mg, 71%), [α]$_D$−7° (c 1, water). $^1$H NMR (D$_2$O) partial: δ 4.90 (m, 2H, J$_{1,2}$=3.5 Hz, H-1$_E$, 1$_{E'}$), 4.82, 4.76, 4.72, 4.67, 4.52, 4.51 (6 bs, 6H, H-1$_A$, 1$_B$, 1$_C$, 1$_{A'}$, 1$_{B'}$, 1$_{C'}$), 4.41 (d, 1H, J$_{1,2}$=8.6 Hz, H-1$_D$*), 4.29 (d, 1H, J$_{1,2}$=8.6 Hz, H-1$_{D'}$*), 1.77 (s, 6H, NHAc), 1.15-0.96 (m, 18H, H-6$_A$, 6$_B$, 6$_C$, 6$_{A'}$, 6$_{B'}$, 6$_{C'}$); $^{13}$C NMR partial (D$_2$O): δ 174.8, 174.7 (2C, C=O), 102.6 (C-1$_D$*), 102.9, 101.8, 101.6, 101.4, 101.3 (6C, C-1$_A$, 1$_B$, 1$_C$, 1$_{A'}$, 1$_{B'}$, 1$_{C'}$), 100.8 (C-1$_{D'}$*), 97.9 (2C, C-1$_E$, 1$_{E'}$), 56.0. 56.4 (2C, 2 C-6$_D$, 6$_{D'}$), 22.7, 22.6 (2C, NHAc), 18.2, 17.2, 17.0, 16.9 (6C, C-6$_A$, 6$_B$, 6$_C$, 6$_{A'}$, 6$_{B'}$, 6$_{C'}$) HRMS: calculated for C$_{66}$H$_{113}$N$_5$O$_{45}$+Na: 1690.6544. Found 1690.6537.

2-Azidoethyl (2-acetamido-3-O-acetyl-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamide-2-deoxy-4,6-O-isopropylidene-β-D-glucopyranoside (621). A mixture of donor 607 (835 mg, 0 44 mmol) and acceptor 617 (590 mg, 0.3 mmol), 4 Å molecular sieves and dry 1,2-DCE (12 mL), was stirred for 1 h, then cooled to −30° C. Triflic acid (35 μL) was added. The stirred mixture was allowed to reach 5° C. in 2.5 h. Et$_3$N (150 μL) was added, and the mixture was filtered. After evaporation, the residue was eluted from a column of silica gel with 1:2 Cyclohexane-EtOAc and 0.2% Et$_3$N to give 621 as a white foam (990 mg, 90%); [α]$_D$+10° (c 1, CHCl$_3$). $^1$H NMR (CDCl$_3$) partial: δ 6.95-7.90 (m, 90H, Ph), 5.98 (d, 1H, J$_{2,NH}$=6.9 Hz, NH$_D$), 5.60 (d, 1H, J$_{2,NH}$=7.5 Hz, NH$_{D'}$), 5.45 (d, 1H, J$_{2,NH}$=8.5 Hz, NH$_{D''}$), 5.22 (dd, 1H, J$_{1,2}$=1.0, J$_{2,3}$=3.0 Hz, H-2$_C$), 5.13 (dd, 1H, J$_{1,2}$=1.0, J$_{2,3}$=3.0 Hz, H-2$_{C'}$), 5.08 (d, 1H, J$_{1,2}$=8.3 Hz, H-1$_D$), 5.07 (bs, 1H, H-1$_A$), 5.04 (bs, 1H, H-1$_{A'}$), 4.97 (d, 1H, J$_{1,2}$=3.0 Hz, H-1$_E$), 4.94 (d, 1H, J$_{1,2}$=3.0 Hz, H-1$_{E'}$), 4.90 (bs, 1H, H-1$_B$), 4.86 (bs, 1H, H-1$_{B'}$), 4.82 (bs, 1H, H-1$_C$), 4.73 (d, 1H, H-1$_D$), 4.70 (bs, 1H, H-1$_{C'}$), 4.43 (d, 1H, H-1$_{D'}$), 4.20-4.80 (m, 16H, CH$_2$Ph), 2.00, 1.85, 1.58 (3s, 9H, NHAc), 1.95 (s, 3H, OAc), 1.37-0.85 (m, 36H, 3 C(CH$_3$)$_2$, H-6$_A$, 6$_B$, 6$_C$, 6$_{A'}$, 6$_{B'}$, 6$_{C'}$); $^{13}$C NMR partial: δ 171.7, 170.8, 169.8, 165.8, 165.4 (6C, C=O), 139.0-127.7 (Ph), 103.9 (C-1$_{D'}$), 102.8 (C-1$_D$), 101.5 (2C, C-1$_B$), 101.3 (C-1$_A$), 101.1 (C-1$_{A'}$), 100.0 (C-1$_D$), 99.5, 99.3 (3C, C(CH$_3$)$_2$), 98 3 (C-1$_{E'}$), 98.1 (2C, C-1$_C$, 1$_E$), 97.8 (C-1$_C$), 82.0, 81.7, 81.6, 81.4, 80.3, 80.2, 80.1, 79.5, 79.2, 78.9, 78.7, 78.4, 78.1, 77.9, 77.8, 77.6, 76.0, 75.8, 75.3, 75.2, 74.7, 74.4, 74.1, 74.0, 73.6, 73.5, 73.4, 73.3, 73.0, 72.7, 71.9, 71.4, 70.9, 70.8, 69.1, 69.0. 68.9, 68.7, 68.6, 68.5, 68.1, 67.8, 67.7, 67.5, 62.6, 62.3, 62.1, 60.8, 59.9, 57.9, 55.0 (3C, C-$2_D$, $2_{D'}$, $2_{D''}$), 51.1 ($CH_2N_3$), 29.5, 29.4, 29.3 (3C, $C(CH_3)_2$), 24.0, 23.9, 23.5 (3C, NHAc), 21.3 (OAc), 19.7, 19.6, 19.2 (3C, $C(CH_3)_2$), 18.9, 18.8, 18.6, 18.5, 18.2, 18.1 (6C, C-$6_A$, $6_B$, $6_C$, $6_{A'}$, $6_{B'}$, $6_{C'}$). FAB-MS for $C_{211}H_{242}N_6O_{53}$ (M, 3710.2) m/z 3733.3 $[M+Na]^+$. Anal. Calcd. for $C_{211}H_{242}N_6O_{53}$: C, 68.31; H, 6.57; N, 2.27. Found: C, 68.17; H, 6.74; N, 2.12.

2- Azidoethyl (2-acetamido-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-4,6-O-isopropylidene-β-D-glucopyranoside (622). The undecasaccharide 621 (990 mg, 0.27 mmol) was dissolved in MeOH (30 mL). MeONa was added until pH 9. The mixture was stirred for 3 h, then treated by IR 120 ($H^+$) until neutral pH. The solution was filtered, and concentrated. The residue was eluted from a column of silica gel with 1:1 toluene-EtOAc and 0.2% of $Et_3N$ to give 622 as a white foam (900 mg, 91%); $[\alpha]_D+15°$ (c 1, $CHCl_3$); $^1H$ NMR partial δ 6.95-8.00 (m, 90H, Ph), 6.19 (bs, 1H, $NH_D*$), 5.96 (d, 1H, $J_{2,NH}$=6.8 Hz, $NH_{D'}*$), 5.57 (d, 1H, $J_{2,NH}$=6.8 Hz, $NH_{D''}*$), 5.22 (dd, 1H, H-$2_C*$), 5.13 (dd, 1H, H-$2_{C'}*$), 5.10 (d, 1H, H-$1_D$), 5.07 (bs, 1H, H-$1_A*$), 5.04 (bs, 1H, H-$1_{A'}*$), 4.96 (d, 1H, H-$1_E*$), 4.94 (d, 1H, H-$1_{E'}*$), 4.85 (bs, 1H, H-$1_B*$), 4.84 (bs, 1H, H-$1_{B'}*$), 4.82 (bs, 1H, H-$1_C*$), 4.70 (d, 1H, H-$1_{C'}*$), 4.67 (d, 1H, H-$1_D*$), 4.44 (d, 1H, H-$1_{D'}*$), 4.20-4.80 (m, 16H, $CH_2Ph$), 2.00, 1.85, 1.58 (3s, 9H, NHAc), 1.37-0.80 (m, 36H, $C(CH_3)_2$, H-$6_A$, $6_B$, $6_C$, $6_{A'}$, $6_{B'}$, $6_{C'}$). $^{13}C$ NMR partial: δ 172.8, 170.9, 170.3, 165.1, 164.7 (5C, C=O), 139.0-127.7 (Ph), 103.5, 103.1 (2C, C-$1_D$, $1_{D'}$), 101.5 (2C, C-$1_B$, $1_{B'}$), 101.2, 101.1 (2C, C-$1_A$, $1_{A'}$), 99.9 (C-$1_{D''}$), 99.0, 98.8. 98.7 (3C, $C(CH_3)_2$), 98.3 (C-$1_E*$), 98.1 (2C, C-$1_C*$, $1_{E'}*$), 97.8 (C-$1_{C'}*$), 82.1, 82.0, 81.9, 81.7, 81.6, 81.5, 80.6, 80.3, 80.2, 80.1, 79.7, 79.1, 78.9, 78.5, 77.9, 77.6, 75.7, 74.9, 74.6, 74.3, 73.3, 73.0, 72.7, 71.9, 71.8, 69.1, 68.9, 68.7, 68.5, 68.0, 67.8, 67.7, 67.6, 67.5, 62.6, 62.3, 61.9, 60.5, 59.9, 57.4, 55.0 (3C, C-$2_D$, $2_{D'}$, $2_{D''}$), 51.0 ($CH_2N_3$), 29.5, 29.3 (3C, $C(CH_3)_2$), 24.0, 23.9, 22.7 (3C, NHAc), 19.7, 19.6, 19.3 (3C, $C(CH_3)_2$), 19.0, 18.9, 18.6, 18.5, 18.2, 18.1 (6C, C-$6_A$, $6_B$, $6_C$, $6_{A'}$, $6_{B'}$, $6_{C'}$). FAD-MS for $C_{209}H_{240}N_6O_{52}$ (M, 3668.1) m/z 3690.8 $[M+Na]^+$. Anal. Calcd. for $C_{211}H_{242}N_6O_{53}$: C, 68.43; H, 6.59; N, 2.29. Found: C, 68.28; H, 6.72; N, 2.11.

2- Azidoethyl (2-O-acetyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido-2-deoxy-4,6-O-isopropylidene-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-4,6-O-isopropylidene-β-D-glucopyranoside (623). A mixture of donor 606 (377 mg, 0.230 mmol) and acceptor 622 (427 mg, 0.115 mmol), 4 Å molecular sieves and dry 1,2-DCE (10 mL), was stirred for 1 h then cooled to −30° C. Triflic acid (20 μL) was added. The stirred mixture was allowed to reach 5° C. in 2.5 h. $Et_3N$ (150 μL) was added, and the mixture filtered. After evaporation, the residue was eluted from a column of silica gel with 3:1 toluene-EtOAc and 0.2% $Et_3N$ to give 623 as a foam (490 mg, 82%); $[\alpha]_D+20°$ (c 1, $CHCl_3$); $^1H$ NMR partial: δ 6.90-8.00 (m, 135H, Ph), 5.95 (d, 1H, $J_{2,NH}$=6.6 Hz, $NH_D*$), 5.60 (d, 1H, $J_{2,NH}$=8.0 Hz, $NH_{D'}*$), 5.59 (d, 1H, $J_{2,NH}$=7.5 Hz, $NH_{D''}*$), 5.44 (dd, 1H, H-$2_C$), 5.22 (dd, 1H, H-$2_{C'}$), 5.10 (dd, 1H, H-$2_C$), 2.20 (s, 3H, OAc), 2.00, 1.85, 1.84 (3s, 9H, AcNH), 1.40-0.80 (m, 45H, 3 $C(CH_3)_2$, H-$6_A$, $6_B$, $6_C$, $6_{A'}$, $6_{B'}$, $6_{C'}$, $6_{A''}$, $6_{B''}$, $6_{C''}$); $^{13}C$ NMR partial: δ 173.2, 172.6, 172.5, 171.3, 167.4, 167.0, 166.9 (C=O), 140.2-126.8 (Ph), 102.8, 102.7, 101.5, 101.3, 101.1, 99.9, 99.8, 98.1, 97.8, 82.0, 81.7, 81.5, 81.4, 80.2, 80.1, 79.6, 79.4, 78.9, 78.6, 78.0, 77.9, 77.6, 75.5, 73.4, 73.3, 73.0, 72.8, 71.9, 71.6, 69.4, 69.1, 69.0, 68.6, 67.8, 67.7. 67.6, 67.5, 62.6, 62.3, 60.0, 57.9, 57.7, 51.0 ($CH_2N_3$), 30.5 (3C, $C(CH_3)_2$), 25.0, 22.4 (3C, NHAc), 22.9 (OAc), 20.7, 20.6, 20.2 (3C, $C(CH_3)_2$), 20.0, 19.9, 19.8, 19.7, 19.6, 19.3, 19.2, 19.1 (9C, C-$6_A$, $6_B$, $6_C$, $6_{A'}$, $6_{B'}$, $6_{C'}$, $6_{A''}$, $6_{B''}$, $6_{C''}$). FAB-MS for $C_{298}H_{334}N_6O_{71}$ (M, 5135.8) m/z 5159.3 $[M+Na]^+$. Anal. Calcd. for $C_{298}H_{334}N_6O_{71}$: C, 69.69; H, 6,55; N. 1.64. Found: C, 69.74; H, 6.72; N, 1.49.

2-Azidoethyl (2-O-acetyl-3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido-2-deoxy-β-D-glucopyranosyl)-(1→2)-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-(2-acetamido-2-deoxy-β-D-glucopyranosyl)-(1→2-(3,4-di-O-benzyl-α-L-rhamnopyranosyl)-(1→2)-(3,4-di-O-benzyl-α-L-rhamnopyranosyl)-(1→3)-[2,3,4,6-tetra-O-benzyl-α-D-glucopyranosyl-(1→4)]-(2-O-benzoyl-α-L-rhamnopyranosyl)-(1→3)-2-acetamido-2-deoxy-β-D-glucopyranoside (624). To a solution of the pentadecasaccharide 623 (480 mg, 93 μmol) in DCM (14 mL) was added dropwise at 0° C., a solution of 50% aq TFA (3.0 mL). The mixture was stirred for 3 h then concentrated by coevaporation first with water, then with toluene. The residue was eluted from a column of silica gel with 1:1 toluene-EtOAc to give 624 as a white foam (390 mg, 83%); $[\alpha]_D+12°$ (c 1, $CHCl_3$); FAB-MS for $C_{289}H_{322}N_6O_{71}$ (M, 5015.6) m/z 5037.2 $[M+Na]^+$.

2-Aminoethyl-α-L-rhamnopyranosyl-(1→2)-α-L-rhamnopyranosyl-(1→3)-[α-D-glucopyranosyl-(1→4)]-α-L-rhamnopyranosyl-(1=3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (604). A solution of the partially deprotected pentadecasaccharide 624 (390 mg, 77 μmol) in MeOH (10 mL) was treated by MeONa until pH 10. The mixture was stirred overnight at 55° C. After cooling at rt, IR 120 ($H^+$) was added until neutral pH. The solution was filtered, concentrated, and the residue was eluted from a column of silica gel with 20:1 DCM-MeOH to give the benzylated residue (252 mg). A solution of this residue in EtOH (3 mL), EtOAc (250 μL) and 1M HCl (106 μL) was hydrogenated in the presence of Pd/C (300 mg) for 48 h at rt. The mixture was filtered and concentrated, and the residue was eluted from a column of C-18 with water/CH$_3$CN, and freeze-dried to afford amorphous 604 (127 mg, 65%); [α]$_D$ −5° (c 1, water). $^1$H NMR (D$_2$O) partial: δ 5.13 (m, 3H, H-1$_E$, 1$_{E'}$, 1$_{E''}$), 5.07, 4.99, 4.95, 4.90, 4.75 (m, 9H, H-1$_A$, 1$_B$, 1$_C$, 1$_{A'}$, 1$_{B'}$, 1$_{C'}$, 1$_{A''}$, 1$_{B''}$, 1$_{C''}$), 4.63, 4.51 (2d, 3H, J$_{1,2}$=8.5 Hz, H-1$_D$, 1$_{D'}$, 1$_{D''}$), 2.00 (s, 9H, NHAc), 1.30-1.18 (m, 27H, H-6$_A$, 6$_B$, 6$_C$, 6$_{A'}$, 6$_{B'}$, 6$_{C'}$, 6$_{A''}$, 6$_{B''}$, 6$_{C''}$); $^{13}$C NMR (D$_2$O) partial: δ 174.8, 174.7 (3C, C=O), 102.9, 102.6, 101.7, 101.3, 100.8, 97.9, 81.8, 81.7, 79.6, 79.0, 76.3, 76.2, 73.0, 72.7, 72.4, 72.1, 71.6, 70.5, 70.1, 70.0, 69.7, 69.6, 69.4, 68.7, 68.6, 66.0, 61.0, 56.0, 55.4, 39.8, 22.7, 22.6 (NHAc), 18.2, 17.2, 17.0, 16.9 (9C, C-6$_A$, 6$_B$, 6$_C$, 6$_{A'}$, 6$_{B'}$, 6$_{C'}$, 6$_{A''}$, 6$_{B''}$, 6$_{C''}$). MALDI-MS for C$_{98}$H$_{166}$N$_4$O$_{67}$Na (M, 2493.96) m/z 2494.96.

(S-Acetylthiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (620). A solution of SAMA-Pfp (2.8 mg, 9.5 μmol) in CH$_3$CN (60 μL) was added to the aminoethyl decasaccharide 603 (6.4 mg, 3.84 μmol) in 0.1M phosphate buffer (pH 7.4, 500 μL). The mixture was stirred at rt for 1 h and purified by RP-HPLC to give 620 (4.2 mg, 61%). HPLC (230 nm): Rt 14.17 min (99.9% pure, Kromasil 5 μm C18 100 Å 4.6×250 mm analytical column, using a 0-20% linear gradient over 20 min of CH$_3$CN in 0.01 M aq TFA at 1 mL/min flow rate). ES-MS for C$_{70}$H$_{117}$N$_3$O$_{47}$S (M, 1784.76) m/z 1784.70.

(S-Acetylthiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (625). A solution of SAMA-Pfp (2.8 mg, 9.6 μmol) in CH$_3$CN (50 μL) was added to the pentadecasaccharide 604 (9.4 mg, 3.8 μmol) in 0.1M phosphate buffer (pH 7.4, 500 μL). The mixture was stirred at rt for 2 h and purified by RP-HPLC to give 625 (6.3 mg, 63%). HPLC (230 nm): Rt 13.97 min (99.0% pure, Kromasil 5 μm C18 100 Å 4.6×250 mm analytical column, using a 0-20% linear gradient over 20 min of CH$_3$CN in 0.01M aq TFA at 1 mL/min flow rate). ES-MS for C$_{102}$H$_{170}$N$_4$O$_{69}$S (M, 2588.53) m/z 2588.67.

PADRE (thiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (601). Compound 620 (6.0 mg, 3.36 μmol) was dissolved in water (300 μL) and added to a solution of PADRE-Mal (7.1 mg, 4.0 μmol) in a mixture of water (630 μL), CH$_3$CN (120 μL) and 0.1M phosphate buffer (pH 5.6, 750 μL). 68 μL of a solution of hydroxylamine hydrochloride (139 mg/mL) in 0.1M phosphate buffer (pH 5.6) was added and the mixture was stirred for 2 h. RP-HPLC purification gave the pure target 601 (5.2 mg, 44%).

HPLC (230 nm): Rt 10.03 min (100% pure, Kromasil 5 μm C18 100 Å 4.6×250 mm analytical column, using a 20-50% linear gradient over 20 min of CH$_3$CN in 0.01M aq TFA at 1 mL/min flow rate). ES-MS Calcd for C$_{153}$H$_{254}$H$_{24}$O$_{65}$S (M, 3501.91) m/z 3501.15.

PADRE (thiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamoopyranosyl-(1→3)-[α-D-glucopyranosyl-(1→4)]-α-L-rhamnopyranosyl-(1→3)-2-acetamido-2-deoxy-β-D-glucopyranoside (602). Compound 625 (10.3 mg, 3.98 μmol) was dissolved in water (350 μL) and added to a solution of PADRE-Mal (9.0 mg, 5.0 μmol) in a mixture of water (740 μL), CH$_3$CN (140 μL) and 0.5M phosphate buffer (pH 5.6, 890 μL). 80 μL of a solution of hydroxylamine hydrochloride (139 mg/mL) in 0.5M phosphate buffer (pH 5.7) was added, and the mixture was stirred for 3 h. RP-HPLC purification gave the pure conjugate 602 (11.5 mg, 67%). HPLC (230 nm): Rt 9.07 min (100% pure, Kromasil 5 μm C18 100 Å 4.6×250 mm analytical column, using a 20-50% linear gradient over 20 min of CH$_3$CN in 0.01M aq TFA at 1 mL/min flow rate). ES-MS Calcd for C$_{185}$H$_{307}$N$_{25}$O$_{87}$S (M, 4305.69) m/z 4305.45.

G. Synthesis of Biotinylated Analogues Oligoligosaccharides Representative of Fragments of the O—SP of *Shigella flexneri* 2a (+)-Biotinyl-3,6-dioxaoctainediaminyl-(thiomethyl)carbonylaminoethyl α-D-glucopyranosyl-(1→4)-α-L-rhamnopyranosyl-(1→3)-2-acetamido-2-deoxy-β-D-glucopyranoside (708). Compound 701 (5.0 mg, 7.26 μmol) was dissolved in water (280 μL) and added to a solution of 707 (3.2 mg, 7.26 μmol) in 0.5 M phosphate buffer (pH 6.0, 400 μL). A 2 M solution of hydroxylamine in 0.5 M phosphate boiler (150 μL) was added and the mixture was stirred at rt for 1 h. More 707 (1.5 mg, 2.85 μmol) in 0.5 M phosphate buffer (300 μL) was added, and the mixture was stirred for 1 h 30 at rt. RP-HPLC purification gave the pure neoglycopeptide 708 (5.7 mg, 67%). ES-MS for C$_{47}$H$_{77}$N$_7$O$_{23}$S$_2$ (M, 1171.5) m/z 1171.45.

(+)-Biotinyl-3,6-dioxaoctainediaminyl-(thiomethyl)carbonylaminoethyl α-L-rhamnopyranosyl-(1→3)-[α-D-glucopyranosyl-(1→4)]-α-L-rhamnopyranosyl-(1→3)-2-acetamido-2-deoxy-β-D-glucopyranoside (709). Compound 702 (10.0 mg, 12.0 μmol) was dissolved in water (500 μL) and added to a solution of 707 (12.6 mg, 20.0 μmol) in 0.5 M phosphate buffer (pH 6, 220 μL). A 2 M solution of hydroxylamine in 0.5 M phosphate buffer (300 μL) was added and the mixture was stirred at rt for 2 h. Since HPLC control showed that some 702 remained, the pH of the mixture was adjusted to 5 by dropwise addition of diluted aq NH$_3$, and the mixture was stirred for 1 h more at rt. RP-HPLC purification gave the pure neoglycopeptide 709 (12.6 mg, 80%). ES-MS Calcd for C$_{109}$H$_{181}$N$_{23}$O$_{35}$S$_2$ (M, 2405.85) m/z 1317.51.

(+)-Biotinyl-3,6-dioxaoctainediaminyl-(thiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (710). Compound 703 (3.8 mg, 3.87 μmol) was dissolved in water (250 μL) and added to a solution of 707 (3 mg, 5.7 μmol) in 0.5 M phosphate buffer (pH 5.8, 250 μL). A 2 M solution of hydroxylamine in 0.5 M phosphate buffer (75 μL) was added and the mixture was stirred at rt for 1 h. RP-HPLC purification gave the pure neoglycopeptide 710 (4.6 mg, 81%). ES-MS Calcd for $C_{59}H_{97}N_7O_{31}S_2$ (M, 1464.6) m/z 1463.57.

(+)-Biotinyl-3,6-dioxaoctainediaminyl-(thiomethyl)carbonylaminoethyl 2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (711). Compound 704 (2.5 mg, 2.11 μmol) was dissolved in water (85 μL) and added to a solution of 707 (1.7 mg, 3.2 μmol) in 0.5 M phosphate buffer (pH 5.9, 215 μL). A 2 M solution of hydroxylamine in 0.5 M phosphate buffer (45 μL) was added and the mixture was stirred at rt for 2 h. RP-HPLC purification gave the pure neoglycopeptide 711 (2.5 mg, 71%). HPLC (230nm): Rt 17.03 min (100% pure, Kromasil 5 ηm C18 100 Å 4.6×250 mm analytical column, using a 0-30% linear gradient over 20 min of $CH_3CN$ in 0.01 M aq TFA at 1 mL/min flow rate). ES-MS for $C_{67}H_{110}N_8O_{36}S_2$ (M, 1667.78) m/z 1667.45.

(+)-Biotinyl-3,6-dioxaoctainediaminyl-(thiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (712). Compound 705 (4.0 mg, 2.24 μmol) was dissolved in water (85 μL) and added to a solution of 707 (1.8 mg, 3.3 μmol) in 0.5 M phosphate buffer (pH 5.9, 220 μL). A 2 M solution of hydroxylamine in 0.5 M phosphate buffer (45 μL) was added and the mixture was stirred at rt for 2 h. RP-HPLC purification gave the pure neoglycopeptide 712 (4.5 mg, 89%). HPLC (230 nm): Rt 16.69 min (100% pure, Kromasil 5 μm C18 100 Å 4.6×250 mm analytical column, using a 0-30% linear gradient over 20 min of $CH_3CN$ in 0.01 M aq TFA at 1 mL/min flow rate). ES-MS for $C_{91}H_{115}N_8O_{53}S_2$ (M, 2268.35) m/z 2267.72.

(+)-Biotinyl-3,6-dioxaoctainediaminyl-(thiomethyl)carbonylaminoethyl α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L--rhamnopyranosyl-(1→2)-L-rhamnopyranosyl-(1→3)-[α-D-glucopyranosyl-(1→4)]-α-L-rhamnopyranosyl-(1→3)-2-acetamido-2-deoxy-β-D-glucopyranosyl-(1→2)-α-L-rhamnopyranosyl-(1→2)-α-L-rhamnopyranosyl-(1→3)-[α-D-glucopyranosyl-(1→4)]-α-L-rhamnopyranosyl-(1→3)-2-acetamido-2-deoxy-β-D-glucopyranoside (713). Compound 706 (5.7 mg, 2.21 μmol) was dissolved in water (85 μL) and added to a solution of 707 (1.7 mg, 3.2 μmol) in 0.5 M phosphate buffer (pH 5.9, 220 μL). A 2 M solution of hydroxylamine in 0.5 M phosphate buffer (45 μL) was added and the mixture was stirred at rt for 2 h. RP-HPLC purification gave the pure neoglycopeptide 713 (4.8 mg, 71%). HPLC (230 nm): Rt 16.35 min (100% pure, Kromasil 5 μm C18 100 Å 4.6×250 mm analytical column, using a 0-30% linear gradient over 20 min of $CH_3CN$ in 0.01 M aq TFA at 1 mL/min flow rate). ES-MS for $C_{123}H_{203}N_9O_{75}S_2$ (M, 3072.13) m/z 3072.17.

Figure 29:
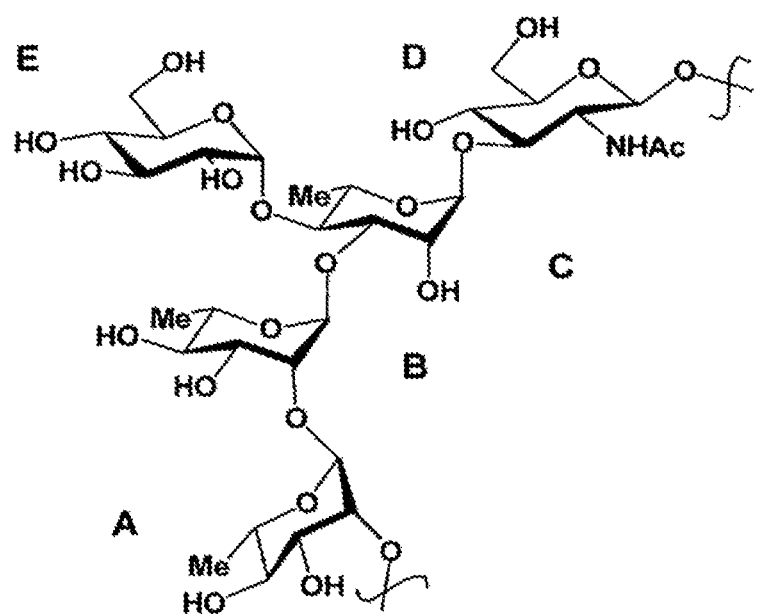

II—The Serum Immunoglobulin G-mediated Response to Serotype-specific Determinants of *Shigella flexneri* Lipopolysaccharide Protects Against Experimental Shigellosis Both intestinal secretory IgA (SIgA) and serum IgG specific for the O-antigen (O—SP, FIG. 29), the polysaccharide part of the bacterial lipopolysaccharide (LPS) are elicited upon *Shigella* infection, the causative agent of bacillary dysentery. However, the respective protective roles of local and systemic humoral immunity remain unclear The ineffectiveness of parenterally injected inactivated whole-cell vaccines in inducing protection, despite the high level of anti-LPS serum IgG antibodies raised, has led to the belief that serum antibodies do not confer protection (Formal et al., ProC; Soc. Exp. Biol. Med., 1967, 125, 347-; Higgins et al., Am. J. Trop. Med., 1955, 4, 281-288). However, several indirect pieces of evidence suggest that anti-O—SP serum IgG may confer protection during natural infection. A correlation was found between the level of anti-LPS IgG antibodies and resistance to shigellosis among Israeli soldiers (Cohen et al., J. Inf. Dis., 1988, 157, 1068; Cohe, et al., J. Clin. Microbial., 1991, 29,386), and an inverse relationship exists between the age of incidence of shigellosis and the presence of IgG antibodies to *Shigella* LPS (Passwell et al., Pediatr. Infect. Dis., 1995, 14, 859-; Van de Verg et al., J. Infect. Dis., 1992, 166, 158-161). In addition, a detoxified LPS-based conjugate vaccine administered parenterally and eliciting mainly, if not only, serum antibodies has been shown to induce protective immunity (Cohen et al., lancet, 1997, 349, 155-).

In the current study, using the mouse model of pulmonary infection and specific polyclonal serum or monoclonal IgG, the protective role of serum IgG recognizing serotype-specific LPS determinants or peptide epitopes on the invasins IpaB and IpaC was addressed.

A) Materials and Methods

1) Bacterial Strains

M90T, an invasive isolate of *S. flexneri* serotype 5a, and 454, an invasive isolate of *S. flexneri* serotype 2a, were the virulent strains of reference, For i.n. infection, bacteria were routinely grown on Luria Bertoni agar plates at 37° C. They were recovered from plates and bacterial dilutions were performed in 0.9% NaCl with the consideration that, for an optical density of 1 at 600 nm, the bacterial concentration was $5×10^8$ colony forming units (c.f.u)/ml. Killed bacteria for systemic immunizations were prepared from bacterial cultures at stationary phase, diluted to $5×10^8$ c.f.u./ml in 0.9% NaCl, and then incubated at 100° C. for 1 h. They were then kept at −20° C. in aliquots.

2) Production and Characterization of mAbs Specific for *S. flexneri* Serotype 2a and 5a LPS BALB/c mice were immunized intraperitoneally (i.p.) with $10^7$ c.f.u. of killed *S. flexneri* 5a or *S. flexneri* 2a bacteria three times at 3 week-intervals. Mice eliciting the highest anti-LPS antibody response were given an intravenous booster injection 3 days before being sacrificed for splenic B cell fusion according to Kohler and Milstein (Eur. J. Immunol., 1976, 6, 511-519). Hybridoma culture supernatants were screened for antibody production by ELISA using LPS purified from *S. flexneri* X, Y, 5a, 5b, 2a, 2b, 1a and 3a, respectively. The hybridoma cells secreting murine IgG (mIgG) reacting specifically with LPS homologous to the strain used for immunization, i. e. recognizing serotype-specific determinants on the LPS O—SP, were selected. A panel of mIgG representative of the four murine IgG subclasses was used for the study. Those selected were then cloned by limiting dilution, and injected i. p. into histocompatible mice for ascitis production. mIgG were precipitated with 50% ammonium sulfate from ascitis fluid, centrifuged, and dialysed against PBS before being purified using ion-exchange chromatography as previously described (Barzu et al., Infect. Immun., 1998, 65, 1599-1605; Phalipon et al., Infect. Immun., 1992, 60, 1919-1926). The avidity of anti-LPS mIgG for LPS was determined as follows: various concentrations of LPS were incubated in solution overnight at 4° C. with a defined amount of a given mIgG until equilibrium was reached. Each mixture was then transferred to a microtiter plate previously coated with homologous purified LPS. Bound antibodies were detected by using peroxidase-conjugated anti-mouse immunoglobulins specific for IgG subclasses. $IC_{50}$ was defined as the concentration of LPS required to inhibit 50% of mIgG binding to LPS.

3) ELISA

Hybridoma culture supernatants were tested by ELISA for the presence of anti-LPS antibodies as previously described (Barzu et al., Infect. Immun., 1993, 61, 3825-3831; Phalipon et al., Infect. Immun., 1992, 60, 1919-1926) except that LPS purified according to Westphal (Methods Carbohydr. Chem., 1965, 5, 83-91) was used at a concentration of 5 µg/ml in PBS. As secondary antibodies, anti-mouse IgG- or IgM- or IgA-alkaline phosphatase-labeled conjugate (SIGMA) were used at a dilution of 1:5,000. To measure the anti-LPS antibody titer in polyclonal serum, biotin-labeled Abs to IgG and its different subclasses (IgG1,-2a, -2b, -3) (PHARMINGEN) and avidin conjugated with alkaline phosphatase (SIGMA) were used at a dilution of 1:5,000. Antibody titers were defined as the last dilution of the sample giving an OD at least twice that of the control.

4) Active and Passive Immunization of Mice

To obtain polyclonal serum, mice were immunized i.p. with $5\times10^7$ killed bacteria, three times at 3 week-intervals. After bleeding, anti-LPS antibody titer in the polyclonal sera was measured by ELISA, as described above, and those ranging from low (1/4,000) to high titer (1/64,000) were used for i.n. passive transfer. Purified mAbs (20 or 2 µg) were also administered intranasally. All i.n. administrations were performed using a volume of 20 µl and mice previously anesthesized via the intramuscular route with 50 µl of a mixture of 12.5% ketamine (MERIAL) and 12.5% acepromazine (VETOQUINOL). Each experiment was performed using 10 mice per group and was repeated three times.

5) Protection Experiments

The protective capacity of the antibodies was analysed using the murine model of pulmonary infection previously described (Voino et al., Acta Morpho., 1961, XI, 440-; Phalipon et al., J. exp. Med., 1995, 182, 769-). Intranasal challenge was performed using either $10^9$ live virulent bacteria when protection was assessed by mortality assay or $10^8$ bacteria when protection was assessed by measurement of the lung-bacterial load. Naive mice were used as controls in each experiment. Mice immunized i.p. were challenged i.n. with virulent bacteria, 3 weeks after the last immunization. Mice passively transferred i.n. with polyclonal sera or with purified mAbs were challenged 1 h after administration of the mAbs. Measurement of lung-bacterial load was performed at 24 h post infection as follows. Mice were sacrificed by cervical dislocation and lungs were removed <<en bloc>> and ground in 10 ml sterile PBS (Ultra Turrax T25 apparatus, Janke and Kunkel IKA Labortechnik GmbH). Dilutions were then plated on Trypticase Soy Broth plates for c.f.u. enumeration. Each experiment was performed using 10 mice per group and was repeated three times.

5) Histopathological Studies

Mice were anesthesized, their trachea catheterized, and 4% formalin injected in order to fill the bronchoalveolar space. Lungs were then removed and fixed in 4% formalin before being processed for histopathological studies. Ten-micrometer paraffin sections were stained with Hematoxiline and Eosin (HE), and observed with a BX50 Olympus microscope (Olympus Optical, Europa, GmhH).

6) Statistical Analysis

Significant differences were compared using the Student's test. Probability values <0.05 were considered significant.

B) Results

1) Protection Conferred upon Systemic Immunization or Intranasal Administration of Specific Immune Serum.

In order to address the role of the systemic anti-LPS IgG antibody response in protection against the mucosal infection, the protection conferred against i.n. challenge with a lethal dose of *S. flexneri* 2a bacteria in mice immunized i.p. with the homologous killed bacteria was assessed. Antibodies induced upon such an immunization were mainly anti-LPS IgG antibodies with all the IgG subclasses similarly elicited (FIG. 30A). No mucosal response was elicited, as reflected by the absence of anti-LPS antibody response detectable in the bronchoalveolar lavage of immunized mice. Only 40% of the immunized mice survived the i.n. challenge; whereas 100% of naive mice succumbed. The low efficacy of systemic immunization in inducing protection could be due to either the inability of anti-LPS lgG to be protective or the absence of the protective antibodies (or their presence but in insufficient amount) in the mucosal compartment at the time of i.n. challenge.

Therefore, it was tested whether the anti-LPS IgG antibodies may confer protection if present locally prior to mucosal challenge. Polyclonal sera exhibiting different anti-LPS antibody titers were intranasally administered to naive mice 1 h prior to i.n. infection with a sublethal dose of *S. flexneri* 2a bacteria. Protection was assessed by the reduction of the lung-bacterial load in comparison to control mice and mice receiving preimmune serum. In contrast to control mice and mice receiving preimmune serum, naive mice receiving anti-LPS IgG serum showed a significant decrease of the lung-bacterial load. The reduction was dependent on the amount of anti-LPS IgG antibodies administered as reflected by the anti-LPS antibody titer of the immune serum used for passive transfer. Thus, the highest reduction was obtained with serum having the highest anti-LPS antibody titer (1/64,000) (FIG. 30B, c); $p=5\times10^{-6}$ in comparison to mice receiving preimmune serum). However, in mice receiving immune serum with lower anti-LPS antibody titer (1/16,000 and 1/4,000) (FIG. 30B, a and b), even if less efficient, the decrease of the bacterial load was still significant in comparison to mice receiving preimmune serum (p=0, 027 and 0, 015, respectively).

These results demonstrated that, if present locally at the time of mucosal challenge, the anti-LPS IgG antibodies were protective, thus limiting bacterial invasion.

2) Protective Capacity of Different Subclasses of mIgG Sspecific for *S. flexneri* 2a LPS Depending on the infecting strain, different subclasses of IgG specific for LPS are induced following natural *Shigella* infection (Islam et al., Infect. Immun., 1995, 63, 2045-2061). To test whether all subclasses exhibit similar protective capacity, murine mIgG specific for serotype deteuuinants on the O—SP and, representative of each of the four marine IgG subclasses were obtained. Upon screening of hybridomas for their reactivity with LPS from *S. flexneri* serotype X, Y, 5a, 5b, 2a, 2b, 1a, 3a, respectively, five mIgG specific for *S. flexneri* 2a LPS were selected: mIgG F22-4 (IgG1), mIgG D15-7 (IgG1), mIgG A2-1 (IgG2a), mIgG E4-1 (IgG2b) and mIgG C1-7 (IgG3). These hybridomas have been deposited on Apr. 20, 2004, at the "Collection National de Culture des Microorganismes" from INSTITUT PASTEUR, 25 rue du Docteur Roux, 75724 PARIS CEDEX 15, FRANCE, under the registration number I-3197, I-3198, I-3199, I-3200 and I-3201, for A2-1, C1-7, D15-7, E4-1 and F22-4, respectively.

Figure 1:
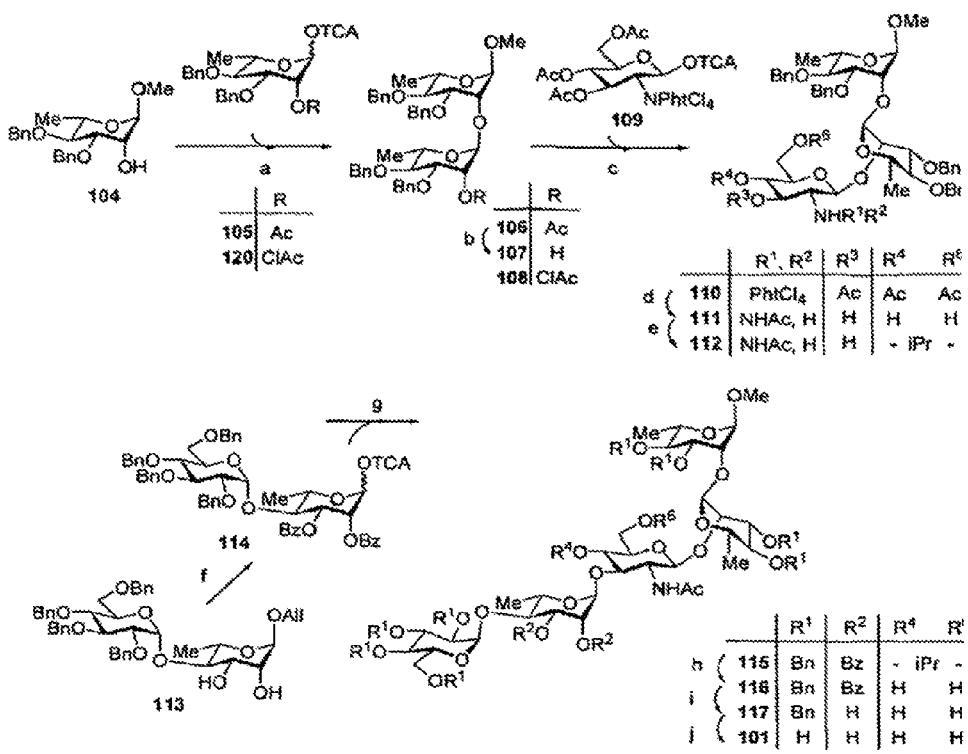
Figure 2:
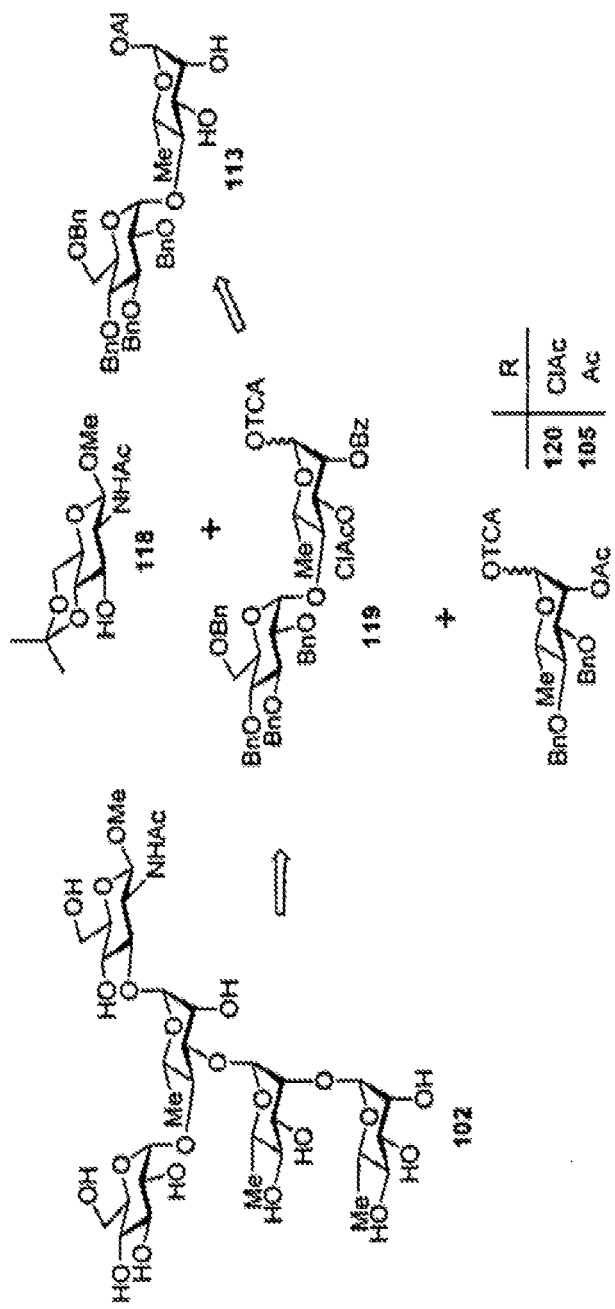
Figure 3:
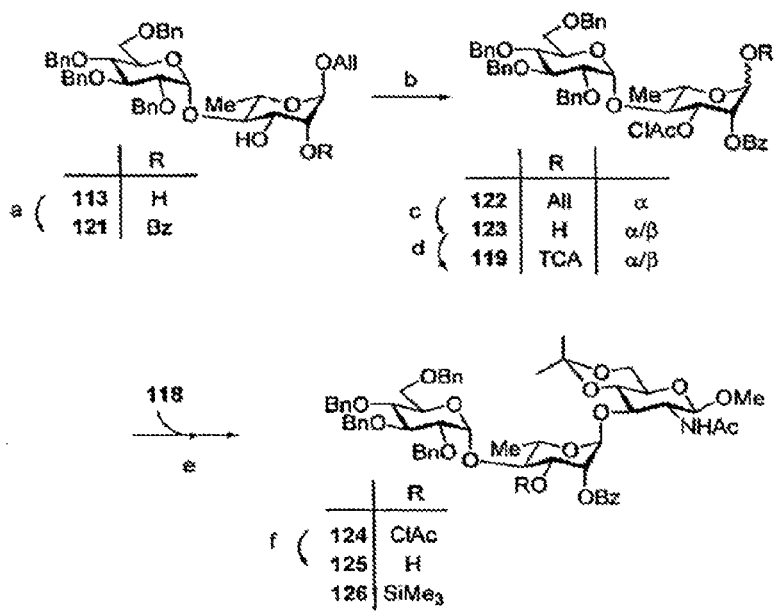
Figure 4:
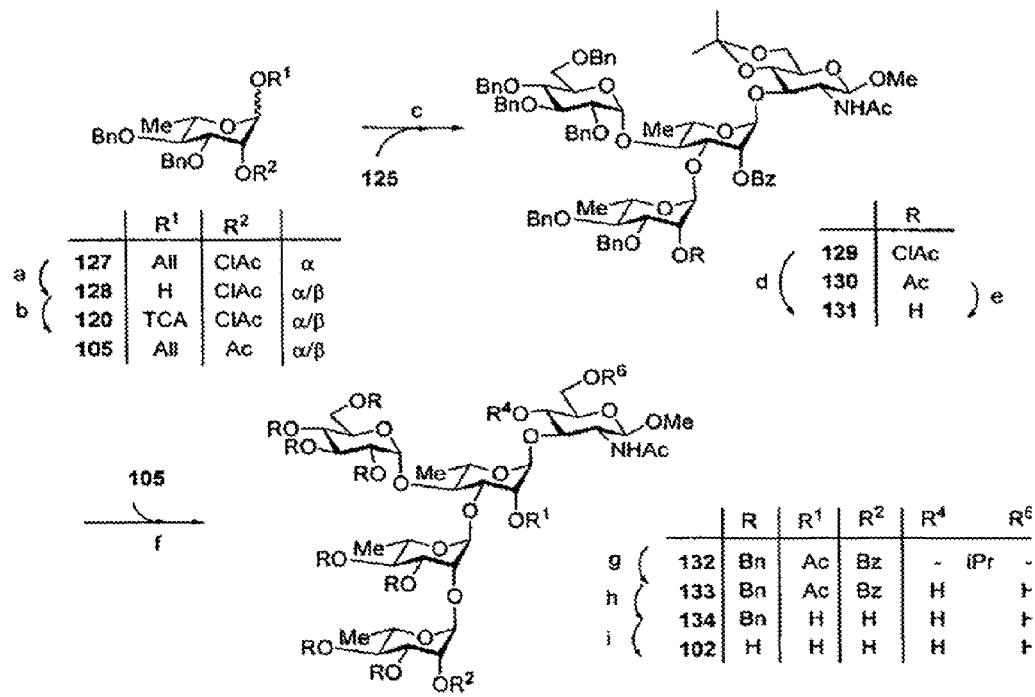
Figure 5:
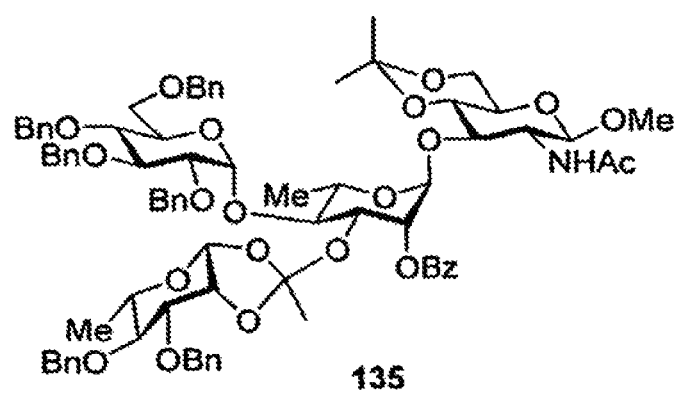
Figure 6:
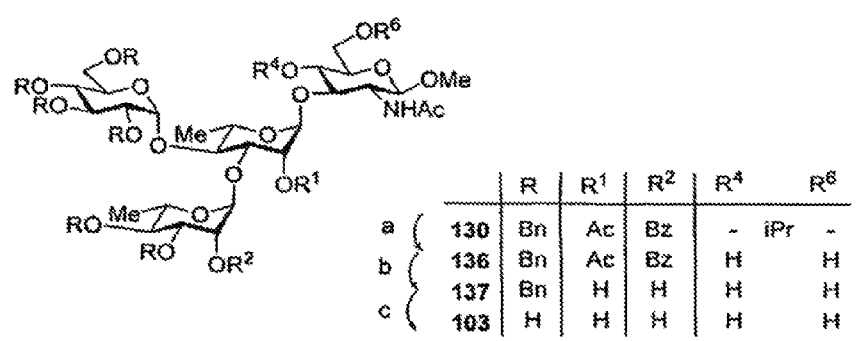
Figure 7:
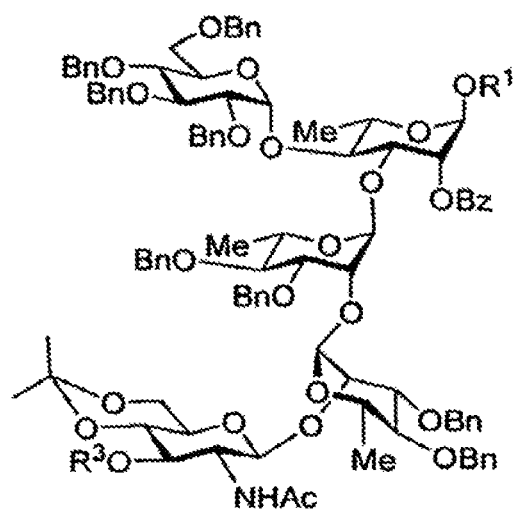
Figure 8:
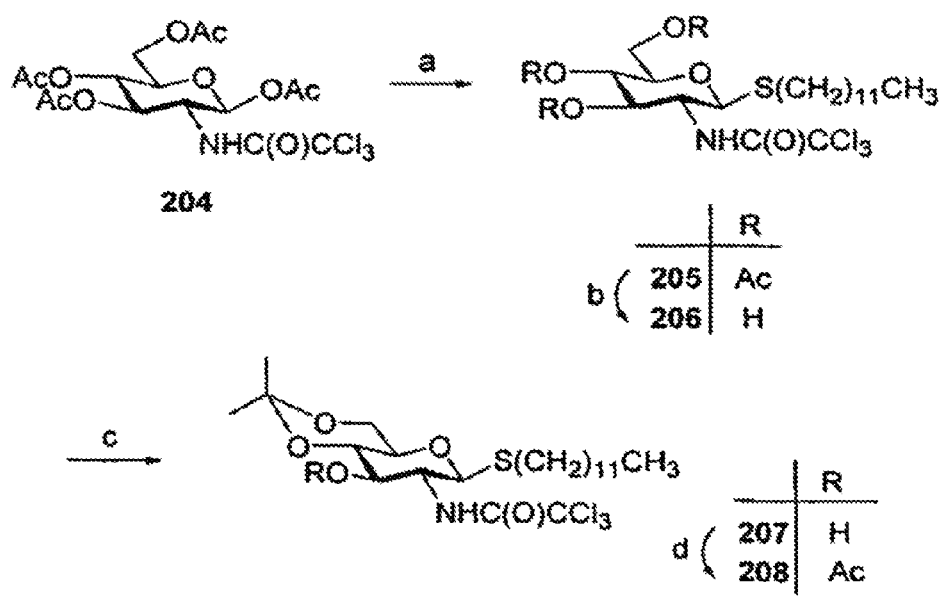
Figure 9:
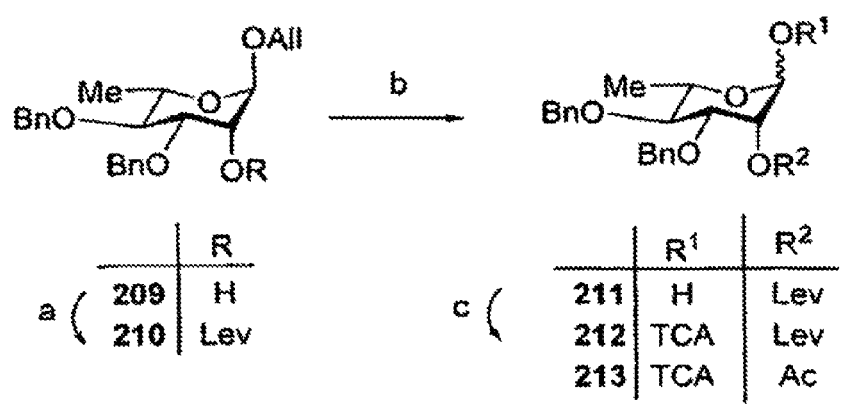
Figure 10:
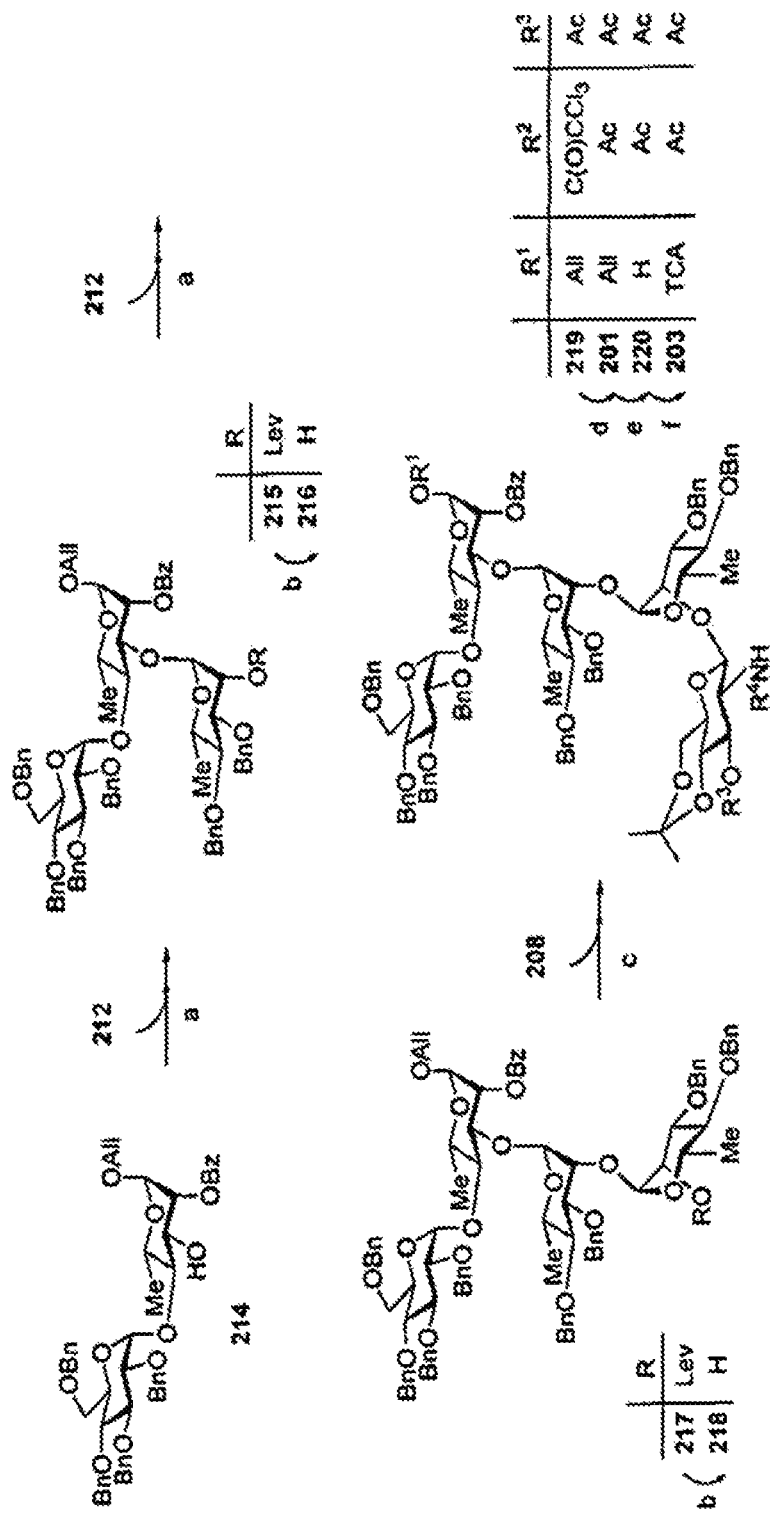
Figure 11:
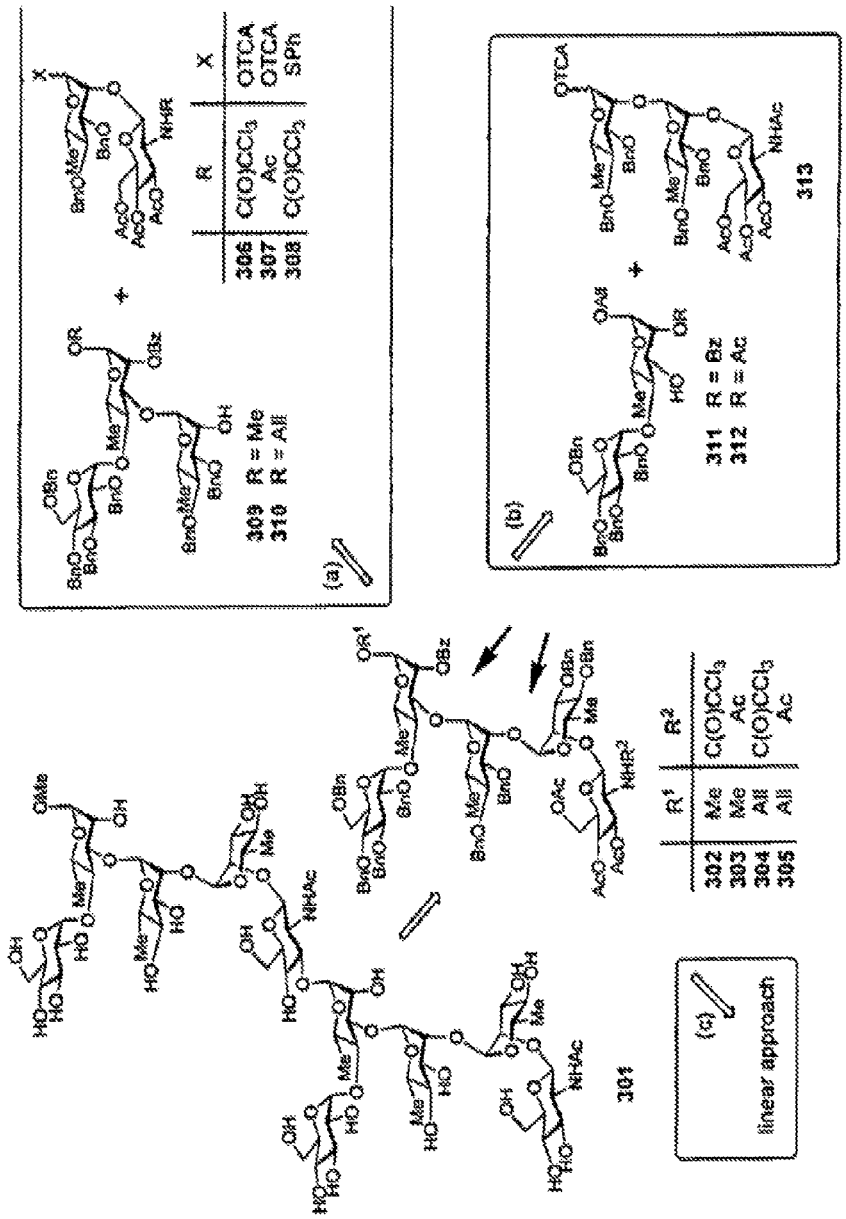
Figure 12:
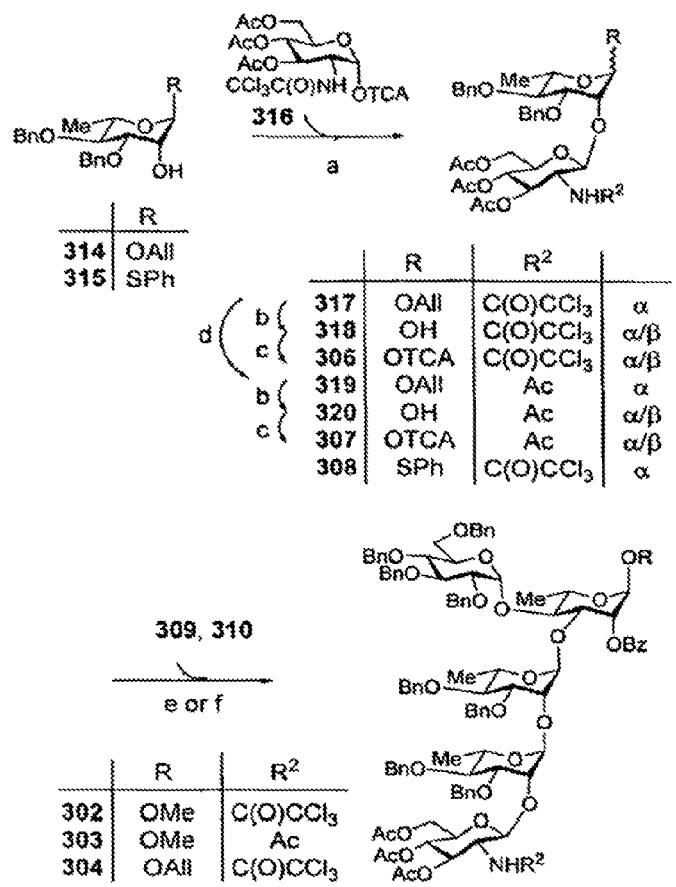
Figure 14:
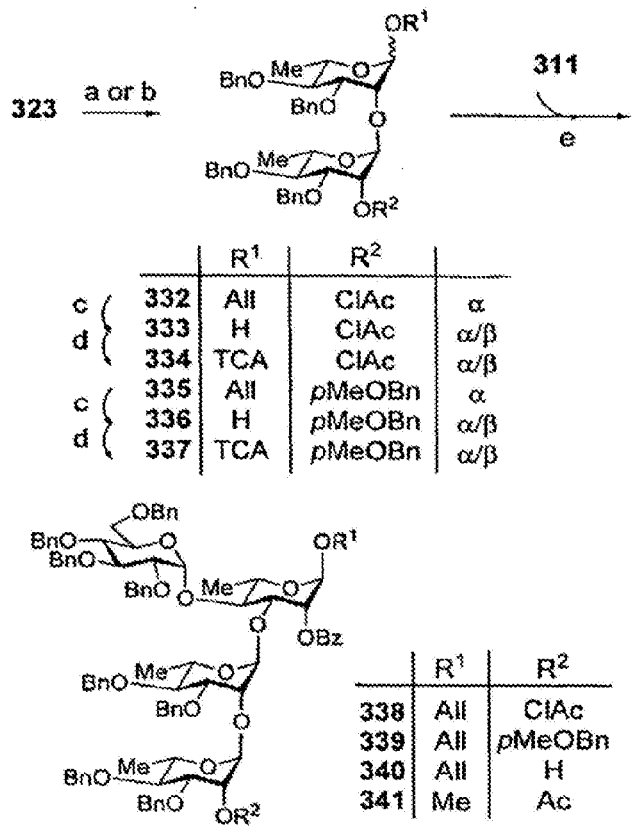
Figure 15:
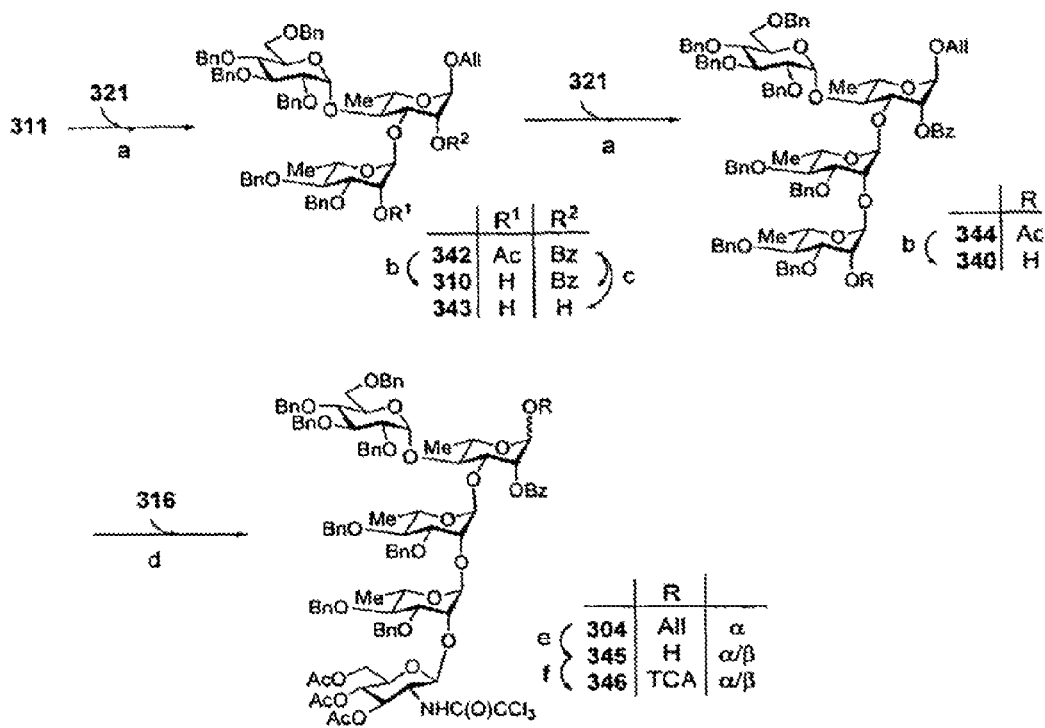
Figure 16:
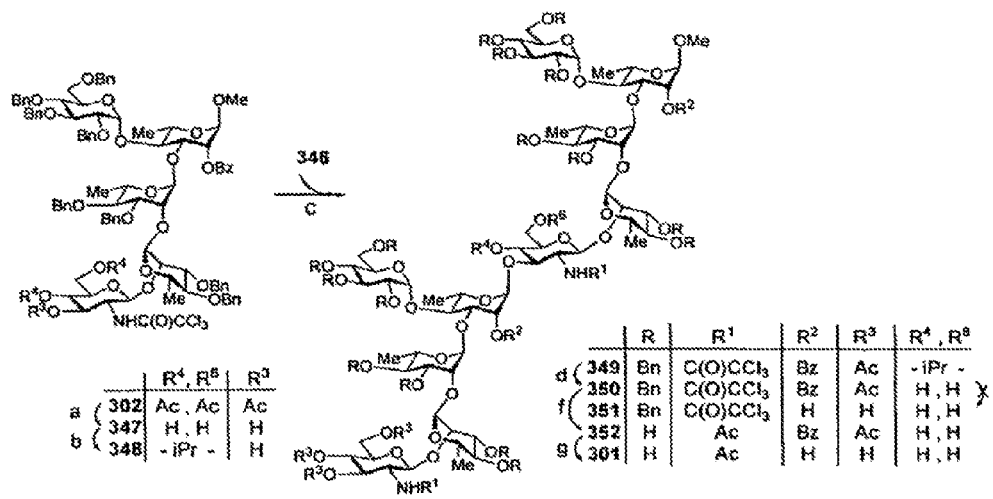
Figure 17:
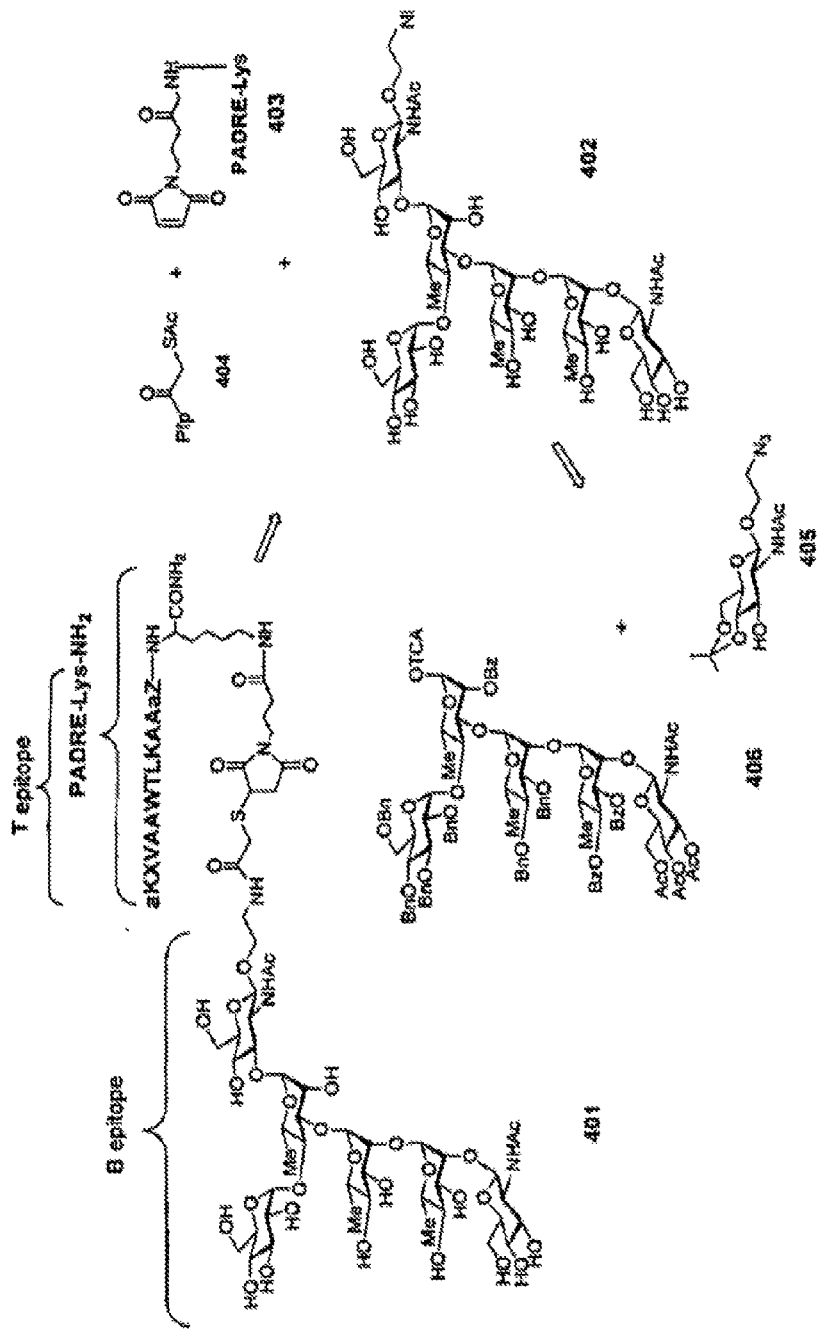
Figure 18:
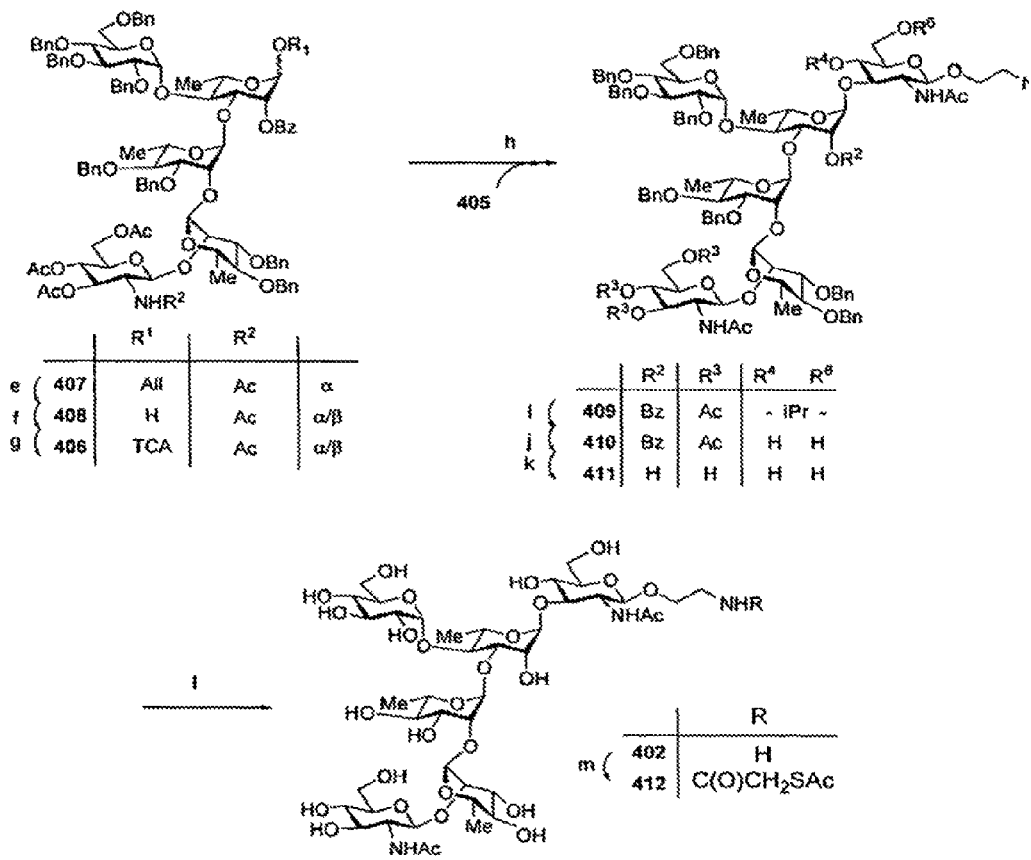
Figure 19:
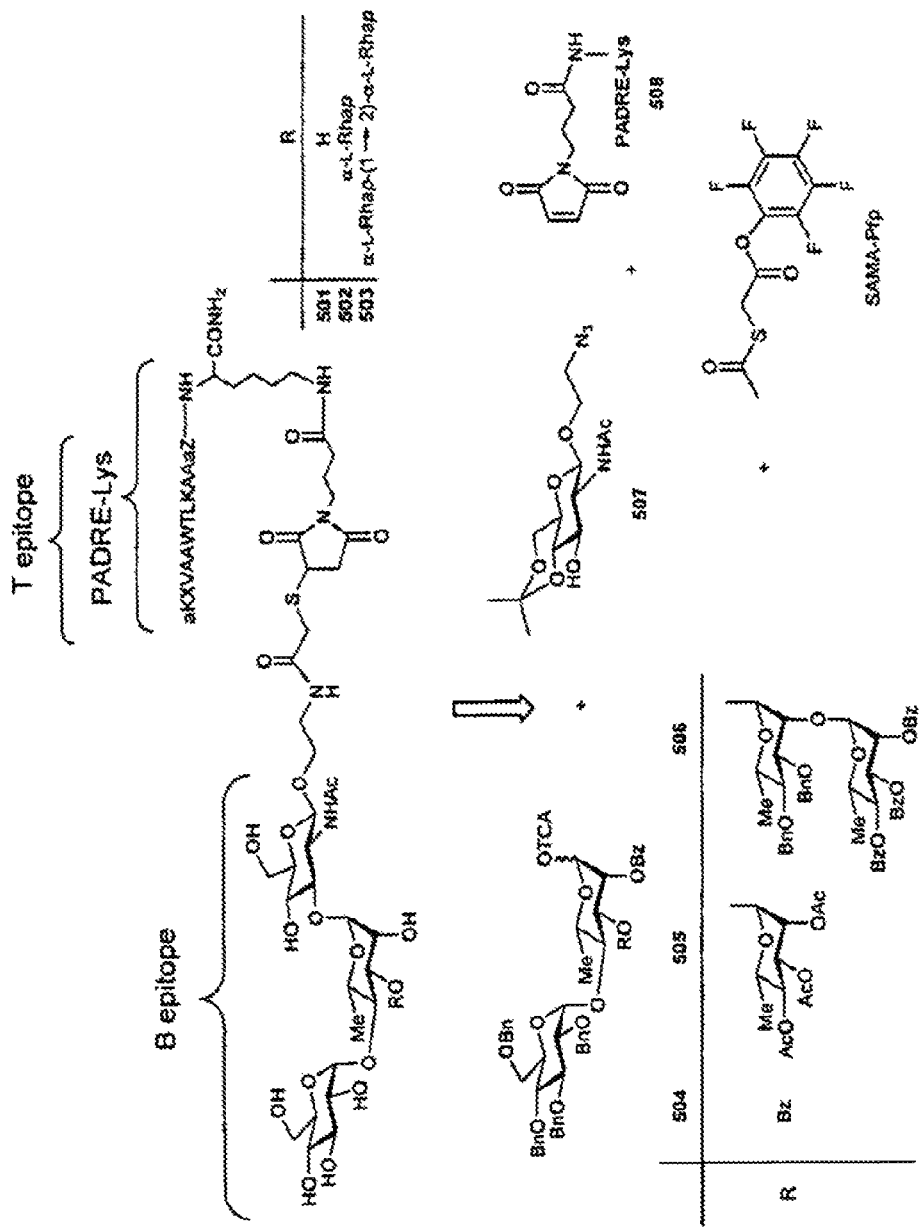
Figure 20:
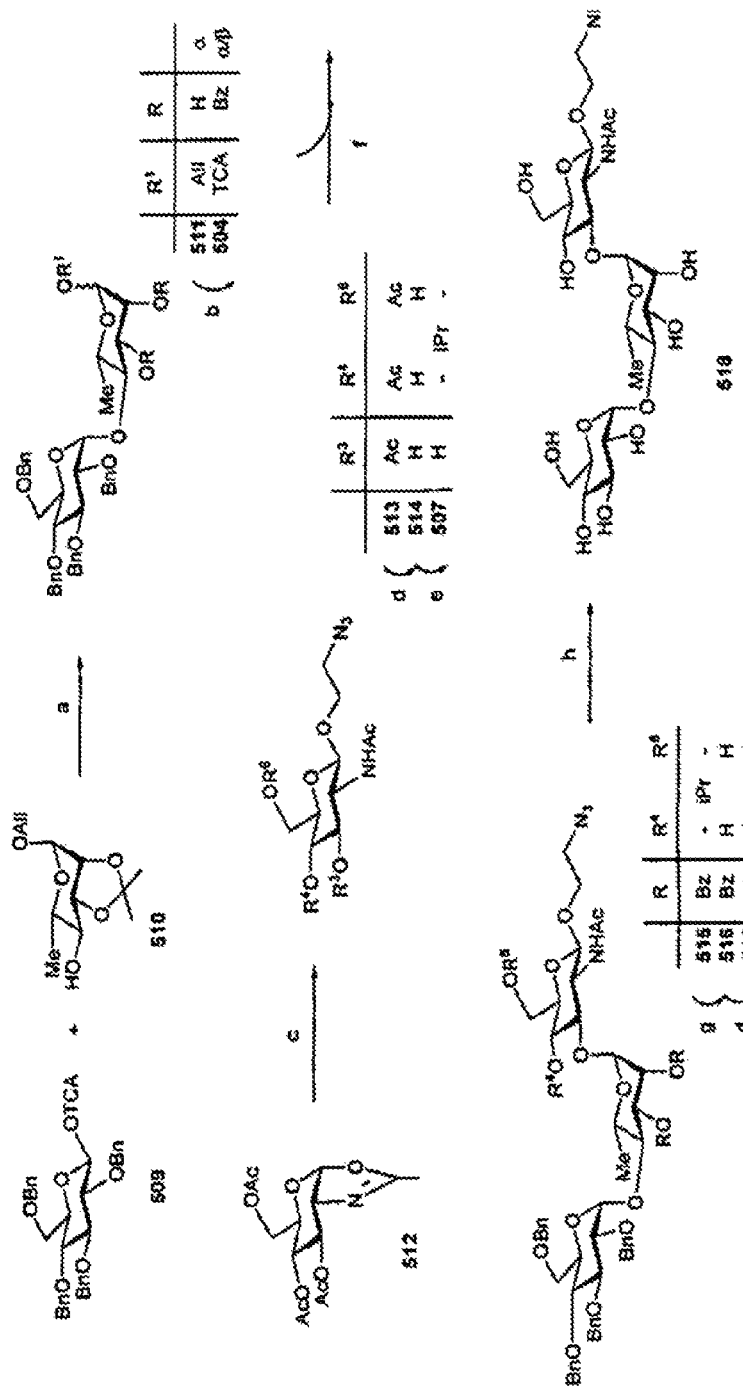
Figure 21:
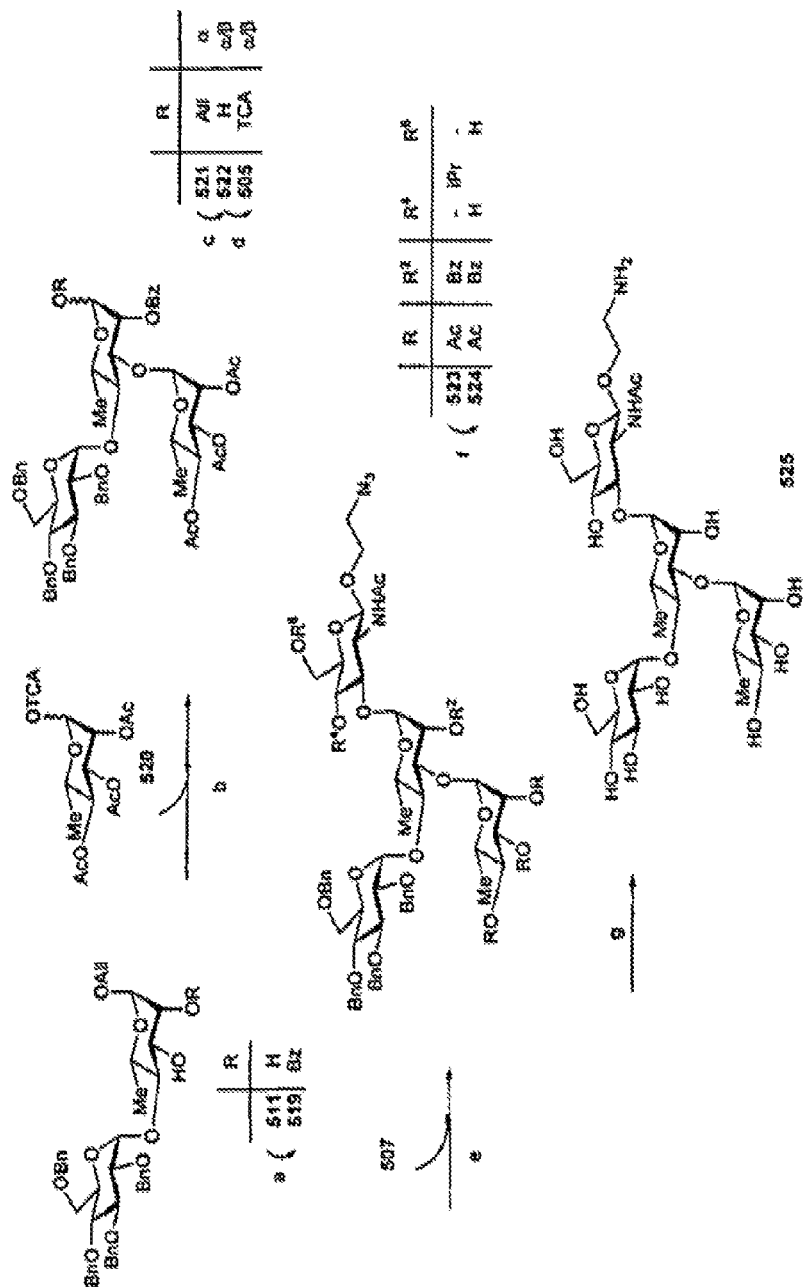
Figure 22:
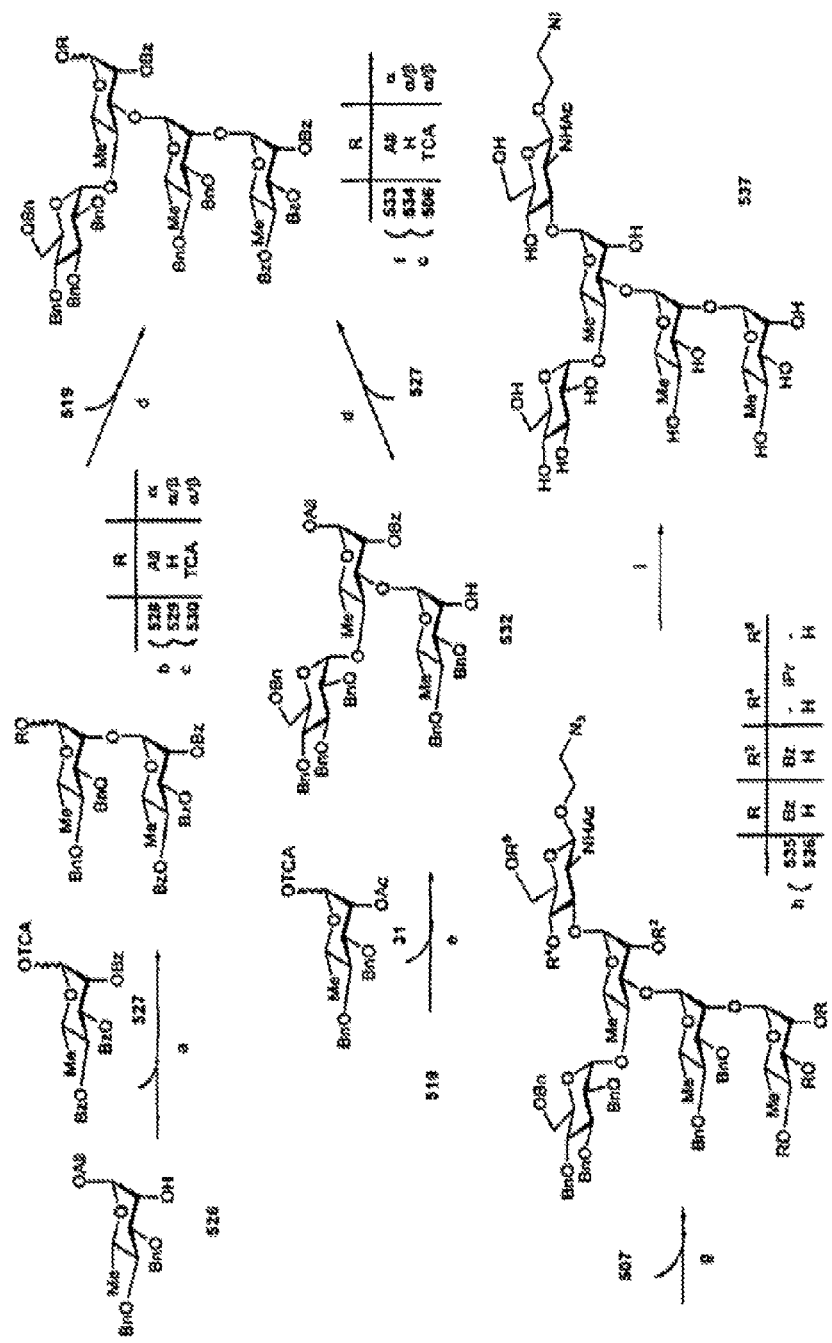
Figure 23:
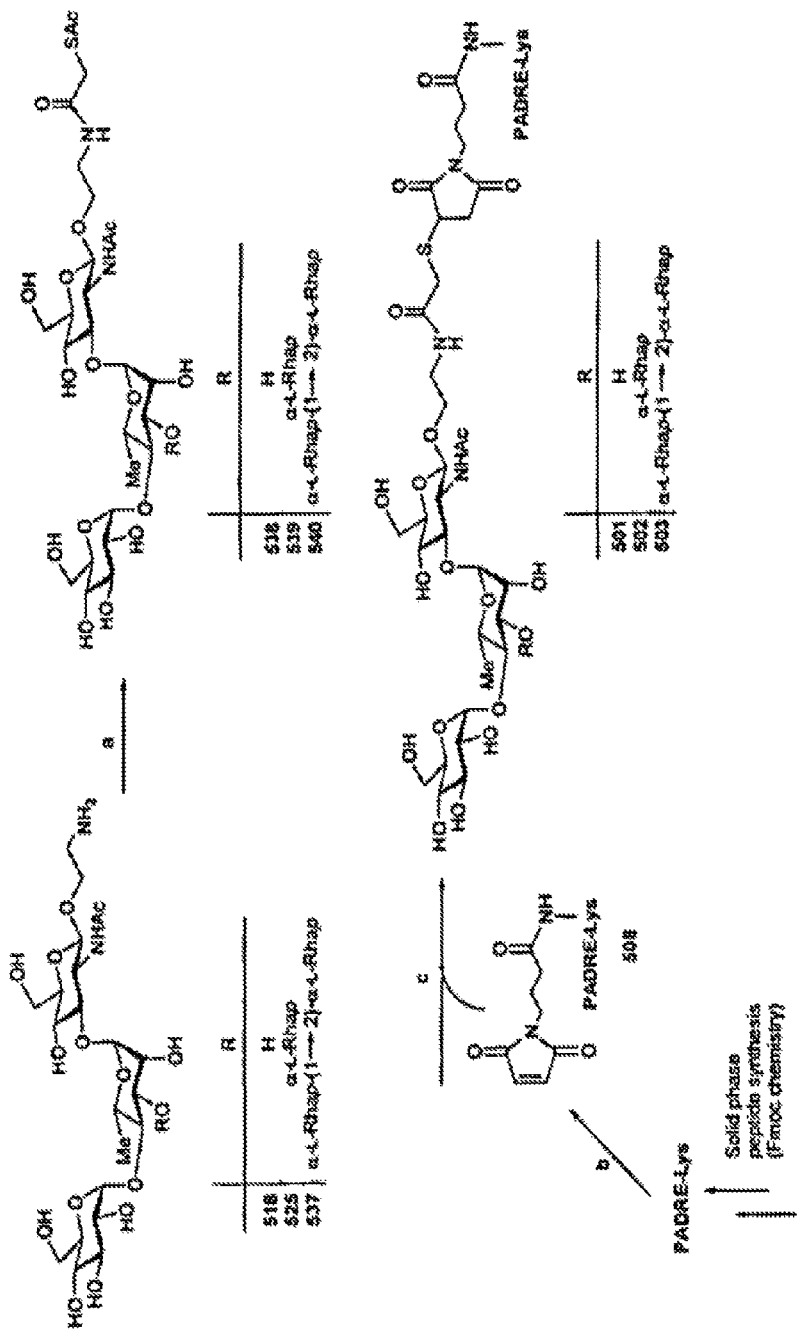
Figure 24:
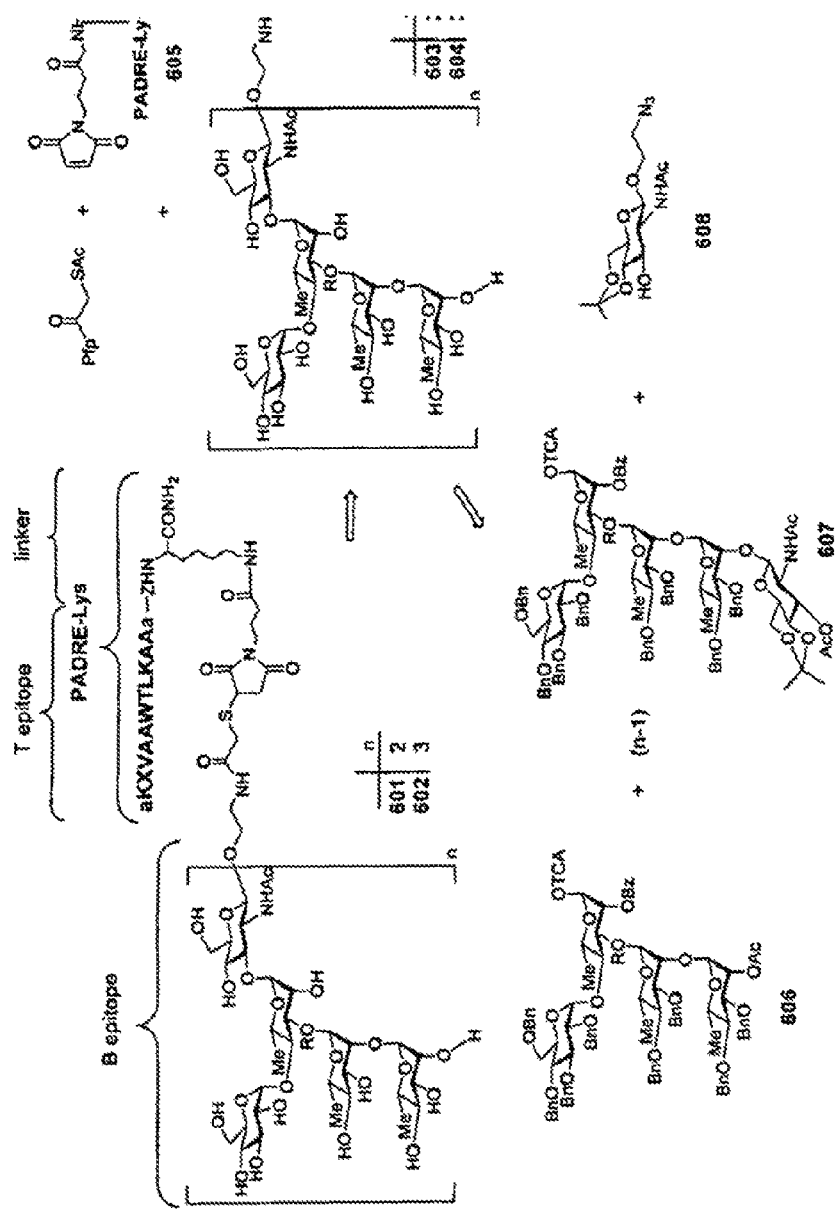
Figure 25:
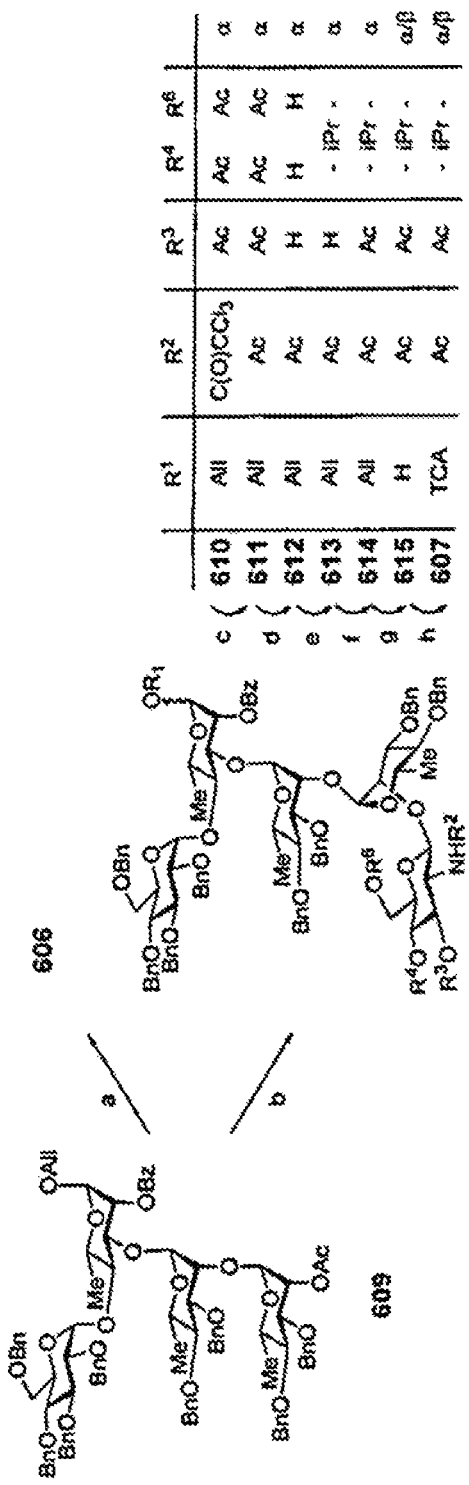
Figure 26:
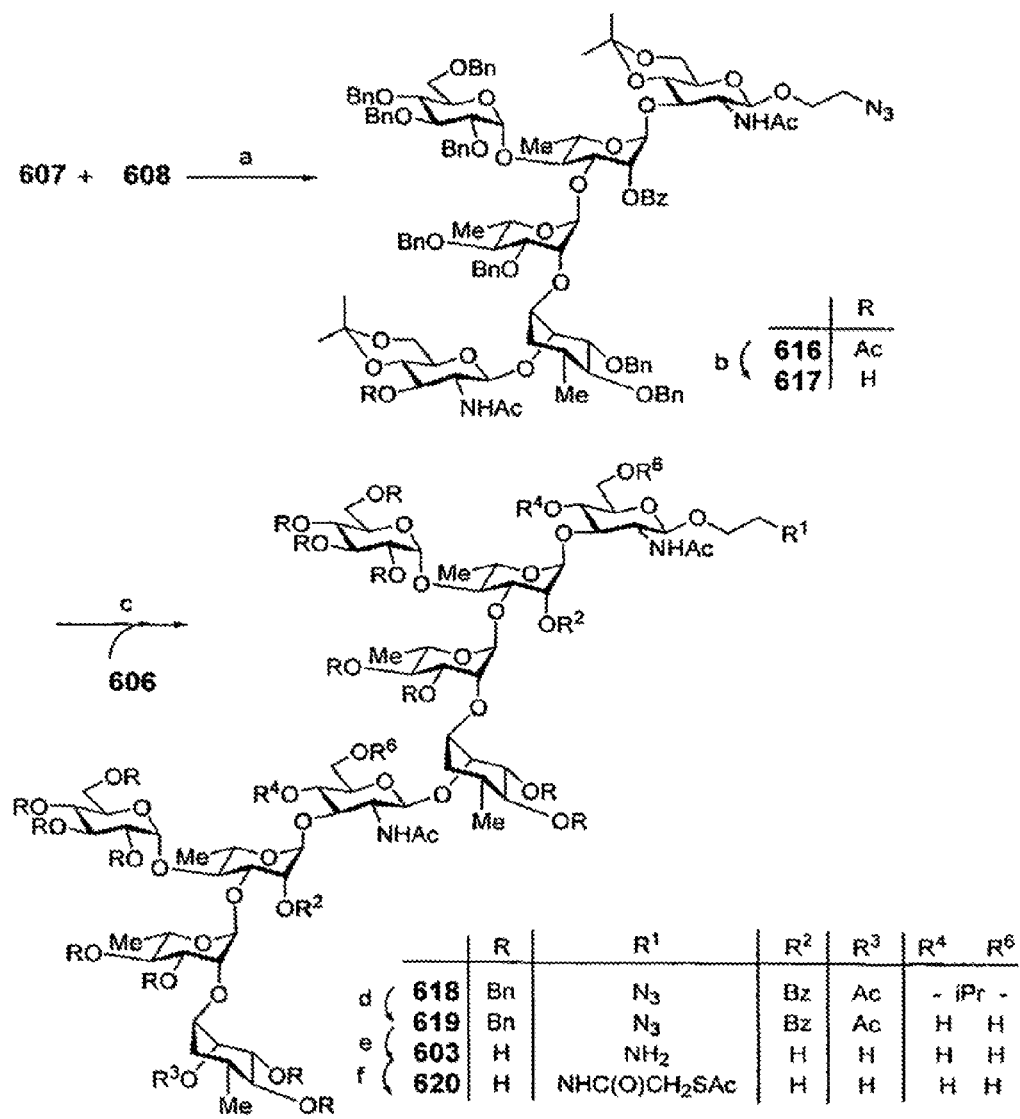
Figure 27:
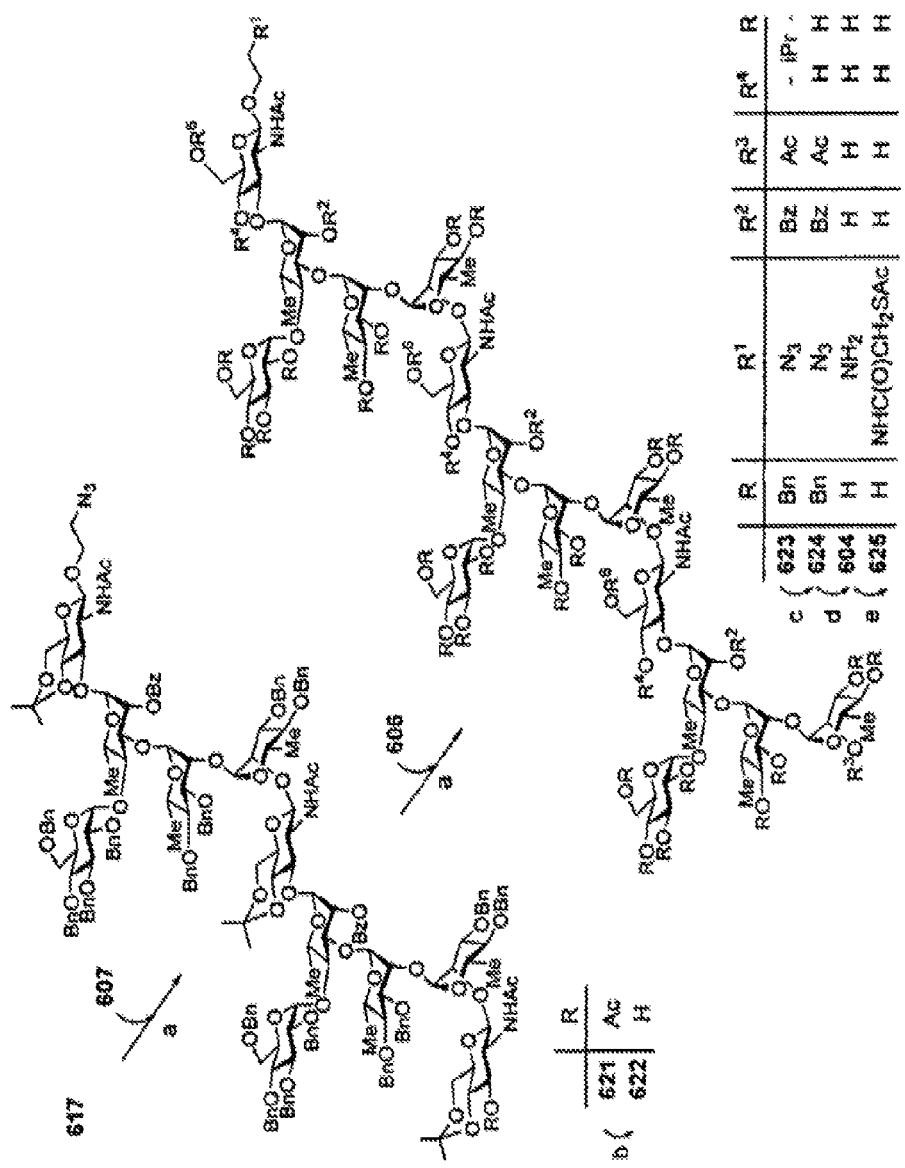
Figure 28A:
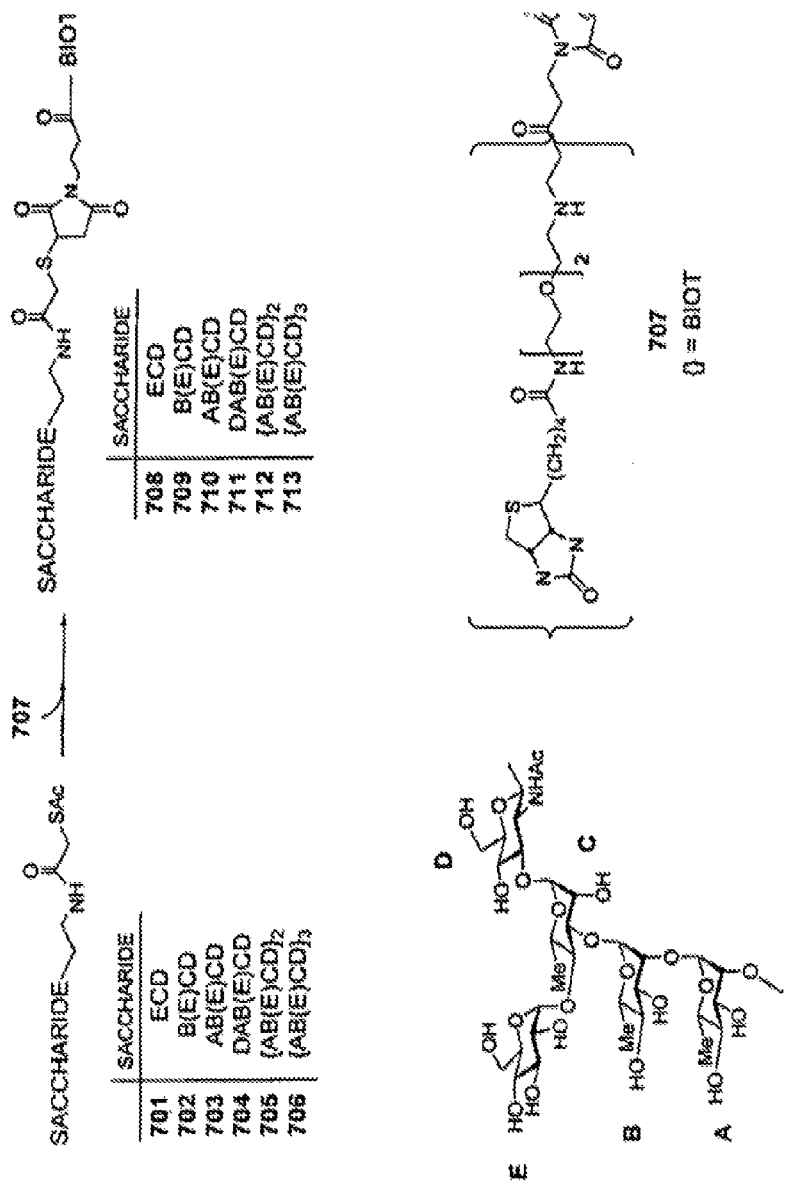
Figure 28B:
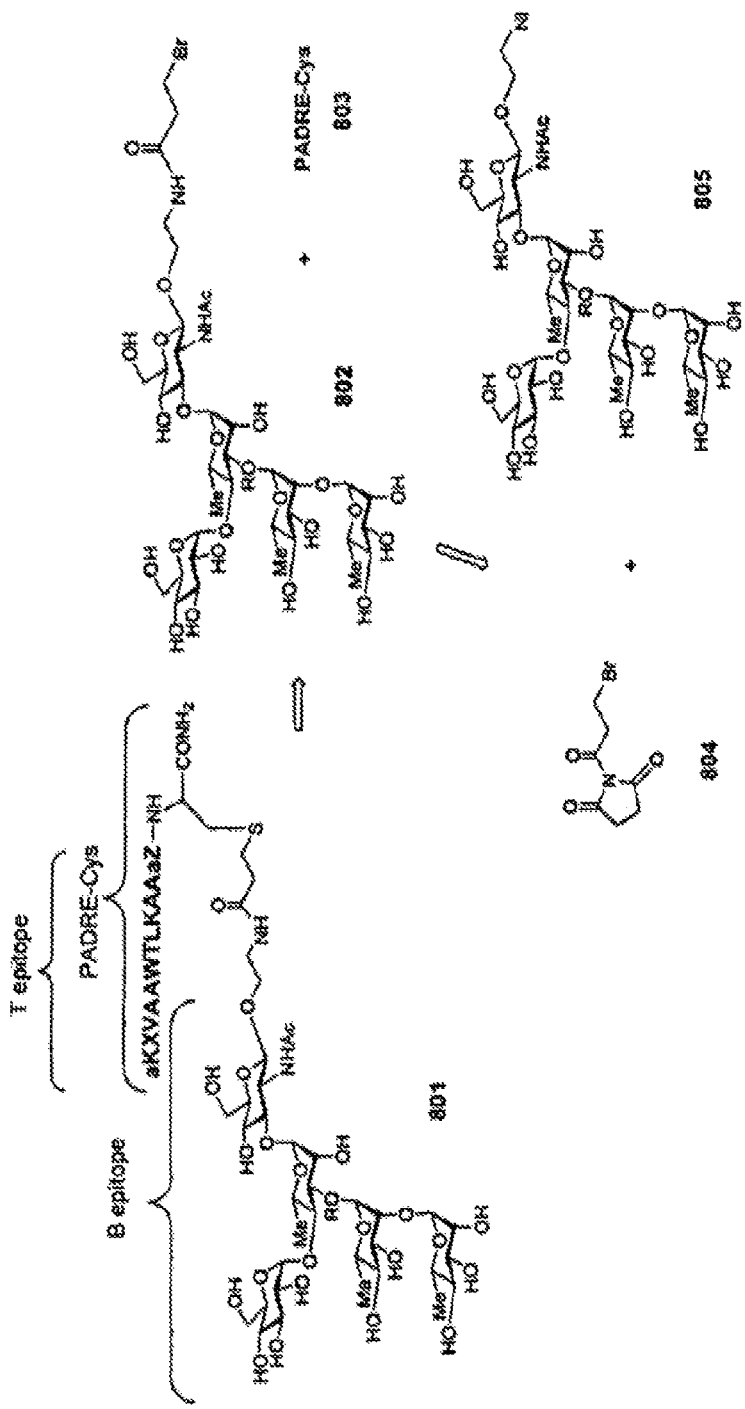

The avidity of each mIgG for LPS, defined by $IC_{50}$, ranged from 2 to 20 ng/ml. To analyse the protective capacity of the selected mAbs, naive mice were administered i.n. with each of the purified mIgG prior to i.n. challenge with a *S. flexneri* sublethal dose. Upon challenge, lung-bacterial load in mice passively administered with 20 µg of each of the mIgG specific for *S. flexneri* 2a LPS was significantly reduced in comparison to mice receiving PBS (FIG. 31A). Upon passive transfer using 2 µg of mIgG, only mIgG D15-7, A2-1 and E4-1 were shown to significantly reduce the lung-bacterial load in comparison to control mice, but with much less efficiency than that observed using 20 µg (FIG. 31A). As shown in FIG. 31B, reduction of lung-bacterial load in mice receiving 20 µg of mIgG was accompanied by a reduction of inflammation and therefore of subsequent tissue destruction. In comparison to control mice showing an acute broncho-alveolitis with diffuse and intense polymorphonuclear cell infiltration (FIG. 31B, a, b) associated with tissular dissemination of bacteria (FIG. 2B, c), only restricted areas of inflammation were observed in antibody-treated mice, essentially at the intra- and peribronchial level (FIG. 31B, d, e), where bacteria localized (FIG. 31B, f). Following passive administration with 2 µg of mIgG, inflammation resembled that of the control mice with a similar pattern of Polymorphonuclear (PMN) infiltration and tissue destruction, in accordance with the very low, if any, reduction in lung-bacterial load.

These results with murine monoclonal antibodies (mAbs) of the G isotype (mIgG) representative of the different IgG subclasses and specific for serotype-specific determinants on the O—SP, demonstrated that each IgG subclass exhibited a similar serotype-specific protective capacity, with significant reduction of the lung-bacterial load and of subsequent inflammation and tissue destruction. These antibodies may confer protection by different pathways involving or not the complement cascade. In the present study, all the different murine IgG subclasses were shown to be protective, suggesting that depending on the subclass, different mechanisms may be involved in IgG-mediated protection. Whereas antibody-dependant cellular cytotoxicity (ADCC) has been reported for *Shigella*-specific secretory IgA and lymphocytes from the gut-associated lymphoid tissues (Tagliabue et al., Nature, 1983, 306, 184-186), *Shigella* IgG-mediated ADCC occurs in vitro with splenic T cells but not with T lymphocytes from the GALT (Tagliabue et al., J. Immunol., Nature, 1984, 133, 988-992). Further studies using mice deficient for T cells or for proteins of the complement cascade will be required to analyze the IgG-mediated protective mechanisms in vivo.

3) Serotype-specific Protection Induced by the Anti-LPS mIgG

Antibodies specific for epitopes common to several serotypes of a given species as well as serotype-specific antibodies are elicited upon natural or experimental infection (Rasolofo-Razanamparany, Infect. Immun., 2001, 69, 5230-5234, Van de Verg et al., Vaccine, 1996, 14, 1062-1068). However, the serotype-specific protection observed following natural or experimental infection suggests that the antibodies directed against serotype determinants play a major protective role (Du Pont et al., J. Infect, Dis., 1972, 125, 12-; Mel et al., Bull. W.H,O., 1968, 39, 375-380). For instance, mIgA specific for *S. flexneri* serotype 5a has been shown to protect only against homologous challenge (Phalipon et al., J. Exp. Med., 1995, 182, 769-). Therefore, it was tested whether the protection observed with the anti-LPS mIgG obtained in this study was also serotype-specific. Mice passively administered with 20 µg of mIgG C1 specific for *S. flexneri* 2a were protected against homologous challenge, but not upon heterologous challenge with *S. flexneri* 5a bacteria (FIG. 32A). Similarly, mice receiving 20 µg of mIgG C20, a mAb specific for *S. flexneri* serotype 5a and, of the same isotype than mIgG C1, i.e. IgG3, showed a significant reduction of lung-bacterial load upon i.n. challenge with *S. flexneri* 5a, but not with *S. flexneri* 2a (FIG. 32A). In mice protected against homologous challenge, inflammation was dramatically reduced with a slight intra- and peribronchial PMN infiltrate remaining present (FIG. 32B, b and c). In contrast, in mice not protected upon heterologous challenge (FIG. 32B, a and d), inflammation and tissue destruction were similar to those observed in control mice (FIG. 32B, and b).

The protective role of the serotype-specific antibody response has been firstly emphasized in a study using a monoclonal dimeric IgA (mIgA) specific for a *S. flexneri* serotype 5a determinant (Phalipon et al., J. Exp. Med., 1995, 182, 769-51). The results presented here demonstrate that mIgGs specific for *S. flexneri* serotype 2a or serotype 5a also confer serotype-specific protection. It seems that whatever the antibody isotype and the bacterial strain, the serotype-specific antibody response is protective against homologous bacterial challenge. It should be noted that using the same amount of mIgA and mIgG specific for *S. flexneri* 5a, both exhibiting a similar $IC_{50}$ for LPS, reduction in lung-bacterial load was much more efficient with mIgA. Actually, in contrast to mIgG, protection was observed in the presence of 2 µg of mIgA. The discrepancy between the two isotypes may be due to the dimeric/polymeric (d/p) form of mIgA, which mimicks the IgA response at the mucosal surface. In contrast to monomeric IgG, interaction of d/p IgA exhibiting at least four antigen-binding sites with a specific determinant highly repeated on the bacterial O—SP surface may lead to the formation of aggregates that are efficiently removed by local physical mechanisms (Corthésy et al., Curr. Top. Microbiol. Immunol., 1999, 236, 93-111). Also, quantitative assessment of IgG and IgA subclass producing cells in the rectal mucosa during shigellosis in humans has revealed the predominance of the IgA response. The IgG response which is about 50 times lower than the IgA response is mainly IgG2 and correlates with the presence of specific IgG2 in serum. This correlation suggests that the majority of the *Shigella* specific serum antibodies are derived from the rectal mucosa (Islam et al., J. Clin. Pathol., 1997, 50, 513-520). Together, these results suggest that in the situation where both local and systemic anti-LPS antibody responses are induced, as for example upon natural infection, the local SIgA-mediated response will be the major protective response, with the IgG-mediated response possibly contributing to a lesser extent to local protection.

On the other hand, the data presented here suggest that in the absence of local SIgA-mediated response, as for example upon vaccination via the systemic route using glycoconjugate vaccines, the systemic anti-O—SP response induced is effective in protecting against homologous *Shigella* infection, if the effectors are present locally. Previous reports have shown that serum IgGs may protect from gastrointestinal infections (Bougoudogo et al., Bull. Inst. Pasteur, 1995, 93, 273-283; Pier et al., Infect. Immun., 1995, 63, 2818-2825). Therefore, it should be admitted that serum IgG efficiently gain access to the intestinal barrier in order to prevent bacterial invasion and dissemination. How IgG crosses the epithelial barrier to function in mucosal immunity remains unclear. One possible pathway is passive transudation from serum to intestinal secretions (Batty et al., J. Pathol., Bacteriol., 1961, 81, 447-458; McCleery et al., Digestion, 1970, 3, 213-221; Wernet et al., J. Infect. Dis., 1971, 124, 223-226). After its passage of the intestinal barrier through M cells and its interaction with resident macrophages and epithelial cells, *Shigella* initiates an inflammatory response leading to infiltration of the infected tissues with polymorphonuclear cells (Philpott et al., Philos. Trans. R. Soc. Lond. B. Biol., 2000, 29, 575-586). It may therefore be reasonably envisioned that specific serum IgGs transudate to the intestinal tissue during this inflammatory process that occurs very soon after bacterial translocation. Another explanation could be the involvement of the FcRn receptor in IgG transport. FcRn was firstly identified as the Fc receptor responsible for transferring maternal IgGs from mother's milk across the intestinal EC of the neonatal gut of rodents. Much evidence supports the concept that FcRn is ubiquitously expressed in adult tissues and plays a role in IgG homeostasis, dealing with IgG half-life (Ghetie et al., Ann. Rev. Immunol., 2000, 18, 739-766). It has been recently reported that this receptor is expressed by enterocytes in human adults and mediates transcytosis of IgG in both direction across the intestinal epithelial monolayer (Ramaligan et al., EMBO J., 1997, 21, 590-601). Further investigation is required to improve the knowledge on the role played by FcRn in IgG-mediated protection of the intestinal barrier against enteropathogens. Nevertheless, the existence of such a pathway already enlarges the current view of the humoral response at mucosal surfaces.

4) Absence of Protection Induced by the mIgG Specific for *S. flexneri* Invasins The invasins IpaB and IpaC are essential to the expression of the *Shigella* invasive phenotype (Ménard et al., J. Bacteriol., 1993, 175, 5899-5906). Moreover, they are targets for the humoral response since antibodies specific for both proteins are detected in sera of patients convalescent from shigellosis (dam et al., J. Clin. Microbial., 1993, 31, 454-457; Oaks et al., Infect. Immun., 1986, 53, 57-63; Oberhelman et al., Infect. Immun., 1991, 59, 2341-2350; Van de Verg et al., J. Infect. Dis., 1992, 166, 158-161). To assess whether the anti-invasin antibody response may contribute to protection, in addition to the anti-LPS antibody response, mIgG recognizing different epitopes on IpaB or IpaC, were used (Barzu et al., Infect. Immun., 1993, 61, 3825-3831; Phalipon et al., Infect. Immun., 1992, 60, 1919-1926). Whatever the dose used, in contrast to mIgG C20, no reduction in lung-bacterial load was measured upon challenge in mice treated with mIgG H16 and mIgG H4 recognizing distinct epitopes in the central region of IpaB or with mIgG J22 and mIgG K24 recognizing the N- and the C-termini domain of IpaC, respectively (FIG. 33). Protection was also not observed upon combining anti-IpaB and anti-IpaC mIgG.

The results presented here demonstrated that mIgG specific for IpaB or IpaC are not protective despite the fact that they are directed against epitopes located in different regions of these proteins (Barzu et al., Infect. Immun., 1993, 61, 3825-3831; Phalipon et al., Infect. Immun., 1992, 60, 1919-1926) and that they have been shown to interfere with their functional properties in in vitro studies (Barzu et al., Infect. Immun., 1998, 65, 1599-1605; Ménard et al., Cell, 1994, 79, 515-525). The most likely explanation is that these invasins, that are secreted through the type III secretion apparatus, are injected straight into the host cell, upon contact of the bacterium with the cell membrane (Ménard et al., EMBO J., 1994, 13, 5291-5302; Blocker et al., Mol. Microbiol., 2001, 39, 652-663). Therefore, there is probably very limited access, if any, for specific antibodies to interact with their targets. Although not tested, it is unlikely that the local SIgA-mediated response to these proteins will be protective.

III—Characterization of the Serotype-specific Antigenic Determinants of *S. flexneri* Serotype 2a Lipopolysaccharide Antigenic determinants recognized by protective monoclonal antibodies were characterized in a competition ELISA using synthetic di-, tri-, tetra- and pentasaccharides obtained by circular permutation of the residues from the repetitive units of the O—SP from *S. flexneri* serotype 2a (FIG. 29), as well as longer fragments (octa- and decasaccharides), as competitors for binding of the antibodies to the homologous LPS.

A) Material and Methods

1) Synthetic Oligosaccharides Representative of *S. flexneri* Serotype 2a O—SP

Oligosaccharides representative of fragments of the O—SP of *S. flexneri* 2a were synthesized by multistep chemical synthesis, as described in the preceding examples.

TABLE A

| Oligosaccharides* representative of fragments of the O-SP of *S. flexneri* 2a | | | | | |
|---|---|---|---|---|---|
| Di-saccharide | Tri-saccharide | Tetra-saccharide | Penta-saccharide | Octa-saccharide | Deca-saccharide |
| AB | ABC | | | | |
| BC | BCD | | | | |
| DA | CDA | | | | |
| (E)C | DAB | | | | |
| (βE)C | B(E)C | AB(E)C | DAB(E)C | | {DAB(E)C}$_2$ |
| | (E)CD | B(E)CD | B(E)CDA | B(E)CDAB(E)C | |
| | A(βE)C | (E)CDA | (E)CDAB | | |
| | | | AB(E)CD | | |

The oligosaccharides were synthesized as methyl glycoside in order to mimic the glycosidic linkages present in the natural polysaccharide and prevent any ambiguity which may otherwise arise due to equilibrium mixtures of the α- and β-anomers corresponding to the furanose and pyranose forms of the reducing residue.

The βEC and A(βE)C compounds, which have a non natural EC glycosidic linkage, were synthesized in order to probe the influence of such linkage on Ab recognition. Since they were estimated to be the easiest chemically accessible targets, the octa- B(E)CDAB(E)C and decasaccharide DAB (E)CDAB(E)C were chosen as the longer fragments in order to gain some knowledge on the length-dependent oligosaccharide-antibody recognition.

2) Monoclonal Antibodies

The monoclonal antibodies specific for serotype 2a used in this study are the five IgG antibodies described in example X+1: F22-4, D15-1, E4-1, A-2, and C1-7. In addition, an IgG monoclonal antibody specific for serotype 5a (C20) was used as control.

3) Inhibition ELISA.

First of all, a standard curve was established for each antibody tested. Different concentrations of the antibody was incubated at 4° C. overnight and then incubated on microtiter plates coated with purified *Shigella flexneri* LPS homologous to the strain used for the obtention of the antibody, at a concentration of 5 µg/ml in carbonate buffer at pH 9.6, and previously incubated with PBS/BSA 1% for 30 min at 4° C. After washing with PBS-Tween 20 (0.05%), alkaline phosphatase-conjugated anti-mouse IgG was added at a dilution of 1:5000 (Sigma Chemical CO.) for 1 h at 37° C. After washing with PBS-Tween 20 (0.05%), the substrate was added (12 mg of p-nitrophenylphosphate in 1.2 ml of Tris, HCl buffer ph 8.8 and 10.8 ml of NaCl 5M). Once the color developped, the plate was read at 405 nm (Dinatech MR 4000 microplate reader). A standard curve OD=f(antibody concentration) was fitted to the quadratic equation $Y=aX^2+bX+c$ where Y is the OD and X is the antibody concentration. Correlation factor ($r^2$) of 0.99 were routinely obtained.

Then, the amount of oligosaccharides giving 50% inhibition of IgG binding to LPS ($IC_{50}$) was then determined as follows. IgG at a given concentration (chosen as the minimal concentration of antibody which gives the maximal OD on the standard curve) was incubated overnight at 4° C. with various concentrations of each of the oligosaccharides to be tested, in PBS/BSA 1%. Measurement of unbound IgG was performed as described in the preceding example, using microtiter plates coated with purified LPS from *S. flexneri* 2a and the antibody concentration was deduced from the standard curve. Then, $IC_{50}$ was determined.

4) mIgG Sequence Analysis

Total RNA was extracted from hybridoma cells by RNAxel kit (EUROBIO). mRNA was converted into cDNA with a reverse transcriptase kit (INVITROGEN) and used as template for PCR amplification using Taq DNA polymerase (GIBCO, BRL) according the manufacturer's protocol. The amplification was performed with the primer of corresponding isotype (SEQ ID NO: 1 to 3; IgG1 : 5' GCA AGG CTT ACT AGT TGA AGA TTT GGG CTC AAC TTT CTT GTC GAC 3'; IgG2a: 5' GTT CTG ACT AGT GGG CAC TCT GGG CTC 3'; IgG3: 5'GGG GGT ACT AGT CTT GGG TAT TCT AGG CTC 3'. The following eight heavy chain variable region (VH) primers were also used (SEQ ID NO: 4 to 11: 5' GAG GTG CAG CTC GAG GAG TCA GGA CC3'; 5' GAG GTC CAG CTC GAG CAG TCT GGA CC 3'; 5' CAG GTC CAA CTC GAG CAG CCT GGG GC 3'; 5' GAG GTT CAG CTC GAG CAG TCT GGG GC 3'; 5' GAG GTG AAG CTC GAG GAA TCT GGA GG 3'; 5' GAG GTA AAG CTC GAG GAG TCT GGA GG 3'; 5' GAA GTG CAG CTC GAG GAG TCT GGG GG 3'; 5' GAG GTT CAG CTC GAG CAG TCT GGA GC 3'). Nucleic acid sequences were carried out by GENOME EXPRESS S.A. using PCR products. Sequence analysis was performed with software package from the Genetics Computer Group, Inc (Madison, Wis.), the Genehank (Los Alamos, N. Mex.) and EMBL (Heidelberg, Germany) databases. For the determination of the genes families, analysis of the nucleotide sequences was performed with the international ImMunoGeneTics database (http://imgt.cines.fr) (Lefranc, M.-P., 2003 *Nucleic Acids Res.*, 31, 307-310).

B) Results

1) Antigenic Determinants of *S. flexneri* Serotype 2a Lipopolysaccharide

The binding of the five available protective mIgGs to 25 synthetic mono- and oligosaccharides was evaluated in inhibition ELISA (Table B).

TABLE B

Minimal sequence recognized by the mIgG

| Motif (*) | F22-4 IgG1 $IC_{50}$ (µmol/L) | D15-7 IgG1 $IC_{50}$ (µmol/L) | A2-1 IgG2a $IC_{50}$ (µmol/L) | E4-1 IgG2b $IC_{50}$ (µmol/L) | C1-7 IgG3 $IC_{50}$ (µmol/L) |
|---|---|---|---|---|---|
| CD | >1000 | >1000 | >1000 | >1000 | >1000 |
| EC | >1000 | >1000 | >1000 | >1000 | >1000 |
| B(E)C | >1000 | >1000 | >1000 | >1000 | >1000 |
| (E)CD | 179 | >1000 | >1000 | >1000 | >1000 |
| (E)CDA | 181 | >1000 | >1000 | >1000 | >1000 |

TABLE B-continued

Minimal sequence recognized by the mIgG

| Motif (*) | F22-4 IgG1 $IC_{50}$ (µmol/L) | D15-7 IgG1 $IC_{50}$ (µmol/L) | A2-1 IgG2a $IC_{50}$ (µmol/L) | E4-1 IgG2b $IC_{50}$ (µmol/L) | C1-7 IgG3 $IC_{50}$ (µmol/L) |
|---|---|---|---|---|---|
| (E)CDAB | 354 | >1000 | >1000 | >1000 | >1000 |
| B(E)CD | 5 | 198 | >1000 | 87 | >1000 |
| B(E)CDA | 2.5 | 240 | 350 | 75 | 400 |
| AB(E)C | >1000 | >1000 | >1000 | >1000 | >1000 |
| DAB(E)C | >1000 | >1000 | >1000 | >1000 | >1000 |
| AB(E)CD | 21 | 490 | 378 | 287 | 734 |

(*) Oligosaccharides are methyl glycosides derivatives

None of the mono- or disaccharides showed any binding when used at a concentration of 1 mM. Evaluation of trisaccharide recognition outlined the unique behaviour of mIgG F22-4, which was the only Ab showing measurable affinity for such short oligosaccharides. ECD was the only trisaccharide recognized by F22-4, pointing out the crucial contribution of both the branched glucosyl residue (E) and the N-acetyl-glucosaminyl residue (D) to Ab recognition. This was supported by the absence of recognition of AB(E)C or DAB(E)C by none of mIgG. Comparison of the recognition of the branched tetrasaccharide B(E)CD to that of the linear ECD indicated that rharnnose B, accounting for an improvement of the $IC_{50}$ by a factor of ~50, was also a key element in the Ab recognition. Indeed, B(E)CD was recognized by all the protective mIgG, except A2-1 and C1-7 for which the minimal sequences necessary for recognition were pentasaccharides AB(E)CD or B(E)CDA. Extension of B(E)CD at the reducing end, yielding the branched pentasaccharide B(E)CDA, did not result in any major improvement of Ab binding for the other mIgGs. The minor, if not absent, contribution of reducing A to binding was also apparent when comparing recognition of ECD and ECDA by F22-4. Further elongation at the reducing end, yielding ECDAB did not improve binding to F22-4. Introduction of residue A at the non reducing end of B(E)CD, leading to AB(E)CD, had a somewhat controversial impact on Ab recognition with a positive effect in the case of A2-1, and only a slight effect in the case of C 7-1, and even negative by a factor ~2 to ~5 when considering the other antibodies. Therefore, for the recognition of short oligosaccharides, two families of mIgGs were identified. The first one represented by F22-4 recognizing the ECD trisaccharide, and the second one, comprising the remaining four mIgGs, that recognized the same common ECD sequence flanked by the B residue at the non reducing end, added or not with A residue at the non reducing or reducing end.

This observation was confirmed when measuring the recognition of longer oligosaccharides (Table C).

TABLE C

Antibody recognition is improved with longer oligosaccharides

| Anticorps | (*) B(E)CDA $IC_{50}$ (µmol/L) | AB(E)CD $IC_{50}$ (µmol/L) | B(E)CDA B(E)C $IC_{50}$ (µmol/L) | DA B(E)CDA B(E)C $IC_{50}$ (µmol/L) |
|---|---|---|---|---|
| F22-4 (IgG1) | 2.5 | 21.6 | 0.22 | 5 |
| D15-7 (IgG1) | 240 | 490 | 60.8 | 11.9 |
| A2-1 (IgG2a) | 350 | 378 | 12.9 | 3 |
| E4-1 (IgG2b) | 75 | 287.7 | 12 | 4.4 |
| C1-7 (IgG3) | 400 | 734 | 242 | 19 |

(*) All oligosaccharides are methylglycosides derivatives

Indeed, the decasaccharide was the highest affinity ligand for all antibodies except F 22-4, In the latter case, the octasaccharide was the best recognized sequence with an $IC_{50}$ of 0.22 µM, corresponding to an improvement by a factor ~10, when compared to pentasaccharide B(E)CDA. Further extension of the octasaccharide by addition of DA at the non reducing end resulted in a loss of recognition by a factor of ~20. Interestingly, the recognition of these two longer oligosaccharides by the other mIgGs differed from that of F22-4. D15-7 and E4-1 behaved similarly, with extension by B(E)C at the reducing end leading to the octasaccharide, and then by DA at the non reducing end, leading to the decasaccharide, both resulting in improving Ab binding by a factor of ~4. C1-7 behaved somewhat differently since contribution of B(E)C to binding appeared to be minor, whereas introduction of DA, resulted, as for the above cited mIgG, in an overall gain in binding of ~20. Finally, in the case of A2-1, addition of B(E)C to the reducing end of pentasaccharide B(E)CDA resulted in a gain in recognition by a factor ~25, and subsequent addition of DA at the non reducing end further contributed to binding improvement by a factor of ~4. To summarize, lengthening the oligosaccharide sequence improved the Ab recognition.

Thus, the data presented indicate the presence of an immunodominant epitope (E)CD of *S. flexneri* serotype 2a lipopolysaccharide, with flanking residues contributing to the reconition depending on the monoclonal antibody. The sequences B(E)CDA and AB(E)CD are almost similarly recognized by all the monoclonal IgG antibodies. In addition, the recognition improvement observed with longer oligosaccharides indicate that multiple epitopes along the polysaccharide chain (17 repetitive units in average) but not one unique epitope at the extremity, are presented on the LPS.

2) Molecular Characterization of the Protective *S. flexneri* Serotype 2a-specific mIgG To analyse whether the differences observed in the recognition of oligosaccharides by the mIgGs reflect differences in the structure of these mAbs, their complementary-determining regions (CDRs) were sequenced (Table D and E).

TABLE D

VH domain CDR sequences

| VH | CDR1 (SEQ ID NO: 12 to 15) | CDR2 (SEQ ID NO: 16 to 19) | CDR3 (SEQ ID NO: 20 to 23) | OLIGO-SACCHARIDE MOTIF |
|---|---|---|---|---|
| F22-4 | NYWMS | EIRLKSDNYATYYAESVKG | PMDY | ECD |
| D15-7 | YSSIH | WINTATGEPTYPDDFKG | YDYAGFYW | B(E)CD |
| A2-1 | DYSLH | WINTETGEPAYADDFKG | YRYDGAY | B(E)CDA |
| E4-1 | DYSMH | WVNTQTGEPSYADDFKG | YRYDGAH | B(E)CD |
| C1-7 | | | | B(E)CDA |

TABLE E

VL domain CDR sequences

| VL | CDR1 (SEQ ID NO: 24 to 27) | CDR2 (SEQ ID NO: 28 to 31) | CDR3 (SEQ ID NO: 32 to 34) | OLIGO-SACCHARIDE MOTIF |
|---|---|---|---|---|
| F22-4 | RSSKSLLHSDGITYLY | HLSNLAS | AHNVELPRT | ECD |
| D15-7 | SASSSVGYIH | DTSKLAS | QQWSRNPLT | B(E)CD |
| A2-1 | RATSSVGYIN | ATSNLAA | QQWSSDPFT | B(E)CDA |
| E4-1 | RARSSVGYM | ATSNQAS | QQWSSDPFT | B(E)CD |
| C1-7 | | | | B(E)CDA |

Only two VH and $V_K$ gene families were expressed among the five studied mIgG (Table F).

TABLE F

| mAb | isotype | VH | D | JH | VK | JK |
|---|---|---|---|---|---|---|
| A2-1 | IgG2a | VGAM3-8 | SP2 | JH3 | VK4/5 | JK4 |
| C1-7 | IgG3 | | | | | |
| D15-7 | IgG1 | VGAM3-8 | SP2 | JH3 | VK4/5 | JK5 |
| E4-1 | IgG2b | VGAM3-8 | SP2 | JH3 | VK4/5 | JK4 |
| F22-4 | IgG1 | J606 | not known | JH4 | VK24/25 | JK1 |

V gene usage

VH J606 (Brodeur et al., *Eur. J. Immunol.*, 1984, 14, 922-930) and VK24/25 (Almagro et al., *Immunogentics*, 1998, 47, 355-363) encoded F22-4 VH and $V_K$, respectively. A2-1, D15-7 and E4-1 VH genes were members of the VGAM3-8 family (Winter et al., *Embo J.*, 1985, 4, 2861-2867) and their $V_K$ genes belonged to the VK4/5 family (Almagro et al., precited). The joining segment of F22-4 heavy chain was encoded by JH4 (Sakano et al., *Nature*, 1980, 86, 676-683), while A2, D15-7 and E4-1 heavy chains shared the same diversity and joining segments, DSP2 (Gu et al., *Cell*, 1991, 65, 47-54) and JH3 (Sakano et al., precited), respectively. The joining segment for the light chain is encoded by JK1 (Max et al., *J. Biol. Chem.,* 1981, 256, 5116-5120) for F22-4, JK4 for A2 and E4-1, and JK5 for D15-7. The four antibody CDRs except for CDRH3, fall into the canonical structure classes (Al-Lazikani et al., *J. Mol Biol,* 1997, 273, 927-948). For all mIgG, the CDRs L2, L3 and H1 were of the same classes, 1/7A, 1/9A and 1/10A, respectively (Martin et al., *J. Mol Biol.,* 1996, 263, 800-815). For F22-4, the canonical form of the loops L1 and H2 were of the classes 4/16A and 4/12A, while those of the three other antibodies fall into classes 1/10A for L1 and 2/10A for H2. The CDR-H3 of A2, D15-7 and E4-1 contained seven residues along with several aromatic ones, while the CDR-H3 of F22-4 was very short, only four amino-acids with a proline residue in the first position.

mIgG F22-4 binds to the O—SP in an unique mode, selecting the linear trisaccharide ECD as the minimal sequence necessary for recognition at a concentration below 1 mM. The specificity of F22-4 suggests that the glucose residue (E) is probably involved in direct interactions with the Ab, while for the other mAbs, E may also constrain the conformation of another part of the oligosaccharide that interacts with the Ab. F22-4 uses a VHJ606/VK24/25 pair. The J606 family comprises VH genes encoding the immune response to β-(1,6)-galactan (Hartman et al., 1984, 3, 2023-2030). The CDRs H1, H2, L1 and L2 are quite similar in sequence and/or length to those of SYA/J6 (Table G), a mAb generated in response to immunization with *S. flexneri* Y.

The other mIgGs require B(E)CD as the minimal sequence recognized at a concentration below or close to 1 mM (A2-1). These mAbs probably bind intrachain epitopes, as it is supported by by the fact that the longer the oligosaccharide, the better the recognition. It is somewhat puzzling to note that although binding to the shorter oligosaccharides is slightly different, all the mIgGs fall into the same pattern of affinity when considering the decasaccharide. The most striking observation concerns A2-1, for which a 100 fold increase in binding was noted when comparing DAB(E)CDAB(E)C to B(E)CDA. It is noteworthy that these mIgGs use a VGAM3-8/VK24/25 pair, thus differing from F22-4. The VGAM3.8 multigene family was isolated from the DNA of mouse B-lymphocytes stimulated by LPS (Winter et al., Embo J., 1985, 4, 2861-22867).

Taken together, these results suggest that the particular behaviour of F22-4 in recognizing of the trisaccharide ECD, in comparison to the other mIgGs, could be related to particular molecular structure.

IV. Preparation of TT Conjugates a) Material and Methods

N-(γ-maleimidobutiryloxy) sulfosuccinimide ester (sulfo-GMBS) was purchased from Pierce. Tetanus toxoid (TT) (MW 150 kDa) (batch n°FA 045644), was purchased from Aventis Pasteur (Marcy l'Etoile, France), and stored at 4° C. in a 39.4 mg.mL$^{-1}$ solution.

TABLE G

Comparison of the sequences of SYA/J6 (SEQ ID NO: 12, 35 to 39) and F22-4 (SEQ ID NO: 12, 16, 20, 24, 28 and 32) CDRs*

| VH | H1 | H2 | H3 |
|---|---|---|---|
| | 31  35 | 52abc | 100a |
| SYA/J6 | NYWMS | EIRLKSNNYATHYAESVKG | GGAVGAMDY |
| F22-4 | NYWMS | EIRLKSDNYATYYAESVKG | PM DY |

| VH | L1 | L2 | L3 |
|---|---|---|---|
| | 27abcde  30 | 50   56 | 89    97 |
| SYA/J6 | RSSQSLLHSDGNTYLH | KVSNRFS | SQTTHVPT |
| F22-4 | RSSKSLLHSDGITYLY | HLSNLAS | AHNVELPRT |

*Kabat numbering

In contrast, the H3 loops, which are the major key of Ab diversity, are very different. In mAb SYA/J6, the CDR-H3 comprises nine amino-acids; its base which possesses three Gly residues, shows the torso-bulged structure (Morea et al., J. Biol. Chem, 1998, 263, 269-294) and this mAb is an example of a groove like site for binding an internal oligosaccharide epitope (Vyas et al., Biochemistry, 2002, 41, 13575-13586). In the case of F22-4, the H3 loop-four residues, which can only form a short hairpin, would allow a more open binding site, than can accommodate the linked glucose.

The improved F22-4 recognition of the tetrasaccharide B(E)CD outlines the key input on the branching site. However, as found in the case of pentasaccharide AB(E)CD and decasaccharide DAB(E)CDAB(E)C, further extension at the non reducing end of this key fragment had a negative impact on binding. These findings suggest that although the Ab combining site is most probably of the groove type, it is somewhat restricted on one side and unable to accommodate inappropriate extension.

Dialyses were performed with Slide-A-Lyzer® Dialysis Cassettes (Pierce) and concentration by centrifugation using Vivaspin 15R centrifugal concentrators (Vivascience, Palaiseau, France), displaying a membrane cut-off of 10000 Da, at a centrifugal force of 4500×g.

i) pmLPS-TT Conjugates

Preparation and Derivatization of *S. flexneri* 2a pmLPS

*S. flexneri* 2a LPS was treated with acetic acid to hydrolyse the lipid A-core linkage: LPS [10 mg in 1% (v/v) aqueous acetic acid (1 mL)], was heated at 100° C. for 60 min. Precipitated lipid A was removed by low-speed centrifugation (350×g for 15 min) at 4° C. The supernatant was extracted with equal volume of chloroform-ethanol (2:1). The reaction mixture was shaken vigorously and centrifuged at 10,000×g for 60 min at 4° C. The aqueous phase was dialyzed against distilled water to remove ethanol and then freeze-dried to give *S. flexneri* 2a pmLPS (5.3 mg, 53%).

*S. flexneri* 2a pmLPS (2.2 mg, 0.13 μmol) was dissolved in water (430 μL) at an actual concentration of 5 mg.mL$^{-1}$. The solution was brought to pH 11 with 2 N NaOH, and an equal weight of CNBr (4.0 µL of a 5 M solution in CH₃CN) was added. The pH was maintained at 11 with 2 N NaOH for 6 min at rt. An equal volume of adipic acid di-hydrazide 430 µL of a 0.5 M solution in 0.5 M NaHCO₃) was added, and the pH was adjusted to 8.5 with 0.5 M HCl. The reaction mixture was kept overnight at 6° C. and dialyzed against 0.1 M potassium phosphate buffer at 4-6° C.

The extent of derivatization of the activated pmLPS was calculated as the ratio of adipic acid dihydrazide/polysaccharide (w/w) and found equal to 3.7% using trinitrobenzenesulfonic acid (TNBS), as titration reagent (Habeeb, A. F., *Anal. Biochem.*, 1966, 14, 328-336).

Preparation and Characterization of the Conjugate

The activated *S. flexneri* 2a pmLPS (1.8 mg), and the succinic anhydride treated TT (1.8 mg) were mixed. Solid 1-ethyl-3-(3-dimethylaminopropyl)carbodimide (EDAC) (5.3 mg), was then added to a final concentration of 0.1 M and the pH of the reaction mixture was maintained at 6 for 4 h at rt. The crude mixture was dialyzed against PBS 1×(3×2 L) at 4-6° C. and passed trough a CL-6B Sepharose column (1 m×160 mm) (Phamiacia Biotech), using 0.05 M PBS, pH 7.4 as eluent at a flow rate of 0.2 mL.min$^{-1}$, with detection by measuring the optical density at 280 nm and the refractive index. The fractions containing the conjugates were pooled and concentrated. The conjugate was stored at 4° C. in the presence of thimerosal (0.1 mg.mL$^{-1}$) and assessed for its total carbohydrate and protein content.

ii) Oligosaccharide-TT Conjugates

Derivatization of TT

In a representative example, to a solution of TT (12 mg, 304 µL, 0.08 µmole) diluted in 0.1 M PBS, pH 7.3 (296 µL), was added N-(γ-maleimidobutiryloxy) sulfosuccinimide ester (GMBS) (3×1.53 mg, 3×58 µL of an 30 mg.mL$^{-1}$ solution in CH₃CN, 3×50 equiv), in three portions every 40 minutes. The pH of the reaction mixture was controlled (indicator paper) and maintained at 7-7.5 by addition of 0.5 M aq NaOH, Following an additional reaction period of 40 minutes, the crude reaction mixture was dialyzed against 3×2 L of 0.1 M potassium phosphate buffer, pH 6.0 at 4° C. to eliminate excess reagent. About 45 maleimide groups were introduced on TT as indicated by SELDI-TOF MS analysis.

Conjugation

Following dialysis, maleimide activated-TT in 0.1 M potassium phosphate buffer solution was divided into several portions which were further reacted with synthetic S-acetylthioacetylated-tri-, tetra penta-, hexa-; deca- and pentadecasaccharides related to *S. flexneri* 2a O—SP in a 1:12 molar ratio, respectively. Reaction mixtures were buffered at a 0.5 M concentration by addition of 1 M potassium phosphate buffer, pH 6.0. Then, NH₂OH, HCl (7.5 µL of a 2 M solution in 1 M potassium phosphate buffer, pH 6), was added to the different mixtures and the couplings were carried out for 2 h at rt. The conjugated products were dialyzed against 3×2 L of 0.05 M PBS, pH 7.4 at 4° C., and further purified by gel permeation chromatography on a sepharose CL-6B column (1 m×160 mm) (Pharmacia Biotech), using 0.05 M PBS, pH 7.4 as eluent at a flow rate of 0.2 mL.min$^{-1}$, with detection by measuring the optical density at 280 nm and the refractive index. The fractions containing the conjugates were pooled and concentrated. The conjugates were stored at 4° C. in the presence of thimerosal (0.1 mg.mL$^{-1}$) and assessed for their total carbohydrate and protein content.

In an attempt to maximize the loading of the protein, the derivatized-TT was reacted as described above but in a 1:56 molar ratio using the pentadecasaccharide related to *S. flexneri* 2a O—SP.

Hexose concentrations were measured by a colorimetric method based on the anthrone reaction, using pmLPS as a standard.

Protein concentrations were measured by the Lowry's spectrophotometric method, using BSA as a standard and/o total acidic hydrolysis (6 N HCl at 110° C. for 20 h), using norleucine as an internal standard.

Determination of Hexoses with Anthrone

Reagents: The reagents are as follows

Stock sulfuric acid. Add 750 mL of concentrated sulfuric acid to 250 mL of distilled water and cool the solution to 4° C.

Anthrone reagent. Dissolve 1.5 g of anthrone in 100 mL of ethyl acetate and cool the solution to 4° C.

Standard oligosaccharide solution: Prepare a solution at a concentration of 4 mg.mL$^{-1}$ in water. Prepare serial dilutions of 400 to 25 µMol of a tetra- or pentasaccharide [B(E)CD and AB(E)CD, respectively] standard solution in water. The tetra- and pentasaccharide standard solutions were used to dose the conjugates obtained using tri-, tetra-, penta- or hexa-, deca- and pentadecasaceharide, respectively.

Procedure:

Prepare serial dilutions of 400 to 25 µMol of the appropriate oligosaccharide standard solution in water (1 mL) in screw-threaded tubes. Prepare similarly a reagent blank containing 1 mL water and control reagents containing a known amount of pmLPS of *S. flexneri* 2a O—SP or glucose in 1 mL water. Prepare samples and make up to 1 mL if necessary by adding water. Cool all tubes in ice-water.

To each tube, add 5 mL of the concentrated H₂SO₄ and 0.5 mL of the anthrone solutions. Heat the tubes at 100° C., caps unscrewed fbr 3 minutes and then caps screwed for 7 minutes. After exactly 10 minutes, return the tubes to an ice-bath and when cool measure the absorbance in a spectrophotometer (Seconam S.7501), at a wavelength of 625 nm. The quantity of carbohydrate in the unknown samples can be read off from the standard curve prepared with the standard solution samples and the blank.

h) Results

Characteristics of representative conjugates are listed in Table L.

TABLE L

| Conjugate reference | Hapten | Isolated yield | carbohydrate/ protein wt/wt (%) | Hapten/protein (mmol/mmol) |
|---|---|---|---|---|
| CGS0303-8-3 | (E)CD | 70% | 5.4 | 12 |
| CGS0303-8-4 | B(E)CD | 64% | 7.4 | 13.3 |
| CGS0303-8-5 | AB(E)CD | 80% | 9.6 | 14.7 |
| CIMG745 | B(E)CD | 66% | 6.5 | 10.8 |
| CIMG746 | AB(E)CD | 85% | 6.5 | 10.9 |
| CGS0703-56-10 | [AB(E)CD]₂ | 71% | 16 | 13.5 |
| CGS0703-56-15 | [AB(E)CD]₃ | 67% | 43 | 24 |
| CGS0104-113-4 | B(E)CD | 52% | 12 | 15.8 |
| CGS0104-113-5 | AB(E)CD | 51% | 10 | 13 |
| CGS0104-113-6 | DAB(E)CD | 72% | 13 | 17 |
| CGS0104-113-10 | [AB(E)CD]₂ | 62% | 22 | 14 |
| CGS0104-113-15 | [AB(E)CD]₃ | 68% | 4 | 26 |
| CGS0204-121 | pmLPS | 88% | 41 | 3.6$^a$ |
| CGS0703-51 | pmLPS | 74% | 25 | 2.2$^a$ |

$^a$Based on an estimated Mr of 17,000 kD for pmLPS (pmLPS stands for LPS detoxified by acid hydrolysis)

V—Immunogenicity of the Oligosaccharides-tetanus Toxoid Conjugates

A) Material and Methods

1) Immunization Protocol

Two immunization assays in the absence of adjuvant were performed with oligosaccharides conjugated to tetanus toxoid, prepared as described in preceding example.

In a first assay, groups of eight mice received four intramuscular injections at three weeks interval of B(E)CD, AB(E)CD, DAB(E)CD, [AB(E)CD]$_2$ or [AB(E)CD]$_3$ oligosaccharides conjugated to tetanus toxoid (10 µg oligosaccharide/mice/injection). Control mice received detoxified LPS from *S. flexneri* 2a conjugated to tetanus toxoid (10 µg polysaccharide/mice/injection) by multipoint attachment, as described by Taylor et al., Infect. Immun., 1993, 61, 3678-3687, or tetanus toxoid alone (140 µg/mice/injection), following the same immunization schedule. One month after the last injection, the mice received a last boost of conjugates, in the same conditions.

In a second assay, groups of seven mice received three intramuscular injections at three weeks interval of B(E)CD, DAB(E)CD, and groups of fourteen mice received three intramuscular injections at three weeks interval [AB(E)CD], [AB(E)CD]$_2$ or [AB(E)CD]$_3$ oligosaccharides conjugated to tetanus toxoid (10 µg oligosaccharide/mice/injection). Control mice received detoxified LPS from *S. flexneri* 2a conjugated to tetanus toxoid (10 µg polysaccharide/mice/injection) by multipoint attachment, as described by Robbins J. B. (J. Infect. Dis. 161: 821-832), or tetanus toxoid alone (140 µg/mice/injection), following the same immunization schedule. Seven days after the last injection, the mice received a last boost of conjugates, in the same conditions.

2) Antibody Response Analysis

The anti-LPS 2a, anti-oligosaccharides and anti-tetanus toxoid (TT) antibody response was analysed by ELISA, seven days after the third immunization (before the boost), and seven days after the boost. Microtiter plates were coated with the corresponding antigen in carbonate buffer pH 9.6, at a concentration of 5 µg/ml, for the LPS. Biotinylated oligosaccharide solutions were adjusted to equimolar concentrations based on the amount of ligand present in the respective glycoconjugate and incubated with PBS/BSA 1% for 30 min at 4° C. Bound antibodies were detected by using peroxidase- conjugated anti-mouse immunoglobulins. After washing with PBS-Tween 20 (0.05%), alkaline phosphatase-conjugated anti-mouse IgG was added at a dilution of 1:5000 (SIGMA) for 1 h at 37° C. After washing with PBS-Tween 20 (0.05%), the substrate was added (12 mg of p-nitrophenylphosphate in 1.2 ml of Tris, HCl buffer ph 8.8 and 10.8 ml of NaCl 5M). Once the color developed, the plate was read at 405 nm (Dinatech MR 4000 microplate reader). Antibody titers were defined as the last dilution of the sample giving an OD at least twice that of the control.

3) Protection Studies

The mice immunized i.m. were challenged i.n. with $10^8$ virulent bacteria, 8 days after the boost. Measurement of bacterial load was performed 24 h post-infection, as described in example II.

B) Results

The anti-LPS 2a, anti-oligosaccharides and anti-tetanus toxoid (TT) antibody response was analysed by ELISA, seven days after the third immunization (before the boost), and seven days after the boost.

TABLE H

Anti-LPS 2a antibody response induced by tetra-and hexasaccharides conjugates J7 after third immunization (1) and J7 after boost (2)

| Mouse n° | TETRA anti-LPS (1) | TETRA anti-LPS (2) | HEXA anti-LPS (1) | HEXA anti-LPS (2) | TT anti-LPS (1) | TT anti-LPS (2) | LPS/TT anti-LPS (1) | LPS/TT anti-LPS (2) |
|---|---|---|---|---|---|---|---|---|
| 1 | 0 | 0 | 0 | 0 | 0 | 0 | 400 | 1600 |
| 2 | 0 | 0 | 0 | 0 | 0 | 0 | 0 | 400 |
| 3 | 0 | 0 | 0 | 0 | 0 | 0 | 0 | 800 |
| 4 | 0 | 0 | 0 | 0 | 0 | 0 | 0 | 200 |
| 5 | 0 | 0 | 0 | 0 | 0 | 0 | 0 | 200 |
| 6 | 0 | 0 | 0 | 0 | 0 | 0 | 0 | 0 |
| 7 | 0 | 0 | 0 | 0 | 0 | 0 | 0 | 0 |

TABLE I

Anti-LPS 2a antibody response induced by penta-, deca- and pentadecasaccharides conjugates J7 after third immunization (1) and J7 after boost (2)

| Mouse n° | PENTA Anti-LPS (1) | PENTA Anti-LPS (2) | DECA Anti-LPS (1) | DECA Anti-LPS (2) | PENTADECA Anti-LPS (1) | PENTADECA Anti-LPS (2) |
|---|---|---|---|---|---|---|
| 1 | 0 | 6400 | 3200 | 12800 | 6400 | 12800 |
| 2 | 0 | 3200 | 3200 | 25600 | 12800 | 51200 |
| 3 | 0 | 400 | 800 | 800 | 12800 | 51200 |
| 4 | 0 | 200 | 1600 | 3200 | 25600 | 25600 |
| 5 | 0 | 0 | 400 | 1600 | 25600 | 51200 |
| 6 | 0 | 0 | 25600 | 400 | 6400 | 12800 |
| 7 | 0 | 0 | 0 | 800 | 3200 | 3200 |
| 8 | 0 | 0 | 0 | 3200 | 12800 | 25600 |
| 9 | 0 | 0 | 0 | 6400 | 6400 | 25600 |
| 10 | 0 | 0 | 0 | 12800 | 12800 | 25600 |
| 11 | 0 | 0 | 0 | 3200 | 6400 | 25600 |
| 12 | 0 | 0 | 0 | 800 | 12800 | 25600 |
| 13 | 0 | 0 | 0 | 0 | 6400 | 12800 |
| 14 | 0 | 0 | 0 | 0 | 3200 | 12800 |
| Percentage of responders | 0% | 28.50% | 42.85% | 85.70% | 100% | 100% |
| Mean of antibody titers |  | 1/728 | 1/2500 | 1/5200 | 1/11000 | 1/26000 |

TABLE J

Anti-oligosaccharide antibody response induced by tetra-and hexasaccharides conjugates J7 after third immunization (1) and J7 after boost (2)

| Mouse n° | TETRA (1) | TETRA (2) | HEXA (1) | HEXA (2) |
|---|---|---|---|---|
| 1 | 51200 | 51200 | 200 | 800 |
| 2 | 51200 | 51200 | 200 | 6400 |
| 3 | 51200 | 51200 | 0 | 12800 |
| 4 | 12800 | 51200 | 0 | 0 |
| 5 | 0 | 51200 | 0 | 0 |
| 6 | 0 | 200 | 0 | 0 |
| 7 | 0 | 0 | 0 | 0 |
| Mean of antibody titers | 1/24000 | 1/36600 | 1/50 | 1/3000 |

TABLE K anti-oligosaccharide antibody response induced by penta-, deca- and pentadecasaccharides conjugates J7 after third immunization (1) and J7 after boost (2)

| Mouse n° | PENTA | | DECA | | PENTADECA | |
|---|---|---|---|---|---|---|
| | (1) | (2) | (1) | (2) | (1) | (2) |
| 1 | 800 | 6400 | 200 | 800 | 3200 | 12800 |
| 2 | 1600 | 12800 | 100 | 25600 | 6400 | 51200 |
| 3 | 200 | 1600 | 100 | 6400 | 6400 | 51200 |
| 4 | 800 | 12800 | 3200 | 800 | 6400 | 51200 |
| 5 | 800 | 1600 | 0 | 400 | 6400 | 102400 |
| 6 | 0 | 12800 | 0 | 12800 | 1600 | 12800 |
| 7 | 0 | 25600 | 0 | 3200 | 6400 | 51200 |
| 8 | 0 | 6400 | 0 | 800 | 3200 | 51200 |
| 9 | 0 | 6400 | 0 | 1600 | 3200 | 51200 |
| 10 | 0 | 25600 | 0 | 6400 | 12800 | 51200 |
| 11 | 0 | 800 | 0 | 200 | 3200 | 51200 |
| 12 | 0 | 1600 | 0 | 0 | 400 | 51200 |
| 13 | 0 | 6400 | 0 | 0 | 3200 | 51200 |
| 14 | 0 | 25600 | 0 | 0 | 800 | 51200 |
| Mean of antibody titers | 1/300 | 1/10500 | 1/250 | 1/4500 | 1/4500 | 1/49000 |

No anti-LPS antibodies are observed in the mice immunized with the tetra- and hexasacacharides conjugates despite of an anti-oligosaccharide antibody response.

Low levels of anti-LPS antibodies are observed in the mice immunized with the detoxified LPS conjugate.

High levels of anti-LPS antibodies are observed in the mice immunized with the penta-, deca and penta decasaccharides conjugates. However, the antibody response is improved with the longer oligosaccharide (pentadecasaccharide); after the third immunization 100% of the mice receiving the pentadecapeptides present anti-LPS antibodies, as compared with 85% and 30% only, for the mice receiving the decasaceharide and the pentasaccharide, respectively. Moreover, the anti-LPS antibody titers as well as the homogeneity of the antibody response is higher in the mice immunized with the pentadecasaccharide.

2) Protection Studies

The ability of the antibodies induced by immunization with the oligosaccharides-TT conjugate to protect against Shigella infection was assayed by active protection studies in the mouse model of pulmonary infection.

Protection as assessed by a reduction of the bacteria load, was observed with the penta, deca and pentadecasaccharides conjugates whereas neither the tetra- and hexa saccharides conjugates, nor the detoxified LPS conjugate induced protection (FIG. 34).

The invention claimed is:

1. A saccharide selected from:

{AB(E)CD}n wherein:
A is an alphaLRhap-(1,2) residue
B is an alphaLRhap-(1,3) residue
C is an alphaLRhap-(1,3) residue
E is an alphaDGlcp-(1,4) residue
D is a betaDGlcNAcp-(1,2) residue
E is branched to C
And n is an integer chosen from 2 and 3.

2. A saccharide derivative selected from:

{AB(E)CD}n—OQ wherein:
A is an alphaLRhap-(1,2) residue
B is an alphaLRhap-(1,3) residue
C is an alphaLRhap-(1,3) residue
E is an [alphaDGlcp-(1,4)] residue
D is a betaDGlcNAcp-(1,2) residue
E is branched to C
Q is selected among alkyl and alkenyl groups comprising 1 to 12 carbon atoms,
O is an oxygen atom
n is chosen from 2 and 3.

3. An immunogenic composition comprising a molecule according to claim 2.

4. A kit for the diagnostic of *Shigella flexneri* type 2a infection wherein said kit comprises a molecule according to claim 2.

5. A molecule selected from:

{AB(E)CD}n—O—R—Z wherein:
A is an alphaLRhap-(1,2) residue
B is an alphaLRhap-(1,3) residue
C is an alphaLRhap-(1,3) residue
E is an [alphaDGlcp-(1,4)] residue
D is a betaDGlcNAcp-(1,2) residue
E is branched to C
R is an alkyl group comprising 1 to 12 carbon atoms, and wherein n is chosen from 2 and 3;
And Z is a functional group.

6. A molecule according to claim 5, selected from:

{AB(E)CD}n—O—R—$NH_2$ wherein:
A is an alphaLRhap-(1,2) residue
B is an alphaLRhap-(1,3) residue
C is an alphaLRhap-(1,3) residue
E is an [alphaDGlcp-(1,4)] residue
D is a betaDGlcNAcp-(1,2) residue
E is branched to C
R is an alkyl group comprising 1 to 12 carbon atoms, and wherein n is chosen from 2 and 3.

7. A process of preparation of a conjugate molecule comprising an oligo- or polysaccharide selected from:

$(X)_x$—{AB(E)CD}n—$(Y)_y$ wherein:
A is an alphaLRhap-(1,2) residue
B is an alphaLRhap-(1,3) residue
C is an alphaLRhap-(1,3) residue
E is an alphaDGlcp-(1,4) residue
D is a betaDGlcNAcp-(1,2) residue
E is branched to C
x and y are independently selected among 0 and 1
X and Y are independently selected among A, B, C, D, E, AB, B(E), (E)C, CD, DA, AB(E), B(E)C, (E)CD, CDA, AB(E)C, B(E)CD, (E)CDA, CDAB, DAB(E) and wherein n is chosen from 2 and 3, covalently bound to a carrier,
said process comprising the direct covalent reaction of a molecule according to any one of claims 5 and 6 with an appropriate carrier.

8. A process of preparation of a conjugate according to claim 7 wherein said covalent reaction comprises the previous activation of the molecule.

9. A process of preparation of a conjugate according to claim 7 wherein said covalent reaction comprises the previous activation of the carrier.

10. A process of preparation of a conjugate molecule comprising an oligo- or polysaccharide selected from the group consisting of:

$(X)_x$—{AB(E)CD}n—$(Y)_y$ wherein:
A is an alphaLRhap-(1,2) residue
B is an alphaLRhap-(1,3) residue
C is an alphaLRhap-(1,3) residue
E is an alphaDGlcp-(1,4) residue
D is a betaDGlcNAcp-(1,2) residue
E is branched to C
x and y are independently selected among 0 and 1
X and Y are independently selected among A, B, C, D, E, AB, B(E), (E)C, CD, DA, AB(E), B(E)C, (E)CD, CDA, AB(E)C, B(E)CD, (E)CDA, CDAB, DAB(E) and wherein n is chosen from 2 and 3 covalently bound to a carrier,
said process comprising the following steps:
a) the conjugation of the molecule according to any one of claims 5 and 6 to a linker to obtain a linker-derivatized molecule,
b) the reaction of said linker-derivatized molecule to the carrier.

11. A process of preparation of a conjugate molecule comprising an oligo- or polysaccharide selected from the group consisting of:

$(X)_x$—{AB(E)CD}n—$(Y)_y$ wherein:
A is an alphaLRhap-(1,2) residue
B is an alphaLRhap-(1,3) residue
C is an alphaLRhap-(1,3) residue
E is an alphaDGlcp-(1,4) residue
D is a betaDGlcNAcp-(1,2) residue
E is branched to C
x and y are independently selected among 0 and 1
X and Y are independently selected among A, B, C, D, E, AB, B(E), (E)C, CD, DA, AB(E), B(E)C, (E)CD, CDA, AB(E)C, B(E)CD, (E)CDA, CDAB, DAB(E) and wherein n is chosen from 2 and 3, covalently bound to a carrier,
said process comprising the following steps:
a) the conjugation of an appropriate carrier to a linker to obtain a linker-derivatized carrier,
b) the reaction of said derivatized carrier to a molecule according to any one of claims 5 and 6.

12. A process of preparation of a conjugate according to claim 10, wherein the linker is a small molecule having a molecular weight of approximately <500 daltons.

13. A process of preparation of a conjugate according to claim 10, wherein the linker is a homobifunctional molecule.

14. A process of preparation of a conjugate according to claim 10, wherein the linker is a heterobifunctional molecule.

15. A process of preparation of a conjugate according to claim 11, wherein the linker is a small molecule having a molecular weight of approximately <500 daltons.

16. A process of preparation of a conjugate according to claim 11, wherein the linker is a homobifunctional molecule.

17. A process of preparation of a conjugate according claim 11, wherein the linker is a heterobifunctional molecule.

18. A process of preparation of a conjugate according to claim 12, wherein the linker is a homobifunctional molecule.

19. A process of preparation of a conjugate according claim 12, wherein the linker is a heterobifunctional molecule.

* * * * *

UNITED STATES PATENT AND TRADEMARK OFFICE
CERTIFICATE OF CORRECTION

PATENT NO. : 9,446,109 B2  
APPLICATION NO. : 13/325511  
DATED : September 20, 2016  
INVENTOR(S) : Armelle Phalipon et al.

Page 1 of 1

It is certified that error appears in the above-identified patent and that said Letters Patent is hereby corrected as shown below:

On the Title Page

Item (73), "Assignee: INSERM (Institut National De La Sante Et De La Recherche Medicale)" should read --INSERM (Institut National De La Sante Et De La Recherche Medicale); INSTITUT PASTEUR; CENTRE NATIONAL DE LA RECHERCHE SCIENTIFIQUE--

Signed and Sealed this  
Sixth Day of June, 2017

Michelle K. Lee  
*Director of the United States Patent and Trademark Office*